US010696979B2

(12) United States Patent
Christensen et al.

(10) Patent No.: US 10,696,979 B2
(45) Date of Patent: Jun. 30, 2020

(54) NUCLEOTIDE SEQUENCES AND POLYPEPTIDES ENCODED THEREBY USEFUL FOR MODIFYING PLANT CHARACTERISTICS IN RESPONSE TO COLD

(71) Applicant: Ceres, Inc., Thousands Oaks, CA (US)

(72) Inventors: Cory Christensen, Simi Valley, CA (US); Jack Okamuro, Oak Park, CA (US); Shing Kwok, Woodland Hills, CA (US); Roger Pennell, Malibu, CA (US)

(73) Assignee: Ceres, Inc., Thousand Oaks, CA (US)

( * ) Notice: Subject to any disclaimer, the term of this patent is extended or adjusted under 35 U.S.C. 154(b) by 0 days.

(21) Appl. No.: 16/275,659

(22) Filed: Feb. 14, 2019

(65) Prior Publication Data

US 2019/0241902 A1 Aug. 8, 2019

Related U.S. Application Data

(60) Division of application No. 15/362,633, filed on Nov. 28, 2016, now Pat. No. 10,240,166, which is a division of application No. 11/779,266, filed on Jul. 17, 2007, now abandoned, which is a continuation-in-part of application No. 11/778,060, filed on Jul. 15, 2007, now abandoned, which is a continuation-in-part of application No. 11/248,547, filed on Oct. 12, 2005, now Pat. No. 7,244,879.

(51) Int. Cl.

| | |
|---|---|
| ***C12N 15/82*** | (2006.01) |
| ***C07K 14/415*** | (2006.01) |
| ***A01H 1/02*** | (2006.01) |
| ***C12Q 1/6895*** | (2018.01) |

(52) U.S. Cl.
CPC ........... *C12N 15/8273* (2013.01); *A01H 1/02* (2013.01); *C07K 14/415* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 5,990,387 | A | 11/1999 | Tomes et al. |
| 2006/0107345 | A1 | 5/2006 | Alexandrov et al. |
| 2006/0150283 | A1 | 7/2006 | Alexandrov et al. |
| 2009/0094717 | A1 | 4/2009 | Troukhan et al. |
| 2009/0265275 | A1 | 10/2009 | Alexandrov et al. |
| 2010/0083407 | A1 | 4/2010 | Feldmann et al. |
| 2016/0369294 | A9* | 12/2016 | Nadzan ................ C07K 14/415 |
| 2018/0223303 | A1 | 8/2018 | Alexandrov et al. |
| 2019/0276836 | A1 | 9/2019 | Christensen et al. |
| 2020/0109412 | A1 | 4/2020 | Christensen et al. |

FOREIGN PATENT DOCUMENTS

| | | | | |
|---|---|---|---|---|
| EP | 1033405 | | 9/2000 | |
| EP | 1033405 | A2 * | 9/2000 | .......... C07K 14/415 |
| WO | WO-9902687 | A1 * | 1/1999 | |
| WO | WO-2004035798 | A2 * | 4/2004 | .......... C07K 14/415 |

OTHER PUBLICATIONS

Wells (Biochemistry 29:8509-8517, 1990).*
Guo et al. (PNAS, 101: 9205-9210, 2004 ).*
Ngo et al., (The Protein Folding Problem and Tertiary Structure Prediction, K. Merz., and S. Le Grand (eds.) pp. 492-495,1994).*
Thornton et al. (Nature structural Biology, structural genomics supplement, Nov. 2000).*
Keskin et al. (Protein Science, 13:1043-1055, 2004).*
USPTO: Notice of Allowance and Fee(s) Due regarding U.S. Appl. No. 16/275,629, dated Aug. 2, 2019.
Kim et al., "Molecular cloning of low temperature-inducible ribosomal proteins from soybean," *Journal of Experimental Botany* 55:1153-1155, 2004.
Lu et al., "*Arabidopsis* Mutants Deficient in Diacylglycerol Acyltransferase Display Increased Sensitivity to Abscisic Acid, Sugards, and Osmotic Stress during Germination and Seedling Development," *Plant Physiology* 129:1352-1358, 2002.
Ngo et al., "Computational Complexity, Protein Structure Prediction, and the Levinthal Pradox," *The Protein Folding Problem and Tertiary Structure Prediction*, K. Merz and S. Le Grand (eds.), pp. 492-495, 1994.
Guo et al., "Protein tolerance to random amino acid change," *PNAS* 101:9205-9210, 2004.
GenBank Accession No. AY117196, dated Sep. 18, 2002.
Keskin et al., "A new, structurally nonredundant, diverse data set of protein-protein interfaces and its implications," *Protein Science* 13:1043-1055, 2004.
Thornton et al., "From structure to function: Approaches and limitations," *Nature Structural Biology, Structural Gemonics Supplement*, Nov. 2000.
Wells, "Additivity of Mutational Effects in Proteins," *Biochemistry* 29:8509-8517, 1990.
U.S. Appl. No. 16/719,390, filed Dec. 18, 2019, Christensen, et al.
U.S. Appl. No. 16/855,674, filed Apr. 22, 2020, Christensen, et al.

* cited by examiner

*Primary Examiner* — Vinod Kumar
(74) *Attorney, Agent, or Firm* — Dentons US LLP

(57) ABSTRACT

Methods and materials for modulating cold tolerance levels in plants are disclosed. For example, nucleic acids encoding cold tolerance-modulating polypeptides are disclosed as well as methods for using such nucleic acids to transform plant cells. Also disclosed are plants having increased levels of cold tolerance and plant products produced from plants having increased cold tolerance levels.

6 Claims, 8 Drawing Sheets

Specification includes a Sequence Listing.

SEQ-ID-NO-4-GI-62526422
SEQ-ID-NO-5-CLONE-1606506
SEQ-ID-NO-2-CLONE-30087
SEQ-ID-NO-52-CLONE-1382611

FIGURE 2

```
SEQ-ID-NO-17-CLONE-839727     MSAAE---GA VVFSEEKEAL VLKSWAIMKK DSANLGLRFF LKIFEIAPSA   47
SEQ-ID-NO-16-CLONE-1554560    MALAEADDGA VVFGEEQEAL VLKSWAVMKK DAANLGLRFF LKVFEIAPSA   50
SEQ-ID-NO-60-CLONE-1802327    MALAE---GN VIFGEEQEAL VLKSWALMKK DSADLGLRFF LKIFEIAPSA   47
SEQ-ID-NO-9-CLONE-30469-FL    -MESE---GK IVFTEEQEAL VVKSWSVMKK NSAELGLKLF IKIFEIAPTT   46
SEQ-ID-NO-10-GI-30909306      -MESE---GK IVFTEEQEAL VVKSWSVMKK NSADLGLKLF IKIFEIAPTA   46
SEQ-ID-NO-13-CLONE-546001     -MTTTLERG- --FSEEQEAL VVKSWNVMKK NSGELGLKFF LKIFEIAPSA   46
SEQ-ID-NO-70-CLONE-1916866    MATYE---GK -VFTEEQEAL VVKSWTVMKK NAAELGLKFF LKIFEIAPSA   46

SEQ-ID-NO-17-CLONE-839727     RQMFPFLRDS DVPLETNPKL KTHAVSVFVM TCEAAAQLRK AGKITVRETT   97
SEQ-ID-NO-16-CLONE-1554560    KQMFSFLRDS DVPLEKNPKL KTHAMSVFVM TCEAAAQLRK AGKVTVRETT  100
SEQ-ID-NO-60-CLONE-1802327    KQMFSFLRDS DVPLEKNPKL KNHAMSVFVM TCEAAAQLRK AGKVTVRETT   97
SEQ-ID-NO-9-CLONE-30469-FL    KKMFSFLRDS PIPAEQNPKL KPHAMSVFVM CCESAVQLRK TGKVTVRETT   96
SEQ-ID-NO-10-GI-30909306      KKLFSFLRDS PIPAEQNPKL KPHAMSVFVM CCESAAQLRK TGKVTVKETT   96
SEQ-ID-NO-13-CLONE-546001     QKLFSFLRDS TVPLEQNPKL KPHAVSVFVM TCDSAVQLRK AGKVTVRESN   96
SEQ-ID-NO-70-CLONE-1916866    KKLFSFLRDS NVPLEQNTKL KPHAMSVFVM TCESAVQLRK AGKVTVRESN   96

SEQ-ID-NO-17-CLONE-839727     LKRLGGTHLK YGVADGHFEV TRFALLETIK EALPADMWGP EMRNAWGEAY  147
SEQ-ID-NO-16-CLONE-1554560    LKRLGATHLR YGVADGHFEV TGFALLETIK EALPADMWSL EMKKAWAEAY  150
SEQ-ID-NO-60-CLONE-1802327    LKRLGATHFK YGVADGHFEV TRFALLETIK EALPADMWSL EMKNAWSEAY  147
SEQ-ID-NO-9-CLONE-30469-FL    LKRLGASHSK YGVVDEHFEV AKYALLETIK EAVP-EMWSP EMKVAWGQAY  145
SEQ-ID-NO-10-GI-30909306      LKRLGANHSK YGVVDEHFEV TKYALLETIK EAVP-EMWSP EMKSAWGQAY  145
SEQ-ID-NO-13-CLONE-546001     LKKLGATHFR TGVANEHFEV TKFALLETIK EAVP-EMWSP AMKNAWGEAY  145
SEQ-ID-NO-70-CLONE-1916866    LKKLGATHFK YGVVDEHFEV TKFALLETIK EAVP-DMWSD EMKNAWGEAY  145

SEQ-ID-NO-17-CLONE-839727     DQLVAAIKQE MKPSE---   162
SEQ-ID-NO-16-CLONE-1554560    SQLVAAIKRE MKPDA---   165
SEQ-ID-NO-60-CLONE-1802327    NQLVAAIKQE MKPAA---   162
SEQ-ID-NO-9-CLONE-30469-FL    DHLVAAIKAE MNLSN---   160
SEQ-ID-NO-10-GI-30909306      DHLVAAIKAE MKPSH---   160
SEQ-ID-NO-13-CLONE-546001     DQLVDAIKSE MKPPSS--   161
SEQ-ID-NO-70-CLONE-1916866    DRLVAAIKIE MKACSQAA   163
```

FIGURE 3

```
SEQ-ID-NO-221-CLONE-839727-T    MSAAE---GA  VVFSEEKEAL  VLKSWAIMKK  DSANLGLRFF  LKIFEIAPSA  47
SEQ-ID-NO-207-CLONE-1554560-T   MALAEADDGA  VVFGEEQEAL  VLKSWAVMKK  DAANLGLRFF  LKVFEIAPSA  50
SEQ-ID-NO-208-CLONE-1802327-T   MALAE---GN  VIFGEEQEAL  VLKSWALMKK  DSADLGLRFF  LKIFEIAPSA  47
SEQ-ID-NO-7-CLONE-30469         MESE----GK  IVFTEEQEAL  VVKSWSVMKK  NSAELGLKLF  IKIFEIAPTT  46
SEQ-ID-NO-227-GI-30909306-T     MESE----GK  IVFTEEQEAL  VVKSWSVMKK  NSADLGLKLF  IKIFEIAPTA  46
SEQ-ID-NO-219-CLONE-546001-T    MTTT----LE  RGFSEEQEAL  VVKSWNVMKK  NSGELGLKFF  LKIFEIAPSA  46
SEQ-ID-NO-212-CLONE-1916866-T   MATY----EG  KVFTEEQEAL  VVKSWTVMKK  NAAELGLKFF  LKIFEIAPSA  46

SEQ-ID-NO-221-CLONE-839727-T    RQMFPFLRDS  DVPLETNPKL  KTHAVSVFVM  --  77
SEQ-ID-NO-207-CLONE-1554560-T   KQMFSFLRDS  DVPLEKNPKL  KTHAMSVFVM  --  80
SEQ-ID-NO-208-CLONE-1802327-T   KQMFSFLRDS  DVPLEKNPKL  KNHAMSVFVM  --  77
SEQ-ID-NO-7-CLONE-30469         KKMFSFLRDS  PIPAEQNPKL  KPHAMSVFVM  YN  78
SEQ-ID-NO-227-GI-30909306-T     KKLFSFLRDS  PIPAEQNPKL  KPHAMSVFVM  --  76
SEQ-ID-NO-219-CLONE-546001-T    QKLFSFLRDS  TVPLEQNPKL  KPHAVSVFVM  --  76
SEQ-ID-NO-212-CLONE-1916866-T   KKLFSFLRDS  NVPLEQNTKL  KPHAMSVFVM  --  76
```

FIGURE 4

| Sequence | | | | | | |
|---|---|---|---|---|---|---|
| SEQ-ID-NO-20-CLONE-271922 | MAKRTKKVGI | VGKYGTRYGA | SIRKQIKKME | VSQHSKYFCE | FCGKYGVKRK | 50 |
| SEQ-ID-NO-54-CLONE-1627907 | MTKRTKKAGI | VGKYGTRYGA | SLRKQIKKME | VSQHAKYFCE | FCGKYAVKRQ | 50 |
| SEQ-ID-NO-25-CLONE-664936 | MTKRTKKAGI | VGKYGTRYGA | SLRKQIKKME | VSQHSKFFCE | FCGKYAVKRK | 50 |
| SEQ-ID-NO-28-CLONE-632613 | MTKRTKKAGI | VGKYGTRYGA | SLRKQIKKME | VSQHSKYFCE | FCGKFAVKRK | 50 |
| SEQ-ID-NO-29-CLONE-1390976 | MTKRTKKAGI | VGKYGTRYGA | SLRKQIKKME | VSQHSKYFCE | FCGKFAVKRK | 50 |
| SEQ-ID-NO-58-CLONE-1783890 | MTKRTKKAGI | VGKYGTRYGA | SLRKQIKKME | VSQHSKYFCE | FCGKFAVKRK | 50 |

| Sequence | | | | | | |
|---|---|---|---|---|---|---|
| SEQ-ID-NO-20-CLONE-271922 | AVGIWGCKDC | GKVKAGGAYT | MNTASAVTVR | STIRRLREQI | EG | 92 |
| SEQ-ID-NO-54-CLONE-1627907 | AVGIWGCKDC | GKVKAGGAYT | LNTASAVTVR | STIRRLREQT | ES | 92 |
| SEQ-ID-NO-25-CLONE-664936 | AVGIWGCKDC | GKVKAGGAYT | LNTASAVTVR | STIRRLREQT | EG | 92 |
| SEQ-ID-NO-28-CLONE-632613 | AVGIWGCKDC | GKVKAGGAYT | MNTASAVTVR | STIRRLREQT | EA | 92 |
| SEQ-ID-NO-29-CLONE-1390976 | AVGIWGCKDC | GKVKAGGAYT | MNTASAVTVR | STIRRLREQT | EA | 92 |
| SEQ-ID-NO-58-CLONE-1783890 | AVGIWGCKDC | GKVKAGGAYT | MNTASAVTVR | STIRRLREQT | EA | 92 |

FIGURE 5

```
SEQ-ID-NO-34-CLONE-2403-FL    MQI FVKTLTG  KTI TLEVESS  DTI DNVKAKI  QDKEGI PPDQ  QRLI FAGKQL   50
SEQ-ID-NO-35-CLONE-1482731    MQI FVKTLTG  KTI TLEVESS  DTI DNVKSKI  QDKEGI PPDQ  QRLI FAGKQL   50
SEQ-ID-NO-36-CLONE-522921     MQI FVKTLTG  KTI TLEVESS  DTI DNVKAKI  QDKEGI PPDQ  QRLI FAGKQL   50
SEQ-ID-NO-37-CLONE-1036726    MQI FVKTLTG  KTI TLEVESS  DTI DNVKAKI  QDKEGI PPDQ  QRLI FAGKQL   50
SEQ-ID-NO-68-CLONE-1884696    MQI FVKTLTG  KTI TLEVESS  DTI DNVKAKI  QDKEGI PPDQ  QRLI FAGKQL   50
SEQ-ID-NO-80-CLONE-2034916    MQI FVKTLTG  KTI TLEVESS  DTI DNVKAKI  QDKEGI PPDQ  QRLI FAGKQL   50

SEQ-ID-NO-34-CLONE-2403-FL    EDGRTLADYN  I QKESTLHLV  LRLRGGTMI K  VKTLTGKEI E  I DI EPTDTI D  100
SEQ-ID-NO-35-CLONE-1482731    EDGRTLADYN  I QKESTLHLV  LRLRGGTMI K  VKTLTGKEI E  I DI EPTDTI D  100
SEQ-ID-NO-36-CLONE-522921     EDGRTLADYN  I QKESTLHLV  LRLRGGTMI K  VKTLTGKEI E  I DI EPTDTI D  100
SEQ-ID-NO-37-CLONE-1036726    EDGRTLADYN  I QKESTLHLV  LRLRGGTMI K  VKTLTGKEI E  I DI EPTDTI D  100
SEQ-ID-NO-68-CLONE-1884696    EDGRTLADYN  I QKESTLHLV  LRLGGGMQI F  VKTLTGKTI T  LEVESSDTI D  100
SEQ-ID-NO-80-CLONE-2034916    EDGRTLADYN  I QKESTLHLV  LRLRGGMQI F  VKTLTGKTI T  LEVESSDTI D  100

SEQ-ID-NO-34-CLONE-2403-FL    RI KERVEEKE  GI PPVQQRLI  YAGKQLADDK  TAKDYAI EGG  SVLHLVLALR  150
SEQ-ID-NO-35-CLONE-1482731    RI KERVEEKE  GI PPVQQRLI  YAGKQLADDK  TAKDYNI EGG  SVLHLVLALR  150
SEQ-ID-NO-36-CLONE-522921     RI KERVEEKE  GI PPVQQRLI  YAGKQLADDK  TAKEYNI EGG  SVLHLVLALR  150
SEQ-ID-NO-37-CLONE-1036726    RI KERVEEKE  GI PPVQQRLI  YAGKQLADDK  TXKDYNI EGG  SVSA------  144
SEQ-ID-NO-68-CLONE-1884696    NVKAKI QDKE  GI PPDQQRLI  FAGKQLEDGR  TLADYNI QKD  STLHLVLRLR  150
SEQ-ID-NO-80-CLONE-2034916    NVKVKI QDKE  GI PPDQQRLI  FAGKQLEDGR  TLADYNI QKE  STLHLVLRLR  150

SEQ-ID-NO-34-CLONE-2403-FL    GGL-------  ----------  ----------  ----------  ----------  153
SEQ-ID-NO-35-CLONE-1482731    GGS-------  ----------  ----------  ----------  ----------  153
SEQ-ID-NO-36-CLONE-522921     GGT-------  ----------  ----------  ----------  ----------  153
SEQ-ID-NO-37-CLONE-1036726    -SG-------  ----------  ----------  ----------  ----------  146
SEQ-ID-NO-68-CLONE-1884696    GG--------  ----------  ----------  ----------  ----------  152
SEQ-ID-NO-80-CLONE-2034916    GGMQI FVKTL  TGKTI TLEVE  SSDTI DNVKA  KI QDKEGI PP  DQQRLI FAGK  200

SEQ-ID-NO-34-CLONE-2403-FL    ----------  --L   154
SEQ-ID-NO-35-CLONE-1482731    ----------  --D   154
SEQ-ID-NO-36-CLONE-522921     ----------  --Y   154
SEQ-ID-NO-37-CLONE-1036726    ----------  --S   147
SEQ-ID-NO-68-CLONE-1884696    ----------  --F   153
SEQ-ID-NO-80-CLONE-2034916    QLEDGRTLAD  YNI   213
```

FIGURE 6

| | | | | | |
|---|---|---|---|---|---|
| SEQ·ID·NO·40·CLONE·2403 | MQI FVKTLTG | KTI TLEVESS | DTI DNVKAKI | QDK | 33 |
| SEQ·ID·NO·205·CLONE·1036726·T | MQI FVKTLTG | KTI TLEVESS | DTI DNVKAKI | QDK | 33 |
| SEQ·ID·NO·211·CLONE·1884696·T | MQI FVKTLTG | KTI TLEVESS | DTI DNVKAKI | QDK | 33 |
| SEQ·ID·NO·213·CLONE·1950105·T | MQI FVKTLTG | KTI TLEVESS | DTI DNVKAKI | QDK | 33 |
| SEQ·ID·NO·218·CLONE·522921·T | MQI FVKTLTG | KTI TLEVESS | DTI DNVKAKI | QDK | 33 |
| SEQ·ID·NO·206·CLONE·1482731·T | MQI FVKTLTG | KTI TLEVESS | DTI DNVKSKI | QDK | 33 |

FIGURE 7

```
SEQ-ID-NO-46-CLONE-1055099   MRKARPPQPQ P----QPSQQ SP-------- ELRYRGVRKR PSGRYAAEIR  38
SEQ-ID-NO-56-CLONE-1761125   MMRDTAAVAV A--------- ---------- APRYRGVRKR PWGRFAAEIR  31
SEQ-ID-NO-83-GI-125550159    MCEAAA---- ---------- ---------- -PRYRGVRKR PWGRFAAEIR  25
SEQ-ID-NO-45-CLONE-273307    MRRRGVAAAD A--------D GD-------V ELRFRGVRKR PWGRYAAEIR  35
SEQ-ID-NO-62-CLONE-1838364   MRRGRGAAAA NAVARRPALQ PS----GSIK EPRYRGVRKR PWGRFAAEIR  46
SEQ-ID-NO-50-CLONE-1240330   MRKGRGGGAS A---AAVDVN GS-----ILK EPRYRGVRKR PWGRFAAEIR  42
SEQ-ID-NO-42-CLONE-674166    MGRGGTAAAA A-EVAEPGLR PV-----YFK EQRYRGVRKR PWGRFAAEIR  44
SEQ-ID-NO-86-GI-56384582     MGRGGATTAA A------AVE PV-----FFK EPRYRGVRKR PWGRFAAEIR  39
SEQ-ID-NO-48-ANNOT-1441430   MGRTRTTTKQ A---VDPNGS ATQNMLVIAK EPRYRGVRKR PWGRFAAEIR  47
SEQ-ID-NO-87-GI-57012880     MRRGRAAAAP APVTGEPNGS GG------SK EIRFRGVRKR PWGRFAAEIR  44
SEQ-ID-NO-44-CLONE-975672    MRKGRGSSAV P-----PALP GS------VK EPRYRGVRKR PWGRFAAEIR  39
SEQ-ID-NO-84-GI-15223609     MRRGRGSSAV AGPTVVAAIN GS------VK EIRFRGVRKR PWGRFAAEIR  44

SEQ-ID-NO-46-CLONE-1055099   DPAKKTPIWL GTFDCAEDAA RAYDSAARSL RGPTARTNFP PSSATQPPPR  88
SEQ-ID-NO-56-CLONE-1761125   DPAKRARVWL GTFDSAEAAA RAYDVAARTL RGPLARTNFP CASSRLPLPS  81
SEQ-ID-NO-83-GI-125550159    DPAKRARVWL GTYDSAEAAA RAYDVAARNL RGPLARTNFP LVSSLPLPSP  75
SEQ-ID-NO-45-CLONE-273307    DPAKKARVWL GTFDSAEDAA RAYDAAARML RGPKARTNFP LPAAAALHHP  85
SEQ-ID-NO-62-CLONE-1838364   DPWKKTRVWL GTFDSAEEAA RAYDTAARTL RGPKAKTNFP INSSNIPAFP  96
SEQ-ID-NO-50-CLONE-1240330   DPLKKARVWL GTFDSAEDAA RAYDAAARTL RGPKAKTNFP P----LSPFC  88
SEQ-ID-NO-42-CLONE-674166    DPLKKARVWL GTFDTAEEAA RAYDTAARTL RGPKAKTNFP L----SPPFY  90
SEQ-ID-NO-86-GI-56384582     DPLKKARVWL GTFDTAEEAA RAYDTAARNL RGPKAKTNFP L----AQPFY  85
SEQ-ID-NO-48-ANNOT-1441430   DPWKKTRVWL GTFDSAEDAA RAYDAAARTL RGAKAKTNFP ISTTNQLFNH  97
SEQ-ID-NO-87-GI-57012880     DPWKKTRVWL GTFDSAEDAA RAYDAAARAL RGPKAKTNFP LPYAHHHQFN  94
SEQ-ID-NO-44-CLONE-975672    DPLKKSRVWL GTFDSAEEAA RAYDAAARNL RGPKAKTNFQ IDCSPSSPLQ  89
SEQ-ID-NO-84-GI-15223609     DPWKKARVWL GTFDSAEEAA RAYDSAARNL RGPKAKTNFP IDSSSPPPPN  94

SEQ-ID-NO-46-CLONE-1055099   ---------- --PPPP---- ---------- ------AAAA AAATSSQSST  106
SEQ-ID-NO-56-CLONE-1761125   ---------- ---------- ----RHQGGC GGGLVAPPPA APTCSS-SST  106
SEQ-ID-NO-83-GI-125550159    ---------- ---------- ----HYHLPG KAAAAAPPVA GPACSA-SST  100
SEQ-ID-NO-45-CLONE-273307    ----HMPAAA AAAAPPY--- ----TTYPTA TGVVSTPPVA RPACSSLSST  124
SEQ-ID-NO-62-CLONE-1838364   ------FETN HHHNEGF--- IDQRRLYPMG EFHDPEVNPQ RPTRSSMSST  137
SEQ-ID-NO-50-CLONE-1240330   --------YP HPTTDPFFYT GFH-DQHHHH NNNNL-NNPQ RPTSSGMSST  128
SEQ-ID-NO-42-CLONE-674166    ---------- --HPDPF--- SDH-RHFA-N TGEDF-HDHR RPTSSGMSST  122
SEQ-ID-NO-86-GI-56384582     --------QN PEAGNPF--- GEL-RFYAGG AGEGF-QDHR RPTSSGMSST  122
SEQ-ID-NO-48-ANNOT-1441430   ------QNQN QSPTDPF--- LDHHSINP-- ---------Q RPTSSSLSST  127
SEQ-ID-NO-87-GI-57012880     ------QGHN PNN-DPF--- VDS-RFYP-- -QDNP-IISQ RPTSSSMSST  129
SEQ-ID-NO-44-CLONE-975672    ------PLHH RNQIDPF--- MDH-RLYG-- -GEQEVVIIS RPASSSMSST  126
SEQ-ID-NO-84-GI-15223609     LRFNQIRNQN QNQVDPF--- MDH-RLFT-D HQQQF-PIVN RPTSSSMSST  138
```

FIGURE 7 (cont)

```
SEQ-ID-NO-46-CLONE-1055099   VESWSGGGP- ---------- -RAPARARSA ARAGTAKEGE EDCRSYCGSS   144
SEQ-ID-NO-56-CLONE-1761125   VESSSGPRGA PRAAAA---- -AAPRIRRRS VKKPRPAAPD IDCHSDCASS   151
SEQ-ID-NO-83-GI-125550159    VESSSGPRGP RPAA------ -TAAAVPRRR VPRPAPPAPD AGCHSDCASS   143
SEQ-ID-NO-45-CLONE-273307    VESFSGARP- ---------- -RPVLPP--R FP--PPSLPD GDCRSDCGSS   158
SEQ-ID-NO-62-CLONE-1838364   VESFSGPRPA QPPQKSAD-- -FAVVSTRKY YPRPPPVEPE -DCHSDCDSS   183
SEQ-ID-NO-50-CLONE-1240330   VESFSGPRPP TTTTTTTTTT ATPFLTATRR YPRTPPLVPE -DCHSDCDSS   177
SEQ-ID-NO-42-CLONE-674166    VESFSGPRAA VPA------- -TAPVATGRR YPRTPPVIPE -DCRSDCDSS   163
SEQ-ID-NO-86-GI-56384582     VESFCGPRPV RPPM------ -PPSAVTGRR YPRTPPVAPG -DCRSDCDSS   164
SEQ-ID-NO-48-ANNOT-1441430   VESFSGPRPP QPTTTT---- -KSGNGPRRS HPRIPPVVPE -DCHSDCDSS   171
SEQ-ID-NO-87-GI-57012880     VESFSGPRPP PAPR------ -QQTTASSRK YTRSPPVVPD -DCHSDCDSS   171
SEQ-ID-NO-44-CLONE-975672    VKSCSGVRPA SS-------- -SVAKAATKR YPRTPPVAPE -DCRSDCDSS   166
SEQ-ID-NO-84-GI-15223609     VESFSGPRPT ---------- -TMKPATTKR YPRTPPVVPE -DCHSDCDSS   176

SEQ-ID-NO-46-CLONE-1055099   SSVLLE---- -----EGADDA AAS------- RSPLPFDLNM PPPQEGAL--   177
SEQ-ID-NO-56-CLONE-1761125   ASV-VD---- -----DGDDAS TV-------- RSRAPFDLNV PAPVDGDH--   182
SEQ-ID-NO-83-GI-125550159    ASV-VD---- -----DADDAS TVR------- SRVAAFDLNL PPPLDRDH--   175
SEQ-ID-NO-45-CLONE-273307    ASV-VD---- -----DDCTDA AAS----ASC PFPLPFDLNL -PPGGGGAGV   194
SEQ-ID-NO-62-CLONE-1838364   SSV-VD---- -----DGDI AL SSC------- RKTLPFDLNF -PPLDEDG--   214
SEQ-ID-NO-50-CLONE-1240330   SSV-VD---- -----DGDDNI VSS----SF- RPPLPFDLNA -LPFDDAA--   210
SEQ-ID-NO-42-CLONE-674166    SSV-VD---- -----DGEGDN VAS----SFP REPLPFDLNA -LPLDDAD--   197
SEQ-ID-NO-86-GI-56384582     SSV-VD---- -----DADNDN AASSTMLSFK RQPLPFDLNA -PPLEEGD--   202
SEQ-ID-NO-48-ANNOT-1441430   SSV-VD---- -----DRDVAS AAS----SLC RKPLPFDLNF -PPLDQVD--   205
SEQ-ID-NO-87-GI-57012880     SSV-VDHGDC EKENDNDNDN I AS----SSF RKPLLFDLNL PPPMDDAG--   214
SEQ-ID-NO-44-CLONE-975672    SSV-VE---- -----DGXDI A SSS----SRR KPPFEFDLNF -XPLDGVD--   200
SEQ-ID-NO-84-GI-15223609     SSV-I D---- -----DDDDI A SSS----RRR NPPFQFDLNF -PPLDCVD--   210

SEQ-ID-NO-46-CLONE-1055099   ---DAEADQM TCRYDTLLRL ---------- ----------   194
SEQ-ID-NO-56-CLONE-1761125   ------ALDL -C---TELRL ---------- ----------   192
SEQ-ID-NO-83-GI-125550159    -------VDL -C---TDLRL ---------- ----------   184
SEQ-ID-NO-45-CLONE-273307    GFYADEEDEL RL---TALRL ---------- ----------   211
SEQ-ID-NO-62-CLONE-1838364   ------RSPV YC-FMSLIAM PVMNDDDRLL DLFFFFKKC    246
SEQ-ID-NO-50-CLONE-1240330   -----ADDDL RR---TALCL ---------- ----------   222
SEQ-ID-NO-42-CLONE-674166    ----VATDDL FC---TVLCL ---------- ----------   210
SEQ-ID-NO-86-GI-56384582     -VANGLGEDL HC---TLLCL ---------- ----------   218
SEQ-ID-NO-48-ANNOT-1441430   -LGSG--DDL HC---TALCL ---------- ----------   219
SEQ-ID-NO-87-GI-57012880     ------ADDL HC---TALCL ---------- ----------   225
SEQ-ID-NO-44-CLONE-975672    -LFVGA-DDX XC---TDLXL ---------- ----------   215
SEQ-ID-NO-84-GI-15223609     -LFNGA-DDL HC---TDLRL ---------- ----------   225
```

NUCLEOTIDE SEQUENCES AND POLYPEPTIDES ENCODED THEREBY USEFUL FOR MODIFYING PLANT CHARACTERISTICS IN RESPONSE TO COLD

This application is a divisional of copending application Ser. No. 15/362,633 filed on Nov. 28, 2016, which application is a divisional of application Ser. No. 11/779,266 filed on Jul. 17, 2007 (Abandoned), which application is a Continuation-In-Part of application Ser. No. 11/778,060 filed on Jul. 15, 2007 (abandoned), which is a Continuation-In-Part of application Ser. No. 11/248,547 filed on Oct. 12, 2005 (now U.S. Pat. No. 7,244,879), the entire contents of which are hereby incorporated by reference and for which priority is claimed under 35 U.S.C. § 120.

FIELD OF THE INVENTION

The present invention relates to isolated polynucleotides, polypeptides encoded thereby, and the use of those products for making transgenic plants with improved tolerances to environmental stresses such as low or chilling temperatures.

BACKGROUND OF THE INVENTION

Plants are constantly exposed to a variety of biotic (i.e. pathogen infection and insect herbivory) and abiotic (i.e. high or low temperature, drought, flood and salinity) stresses. To survive these challenges to their sessile life, plants have developed elaborate mechanisms to perceive external signals and to manifest adaptive responses with proper physiological and morphological changes (Bohnert et al. 1995). Plants exposed to cold or chilling conditions typically have low yields of biomass, seeds, fruit and other edible products. The term "chilling sensitivity" is used for the description of physiological and developmental damages in the plant caused by low, but above freezing, temperatures. Important agricultural crop plants such as corn, soybean, rice and cotton have tropical ancestors that make them chilling sensitive. In some countries or agricultural regions of the world chilling temperatures are a significant cause of crop losses and a primary factor limiting the geographical range and growing season of many crop species. Another example is that chilling conditions can cause significant concern in early spring planting of corn or canola. Poor germination and reduced growth of chilling sensitive crops in the spring results in less ground coverage, more erosion and increased occurrence of weeds leading to less nutrient supply for the crop.

Typically, chilling damage includes wilting, necrosis or ion leakage from cell membranes, especially calcium leakage, and decreased membrane fluidity, which consequently impacts membrane dependent processes such as: photosynthesis, protein synthesis, ATPase activity, uptake of nitrogen, etc. (see Levitt J (1980) Chilling injury and resistance. In Chilling, Freezing, and High Temperature Stresses: Responses of Plant to Environmental Stresses, Vol 1., T T Kozlowsky, ed, Academic Press, New York, pp 23-64; Graham and Patterson (1982) *Annu Rev Plant Physiol* 33: 347-372; Guy (1990) *Annu Rev Plant Physiol Plant Mol Biol* 41: 187-223; and Nishida and Murata (1996) *Annu Rev Plant Physiol Plant Mol Biol* 47: 541-568.). In addition, cold temperatures are often associated with wet conditions. The combination of cold and wet can result in hypoxic stress on the roots, causing an even more severe reduction of growth rate but, more critically, can be lethal to the plants, especially sensitive plant species such as corn and cotton.

Yet it has been observed that environmental factors, such as low temperature, can serve as triggers to induce cold acclimation processes allowing plants responding thereto to survive and thrive in low temperature environments. It would, therefore, be of great interest and importance to be able to identify genes that regulate or confer improved cold acclimation characteristics to enable one to create transformed plants (such as crop plants) with improved cold tolerance characteristics such as faster germination and/or growth and/or improved nitrogen uptake under cold conditions to improve survival or performance under low or chilling temperatures.

In the fields of agriculture and forestry efforts are constantly being made to produce plants with an increased growth potential in order to feed the ever-increasing world population and to guarantee the supply of reproducible raw materials. This is done conventionally through plant breeding. The breeding process is, however, both time-consuming and labor-intensive. Furthermore, appropriate breeding programs must be performed for each relevant plant species.

Progress has been made in part by the genetic manipulation of plants; that is by introducing and expressing recombinant nucleic acid molecules in plants. Such approaches have the advantage of not usually being limited to one plant species, but instead being transferable among plant species. There is a need for generally applicable processes that improve forest or agricultural plant growth potential. Therefore, the present invention relates to a process for increasing the growth potential in plants under low temperature, chilling or cold conditions, characterized by expression of recombinant DNA molecules stably integrated into the plant genome.

SUMMARY OF THE INVENTION

The present invention, therefore, relates to isolated polynucleotides, polypeptides encoded thereby and the use of those products for making transgenic plants with improved cold tolerance.

The present invention also relates to processes for increasing the growth potential in plants due to cold acclimation, recombinant nucleic acid molecules and polypeptides used for these processes and their uses, as well as to plants with an increased growth potential due to improved cold acclimation. Unless otherwise defined, all scientific and technical terms used herein have the same meaning as commonly understood by one of ordinary skilled in the art to which this invention belongs.

BRIEF DESCRIPTION OF THE FIGURES

FIG. 1 and the other alignment figures provided herein were generated using the program MUSCLE (Edgar (2004) Nuc. Acids Res. 32(5):1792-1797).

FIG. 2 is an alignment of ME02779.

FIG. 3 is an alignment of truncated mutant of ME02779.

FIG. 4 is an alignment of ME03944.

FIG. 5 is an alignment of ME05304.

FIG. 6 is an alignment of truncated mutant of ME05304.

FIG. 7 is an alignment of ME03186.

DETAILED DESCRIPTION OF THE INVENTION

1. Definitions

Figure 1:
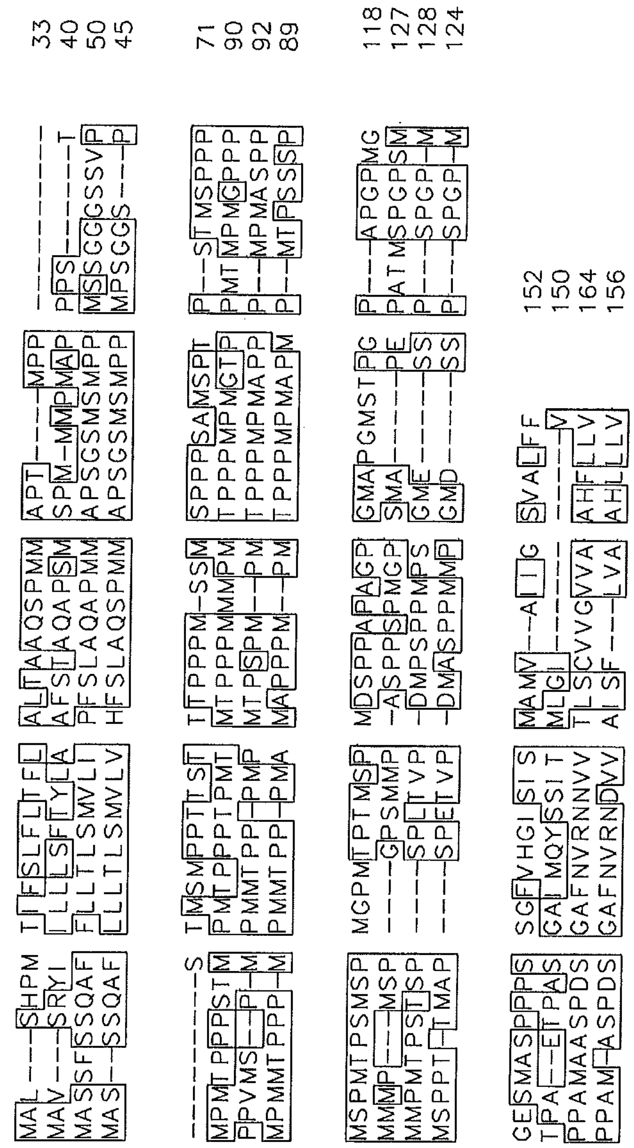
FIG. 1 is an alignment of ME01451. In all the alignment figures shown herein, a dash in an aligned sequence represents a gap, i.e., a lack of an amino acid at that position. Identical amino acids or conserved amino acid substitutions among aligned sequences are identified by boxes.

The following terms are utilized throughout this application:

Amino acid: As used herein, "amino acid" refers to one of the twenty biological occurring amino acids and to synthetic amino acids, including D/L optical isomers.

Cell type-preferential promoter or Tissue-preferential promoter: As used herein, these phrases refer to a promoter that drives expression preferentially in a target cell type or tissue, respectively, but may also lead to some transcription in other cell types or tissues as well.

Cold: Plant species vary in their capacity to tolerate low temperatures. Chilling-sensitive plant species, including many agronomically important species, can be injured by cold, above-freezing temperatures. At temperatures below the freezing-point of water most plant species will be damaged. Thus, "cold" can be defined as the temperature at which a given plant species will be adversely affected as evidenced by symptoms such as decreased photosynthesis and membrane damage (measured by electrolyte leakage). Since plant species vary in their capacity to tolerate cold, the precise environmental conditions that cause cold stress can not be generalized. However, cold tolerant plants are characterized by their ability to retain their normal appearance or recover quickly from low temperature conditions. Such cold tolerant plants produce higher biomass and yield than plants that are not cold tolerant. Differences in physical appearance, recovery and yield can be quantified and statistically analyzed using well known measurement and analysis methods.

Plant seeds vary considerably in their ability to germinate under cold conditions. Seeds of many plant species will not germinate at temperatures less than 10° C. Once seeds have imbibed water they become very susceptible to disease, water and chemical damage. Seeds that are tolerant to cold stress during germination can survive for relatively long periods under which the temperature is too low to germinate. Since plant species vary in their capacity to tolerate cold during germination, the precise environmental conditions that cause cold stress during germination can not be generalized. However, plants that tolerate cold during germination are characterized by their ability to remain viable or recover quickly from low temperature conditions. Such cold tolerant plants germinate, become established, grow more quickly and ultimately produce more biomass and yield than plants that are not cold tolerant. Differences in germination rate, appearance, recovery and yield can be quantified and statistically analyzed using well known measurement and analysis methods.

Constitutive Promoter: Promoters referred to herein as "constitutive promoters" actively promote transcription under most, but not necessarily all, environmental conditions and states of development or cell differentiation. Examples of constitutive promoters include the cauliflower mosaic virus (CaMV) 35S transcript initiation region, the 1' or 2' promoter derived from T-DNA of *Agrobacterium tumefaciens* and other transcription initiation regions from various plant genes, such as the maize ubiquitin-1 promoter, known to those of skill.

Control Plant: "Control plant" refers to a plant that does not contain the exogenous nucleic acid present in the transgenic plant of interest, but otherwise has the same of similar genetic background as such a transgenic plant. A suitable control plant can be a non-transgenic segregant from a transformation experiment, or a transgenic plant that contains an exogenous nucleic acid other than the exogenous nucleic acid of interest.

Domain: "Domains" are groups of substantially contiguous amino acids in a polypeptide that can be used to characterize protein families and/or parts of proteins. Such domains have a "fingerprint" or "signature" that can comprise conserved primary sequence, secondary structure, and/or three-dimensional conformation. Generally, domains are correlated with specific in vitro and/or in vivo activities. A domain can have a length of from 10 amino acids to 400 amino acids, e.g., 10 to 50 amino acids, or 25 to 100 amino acids, or 35 to 65 amino acids, or 35 to 55 amino acids, or 45 to 60 amino acids, or 200 to 300 amino acids, or 300 to 400 amino acids.

Down-regulation: "Down-regulation" refers to regulation that decreases production of expression products (mRNA, polypeptide, or both) relative to basal or native states.

Endogenous: The term "endogenous," within the context of the current invention refers to any polynucleotide, polypeptide or protein sequence which is a natural part of a cell or organism regenerated from said cell.

Exogenous: "Exogenous" with respect to a nucleic acid indicates that the nucleic acid is part of a recombinant nucleic acid construct, or is not in its natural environment. For example, an exogenous nucleic acid can be a sequence from one species introduced into another species, i.e., a heterologous nucleic acid. Typically, such an exogenous nucleic acid is introduced into the other species via a recombinant nucleic acid construct. An exogenous nucleic acid can also be a sequence that is native to an organism and that has been reintroduced into cells of that organism. An exogenous nucleic acid that includes a native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found. It will be appreciated that an exogenous nucleic acid may have been introduced into a progenitor and not into the cell under consideration. For example, a transgenic plant containing an exogenous nucleic acid can be the progeny of a cross between a stably transformed plant and a non-transgenic plant. Such progeny are considered to contain the exogenous nucleic acid.

Expression: As used herein, "expression" refers to the process of converting genetic information of a polynucleotide into RNA through transcription, which is catalyzed by an enzyme, RNA polymerase, and into protein, through translation of mRNA on ribosomes.

Functionally Comparable Proteins: This phrase describes those proteins that have at least one characteristic in common. Such characteristics include sequence similarity, biochemical activity, transcriptional pattern similarity and phenotypic activity. Typically, the functionally comparable proteins share some sequence similarity or at least one biochemical. Within this definition, homologs, orthologs and analogs are considered to be functionally comparable. In addition, functionally comparable proteins generally share at least one biochemical and/or phenotypic activity.

Functionally comparable proteins will give rise to the same characteristic to a similar, but not necessarily the same, degree. Typically, comparable proteins give the same characteristics where the quantitative measurement due to one of the comparables is at least 20% of the other; more typically, between 30 to 40%; even more typically, between 50-60%; even more typically between 70 to 80%; even more typically between 90 to 100% of the other.

Heterologous polypeptide: "Heterologous polypeptide" as used herein refers to a polypeptide that is not a naturally occurring polypeptide in a plant cell, e.g., a transgenic Panicum plant transformed with and expressing the coding sequence for a nitrogen transporter from a Zea plant.

Heterologous sequences: "Heterologous sequences" are those that are not operatively linked or are not contiguous to each other in nature. For example, a promoter from corn is considered heterologous to an Arabidopsis coding region sequence. Also, a promoter from a gene encoding a growth factor from corn is considered heterologous to a sequence encoding the corn receptor for the growth factor. Regulatory element sequences, such as UTRs or 3' end termination sequences that do not originate in nature from the same gene as the coding sequence, are considered heterologous to said coding sequence. Elements operatively linked in nature and contiguous to each other are not heterologous to each other. On the other hand, these same elements remain operatively linked but become heterologous if other filler sequence is placed between them. Thus, the promoter and coding sequences of a corn gene expressing an amino acid transporter are not heterologous to each other, but the promoter and coding sequence of a corn gene operatively linked in a novel manner are heterologous.

Inducible Promoter: An "inducible promoter" in the context of the current invention refers to a promoter which is regulated under certain conditions, such as light, chemical concentration, protein concentration, conditions in an organism, cell, or organelle, etc. A typical example of an inducible promoter which can be utilized with the polynucleotides of the present invention is rd29a, the promoter from an Arabidopsis gene and which is induced by cold or dehydration (Baker et al. (1994) *Plant Mol. Biol.* 24:701). Examples of environmental conditions that may affect transcription by inducible promoters include anaerobic conditions, elevated temperature and/or the presence of light.

Isolated nucleic acid: "Isolated nucleic acid" as used herein includes a naturally-occurring nucleic acid, provided one or both of the sequences immediately flanking that nucleic acid in its naturally-occurring genome is removed or absent. Thus, an isolated nucleic acid includes, without limitation, a nucleic acid that exists as a purified molecule or a nucleic acid molecule that is incorporated into a vector or a virus. A nucleic acid existing among hundreds to millions of other nucleic acids within, for example, cDNA libraries, genomic libraries, or gel slices containing a genomic DNA restriction digest, is not to be considered an isolated nucleic acid.

Masterpool: The "master pools" discussed in these experiments are a pool of seeds from five independent transformation events of the same exogenous nucleotide sequence.

Modulation: As used herein, "Modulation" of the level of a compound or constituent refers to the change in the level of the indicated compound or constituent that is observed as a result of expression of, or transcription from, an exogenous nucleic acid in a plant cell. The change in level is measured relative to the corresponding level in control plants.

Misexpression: The term "misexpression" refers to an increase or a decrease in the transcription of a coding region into a complementary RNA sequence as compared to the wild-type. This term also encompasses expression of a gene or coding region for a different time period as compared to the wild-type and/or from a non-natural location within the plant genome.

Nucleic acid and polynucleotide: "Nucleic acid" and "polynucleotide" are used interchangeably herein, and refer to both RNA and DNA, including cDNA, genomic DNA, synthetic DNA, and DNA or RNA containing nucleic acid analogs. Polynucleotides can have any three-dimensional structure. A nucleic acid can be double-stranded or single-stranded (i.e., a sense strand or an antisense strand). Non-limiting examples of polynucleotides include genes, gene fragments, exons, introns, messenger RNA (mRNA), transfer RNA, ribosomal RNA, siRNA, micro-RNA, ribozymes, cDNA, recombinant polynucleotides, branched polynucleotides, nucleic acid probes and nucleic acid primers. A polynucleotide may contain unconventional or modified nucleotides.

Operably linked: As used herein, "operably linked" refers to the positioning of a regulatory region and a sequence to be transcribed in a nucleic acid so that the regulatory region is effective for regulating transcription or translation of the sequence. For example, to operably link a coding sequence and a regulatory region, the translation initiation site of the translational reading frame of the coding sequence is typically positioned between one and about fifty nucleotides downstream of the regulatory region. A regulatory region can, however, be positioned as much as about 5,000 nucleotides upstream of the translation initiation site, or about 2,000 nucleotides upstream of the transcription start site.

Percentage of sequence identity: "Percentage of sequence identity," as used herein, is determined by comparing two optimally aligned sequences over a comparison window defined by the length of the longest sequence, where the polynucleotide or amino acid sequence in the comparison window may comprise additions or deletions (e.g., gaps or overhangs) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman (1981) *Add. APL. Math.* 2:482, by the homology alignment algorithm of Needleman and Wunsch (1970) *J. Mol. Biol.* 48:443), by the search for similarity method of Pearson and Lipman (1988) *Proc. Natl. Acad. Sci.* (*USA*) 85: 2444, by computerized implementations of these algorithms (GAP, BESTFIT, BLAST, PASTA, and TFASTA in the Wisconsin Genetics Software Package, Genetics Computer Group (GCG), 575 Science Dr., Madison, Wis.), or by inspection. Given that two sequences have been identified for comparison, GAP and BESTFIT are preferably employed to determine their optimal alignment. Typically, the default values of 5.00 for gap weight and 0.30 for gap weight length are used. The term "substantial sequence identity" between polynucleotide or polypeptide sequences refers to polynucleotide or polypeptide comprising a sequence that has at least 80% sequence identity, preferably at least 85%, more preferably at least 90% and most preferably at least 95%, even more preferably, at least 96%, 97%, 98% or 99% sequence identity compared to a reference sequence using the programs.

Query nucleic acid and amino acid sequences were searched against subject nucleic acid or amino acid sequences residing in public or proprietary databases. Such searches were done using the Washington University Basic Local Alignment Search Tool Version 1.83 (WU-Blast2) program. The WU-Blast2 program is available on the internet from Washington University. A WU-Blast2 service for Arabidopsis can also be found on the internet. Typically the following parameters of WU-Blast2 were used: Filter options were set to "default," Output format was set to "gapped alignments," the Comparison Matrix was set to "BLOSUM62," Cutoff Score (S value) was set to "default," the Expect (E threshold) was set to "default," the Number of best alignments to show was set to "100," and the "Sort output" option was set to sort the output by "pvalue."

Plant Promoter: A "plant promoter" is a promoter capable of initiating transcription in plant cells and can drive or facilitate transcription of a nucleotide sequence or fragment thereof of the instant invention. Such promoters need not be of plant origin. For example, promoters derived from plant viruses, such as the CaMV35S promoter or from *Agrobacterium tumefaciens*, such as the T-DNA promoters, can be plant promoters. A typical example of a plant promoter of plant origin is the maize ubiquitin-1 (ubi-1) promoter known to those of skill.

Polypeptide: "Polypeptide" as used herein refers to a compound of two or more subunit amino acids, amino acid analogs, or other peptidomimetics, regardless of post-translational modification, e.g., phosphorylation or glycosylation. The subunits may be linked by peptide bonds or other bonds such as, for example, ester or ether bonds. Full-length polypeptides, truncated polypeptides, point mutants, insertion mutants, splice variants, chimeric proteins, and fragments thereof are encompassed by this definition.

Progeny: As used herein, "progeny" includes descendants of a particular plant or plant line. Progeny of an instant plant include seeds formed on $F_1$, $F_2$, $F_3$, $F_4$, $F_5$, $F_6$ and subsequent generation plants, or seeds formed on $BC_1$, $BC_2$, $BC_3$, and subsequent generation plants, or seeds formed on $F_1BC_1$, $F_1BC_2$, $F_1BC_3$, and subsequent generation plants. The designation $F_1$ refers to the progeny of a cross between two parents that are genetically distinct. The designations $F_2$, $F_3$, $F_4$, $F_5$ and $F_6$ refer to subsequent generations of self- or sib-pollinated progeny of an $F_1$ plant.

Regulatory region: As used herein, "regulatory region" refers to a nucleic acid having nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns, and combinations thereof. A regulatory region typically comprises at least a core (basal) promoter. A regulatory region also may include at least one control element, such as an enhancer sequence, an upstream element or an upstream activation region (UAR). For example, a suitable enhancer is a cis-regulatory element (−212 to −154) from the upstream region of the octopine synthase (ocs) gene. Fromm et al., *The Plant Cell*, 1:977-984 (1989).

Specific Promoter: In the context of the current invention, "specific promoters" refers to promoters that have a high preference for being active in a specific tissue or cell and/or at a specific time during development of an organism. By "high preference" is meant at least a 3-fold, preferably 5-fold, more preferably at least 10-fold still more preferably at least a 20-fold, 50-fold or 100-fold increase in transcription in the desired tissue over the transcription in any other tissue. Typical examples of temporal and/or tissue specific promoters of plant origin that can be used with the polynucleotides of the present invention, are: SH-EP from *Vigna mungo* and EP-C1 from *Phaseolus vulgaris* (Yamauchi et al. (1996) *Plant Mol Biol.* 30:321-9.); RCc2 and RCc3, promoters that direct root-specific gene transcription in rice (Xu et al. (1995) *Plant Mol. Biol.* 27:237) and TobRB27, a root-specific promoter from tobacco (Yamamoto et al. (1991) *Plant Cell* 3:371).

Stringency: "Stringency" as used herein is a function of probe length, probe composition (G+C content), salt concentration, organic solvent concentration and temperature of hybridization or wash conditions. Stringency is typically compared by the parameter $T_m$, which is the temperature at which 50% of the complementary molecules in the hybridization are hybridized, in terms of a temperature differential from $T_m$. High stringency conditions are those providing a condition of $T_m$−5° C. to $T_m$−10° C. Medium or moderate stringency conditions are those providing $T_m$−20° C. to $T_m$−29° C. Low stringency conditions are those providing a condition of $T_m$−40° C. to $T_m$−48° C. The relationship of hybridization conditions to $T_m$ (in ° C.) is expressed in the mathematical equation $$T_m=81.5-16.6(\log_{10}[Na^+])+0.41(\%\ G+C)-(600/N) \quad (1)$$

where N is the length of the probe. This equation works well for probes 14 to 70 nucleotides in length that are identical to the target sequence. The equation below for $T_m$ of DNA-DNA hybrids is useful for probes in the range of 50 to greater than 500 nucleotides, and for conditions that include an organic solvent (formamide).

$$T_m=81.5+16.6\log\{[Na^+]/(1+0.7[Na^+])\}+0.41(\%\ G+C)-500/L0.63(\%\ \text{formamide}) \quad (2)$$

where L is the length of the probe in the hybrid (P. Tijessen, "Hybridization with Nucleic Acid Probes" In Laboratory Techniques in Biochemistry and Molecular Biology, P. C. vand der Vliet, ed., c. 1993 by Elsevier, Amsterdam.) The $T_m$ of equation (2) is affected by the nature of the hybrid; for DNA-RNA hybrids $T_m$ is 10-15° C. higher than calculated, for RNA-RNA hybrids $T_m$ is 20-25° C. higher. Because the $T_m$ decreases about 1° C. for each 1% decrease in homology when a long probe is used (Bonner et al., (1973) *J. Mol. Biol.* 81:123), stringency conditions can be adjusted to favor detection of identical genes or related family members.

Equation (2) is derived assuming equilibrium. Therefore, hybridizations according to the present invention are most preferably performed under conditions of probe excess and for sufficient time to achieve equilibrium. The time required to reach equilibrium can be shortened by using a hybridization buffer that includes a hybridization accelerator such as dextran sulfate or another high volume polymer.

Stringency can be controlled during the hybridization reaction or after hybridization has occurred by altering the salt and temperature conditions of the wash solutions used. The formulas shown above are equally valid when used to compute the stringency of a wash solution. Preferred wash solution stringencies lie within the ranges stated above; high stringency is 5-8° C. below $T_m$, medium or moderate stringency is 26-29° C. below $T_m$ and low stringency is 45-48° C. below $T_m$.

Superpool: As used in the context of the current invention, a "superpool" refers to a mixture of seed from 100 different "master pools." The master pools are of 5 different events with the same exogenous nucleotide sequence transformed into them. Thus, while the superpool contains an equal amount of seed from 500 different events, it only represents 100 transgenic plants with a distinct exogenous nucleotide sequence transformed into them.

$T_0$: As used in the current application, the term "$T_0$" refers to the whole plant, explant or callus tissue inoculated with the transformation medium.

$T_1$: As used in the current application, the term $T_1$ refers to either the progeny of the $T_0$ plant, in the case of whole-plant transformation, or the regenerated seedling in the case of explant or callous tissue transformation.

$T_2$: As used in the current application, the term $T_2$ refers to the progeny of the $T_1$ plant. $T_2$ progeny are the result of self-fertilization or cross pollination of a $T_1$ plant.

$T_3$: As used in the current application, the term $T_3$ refers to second generation progeny of the plant that is the direct result of a transformation experiment. $T_3$ progeny are the result of self-fertilization or cross pollination of a $T_2$ plant.

Up-regulation: "Up-regulation" refers to regulation that increases the level of an expression product (mRNA, polypeptide, or both) relative to basal or native states.

Vector: "Vector" refers to a replicon, such as a plasmid, phage, or cosmid, into which another DNA segment may be inserted so as to bring about the replication of the inserted segment. Generally, a vector is capable of replication when associated with the proper control elements. The term "vector" includes cloning and expression vectors, as well as viral vectors and integrating vectors. An "expression vector" is a vector that includes a regulatory region.

2. Important Characteristics of the Polynucleotides of the Invention

The genes and polynucleotides of the present invention are of interest because when they are misexpressed (i.e. when expressed at a non-natural location or in an increased or decreased amount) they produce plants with improved low temperature, chilling or cold tolerance as discussed below and as evidenced by the results of various experiments. These traits can be used to exploit or maximize plant products. For example, the genes and polynucleotides of the present invention are used to increase the expression of genes that render the plant more tolerant to low temperature, chilling or cold conditions. As a consequence, such transgenic plants do better and grow faster under low temperature, chilling or cold conditions, leading to reduced costs for the fanner and, better yield under low temperatures.

3. The Polynucleotides and Polypeptides of the Invention

The polynucleotides of the invention and the proteins expressed thereby are set forth in the Sequence Listing. Such Sequence Listing consists of functionally comparable proteins.

Functionally comparable proteins are those proteins that have at least one characteristic in common. Such characteristics can include sequence similarity, biochemical activity and phenotypic activity. Typically, the functionally comparable proteins share some sequence similarity. Within this definition homologs, orthologs and analogs are considered to be functionally comparable.

Also, these comparables generally share at least one biochemical and/or phenotypic activity. For example, biochemical activity comparables are proteins that act on the same reactant to give the same product.

Another class of comparables is phenotypic comparables that both give the same physical characteristic, such as increased low temperature, chilling or cold tolerance. Proteins can be considered phenotypic comparables even if the proteins give rise to the same physical characteristic, but to a different degree.

4. Use of the Polynucleotides and Polypeptides to Make Transgenic Plants

To use the sequences of the present invention or a combination of them or parts and/or mutants and/or fusions and/or variants of them, recombinant DNA constructs are prepared which comprise the polynucleotide sequences of the invention inserted into a vector and which are suitable for transformation of plant cells. The construct can be made using standard recombinant DNA techniques (see Sambrook et al., Molecular Cloning: A Laboratory Manual, Second Edition, Cold Spring Harbor Laboratory Press, 1989, New York) and can be introduced to the species of interest by *Agrobacterium*-mediated transformation or by other means of transformation as referenced below.

The vector backbone can be any of those typical in the art such as plasmids, viruses, artificial chromosomes, BACs, YACs and PACs and vectors of the sort described by (a) BAC: Shizuya et al. (1992) *Proc. Natl. Acad. Sci. USA* 89: 8794-8797; Hamilton et al. (1996) *Proc. Natl. Acad. Sci. USA* 93: 9975-9979;

(b) YAC: Burke et al. (1987) *Science* 236:806-812;

(c) PAC: Sternberg N. et al. (1990) *Proc Natl Acad Sci USA. January;* 87:103-7;

(d) Bacteria-Yeast Shuttle Vectors: Bradshaw et al. (1995) *Nucl Acids Res* 23: 4850-4856;

(e) Lambda Phage Vectors: Replacement Vector, e.g., Frischauf et al. (1983) *J. Mol Biol* 170: 827-842; or Insertion vector, e.g., Huynh et al., In: Glover N M (ed) DNA Cloning: A practical Approach, Vol. 1 Oxford: IRL Press (1985); T-DNA gene fusion vectors: Walden et al. (1990) *Mol Cell Biol* 1: 175-194; and (g) Plasmid vectors: Sambrook et al., infra.

Typically, the construct comprises a vector containing a sequence of the present invention with any desired transcriptional and/or translational regulatory sequences such as promoters, UTRs, and 3' end termination sequences. Vectors can also include origins of replication, scaffold attachment regions (SARs), markers, homologous sequences, introns, etc. The vector may also comprise a marker gene that confers a selectable phenotype on plant cells. The marker typically encodes biocide resistance, particularly antibiotic resistance, such as resistance to kanamycin, bleomycin, or hygromycin, or herbicide resistance, such as resistance to glyphosate, chlorosulfuron or phosphinotricin.

A plant promoter is used that directs transcription of the gene in all tissues of a regenerated plant and may be a constitutive promoter, such as the Cauliflower Mosaic Virus 35S. Alternatively, the plant promoter directs transcription of a sequence of the invention in a specific tissue (tissue-specific promoters) or is otherwise under more precise environmental or developmental control (inducible promoters). Typically, preferred promoters to use in the present invention are cold inducible promoters. Many cold-inducible genes, including the cis-elements which confer cold induction, have been identified (Shinozaki et al. (2003) *Curr. Opin. Plant Biol.* 6:410). Examples of such cold-inducible genes include RD29A (Yamaguchi-Shinozaki and Shinozaki (1994) *Plant Cell* 6:251) and CBF/DREB1 (Stockinger et al. (1997) *PNAS* 94:1035. Another preferred embodiment of the present invention is to use seedling specific promoters, endosperm specific promoters and leaf specific promoters. Various plant promoters, including constitutive, tissue-specific and inducible, are known to those skilled in the art and can be utilized in the present invention.

Alternatively, misexpression can be accomplished using a two component system, whereby the first component consists of a transgenic plant comprising a transcriptional activator operatively linked to a promoter and the second component consists of a transgenic plant that comprises sequence of the invention operatively linked to the target-binding sequence/region of the transcriptional activator. The two transgenic plants are crossed and the sequence of the invention is expressed in their progeny. In another alternative, the misexpression can be accomplished by having the sequences of the two component system transformed in one transgenic plant line.

Transformation

Nucleotide sequences of the invention are introduced into the genome or the cell of the appropriate host plant by a variety of techniques. These techniques for transforming a wide variety of higher plant species are well known and described in the technical and scientific literature. See, e.g. Weising et al. (1988) *Ann. Rev. Genet.* 22:421; and Christou (1995) *Euphytica*, v. 85, n. 1-3:13-27.

Processes for the transformation of monocotyledonous and dicotyledonous plants are known to the person skilled in the art. A variety of techniques is available for the introduction of DNA into a plant host cell. These techniques include transformation of plant cells by injection, microinjection, electroporation of DNA, PEG, use of biolistics, fusion of cells or protoplasts, and via T-DNA using *Agrobacterium tumefaciens* or *Agrobacterium rhizogenes* or other bacterial hosts, as well as further possibilities.

In addition, a number of non-stable transformation methods that are well known to those skilled in the art may be desirable for the present invention. Such methods include, but are not limited to, transient expression and viral transfection.

Seeds are obtained from the transformed plants and used for testing stability and inheritance. Generally, two or more generations are cultivated to ensure that the phenotypic feature is stably maintained and transmitted.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

The nucleic acids of the invention can be used to confer the trait of increased tolerance to low temperature, chilling or cold conditions without reduction in fertility on essentially any plant, including chilling sensitive crop plants such as corn, soybean, rice and cotton.

The nucleotide sequences according to the invention encode appropriate proteins from any organism, in particular from plants, fungi, bacteria or animals.

The process according to the invention can be applied to any plant, preferably higher plants, pertaining to the classes of Angiospermae and Gymnospermae. Plants of the subclasses of the Dicotylodenae and the Monocotyledonae are particularly suitable. Dicotyledonous plants belong to the orders of the Magniolales, Illiciales, Laurales, Piperales Aristochiales, Nymphaeales, Ranunculales, Papeverales, Sarraceniaceae, Trochodendrales, Hamamelidales, Eucomiales, Leitneriales, Myricales, Fagales, Casuarinales, Caryophyllales, Batales, Polygonales, Plumbaginales, Dilleniales, Theales, Malvales, Urticales, Lecythidales, Violales, Salicales, Capparales, Ericales, Diapensales, Ebenales, Primulales, Rosales, Fabales, Podostemales, Haloragales, Myrtales, Cornales, Proteales, Santales, Rafflesiales, Celastrales, Euphorbiales, Rhamnales, Sapindales, Juglandales, Geraniales, Polygalales, Umbellales, Gentianales, Polemoniales, Lamiales, Plantaginales, Scrophulariales, Campanulales, Rubiales, Dipsacales, and Asterales. Monocotyledonous plants belong to the orders of the Alismatales, Hydrocharitales, Najadales, Triuridales, Commelinales, Eriocaulales, Restionales, Poales, Juncales, Cyperales, Typhales, Bromeliales, Zingiberales, Arecales, Cyclanthales, Pandanales, Arales, Lilliales, and Orchidales. Plants belonging to the class of the Gymnospermae are Pinales, Ginkgoales, Cycadales and Gnetales.

The process is preferably used with plants that are important or interesting for agriculture, horticulture, biomass for bioconversion and/or forestry. Examples are tobacco, oilseed rape, sugar beet, potatoes, tomatoes, cucumbers, peppers, beans, peas, citrus fruits, avocados, peaches, apples, pears, berries, plumbs, melons, eggplants, cotton, soybean, sunflowers, roses, poinsettia, petunia, guayule, cabbages, spinach, alfalfa, artichokes, corn, wheat, rice, rye, barley, grasses such as switch grass or turf grass, millet, hemp, bananas, poplars, eucalyptus trees and conifers.

Homologs Encompassed by the Invention

It is well known in the art that one or more amino acids in a native sequence can be substituted with other amino acid(s), the charge and polarity of which are similar to that of the native amino acid, i.e. a conservative amino acid substitution, resulting in a silent change. Conservative substitutes for an amino acid within the native polypeptide sequence can be selected from other members of the class to which the amino acid belongs. Amino acids can be divided into the following four groups: |(1) acidic (negatively charged) amino acids, such as aspartic acid and glutamic acid; (2) basic (positively charged) amino acids, such as arginine, histidine, and lysine; (3) neutral polar amino acids, such as serine, threonine, tyrosine, asparagine, and glutamine; and (4) neutral nonpolar (hydrophobic) amino acids such as glycine, alanine, leucine, isoleucine, valine, proline, phenylalanine, tryptophan, cysteine, and methionine.

In a further aspect of the present invention, nucleic acid molecules of the present invention can comprise sequences that differ from those encoding a protein or fragment thereof selected from the group consisting of SEQ ID NOs: 2-5, 7, 9-18, 20-32, 34-38, 40 and 42-46 due to the fact that the different nucleic acid sequence encodes a protein having one or more conservative amino acid changes.

Polypeptides

Polypeptides described herein include cold tolerance-modulating polypeptides. Cold tolerance-modulating polypeptides can be effective to modulate cold tolerance levels when expressed in a plant or plant cell. Such polypeptides typically contain at least one domain indicative of cold tolerance-modulating polypeptides, as described in more detail herein. Cold tolerance-modulating polypeptides typically have an HMM bit score that is greater than 20, as described in more detail herein. In some embodiments, cold tolerance-modulating polypeptides have greater than 80% identity to SEQ ID NOs: 2, 7, 9, 20, 34, 40, and 42, as described in more detail herein.

In some embodiments, a cold tolerance-modulating polypeptide is truncated at the amino- or carboxy-terminal end of a naturally occurring polypeptide. A truncated polypeptide may retain certain domains of the naturally occurring polypeptide while lacking others. Thus, length variants that are up to 5 amino acids shorter or longer typically exhibit the cold tolerance-modulating activity of a truncated polypeptide. In some embodiments, a truncated polypeptide is a dominant negative polypeptide. SEQ ID NOs 7 and 40 set forth the amino sequences of cold tolerance-modulating polypeptides that are truncated at the 3' end relative to the naturally occurring polypeptides SEQ ID NOs 9 and 34, respectively. Expression in a plant of such a truncated polypeptide confers a difference in the level of cold tolerance in a tissue of the plant as compared to the corresponding level in tissue of a control plant that does not comprise the truncation.

A. Functional Homologs Identified by Reciprocal BLAST

In some embodiments, one or more functional homologs of a reference cold tolerance-modulating polypeptide defined by one or more of the pfam descriptions indicated above are suitable for use as cold tolerance-modulating polypeptides. A functional homolog is a polypeptide that has sequence similarity to a reference polypeptide, and that carries out one or more of the biochemical or physiological function(s) of the reference polypeptide. A functional homolog and the reference polypeptide may be natural occurring polypeptides, and the sequence similarity may be due to convergent or divergent evolutionary events. As such, functional homologs are sometimes designated in the literature as homologs, or orthologs, or paralogs. Variants of a naturally occurring functional homolog, such as polypeptides encoded by mutants of a wild type coding sequence, may themselves be functional homologs. Functional homologs can also be created via site-directed mutagenesis of the coding sequence for a cold tolerance-modulating polypeptide, or by combining domains from the coding sequences for different naturally-occurring cold tolerance-modulating polypeptides ("domain swapping"). The term "functional homolog" is sometimes applied to the nucleic acid that encodes a functionally homologous polypeptide.

Functional homologs can be identified by analysis of nucleotide and polypeptide sequence alignments. For example, performing a query on a database of nucleotide or polypeptide sequences can identify homologs of cold tolerance-modulating polypeptides. Sequence analysis can involve BLAST, Reciprocal BLAST, or PSI-BLAST analysis of nonredundant databases using a cold tolerance-modulating polypeptide amino acid sequence as the reference sequence. Amino acid sequence is, in some instances, deduced from the nucleotide sequence. Those polypeptides in the database that have greater than 40% sequence identity are candidates for further evaluation for suitability as a cold tolerance-modulating polypeptide. Amino acid sequence similarity allows for conservative amino acid substitutions, such as substitution of one hydrophobic residue for another or substitution of one polar residue for another. If desired, manual inspection of such candidates can be carried out in order to narrow the number of candidates to be further evaluated. Manual inspection can be performed by selecting those candidates that appear to have domains present in cold tolerance-modulating polypeptides, e.g., conserved functional domains.

Conserved regions can be identified by locating a region within the primary amino acid sequence of a cold tolerance-modulating polypeptide that is a repeated sequence, forms some secondary structure (e.g., helices and beta sheets), establishes positively or negatively charged domains, or represents a protein motif or domain. See, e.g., the Pfam web site describing consensus sequences for a variety of protein motifs and domains on the World Wide Web at the Welcome Trust Sanger Institute and HMMI janelia farm research campus. A description of the information included at the Pfam database is described in Sonnhammer et al., *Nucl. Acids Res.,* 26:320-322 (1998); Sonnhammer et al., *Proteins,* 28:405-420 (1997); and Bateman et al., *Nucl. Acids Res.,* 27:260-262 (1999). Conserved regions also can be determined by aligning sequences of the same or related polypeptides from closely related species. Closely related species preferably are from the same family. In some embodiments, alignment of sequences from two different species is adequate.

Typically, polypeptides that exhibit at least about 40% amino acid sequence identity are useful to identify conserved regions. Conserved regions of related polypeptides exhibit at least 45% amino acid sequence identity (e.g., at least 50%, at least 60%, at least 70%, at least 80%, or at least 90% amino acid sequence identity). In some embodiments, a conserved region exhibits at least 92%, 94%, 96%, 98%, or 99% amino acid sequence identity.

Amino acid sequences of functional homologs of the polypeptide set forth in SEQ ID NOs 2, 7, 9, 20, 34, 40 and 42 are provided in FIGS. 1-7, respectively. In some cases, a functional homolog of SEQ ID NOs 2, 7, 9, 20, 34, 40 and 42 has an amino acid sequence with at least 80% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in the Sequence Listing.

The identification of conserved regions in a cold tolerance-modulating polypeptide facilitates production of variants of cold tolerance-modulating polypeptides. Variants of cold tolerance-modulating polypeptides typically have 10 or fewer conservative amino acid substitutions within the primary amino acid sequence, e.g., 7 or fewer conservative amino acid substitutions, 5 or fewer conservative amino acid substitutions, or between 1 and 5 conservative substitutions. A useful variant polypeptide can be constructed based on one of the alignments set forth in any one of FIGS. 1-7. Such a polypeptide includes the conserved regions, arranged in the order depicted in the Figure from amino-terminal end to carboxy-terminal end. Such a polypeptide may also include zero, one, or more than one amino acid in positions marked by dashes. When no amino acids are present at positions marked by dashes, the length of such a polypeptide is the sum of the amino acid residues in all conserved regions. When amino acids are present at all positions marked by dashes, such a polypeptide has a length that is the sum of the amino acid residues in all conserved regions and all dashes.

B. Functional Homologs Identified by HMMER

In some embodiments, useful cold tolerance-modulating polypeptides include those that fit a Hidden Markov Model based on the polypeptides set forth in any one of FIGS. 1-7. A Hidden Markov Model (HMM) is a statistical model of a consensus sequence for a group of functional homologs. See, Durbin et al., *Biological Sequence Analysis: Probabilistic Models of Proteins and Nucleic Acids*, Cambridge University Press, Cambridge, UK (1998). An HMM is generated by the program HMMER 2.3.2 with default program parameters, using the sequences of the group of functional homologs as input. The multiple sequence alignment is generated by ProbCons (Do et al., Genome Res., 15(2):330-40 (2005)) version 1.11 using a set of default parameters: -c, —consistency REPS of 2; -ir, —iterative-refinement REPS of 100; -pre, —pre-training REPS of 0. ProbCons is a public domain software program provided by Stanford University.

The default parameters for building an HMM (hmmbuild) are as follows: the default "architecture prior" (archpri) used by MAP architecture construction is 0.85, and the default cutoff threshold (idlevel) used to determine the effective sequence number is 0.62. HMMER 2.3.2 was released Oct. 3, 2003 under a GNU general public license, and is available from various sources on the World Wide Web such as the HMMER page on the HHMI janelia farm research campus website; the Eddy Lab Home page on the HHMI janelia farm research campus website; and HMMER 2.3.2 download available on the Fish & Richardson website. Hmmbuild outputs the model as a text file.

The HMM for a group of functional homologs can be used to determine the likelihood that a candidate cold tolerance-modulating polypeptide sequence is a better fit to that particular HMM than to a null HMM generated using a group of sequences that are not structurally or functionally related. The likelihood that a subject polypeptide sequence is a better fit to an HMM than to a null HMM is indicated by the HMM bit score, a number generated when the candidate sequence is fitted to the HMM profile using the HMMER hmmsearch program. The following default parameters are used when running hmmsearch: the default E-value cutoff (E) is 10.0, the default bit score cutoff (T) is negative infinity, the default number of sequences in a database (Z) is the real number of sequences in the database, the default E-value cutoff for the per-domain ranked hit list (domE) is infinity, and the default bit score cutoff for the per-domain ranked hit list (domT) is negative infinity. A high HMM bit score indicates a greater likelihood that the subject sequence carries out one or more of the biochemical or physiological function(s) of the polypeptides used to generate the HMM. A high HMM bit score is at least 20, and often is higher.

The cold tolerance-modulating polypeptides discussed below fit the indicated HMM with an HMM bit score greater than 20 (e.g., greater than 30, 40, 50, 60, 70, 80, 90, 100, 200, 300, 400, or 500). In some embodiments, the HMM bit score of a cold tolerance-modulating polypeptide discussed below is about 50%, 60%, 70%, 80%, 90%, or 95% of the HMM bit score of a functional homolog provided in one of Table 7. In some embodiments, a cold tolerance-modulating polypeptide discussed below fits the indicated HMM with an HMM bit score greater than 20, and has a domain indicative of an cold tolerance-modulating polypeptide. In some embodiments, a cold tolerance-modulating polypeptide discussed below fits the indicated HMM with an HMM bit score greater than 20, and has 80% or greater sequence identity (e.g., 75%, 80%, 85%, 90%, 95%, or 100% sequence identity) to an amino acid sequence shown in any one of FIGS. 1-7.

Polypeptides are shown in Table 7 that have HMM bit scores greater than 20 when fitted to an HMM generated from the amino acid sequences set forth in FIGS. 1-7, respectively.

In another aspect, biologically functional equivalents of the proteins or fragments thereof of the present invention can have about 10 or fewer conservative amino acid changes, more preferably about 7 or fewer conservative amino acid changes and most preferably about 5 or fewer conservative amino acid changes. In a preferred embodiment, the protein has between about 5 and about 500 conservative changes, more preferably between about 10 and about 300 conservative changes, even more preferably between about 25 and about 150 conservative changes, and most preferably between about 5 and about 25 conservative changes or between 1 and about 5 conservative changes.

Inhibition of Expression of a Cold Tolerance-Modulating Polypeptide

Polynucleotides and recombinant constructs described herein can be used to inhibit expression of a cold tolerance-modulating polypeptide in a plant species of interest. See, e.g., Matzke and Birchler, *Nature Reviews Genetics* 6:24-35 (2005); Akashi et al., *Nature Reviews Mol. Cell Biology* 6:413-422 (2005); Mittal, *Nature Reviews Genetics* 5:355-365 (2004); Dorsett and Tuschl, *Nature Reviews Drug Discovery* 3: 318-329 (2004); and *Nature Reviews RNA interference collection*, October 2005 at nature.com/reviews/focus/mai. A number of nucleic acid based methods, including antisense RNA, ribozyme directed RNA cleavage, post-transcriptional gene silencing (PTGS), e.g., RNA interference (RNAi), and transcriptional gene silencing (TGS) are known to inhibit gene expression in plants. Antisense technology is one well-known method. In this method, a nucleic acid segment from a gene to be repressed is cloned and operably linked to a regulatory region and a transcription termination sequence so that the antisense strand of RNA is transcribed. The recombinant construct is then transformed into plants, as described herein, and the antisense strand of RNA is produced. The nucleic acid segment need not be the entire sequence of the gene to be repressed, but typically will be substantially complementary to at least a portion of the sense strand of the gene to be repressed. Generally, higher homology can be used to compensate for the use of a shorter sequence. Typically, a sequence of at least 30 nucleotides is used, e.g., at least 40, 50, 80, 100, 200, 500 nucleotides or more.

In another method, a nucleic acid can be transcribed into a ribozyme, or catalytic RNA, that affects expression of an mRNA. See, U.S. Pat. No. 6,423,885. Ribozymes can be designed to specifically pair with virtually any target RNA and cleave the phosphodiester backbone at a specific location, thereby functionally inactivating the target RNA. Heterologous nucleic acids can encode ribozymes designed to cleave particular mRNA transcripts, thus preventing expression of a polypeptide. Hammerhead ribozymes are useful for destroying particular mRNAs, although various ribozymes that cleave mRNA at site-specific recognition sequences can be used. Hammerhead ribozymes cleave mRNAs at locations dictated by flanking regions that form complementary base pairs with the target mRNA. The sole requirement is that the target RNA contains a 5'-UG-3' nucleotide sequence. The construction and production of hammerhead ribozymes is known in the art. See, for example, U.S. Pat. No. 5,254,678 and WO 02/46449 and references cited therein. Hammerhead ribozyme sequences can be embedded in a stable RNA such as a transfer RNA (tRNA) to increase cleavage efficiency in vivo. Perriman et al., *Proc. Natl. Acad. Sci. USA,* 92(13):6175-6179 (1995); de Feyter and Gaudron, Methods in Molecular Biology, Vol. 74, Chapter 43, "Expressing Ribozymes in Plants", Edited by Turner, P. C., Humana Press Inc., Totowa, N.J. RNA endoribonucleases which have been described, such as the one that occurs naturally in *Tetrahymena thermophila*, can be useful. See, for example, U.S. Pat. Nos. 4,987,071 and 6,423,885.

PTGS, e.g., RNAi, can also be used to inhibit the expression of a gene. For example, a construct can be prepared that includes a sequence that is transcribed into an RNA that can anneal to itself, e.g., a double stranded RNA having a stem-loop structure. In some embodiments, one strand of the stem portion of a double stranded RNA comprises a sequence that is similar or identical to the sense coding sequence of a cold tolerance-modulating polypeptide, and that is from about 10 nucleotides to about 2,500 nucleotides in length. The length of the sequence that is similar or identical to the sense coding sequence can be from 10 nucleotides to 500 nucleotides, from 15 nucleotides to 300 nucleotides, from 20 nucleotides to 100 nucleotides, or from 25 nucleotides to 100 nucleotides. The other strand of the stem portion of a double stranded RNA comprises a sequence that is similar or identical to the antisense strand of the coding sequence of the cold toleran ce-modulating polypeptide, and can have a length that is shorter, the same as, or longer than the corresponding length of the sense sequence. In some cases, one strand of the stem portion of a double stranded RNA comprises a sequence that is similar or identical to the 3' or 5' untranslated region of an mRNA encoding a cold tolerance-modulating polypeptide, and the other strand of the stem portion of the double stranded RNA comprises a sequence that is similar or identical to the sequence that is complementary to the 3' or 5' untranslated region, respectively, of the mRNA encoding the cold tolerance-modulating polypeptide. In other embodiments, one strand of the stem portion of a double stranded RNA comprises a sequence that is similar or identical to the sequence of an intron in the pre-mRNA encoding a cold tolerance-modulating polypeptide, and the other strand of the stem portion comprises a sequence that is similar or identical to the sequence that is complementary to the sequence of the intron in the pre-mRNA. The loop portion of a double stranded RNA can be from 3 nucleotides to 5,000 nucleotides, e.g., from 3 nucleotides to 25 nucleotides, from 15 nucleotides to 1,000 nucleotides, from 20 nucleotides to 500 nucleotides, or from 25 nucleotides to 200 nucleotides. The loop portion of the RNA can include an intron. A double stranded RNA can have zero, one, two, three, four, five, six, seven, eight, nine, ten, or more stem-loop structures. A construct including a sequence that is operably linked to a regulatory region and a transcription termination sequence, and that is transcribed into an RNA that can form a double stranded RNA, is transformed into plants as described herein. Methods for using RNAi to inhibit the expression of a gene are known to those of skill in the art. See, e.g., U.S. Pat. Nos. 5,034,323; 6,326,527; 6,452,067; 6,573,099; 6,753,139; and 6,777,588. See also WO 97/01952; WO 98/53083; WO 99/32619; WO 98/36083; and U.S. Patent Publications 20030175965, 20030175783, 20040214330, and 20030180945.

Constructs containing regulatory regions operably linked to nucleic acid molecules in sense orientation can also be used to inhibit the expression of a gene. The transcription product can be similar or identical to the sense coding sequence of a cold tolerance-modulating polypeptide. The transcription product can also be unpolyadenylated, lack a 5' cap structure, or contain an unsplicable intron. Methods of inhibiting gene expression using a full-length cDNA as well as a partial cDNA sequence are known in the art. See, e.g., U.S. Pat. No. 5,231,020.

In some embodiments, a construct containing a nucleic acid having at least one strand that is a template for both sense and antisense sequences that are complementary to each other is used to inhibit the expression of a gene. The sense and antisense sequences can be part of a larger nucleic acid molecule or can be part of separate nucleic acid molecules having sequences that are not complementary. The sense or antisense sequence can be a sequence that is identical or complementary to the sequence of an mRNA, the 3' or 5' untranslated region of an mRNA, or an intron in a pre-mRNA encoding a cold tolerance-modulating polypeptide. In some embodiments, the sense or antisense sequence is identical or complementary to a sequence of the regulatory region that drives transcription of the gene encoding a cold tolerance-modulating polypeptide. In each case, the sense sequence is the sequence that is complementary to the antisense sequence.

The sense and antisense sequences can be any length greater than about 12 nucleotides (e.g., 13, 14, 15, 16, 17, 18, 19, 20, 21, 22, 23, 24, 25, 26, 27, 28, 29, 30, or more nucleotides). For example, an antisense sequence can be 21 or 22 nucleotides in length. Typically, the sense and antisense sequences range in length from about 15 nucleotides to about 30 nucleotides, e.g., from about 18 nucleotides to about 28 nucleotides, or from about 21 nucleotides to about 25 nucleotides.

In some embodiments, an antisense sequence is a sequence complementary to an mRNA sequence encoding a cold tolerance-modulating polypeptide described herein. The sense sequence complementary to the antisense sequence can be a sequence present within the mRNA of the cold tolerance-modulating polypeptide. Typically, sense and antisense sequences are designed to correspond to a 15-30 nucleotide sequence of a target mRNA such that the level of that target mRNA is reduced.

In some embodiments, a construct containing a nucleic acid having at least one strand that is a template for more than one sense sequence (e.g., 2, 3, 4, 5, 6, 7, 8, 9, 10 or more sense sequences) can be used to inhibit the expression of a gene. Likewise, a construct containing a nucleic acid having at least one strand that is a template for more than one antisense sequence (e.g., 2, 3, 4, 5, 6, 7, 8, 9, 10 or more antisense sequences) can be used to inhibit the expression of a gene. For example, a construct can contain a nucleic acid having at least one strand that is a template for two sense sequences and two antisense sequences. The multiple sense sequences can be identical or different, and the multiple antisense sequences can be identical or different. For example, a construct can have a nucleic acid having one strand that is a template for two identical sense sequences and two identical antisense sequences that are complementary to the two identical sense sequences. Alternatively, an isolated nucleic acid can have one strand that is a template for (1) two identical sense sequences 20 nucleotides in length, (2) one antisense sequence that is complementary to the two identical sense sequences 20 nucleotides in length, (3) a sense sequence 30 nucleotides in length, and (4) three identical antisense sequences that are complementary to the sense sequence 30 nucleotides in length. The constructs provided herein can be designed to have any arrangement of sense and antisense sequences. For example, two identical sense sequences can be followed by two identical antisense sequences or can be positioned between two identical antisense sequences.

A nucleic acid having at least one strand that is a template for one or more sense and/or antisense sequences can be operably linked to a regulatory region to drive transcription of an RNA molecule containing the sense and/or antisense sequence(s). In addition, such a nucleic acid can be operably linked to a transcription terminator sequence, such as the terminator of the nopaline synthase (nos) gene. In some cases, two regulatory regions can direct transcription of two transcripts: one from the top strand, and one from the bottom strand. See, for example, Yan et al., *Plant Physiol.,* 141: 1508-1518 (2006). The two regulatory regions can be the same or different. The two transcripts can form double-stranded RNA molecules that induce degradation of the target RNA. In some cases, a nucleic acid can be positioned within a T-DNA or plant-derived transfer DNA (P-DNA) such that the left and right T-DNA border sequences, or the left and right border-like sequences of the P-DNA, flank or are on either side of the nucleic acid. See, US 2006/0265788. The nucleic acid sequence between the two regulatory regions can be from about 15 to about 300 nucleotides in length. In some embodiments, the nucleic acid sequence between the two regulatory regions is from about 15 to about 200 nucleotides in length, from about 15 to about 100 nucleotides in length, from about 15 to about 50 nucleotides in length, from about 18 to about 50 nucleotides in length, from about 18 to about 40 nucleotides in length, from about 18 to about 30 nucleotides in length, or from about 18 to about 25 nucleotides in length.

In some nucleic-acid based methods for inhibition of gene expression in plants, a suitable nucleic acid can be a nucleic acid analog. Nucleic acid analogs can be modified at the base moiety, sugar moiety, or phosphate backbone to improve, for example, stability, hybridization, or solubility of the nucleic acid. Modifications at the base moiety include deoxyuridine for deoxythymidine, and 5-methyl-2'-deoxycytidine and 5-bromo-2'-deoxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six-membered morpholino ring, or peptide nucleic acids, in which the deoxyphosphate backbone is replaced by a pseudopeptide backbone and the four bases are retained. See, for example, Summerton and Weller, 1997, *Antisense Nucleic Acid Drug Dev.,* 7:187-195; Hyrup et al., *Bioorgan. Med. Chem.,* 4:5-23 (1996). In addition, the deoxyphosphate backbone can be replaced with, for example, a phosphorothioate or phosphorodithioate backbone, a phosphoroamidite, or an alkyl phosphotriester backbone.

In some embodiments, nucleic acid based inhibition of gene expression does not require transcription of the nucleic acid.

Identification of Useful Nucleotide Sequences

The nucleotide sequences of the invention were identified by use of a variety of screens under low temperature, chilling or cold conditions recognized by those skilled in the art to be predictive of nucleotide sequences that provide plants with improved tolerance to low temperature, chilling or cold conditions. One or more of the following screens were, therefore, utilized to identify the nucleotide (and amino acid) sequences of the invention.

1. Cold Germination Superpool Screen 0.5× MS Media is prepared and the pH adjusted to 5.7 using 10N KOH. Seven g/l of Phytagar is added prior to autoclaving.

Individual superpool and control seeds are sterilized in a 30% bleach solution for 5 minutes. Seeds are then rinsed repeatedly with sterile water to eliminate all bleach solution. Seeds are sown on media plates in a monolayer, including wild-type and positive controls. Plates are wrapped in aluminum foil and placed at 4° C. for three days to stratify. At the end of this time, the foil is removed and plates are transferred to an 8° C. Percival with fluorescent bulbs emitting a light intensity of ~100 μEinsteins.

Approximately 10 days after transfer to 8° C., seeds are examined microscopically to identify those that have germinated (defined as cotyledon emergence and expansion). Seedlings with more expanded and greener cotyledons compared to the wild-type population in the same plate are collected. DNA from these candidate seedlings is extracted and the transgene amplified using PCR. The PCR product is sequenced to determine the identity of the transgene and consequently the ME line from which the candidate is derived.

2. Cold Germination Assay

Independent transformation events of the ME lines identified in the Superpool screen are assayed in two generations to validate the cold tolerance phenotype. Media is prepared and seeds sterilized as described above for the Cold Germination Superpool Screen.

Two events with 27 seeds from each event are sown in a Latin square layout on square Petri dishes together with 27 wild-type control seeds. Following 3 days of stratification at 4° C., plates are transferred to 8° C. in the light and grown as above. Approximately 10 days after transfer, plates are imaged on a flat-bed scanner. Plate images are analyzed using WinRhizo software to determine the area of each seedling. Subsequently, plates are transferred to 22° C. for several days of growth and then sprayed with Finale™ to identify transgenic seedlings. Seedling area and transgene status data are entered into a database. Events are considered positive for the low temperature, chilling or cold-tolerant phenotype if the seedling area of the transgenic plants within an event is significantly different by a one-tailed student's t-test than the seedling area of the pooled non-transgenic seedlings across all the events for that ME line.

REFERENCES

Levitt (1980) Chilling injury and resistance. In T T Kozlowsky, ed, Chilling, Freezing, and High Temperature Stresses: Responses of Plant to Environmental Stresses, Vol 1. Academic Press, New York, pp 23-64.

Graham and Patterson (1982) *Annu Rev Plant Physiol* 33: 347-372.

Guy (1990) *Annu Rev Plant Physiol Plant Mol Biol* 41: 187-223.

Nishida and Murata (1996) *Annu Rev Plant Physiol Plant Mol Biol* 47: 541-568.

EXAMPLES

Summary

| | |
|---|---|
| Trait area(s) | Cold |
| Sub-trait Area | Cold - germination and vigor |
| Coding sequence/ Species of Origin | 1. Vector Construct Sequence Identifier 14298746 corresponding to Clone 30087 - ME01451; encodes a 164 amino acid protein of unknown function from *Arabidopsis*.<br>2. Vector Construct Sequence Identifier 14298770 corresponding to Clone 30469 - ME02779 encodes a 78 amino acid protein with identity to the N-terminal half of an *Arabidopsis* class I nonsymbiotic hemoglobin.<br>3. Vector Construct Sequence Identifier 14301197 corresponding to Clone 271922 - ME03944 encodes a 92 amino acid 60s ribosomal protein L37a protein from *Arabidopsis*.<br>4. Vector Construct Sequence Identifier 14296769 corresponding to Clone 2403 - ME05304 encodes a truncated ubiquitin-like protein from *Arabidopsis*.<br>5. Vector Construct Sequence Identifier 14301334 corresponding to Clone 674166 - ME03186 from Glycine max encodes a 210 amino acid protein with similarity to the ethylene-responsive element binding protein (ERF) family. |

-continued

| | |
|---|---|
| Species in which Clone was Tested | *Arabidopsis thaliana* |
| Promoter | 35S, a strong constitutive promoter |
| Insert DNA type | cDNA |

Introduction

How plants respond to stress in the environment dictates their ability to survive and reproduce. There are probably many mechanisms by which plants regulate the temperatures under which they will germinate (Lu and Hills, 2003). Finding genes that result in stress tolerance when over-expressed has proved difficult because of the large amount of cross-talk and regulation among gene families.

Over-expression of these genes could be useful for increasing low temperature, chilling or cold tolerance in crops. If successfully deployed, low temperature, chilling or cold tolerant genes could enhance crop productivity following intermittent or sustained low temperature, chilling or cold periods that occur early in the growing season when seeds are germinating. Assuming conservation of processes controlling vegetative physiology across species, these genes and proteins are likely to function similarly in other species.

Assays described here focus on low temperature, chilling or cold tolerance in germinating seedlings. The ability to germinate and grow under low temperature, chilling or cold, and wet conditions would allow a longer growing season and mitigate damage caused by unexpected low temperature, chilling or cold periods. If this trait is recapitulated in crops overexpressing these genes, the result could be very valuable in agriculture in many crops and environments and make a significant contribution to sustainable farming. Furthermore, low temperature, chilling or cold tolerance may be modulated by expressing these clones under the control of a low temperature, chilling or cold inducible promoter.

Materials and Methods:

Generation and Phenotypic Evaluation of $T_1$ Events.

Wild-type Arabidopsis Wassilewskija (Ws) plants were transformed with a Ti plasmid containing different Clones in the sense orientation relative to the 35S promoter, by *Agrobacterium*-Mediated Transformation. The Ti plasmid vector *used for this construct, CRS 338, contains the Ceres-constructed, plant selectable marker gene phosphinothricin acetyltransferase (PAT) which confers herbicide resistance to transformed plants. Ten independent transformation events were selected and evaluated for their qualitative phenotype in the $T_1$ generation by selecting Finale™-resistant plants and observing their physical characteristics.*

Screening for Low Temperature, Chilling or Cold Germination Candidates.

All superpools (n=91) were screened for cold germination by plating seeds on MS media and germinating them at 8° C. Candidates were chosen based on a comparison to wild-type controls. The candidates were processed as follows.

Process Flow:

Procedure for 1) identifying the candidate from a cold germination superpool screen, 2) confirming the phenotype in the second and third generations and 3) determining the lack of significant negative phenotypes.

1. Superpools screened for Cold Germination
2. Cold tolerant candidates identified
3. Independent events tested for Cold Germination and Finale™ resistance in two generations
4. For all candidates, at least 2 Events were significantly tolerant to cold in 2 generations
5. Tested positive events for negative phenotypes Growth Conditions and Planting Schema Under Cold Germination.

Up to five independent $T_2$ transformation events were evaluated for each line under cold conditions. Subsequently, $T_3$ generation seeds for up to five events were evaluated under cold germination conditions. In these assays, the seedling area (a measure of timing of germination and cotyledon expansion) for transgenic plants within an event was compared to the seedling area for non-transgenic segregants pooled across all plates for that line.

Preparation of plates and seed sowing were performed by sowing seeds on 0.5× MS plates and grown at 8° C. Plates were scored on day 10, and analyzed for cotyledon area. After the Cold Germination Assay was complete, plates were transferred to 22° C. and insert-containing plants were identified by spraying the seedlings with Finale™. Transgenic plants are Finale™ resistant.

Screening for Negative Phenotypes.

The events described in this report were analyzed for negative phenotypes. None of the events had (a) reduction in germination of more than 25%, (b) delay in onset of flowering more than 4 days in 50% or more of plants relative to in-flat control, (c) reduction in fertility as evidenced by visual observation of reduction in silique fill or silique number, (d) a reduction in seed dry weight by 25% or more relative to control, or (e) more than 30% reduction in rosette diameter at maturity.

Results

Example 1: ME01451

TABLE 1-1

| Construct | Event/Generation | Plant Stage | Assay | Result |
|---|---|---|---|---|
| 35S:: 30087 | −01/$T_2$ Finale resistant plants | Seedling | Cold Germination | Significant at p ≤.05 |
| 35S:: 30087 | −05/$T_2$ Finale resistant plants | Seedling | Cold Germination | Significant at p ≤.05 |
| 35S:: 30087 | −01/$T_3$ Finale resistant plants | Seedling | Cold Germination | Significant at p ≤.05 |
| 35S:: 30087 | −05/$T_3$ Finale resistant plants | Seedling | Cold Germination | Significant at p ≤.05 |

Ectopic expression of Clone 30087 under the control of the 35S promoter induces the following phenotypes:

Early germination at 8° C. resulting in larger seedlings after 10 days of growth in the cold.

Plants from Events -01 and -05 which are heterozygous or homozygous for Clone 30087 do not show any negative phenotypes under long-day conditions.

The gene corresponding to Clone 30087 is up-regulated in developing seedlings, seeds and siliques and down-regulated in drought, heat and ABA.

Two Events of ME01451 Showed Significant Early Germination Under Cold Conditions in Both Generations.

All five events of ME01451 were sown as described in the Cold Germination Assay in both the $T_2$ and the $T_3$ generations. Two events, -01 and -05, were significant in both generations at p=0.05 using a one-tailed t-test assuming unequal variance (Table 1-2). ME01451 transgenic seedlings were significantly larger than the pooled non-transgenic segregants.

TABLE 1-2

T-test comparison of seedling area between transgenic seedlings and pooled non-transgenic segregants after 10 days at 8° C.

| | | Transgenic | | | Pooled Non-Transgenics | | | t-test |
|---|---|---|---|---|---|---|---|---|
| Line | Events | Avg | SE | N | Avg | SE | N | p-value |
| ME01451 | ME01451-01 | 0.0086 | 0.0005 | 25 | 0.0067 | 0.0006 | 54 | 0.00702 |
| ME01451 | ME01451-01-99 | 0.0106 | 0.0006 | 22 | 0.0079 | 0.0010 | 14 | 0.01374 |
| ME01451 | ME01451-05 | 0.0104 | 0.0006 | 18 | 0.0067 | 0.0006 | 54 | 0.00002 |
| ME01451 | ME01451-05-99 | 0.0125 | 0.0007 | 25 | 0.0079 | 0.0010 | 14 | 0.00035 |

Two Events of ME01451 Show 3:1 and 15:1 Segregation for Finale™ Resistance.

Events -01 and -05 segregated 15:1 and 3:1 (R:S), respectively, for Finale™ resistance in the $T_2$ generation (data not shown).

Qualitative Analysis of the $T_1$ Plants:

The physical appearance of all ten $T_1$ plants was identical to the controls.

Qualitative and Quantitative Analysis of the $T_2$ Plants:

Events -01 and -05 of ME01451 exhibited no statistically relevant negative phenotypes.

- Germination
  - No detectable reduction in germination rate.
- General morphology/architecture
  - Plants appeared wild-type in all instances.
  - Days to flowering
  - No observable or statistical differences between experimentals and controls.
- Rosette area 7 days post-bolting
  - No observable or statistical differences between experimentals and controls.
- Fertility (silique number and seed fill)
  - No observable or statistical differences between experimentals and controls Example 2: ME02779

TABLE 2-1

| Construct | Event/Generation | Plant Stage | Assay | Result |
|---|---|---|---|---|
| 35S:: 30469 | −01/$T_2$ Finale resistant plants | Seedling | Cold Germination | Significant at p ≤.05 |
| 35S:: 30469 | −03/$T_2$ Finale resistant plants | Seedling | Cold Germination | Significant at p ≤.05 |
| 35S:: 30469 | −01/$T_3$ Finale resistant plants | Seedling | Cold Germination | Significant at p ≤.05 |
| 35S:: 30469 | −03/$T_3$ Finale resistant plants | Seedling | Cold Germination | Significant at p ≤.05 |

- Ectopic expression of Clone 30469 under the control of the 35S promoter induces the following phenotypes:
  - Early germination at 8° C. resulting in larger seedlings after 10 days at 8° C.
- Plants from Events -01 and -03 which are heterozygous or homozygous for Clone 30469 do not show any negative phenotypes under long-day conditions.
- The gene corresponding to Clone 30469 is down-regulated in ABA, heat, and germinating seeds and up-regulated in high nitrogen and most cold and drought treatments.
- Clone 30469 encodes a class I nonsymbiotic hemoglobin. These proteins can play a role in acclimation to hypoxic conditions, possibly explaining the cold tolerance phenotype (Hunt et al., 2001). Clone 30469 is a splice variant of a gene that encodes a longer protein.

Two Events of ME02779 Showed Significant Early Germination Under Cold Conditions in Both Generations.

Five events of ME02779 were sown as described in the Cold Germination Assay in both the $T_2$ and the $T_3$ generations. Two events, -01 and -03 were significant in both generations at p=0.05 using a one-tailed t-test assuming unequal variance (Table 2-2). ME02779 transgenic seedlings were significantly larger than the pooled non-transgenic segregants.

TABLE 2-2

T-test comparison of seedling area between transgenic seedlings and pooled non-transgenic segregants after 10 days at 8° C.

| | | Transgenic | | | Pooled Non-Transgenics | | | t-test |
|---|---|---|---|---|---|---|---|---|
| Line | Events | Avg | SE | N | Avg | SE | N | p-value |
| ME02779 | ME02779-01 | 0.0077 | 0.0007 | 12 | 0.0040 | 0.0014 | 3 | 0.01738 |
| ME02779 | ME02779-01-99 | 0.0051 | 0.0005 | 21 | 0.0034 | 0.0002 | 29 | 0.00077 |
| ME02779 | ME02779-03 | 0.0111 | 0.0007 | 19 | 0.0085 | 0.0007 | 40 | 0.00433 |
| ME02779 | ME02779-03-99 | 0.0052 | 0.0006 | 20 | 0.0034 | 0.0002 | 29 | 0.00293 |

Two Events of ME02779 Show 3:1 Segregation for Finale™ Resistance.

Events -01 and -03 segregated 3:1 (R:S) for Finale™ resistance in the $T_2$ generation (data not shown).

Qualitative Analysis of the $T_1$ Plants:

The physical appearance of nine of the ten $T_1$ plants was identical to the controls except for Event -09, which exhibited small rosettes and reduced fertility.

Qualitative and Quantitative Analysis of the $T_2$ Plants:

Events -01 and -03 of ME02779 exhibited no statistically relevant negative phenotypes.

Germination
- No detectable reduction in germination rate.

General morphology/architecture
- Plants appeared wild-type in all instances.

Days to flowering
- No observable or statistical differences between experimentals and controls.

Rosette area 7 days post-bolting
- No observable or statistical differences between experimentals and controls.

Fertility (silique number and seed fill)
- No observable or statistical differences between experimentals and controls

Example 3: ME03944

TABLE 3-1

| Construct | Event/Generation | Plant Stage | Assay | Result |
|---|---|---|---|---|
| 35S:: 271922 | −02/$T_2$ Finale resistant plants | Seedling | Cold Germination | Significant at p ≤.05 |
| 35S:: 271922 | −06/$T_2$ Finale resistant plants | Seedling | Cold Germination | Significant at p ≤.05 |
| 35S:: 271922 | −02/$T_3$ Finale resistant plants | Seedling | Cold Germination | Significant at p ≤.05 |
| 35S:: 271922 | −06/$T_3$ Finale resistant plants | Seedling | Cold Germination | Significant at p ≤.05 |

Ectopic expression of Clone 271922 under the control of the 35S promoter induces the following phenotypes:
- Early germination at 8° C. resulting in larger seedlings after 10 days at 8° C.

Plants from Events -02 and -06 which are heterozygous or homozygous for Clone 271922 do not show any negative phenotypes under long-day conditions.

The gene corresponding to Clone 271922 shows little differential regulation in transcription profiling experiments on wildtype.

Clone 271922 encodes a 60s ribosomal protein L37a.

Two Events of ME03944 Showed Significant Early Germination Under Cold Conditions in Both Generations.

Four events of ME03944 were sown as described in the Cold Germination Assay in both the $T_2$ and the $T_3$ generations. Two events, -02 and -06, were significant in both generations at p≤0.05 using a one-tailed t-test assuming unequal variance (Table 3-2). The $T_3$ lines are indicated as -99 which indicates that the seeds are the bulked progeny from several $T_2$ plants. ME03944 transgenic seedlings were significantly larger than the pooled non-transgenic segregants.

TABLE 3-2

T-test comparison of seedling area between transgenic seedlings and pooled non-transgenic segregants after 10 days at 8° C.

| | | Transgenic | | | Pooled Non-Transgenics | | | t-test |
|---|---|---|---|---|---|---|---|---|
| Line | Events | Avg | SE | N | Avg | SE | N | p-value |
| ME03944 | ME03944-02 | 0.0115 | 0.0004 | 23 | 0.0069 | 0.0006 | 35 | 3.4023E-08 |
| ME03944 | ME03944-02-99 | 0.0070 | 0.0008 | 15 | 0.0051 | 0.0004 | 29 | 0.0173 |
| ME03944 | ME03944-06 | 0.0106 | 0.0006 | 18 | 0.0069 | 0.0006 | 35 | 2.7850E-05 |
| ME03944 | ME03944-06-99 | 0.0077 | 0.0007 | 21 | 0.0051 | 0.0004 | 29 | 0.0011 |

Two Events of ME03944 Show 3:1 Segregation for Finale™ Resistance.

Events -02 and -06 segregated 3:1 (R:S) for Finale™ resistance in the $T_2$ generation (data not shown).

Qualitative Analysis of the $T_1$ Plants:

The physical appearance of five of the six $T_1$ plants was identical to the controls. Event -03 exhibited a small rosette and curled leaves.

Other Characteristics:

Seedlings from ME03944-06 exhibited elongated hypocotyls. This phenotype co-segregated with Finale™ resistance.

Qualitative and Quantitative Analysis of the $T_2$ Plants:

Events -02 and -06 of ME03944 exhibited no statistically relevant negative phenotypes.

Germination
- No detectable reduction in germination rate.

General morphology/architecture
- Plants appeared wild-type in all instances.

Days to flowering
- No observable or statistical differences between experimentals and controls.

Rosette area 7 days post-bolting
- No observable or statistical differences between experimentals and controls.

Fertility (silique number and seed fill)
- No observable or statistical differences between experimentals and controls

Example 4: ME05304

TABLE 4-1

| Construct | Event/Generation | Plant Stage | Assay | Result |
|---|---|---|---|---|
| 35S:: 2403 | −01/$T_2$ Finale resistant plants | Seedling | Cold Germination | Significant at p ≤.05 |
| 35S:: 2403 | −04/$T_2$ Finale resistant plants | Seedling | Cold Germination | Significant at p ≤.05 |
| 35S:: 2403 | −01/$T_3$ Finale resistant plants | Seedling | Cold Germination | Significant at p ≤.05 |
| 35S:: 2403 | −04/$T_3$ Finale resistant plants | Seedling | Cold Germination | Significant at p ≤.05 |

Ectopic expression of Clone 2403 under the control of the 35S promoter induces the following phenotypes:

Early germination at 8° C. resulting in larger seedlings after 10 days at 8° C.

Plants from Events -01 and -04 which are heterozygous or homozygous for Clone 2403 do not show any negative phenotypes under long-day conditions.

The gene corresponding to Clone 2403 shows little differential regulation in transcript profiling experiments on wildtype.

Clone 2403 encodes a truncated ubiquitin-like protein.

Two Events of ME05304 Showed Significant Early Germination Under Cold Conditions in Both Generations.

Four events of ME05304 were sown as described in the Cold Germination Assay in both the $T_2$ and the $T_3$ generations. Two events, -01 and -04 were significant in both generations at p≤0.05 using a one-tailed t-test assuming unequal variance (Table 4-2). The $T_3$ lines are indicated as -99 which indicates that the seeds are the bulked progeny from several $T_2$ plants.

TABLE 4-2

T-test comparison of seedling area between transgenic seedlings and pooled non-transgenic segregants after 10 days at 8° C.

| | | Transgenic | | | Pooled Non-Transgenics | | | t-test |
|---|---|---|---|---|---|---|---|---|
| Line | Events | Avg | SE | N | Avg | SE | N | p-value |
| ME05304 | ME05304-01 | 0.0142 | 0.0009 | 20 | 0.0079 | 0.0006 | 39 | 0.0000 |
| ME05304 | ME05304-01-99 | 0.0061 | 0.0005 | 17 | 0.0049 | 0.0003 | 27 | 0.0213 |
| ME05304 | ME05304-04 | 0.0101 | 0.0007 | 15 | 0.0079 | 0.0006 | 39 | 0.0099 |
| ME05304 | ME05304-04-99 | 0.0067 | 0.0005 | 22 | 0.0049 | 0.0003 | 27 | 0.0014 |

Two Events of ME05304 Show 3:1 Segregation for Finale™ Resistance.

Events -01 and -04 segregated 3:1 (R:S) for Finale™ resistance in the $T_2$ generation (data not shown).

Qualitative Analysis of the $T_1$ Plants:

The physical appearance of seven of the ten $T_1$ plants was identical to the controls. The other three events exhibited the following phenotypes: late flowering (Events -01, -02 and -08), dark green rosette leaves (Events -01 and -08) and shorter petioles (Events -02 and -08). Event -01 did not reproduce the late-flowering phenotype in the $T_2$ generation.

Qualitative and Quantitative Analysis of the $T_2$ Plants:

Events -01 and -04 of ME05304 exhibited no statistically relevant negative phenotypes.

Germination
- No detectable reduction in germination rate.

General morphology/architecture
- Plants appeared wild-type in all instances.

Days to flowering
- No observable or statistical differences between experimentals and controls.

Rosette area 7 days post-bolting
- No observable or statistical differences between experimentals and controls.

Fertility (silique number and seed fill)
- No observable or statistical differences between experimentals and controls.

Example 5: ME03186

TABLE 5-1

| Construct | Event/Generation | Plant Stage | Assay | Result |
|---|---|---|---|---|
| 35S::674166 | −04/$T_3$ Finale resistant plants | Seedling | Cold Germination | Significant at p ≤.05 |
| 35S::674166 | −04/$T_4$ Finale resistant plants | Seedling | Cold Germination | Significant at p ≤.05 |
| 35S::674166 | −05/$T_2$ Finale resistant plants | Seedling | Cold Germination | Significant at p ≤.05 |
| 35S::674166 | −05/$T_3$ Finale resistant plants | Seedling | Cold Germination | Significant at p ≤.05 |

- Ectopic expression of Clone 674166 under the control of the 35S promoter results in early germination at 8° C. resulting in larger seedlings after 10 days at 8° C.
- Plants from Events -04 and -05 which are hemizygous or homozygous for Clone 674166 do not show any negative phenotypes under long-day conditions.

Two Events of ME03186 Showed Significant Early Germination Under Cold Conditions in Both Generations.

Two events, -04 and -05 were significant in two generations at p≤0.05 using a one-tailed t-test assuming unequal variance (Table 5-2). '-99' signifies that seeds were pooled from several plants.

TABLE 5-2

T-test comparison of seedling area between transgenic seedlings and control non-transgenic segregants after 10 days at 8° C.

| | Event- | Transgenic | | | Control Non-Transgenics[a] | | | t-test |
|---|---|---|---|---|---|---|---|---|
| Events | Gen | Avg | SE | N | Avg | SE | N | p-value |
| ME03186-04-99[b] | 04-T3 | 0.0045 | 0.0003 | 35 | 0.0030 | 0.0002 | 31 | 1.37E-05 |
| ME03186-04-99 | 04-T3 | 0.0092 | 0.0003 | 48 | 0.0051 | 0.0005 | 12 | 3.72E-10 |
| ME03186-04-99-03 | 04-T4 | 0.0107 | 0.0002 | 70 | 0.0083 | 0.0005 | 34 | 2.72E-05 |

TABLE 5-2-continued

T-test comparison of seedling area between transgenic seedlings and control non-transgenic segregants after 10 days at 8° C.

| Events | Event-Gen | Transgenic Avg | Transgenic SE | Transgenic N | Control Non-Transgenics[a] Avg | Control Non-Transgenics[a] SE | Control Non-Transgenics[a] N | t-test p-value |
|---|---|---|---|---|---|---|---|---|
| ME03186-04-99-04 | 04-T4 | 0.0120 | 0.0004 | 62 | 0.0083 | 0.0005 | 34 | 3.61E-08 |
| ME03186-04-99-07 | 04-T4 | 0.0107 | 0.0003 | 69 | 0.0083 | 0.0005 | 34 | 4.91E-05 |
| ME03186-04-99-08 | 04-T4 | 0.0110 | 0.0003 | 69 | 0.0083 | 0.0005 | 34 | 5.53E-06 |
| ME03186-05[b] | 05-T2 | 0.0051 | 0.0005 | 22 | 0.0038 | 0.0005 | 6 | 0.0332 |
| ME03186-05 | 05-T2 | 0.0067 | 0.0003 | 53 | 0.0054 | 0.0005 | 9 | 0.0106 |
| ME03186-05-04 | 05-T3 | 0.0050 | 0.0003 | 50 | 0.0037 | 0.0003 | 9 | 0.0008 |

[a]Transgenic seedlings were compared to non-transgenic segregants within a seed line except for the $T_4$ generation of Event-04. Since these seed lines were homozygous, they were compared to pooled non-transgenic segregants from another $T_4$ generation event that was grown in the same flat as the $T_4$ generation of Event-04.
[b]These events were sown twice. The first time was to identify ME03186 as a hit. They were repeated the second time with two generations to identify ME03186 as a candidate.

Two Events of ME03186 Show 3:1 Segregation for Finale™ Resistance.

Event -05 segregated 3:1 (R:S) for Finale™ resistance in the $T_2$ generation. $T_2$ generation seed was not available for Event -04. However, the $T_3$ generation seeds that were pooled from several $T_2$ plants segregated approximately 2:1 in a manner consistent with a single insert (see Table 5-2).

Qualitative and Quantitative Analysis of the $T_2$ Plants (Screening for Negative Phenotypes):

Events -04 and -05 of ME03186 exhibited no statistically significant negative phenotypes.

Germination

No detectable reduction in germination rate.

General morphology/architecture

Plants appeared wild-type in all instances.

Days to flowering

No observable or statistical differences between experimentals and controls.

Rosette area 7 days post-bolting

REFERENCES

Hunt et al, (2001) *Plant Mol Biol* 47: 677-692.

Lu and Hills (2002) *Plant Physiol.* 129:1352-8

Example 6: Clone 1055099 (SEQ ID NO: 46)—ME 24967

In the same manner as Example 5, transgenics made with a construct of 35S—Clone 1055099 were screened for cold tolerance. Clone 1055099 (SEQ ID NO: 46) is a wheat functional homolog of clone 674166 (SEQ ID NO: 42), and showed the following results in the seedling cold tolerance assay.

TABLE 6-1

Cold Germination Assay results for ME24967.

| Event | p-values Internal[a] | p-values Pooled[b] | Avg. Seedling Area Transgenic | Avg. Seedling Area Internal | Avg. Seedling Area Pooled | Sample No. Transgenic | Sample No. Internal | Sample No. Pooled |
|---|---|---|---|---|---|---|---|---|
| ME03186-04-99[c] | 0.00224438 | 0.00224438 | 0.0032 | 0.0017 | 0.0017 | 30 | 40 | 40 |
| ME24967-02 | 0.12660455 | 0.45511103 | 0.0053 | 0.0071 | 0.0054 | 29 | 5 | 83 |
| ME24967-03[d] | 0.01488322 | 0.04610112 | 0.0069 | 0.0031 | 0.0054 | 31 | 3 | 83 |
| ME24967-05[d] | 0.08783497 | 3.0406E-08 | 0.0115 | 0.0092 | 0.0054 | 23 | 12 | 83 |
| ME24967-10 | 0.40686041 | 0.25206736 | 0.0049 | 0.0053 | 0.0054 | 28 | 6 | 83 |
| ME24967-11 | 0.19290195 | 0.40123421 | 0.0051 | 0.0038 | 0.0054 | 5 | 25 | 83 |
| ME24967-12 | 0.3021565 | 0.00329335 | 0.0032 | 0.0050 | 0.0054 | 27 | 2 | 83 |
| ME24967-13 | 0.24672812 | 0.31347649 | 0.0060 | 0.0077 | 0.0054 | 23 | 7 | 83 |
| ME24967-14 | 0.17548824 | 0.29369895 | 0.0050 | 0.0032 | 0.0054 | 26 | 5 | 83 |
| ME24967-15 | 0.29278326 | 0.38586196 | 0.0057 | 0.0048 | 0.0054 | 22 | 11 | 83 |
| ME24967-16 | | 0.05451794 | 0.0041 | 0.0018 | 0.0054 | 34 | 1 | 83 |

TABLE 6-1-continued

| Cold Germination Assay results for ME24967. | | | | | | | | |
|---|---|---|---|---|---|---|---|---|
| | p-values | | Avg. Seedling Area | | | Sample No. | | |
| Event | Internal[a] | Pooled[b] | Transgenic | Internal | Pooled | Transgenic | Internal | Pooled |
| ME24967-17 | 0.27484717 | 0.13660585 | 0.0044 | 0.0058 | 0.0054 | 26 | 6 | 83 |

[a]Internal controls are segregating non-transgenic seedlings within an Event.

[b]Pooled controls are all of the segregating non-transgenic seedlings from all of the Events within a line.

[c]ME03186 is a positive control to verify that the experimental conditions were appropriate.

[d]These events show significantly improved seedling area for at least internal or pooled controls.

Example 7—Determination of Functional Homologs by Reciprocal BLAST

A candidate sequence was considered a functional homolog of a reference sequence if the candidate and reference sequences encoded proteins having a similar function and/or activity. A process known as Reciprocal BLAST (Rivera et al., *Proc. Natl. Acad. Sci. USA,* 95:6239-6244 (1998)) was used to identify potential functional homolog sequences from databases consisting of all available public and proprietary peptide sequences, including NR from NCBI and peptide translations from Ceres clones.

Before starting a Reciprocal BLAST process, a specific reference polypeptide was searched against all peptides from its source species using BLAST in order to identify polypeptides having BLAST sequence identity of 80% or greater to the reference polypeptide and an alignment length of 85% or greater along the shorter sequence in the alignment. The reference polypeptide and any of the aforementioned identified polypeptides were designated as a cluster.

The BLASTP version 2.0 program from Washington University at Saint Louis, Mo., USA was used to determine BLAST sequence identity and E-value. The BLASTP version 2.0 program includes the following parameters: 1) an E-value cutoff of 1.0e−5; 2) a word size of 5; and 3) the -postsw option. The BLAST sequence identity was calculated based on the alignment of the first BLAST HSP (High-scoring Segment Pairs) of the identified potential functional homolog sequence with a specific reference polypeptide. The number of identically matched residues in the BLAST HSP alignment was divided by the HSP length, and then multiplied by 100 to get the BLAST sequence identity. The HSP length typically included gaps in the alignment, but in some cases gaps were excluded.

The main Reciprocal BLAST process consists of two rounds of BLAST searches; forward search and reverse search. In the forward search step, a reference polypeptide sequence, "polypeptide A," from source species SA was BLASTed against all protein sequences from a species of interest. Top hits were determined using an E-value cutoff of $10^{-5}$ and a sequence identity cutoff of 35%. Among the top hits, the sequence having the lowest E-value was designated as the best hit, and considered a potential functional homolog or ortholog. Any other top hit that had a sequence identity of 80% or greater to the best hit or to the original reference polypeptide was considered a potential functional homolog or ortholog as well. This process was repeated for all species of interest.

In the reverse search round, the top hits identified in the forward search from all species were BLASTed against all protein sequences from the source species SA. A top hit from the forward search that returned a polypeptide from the aforementioned cluster as its best hit was also considered as a potential functional homolog.

Functional homologs were identified by manual inspection of potential functional homolog sequences. Representative functional homologs for SEQ ID NOs: 2, 7, 9, 20, 34, 40 and 42 are shown in FIGS. 1-7, respectively. The BLAST percent identities and E-values of functional homologs to SEQ ID NOs: 2, 7, 9, 20, 34, 40 and 42 are shown in the Sequence Listing. The BLAST sequence identities and E-values given in the Sequence Listing were taken from the forward search round of the Reciprocal BLAST process.

Example 8—Determination of Functional Homologs by Hidden Markov Models

Hidden Markov Models (HMMs) were generated by the program HMMER 2.3.2. To generate each HMM, the default HMMER 2.3.2 program parameters, configured for glocal alignments, were used.

An HMM was generated using the sequences shown in each of FIGS. 1-7 as input. Additional sequences were input into the model, and the HMM bit scores for the additional sequences are shown in the Sequence Listing. The results indicate that these additional sequences are functional homologs of SEQ ID NOs: 2, 7, 9, 20, 34, 40 and 42, respectively. The bit score results are provided in Table 7.

TABLE 7

| Query Identifier | Functional Homolog | Sequence Type | Species | Seq Id No | Length | Pfam | Pfam Description | Start | End | Profile | HMM Bit Score | FL_Profile | FL_Score |
|---|---|---|---|---|---|---|---|---|---|---|---|---|---|
| | Ceres CLONE ID no. 30087 | DNA | *Arabidopsis thaliana* | 1 | 828 | | | | | | | | |
| Ceres CLONE ID no. 30087 | Ceres CLONE ID no. 30087 | PRT | *Arabidopsis thaliana* | 2 | 164 | | | | | Y | | | |
| Ceres Clone ID no. 30087 | Ceres CLONE ID no. 947579 | PRT | *Brassica napus* | 3 | 155 | | | | | Y | | | |
| Ceres Clone ID no. 30087 | Public GI no. 62526422 | PRT | *Brassica napus* | 4 | 152 | | | | | | | | |
| Ceres Clone ID no. 30087 | Ceres CLONE ID no. 1606506 | PRT | *Parthenium argantatum* | 5 | 150 | | | | | Y | | | |
| | Ceres CLONE ID no. 30469 | DNA | Artificial Sequence | 6 | 586 | | | | | | | | |
| Ceres CLONE ID no. 30469 | Ceres CLONE ID no. 30469 | PRT | Artificial Sequence | 7 | 78 | Globin | Globin | 13 | 74 | Y | 184.6 | | 66 |
| | Ceres CLONE ID no. 30469_FL | DNA | *Arabidopsis thaliana* | 8 | 483 | | | | | | | | |
| Ceres Clone ID no. 30469 | Ceres CLONE ID no. 30469_FL | PRT | *Arabidopsis thaliana* | 9 | 160 | Globin | Globin | 13 | 152 | | 184.6 | Y | 404.9 |
| Ceres Clone ID no. 30469 | Public GI no. 30909306 | PRT | *Raphanus sativus* | 10 | 160 | Globin | Globin | 13 | 152 | | 185.7 | Y | 410.4 |
| Ceres Clone ID no. 30469 | Public GI no. 37903656 | PRT | *Arabidopsis thaliana* | 11 | 158 | Globin | Globin | 10 | 149 | | 172.6 | | 387.2 |
| Ceres Clone ID no. 30469 | Public GI no. 15824736 | PRT | *Arabidopsis thaliana* | 12 | 163 | Globin | Globin | 13 | 152 | | 184.2 | | 405.4 |
| Ceres Clone ID no. 30469 | Ceres CLONE ID no. 546001 | PRT | Glycine max | 13 | 161 | Globin | Globin | 13 | 152 | | 182.8 | Y | 402.3 |
| Ceres Clone ID no. 30469 | Public GI no. 11095158 | PRT | Glycine max | 14 | 160 | Globin | Globin | 13 | 152 | | 167.8 | | 387.2 |
| Ceres Clone ID no. 30469 | Public GI no. 12963875 | PRT | Glycine max | 15 | 152 | Globin | Globin | 8 | 147 | | 145.8 | | 337.1 |
| Ceres Clone ID no. 30469 | Ceres CLONE ID no. 1554560 | PRT | *Zea mays* | 16 | 165 | Globin | Globin | 17 | 157 | | 185.7 | Y | 404.5 |
| Ceres Clone ID no. 30469 | Ceres CLONE ID no. 839727 | PRT | *Triticum aestivum* | 17 | 162 | Globin | Globin | 14 | 154 | | 187.8 | Y | 415.2 |
| Ceres Clone ID no. 30469 | Public GI no. 14701800 | PRT | *Triticum aestivum* | 18 | 169 | Globin | Globin | 21 | 161 | | 170.1 | | 386.9 |
| | Ceres CLONE ID no. 271922 | DNA | *Arabidopsis thaliana* | 19 | 416 | | | | | | | | |
| Ceres CLONE ID no. 271922 | Ceres CLONE ID no. 271922 | PRT | *Arabidopsis thaliana* | 20 | 92 | Ribosomal_L37ae; | Ribosomal L37ae protein family | 2 | 91 | Y | 266.3 | | |
| Ceres Clone ID no. 271922 | Public Gl no. 4090257 | PRT | *Arabidopsis thaliana* | 21 | 92 | Ribosomal_L37ae | Ribosomal L37ae protein family | 2 | 91 | | 265 8 | | |
| Ceres Clone ID no. 271922 | Public GI no. 4741896 | PRT | *Arabidopsis thaliana* | 22 | 92 | Ribosomal_L37ae | Ribosomal L37ae protein family | 2 | 91 | | 264 | | |
| Ceres Clone ID no. 271922 | Ceres CLONE ID no. 36046 | PRT | *Arabidopsis thaliana* | 23 | 92 | Ribosomal_L37ae | Ribosomal L37ae protein family | 2 | 91 | | 257.8 | | |
| Ceres Clone ID no. 271922 | Public GI no. 6016699 | PRT | *Arabidopsis thaliana* | 24 | 92 | Ribosomal_L37ae | Ribosomal L37ae protein family | 2 | 91 | | 257.4 | | |
| Ceres Clone ID no. 271922 | Ceres CLONE ID no. 664936 | PRT | Glycine max | 25 | 92 | Ribosomal_L37ae | Ribosomal L37ae protein family | 2 | 91 | Y | 268.8 | | |
| Ceres Clone ID no. 271922 | Ceres CLONE ID no. 658438 | PRT | Glycine max | 26 | 92 | Ribosomal_L37ae | Ribosomal L37ae protein family | 2 | 91 | | 269 | | |
| Ceres Clone ID no. 271922 | Ceres CLONE ID no. 1049262 | PRT | Glycine max | 27 | 92 | Ribosomal_L37ae | Ribosomal L37ae protein family | 2 | 91 | | 268.9 | | |
| Ceres Clone ID no. 271922 | Ceres CLONE ID no. 632613 | PRT | *Triticum aestivum* | 28 | 92 | Ribosomal_L37ae | Ribosomal L37ae protein family | 2 | 91 | Y | 269 | | |
| Ceres Clone ID no. 271922 | Ceres CLONE ID no. 1390976 | PRT | *Zea mays* | 29 | 92 | Ribosomal_L37ae | Ribosomal L37ae protein family | 2 | 91 | Y | 269 | | |
| Ceres Clone ID no. 271922 | Ceres CLONE ID no. 1457185 | PRT | *Zea mays* | 30 | 92 | Ribosomal_L37ae | Ribosomal L37ae protein family | 2 | 91 | | 269 | | |
| Ceres Clone ID no. 271922 | Public Gl no. 56202147 | PRT | *Zea mays* | 31 | 92 | Ribosomal_L37ae | Ribosomal L37ae protein family | 2 | 91 | | 269 | | |

TABLE 7-continued

| Query Identifier | Functional Homolog | Sequence Type | Species | Seq Id No | Length | Pfam | Pfam Description | Start | End | Profile | HMM Bit Score | FL_Profile | FL_Score |
|---|---|---|---|---|---|---|---|---|---|---|---|---|---|
| Ceres Clone ID no. 271922 | Public GI no. 58578274 | PRT | *Zea mays* | 32 | 92 | Ribosomal_L37ae | Ribosomal L37ae protein family | 2 | 91 | | 267.2 | | |
| | Ceres CLONE ID no. 2403_FL | DNA | *Arabidopsis thaliana* | 33 | 632 | | | | | | | | |
| Ceres CLONE ID no. 2403 | Ceres CLONE ID no. 2403_FL | PRT | *Arabidopsis thaliana* | 34 | 154 | ubiquitin; | Ubquitin family | 1 | 74 | | 118.7 | | 416.2 |
| Ceres CLONE ID no. 2403 | Ceres CLONE ID no. 2403_ FL | PRT | *Arabidopsis thaliana* | 34 | 154 | ubiquitin; | Ubiquitin family | 77 | 150 | | 118.7 | Y | 416.2 |
| Ceres Clone ID no. 2403 | Ceres CLONE ID no. 1482731 | PRT | *Zea Mays* | 35 | 169 | ubiquitin | Ubiquitin family | 1 | 74 | | 118.3 | Y | 417 |
| Ceres Clone ID no. 2403 | Ceres CLONE ID no. 1482731 | PRT | *Zea mays* | 35 | 169 | ubiquitin | Ubiquitin family | 77 | 150 | | 118.3 | Y | 417 |
| Ceres Clone ID no. 2403 | Ceres CLONE ID no. 522921 | PRT | Glycine max | 36 | 154 | ubiquitin | Ubiquitin family | 1 | 74 | | 118.7 | Y | 418.4 |
| Ceres Clone ID no. 2403 | Ceres CLONE ID no. 522921 | PRT | Glycine max | 36 | 154 | ubiquitin | Ubiquitin family | 77 | 150 | | 118.7 | Y | 418.4 |
| Ceres Clone ID no. 2403 | Ceres CLONE ID no. 1036726 | PRT | *Brassica napus* | 37 | 160 | ubiquitin | Ubiquitin family | 1 | 74 | | 118.7 | Y | 384.4 |
| Ceres Clone ID no. 2403 | Ceres CLONE ID no. 1036726 | PRT | *Brassica napus* | 37 | 160 | ubiquitin | Ubiquitin family | 77 | 142 | | 118.7 | Y | 384.4 |
| Ceres Clone ID no. 2403 | Ceres CLONE ID no. 513071 | PRT | Glycine max | 38 | 188 | ubiquitin | Ubiquitin family | 1 | 74 | | 114.3 | | 408.6 |
| Ceres Clone ID no. 2403 | Ceres CLONE ID no. 513071 | PRT | Glycine max | 38 | 188 | ubiquitin | Ubiquitin family | 77 | 150 | | 114.3 | | 408.6 |
| | Ceres CLONE ID no. 2403 | DNA | Artificial Sequence | 39 | 620 | | | | | | | | |
| Ceres CLONE ID no. 2403 | Ceres CLONE ID no. 2403 | PRT | Artificial Sequence | 40 | 33 | ubiquitin; | Ubiquitin family | 1 | 33 | Y | 87.6 | | −83.1 |
| | Ceres CLONE ID no. 674166 | DNA | Glycine max | 41 | 1106 | | | | | | | | |
| Ceres CLONE ID no. 674166 | Ceres CLONE ID no. 674166 | PRT | Glycine max | 42 | 210 | AP2; | AP2 domain | 26 | 89 | Y | 491.8 | | |
| Ceres Clone ID no. 674166 | Public GI no. 12322345 | PRT | Glycine max | 43 | 225 | AP2 | AP2 domain | 26 | 89 | | 522.4 | | |
| Ceres Clone ID no. 674166 | Ceres CLONE ID no. 975672 | PRT | *Brassica napus* | 44 | 215 | AP2 | AP2 domain | 21 | 84 | Y | 481.7 | | |
| Ceres Clone ID no. 674166 | Ceres CLONE ID no. 273307 | PRT | *Zea mays* | 45 | 211 | AP2 | AP2 domain | 17 | 80 | Y | 419.7 | | |
| Ceres Clone ID no. 674166 | Ceres CLONE ID no. 1055099 | PRT | *Triticum aestivum* | 46 | 194 | AP2 | AP2 domain | 20 | 83 | Y | 358.4 | | |
| | Ceres ANNOT ID no. 1441430 | DNA | *Populus balsamifera* subsp. *trichocarpa* | 47 | 660 | | | | | | | | |
| Ceres CLONE ID no. 674166 | Ceres ANNOT ID no. 1441430 | PRT | *Populus balsamifera* subsp. *trichocarpa* | 48 | 219 | AP2 | AP2 domain | 29 | 92 | Y | 504.4 | | |
| | Ceres CLONE ID no. 1240330 | DNA | Glycine max | 49 | 985 | | | | | | | | |
| Ceres CLONE ID no. 674166 | Ceres CLONE ID no. 1240330 | PRT | Glycine max | 50 | 222 | AP2 | AP2 domain | 24 | 87 | | 483.3 | | |
| | Ceres CLONE ID no. 1382611 | DNA | *Zea mays* | 51 | 726 | | | | | | | | |
| Ceres CLONE ID no. 30087 | Ceres CLONE ID no. 1382611 | PRT | *Zea mays* | 52 | 156 | | | | | Y | | | |
| | Ceres CLONE ID no. 1627907 | DNA | *Papaver somniferum* | 53 | 580 | | | | | | | | |
| Ceres CLONE ID no. 271922 | Ceres CLONE ID no. 1627907 | PRT | *Papaver somniferum* | 54 | 92 | Ribosomal_L37ae | Ribosomal L37ae protein family | 2 | 91 | Y | 268.1 | | |
| | Ceres CLONE ID no. 1761125 | DNA | *Panicum virgatum* | 55 | 983 | | | | | | | | |
| Ceres CLONE ID no. 674166 | Ceres CLONE ID no. 1761125 | PRT | *Panicum virgatum* | 56 | 192 | AP2 | AP2 domain | 13 | 76 | Y | 363 | | |
| | Ceres CLONE ID no. 1783890 | DNA | *Panicum virgatum* | 57 | 694 | | | | | | | | |
| Ceres CLONE ID no. 271922 | Ceres CLONE ID no. 1783890 | PRT | *Panicum virgatum* | 58 | 92 | Ribosomal_L37ae | Ribosomal L37ae protein family | 2 | 91 | Y | 269 | | |
| | Ceres CLONE ID no. 1802327 | DNA | *Panicum virgatum* | 59 | 880 | | | | | | | | |
| Ceres Clone ID no. 30469 | Ceres CLONE ID no. 1802327 | PRT | *Panicum virgatum* | 60 | 162 | Globin | Globin | 14 | 154 | | 191.4 | Y | 417.9 |
| | Ceres CLONE ID no. 1838364 | DNA | *Gossypium hirsutum* | 61 | 1017 | | | | | | | | |
| Ceres CLONE ID no. 674166 | Ceres CLONE ID no. 1838364 | PRT | *Gossypium hirsutum* | 62 | 246 | AP2 | AP2 domain | 28 | 91 | Y | 484.1 | | |
| | Ceres CLONE ID no. 1876458 | DNA | *Panicum virgatum* | 63 | 708 | | | | | | | | |
| Ceres Clone ID no. 30469 | Ceres CLONE ID no. 1876458 | PRT | *Panicum virgatum* | 64 | 162 | Globin | Globin | 14 | 154 | | 191.9 | | 415.3 |
| | Ceres CLONE ID no. 1879148 | DNA | *Panicum virgatum* | 65 | 712 | | | | | | | | |
| Ceres Clone ID no. 30469 | Ceres CLONE ID no. 1879148 | PRT | *Panicum virgatum* | 66 | 164 | Globin | Globin | 16 | 156 | | 185.7 | | 411.2 |
| | Ceres CLONE ID no. 1884696 | DNA | *Gossypium hirsutum* | 67 | 1129 | | | | | | | | |

TABLE 7-continued

| Query Identifier | Functional Homolog | Sequence Type | Species | Seq Id No | Length | Pfam | Pfam Description | Start | End | Profile | HMM Bit Score | FL_Profile | FL_Score |
|---|---|---|---|---|---|---|---|---|---|---|---|---|---|
| Ceres CLONE ID no. 2403 | Ceres CLONE ID no. 1884696 | PRT | *Gossypium hirsutum* | 68 | 153 | ubiquitin | Ubiquitin family | 1 | 74 | | 175.2 | Y | 408 |
| Ceres CLONE ID no. 2403 | Ceres CLONE ID no. 1884696 | PRT | *Gossypium hirsutum* | 68 | 153 | ubiquitin | Ubiquitin family | 77 | 150 | | 175.2 | Y | 408 |
| | Ceres CLONE ID no. 1916866 | DNA | *Gossypium hirsutum* | 69 | 679 | | | | | | | | |
| Ceres Clone ID no. 30469 | Ceres CLONE ID no. 1916866 | PRT | *Gossypium hirsutum* | 70 | 163 | Globin | Globin | 13 | 152 | | 188.3 | Y | 409.8 |
| | Ceres CLONE ID no. 1950105 | DNA | *Panicum virgatum* | 71 | 1003 | | | | | | | | |
| Ceres CLONE ID no. 2403 | Ceres CLONE ID no. 1950105 | PRT | *Panicum virgatum* | 72 | 229 | ubiquitin | Ubiquitin family | 1 | 74 | | 262.8 | | 504.1 |
| Ceres CLONE ID no. 2403 | Ceres CLONE ID no. 1950105 | PRT | *Panicum virgatum* | 72 | 229 | ubiquitin | Ubiquitin family | 77 | 150 | | 262.8 | | 504.1 |
| Ceres CLONE ID no. 2403 | Ceres CLONE ID no. 1950105 | PRT | *Panicum virgatum* | 72 | 229 | ubiquitin | Ubiquitin family | 153 | 226 | | 262.8 | | 504.1 |
| | Ceres CLONE ID no. 1990746 | DNA | *Panicum virgatum* | 73 | 724 | | | | | | | | |
| Ceres Clone ID no. 30469 | Ceres CLONE ID no. 1990746 | PRT | *Panicum virgatum* | 74 | 164 | Globin | Globin | 16 | 156 | | 184.9 | | 405.6 |
| | Ceres CLONE ID no. 2007485 | DNA | *Panicum virgatum* | 75 | 696 | | | | | | 369.2 | | |
| Ceres CLONE ID no. 674166 | Ceres CLONE ID no. 2007485 | PRT | *Panicum virgatum* | 76 | 201 | AP2 | AP2 domain | 17 | 80 | | 271.2 | | |
| | Ceres CLONE ID no. 2033803 | DNA | *Panicum virgatum* | 77 | 698 | | | | | | | | |
| Ceres Clone ID no. 30469 | Ceres CLONE ID no. 2033803 | PRT | *Panicum virgatum* | 78 | 156 | Globin | Globin | 16 | 148 | | 184.9 | | 369.2 |
| | Ceres CLONE ID no. 2034916 | DNA | *Panicum virgatum* | 79 | 724 | | | | | | | | |
| Ceres CLONE ID no. 2403 | Ceres CLONE ID no. 2034916 | PRT | *Panicum virgatum* | 80 | 213 | ubiquitin | Ubiquitin family | 1 | 74 | | 259.2 | Y | 460.4 |
| Ceres CLONE ID no. 2403 | Ceres CLONE ID no. 2034916 | PRT | *Panicum virgatum* | 80 | 213 | ubiquitin | Ubiquitin family | 77 | 150 | | 259.2 | Y | 460.4 |
| Ceres CLONE ID no. 2403 | Ceres CLONE ID no. 2034916 | PRT | *Panicum virgatum* | 80 | 213 | ubiquitin | Ubiquitin family | 153 | 213 | | 259.2 | Y | 460.4 |
| | Ceres CLONE ID no. 651581 | DNA | Glycine max | 81 | 1194 | | | | | | | | |
| Ceres CLONE ID no. 674166 | Ceres CLONE ID no. 651581 | PRT | Glycine max | 82 | 224 | AP2 | AP2 domain | 24 | 87 | | 469.5 | | |
| Ceres CLONE ID no. 674166 | Public GI ID no. 125550159 | PRT | *Oryza saliva* subsp. *indica* | 83 | 184 | AP2 | AP2 domain | 7 | 70 | Y | 344 | | |
| Ceres CLONE ID no. 674166 | Public GI ID no. 15223609 | PRT | *Arabidopsis thaliana* | 84 | 225 | AP2 | AP2 domain | 26 | 89 | Y | 522.4 | | |
| Ceres CLONE ID no. 30087 | Public GI ID no. 30683885 | PRT | *Arabidopsis thaliana* | 85 | 164 | | | | | | | | |
| Ceres CLONE ID no. 674166 | Public GI ID no. 56384582 | PRT | *Pisum sativum* | 86 | 218 | AP2 | AP2 domain | 21 | 84 | Y | 484.2 | | |
| Ceres CLONE ID no. 674166 | Public G1 ID no. 57012880 | PRT | *Nicotiana tabacum* | 87 | 225 | AP2 | AP2 domain | 26 | 89 | Y | 521.4 | | |
| Ceres Clone ID no. 30469 | Public GI ID no. 62548111 | PRT | *Gossypium hirsutum* | 88 | 163 | Globin | Globin | 13 | 152 | | 188.3 | | 409.8 |
| Ceres CLONE ID no. 2403 | Ceres CLONE ID no. 100021733 | PRT | *Gossypium hirsutum* | 89 | 153 | ubiquitin | Ubiquitin family | 1 | 74 | | 175.2 | | 410.3 |
| Ceres CLONE ID no. 2403 | Ceres CLONE ID no. 100021733 | PRT | *Gossypium hirsutum* | 89 | 153 | ubiquitin | Ubiquitin family | 77 | 150 | | 175.2 | | 410.3 |
| | Ceres CLONE ID no. 947579 | DNA | *Brassica napus* | 90 | 775 | | | | | | | | |
| | Ceres CLONE ID no. 36046 | DNA | *Arabidopsis thaliana* | 91 | 1032 | | | | | | | | |
| | Ceres CLONE ID no. 1606506 | DNA | *Parthenium argantatum* | 92 | 492 | | | | | | | | |
| | Ceres CLONE ID no. 546001 | DNA | Glycine max | 93 | 970 | | | | | | | | |
| | Ceres CLONE ID no. 1554560 | DNA | *Zea mays* | 94 | 604 | | | | | | | | |
| | Ceres CLONE ID no. 839727 | DNA | *Triticum aestivum* | 95 | 846 | | | | | | | | |
| | Ceres CLONE ID no. 664936 | DNA | Glycine max | 96 | 440 | | | | | | | | |
| | Ceres CLONE ID no. 658438 | DNA | Glycine max | 97 | 463 | | | | | | | | |
| | Ceres CLONE ID no. 1049262 | DNA | Glycine max | 98 | 458 | | | | | | | | |
| | Ceres CLONE ID no. 632613 | DNA | *Triticum aestivum* | 99 | 600 | | | | | | | | |
| | Ceres CLONE ID no. 1390976 | DNA | *Zea mays* | 100 | 546 | | | | | | | | |
| | Ceres CLONE ID no. 1457185 | DNA | *Zea mays* | 101 | 550 | | | | | | | | |
| | Ceres CLONE ID no. 1482731 | DNA | *Zea mays* | 102 | 668 | | | | | | | | |
| | Ceres CLONE ID no. 522921 | DNA | Glycine max | 103 | 752 | | | | | | | | |
| | Ceres CLONE ID no. 1036726 | DNA | *Brassica napus* | 104 | 484 | | | | | | | | |
| | Ceres CLONE ID no. 513071 | DNA | Glycine max | 105 | 580 | | | | | | | | |
| | Ceres CLONE ID no. 975672 | DNA | *Brassica napus* | 106 | 987 | | | | | | | | |
| | Ceres CLONE ID no. 273307 | DNA | *Zea mays* | 107 | 1034 | | | | | | | | |
| | Ceres CLONE ID no. 1055099 | DNA | *Triticum aestivum* | 108 | 911 | | | | | | | | |

TABLE 7-continued

| Query Identifier | Functional Homolog | Sequence Type | Species | Seq Id No | Length | Pfam | Pfam Description | Start | End | Profile | HMM Bit Score | FL_Profile | FL_Score |
|---|---|---|---|---|---|---|---|---|---|---|---|---|---|
| Ceres Clone ID no. 30469 | Ceres GI ID no. GI 15226675 | PRT | *Arabidopsis thaliana* | 109 | 160 | Globin | Globin | 13 | 152 | | 184.6 | | 404.9 |
| | Ceres Promoter 21876 | DNA | *Arabidopsis thaliana* | 110 | 1823 | | | | | | | | |
| | Ceres Promoter PT0668 | DNA | *Arabidopsis thaliana* | 111 | 1000 | | | | | | | | |
| | Ceres Promoter PT0535 | DNA | *Arabidopsis thaliana* | 112 | 1000 | | | | | | | | |
| | Ceres Promoter PT0585 | DNA | *Arabidopsis thaliana* | 113 | 999 | | | | | | | | |
| | Ceres Promoter PT0613 | DNA | *Arabidopsis thaliana* | 114 | 1000 | | | | | | | | |
| | Ceres Promoter PT0625 | DNA | *Arabidopsis thaliana* | 115 | 351 | | | | | | | | |
| | Ceres Promoter PT0633 | DNA | *Arabidopsis thaliana* | 116 | 1022 | | | | | | | | |
| | Ceres Promoter PT0650 | DNA | *Arabidopsis thaliana* | 117 | 1000 | | | | | | | | |
| | Ceres Promoter PT0660 | DNA | *Arabidopsis thaliana* | 118 | 998 | | | | | | | | |
| | Ceres Promoter PT0665 | DNA | *Arabidopsis thaliana* | 119 | 1000 | | | | | | | | |
| | Ceres Promoter PT0672 | DNA | *Arabidopsis thaliana* | 120 | 999 | | | | | | | | |
| | Ceres Promoter PT0676 | DNA | *Arabidopsis thaliana* | 121 | 1000 | | | | | | | | |
| | Ceres Promoter PT0678 | DNA | *Arabidopsis thaliana* | 122 | 998 | | | | | | | | |
| | Ceres Promoter PT0683 | DNA | *Arabidopsis thaliana* | 123 | 1000 | | | | | | | | |
| | Ceres Promoter PT0688 | DNA | *Arabidopsis thaliana* | 124 | 1000 | | | | | | | | |
| | Ceres Promoter PT0695 | DNA | *Arabidopsis thaliana* | 125 | 1000 | | | | | | | | |
| | Ceres Promoter PT0708 | DNA | *Arabidopsis thaliana* | 126 | 1000 | | | | | | | | |
| | Ceres Promoter PT0710 | DNA | *Arabidopsis thaliana* | 127 | 1000 | | | | | | | | |
| | Ceres Promoter PT0723 | DNA | *Arabidopsis thaliana* | 128 | 1002 | | | | | | | | |
| | Ceres Promoter PT0740 | DNA | *Arabidopsis thaliana* | 129 | 1001 | | | | | | | | |
| | Ceres Promoter PT0743 | DNA | *Arabidopsis thaliana* | 130 | 1024 | | | | | | | | |
| | Ceres Promoter PT0758 | DNA | *Arabidopsis thaliana* | 131 | 1000 | | | | | | | | |
| | Ceres Promoter PT0829 | DNA | *Arabidopsis thaliana* | 132 | 921 | | | | | | | | |
| | Ceres Promoter PT0837 | DNA | *Arabidopsis thaliana* | 133 | 763 | | | | | | | | |
| | Ceres Promoter PT0838 | DNA | *Arabidopsis thaliana* | 134 | 751 | | | | | | | | |
| | Ceres Promoter PT0848 | DNA | *Arabidopsis thaliana* | 135 | 669 | | | | | | | | |
| | Ceres Promoter PT0863 | DNA | *Arabidopsis thaliana* | 136 | 702 | | | | | | | | |
| | Ceres Promoter PT0879 | DNA | *Arabidopsis thaliana* | 137 | 435 | | | | | | | | |
| | Ceres Promoter PT0886 | DNA | *Arabidopsis thaliana* | 138 | 397 | | | | | | | | |
| | Ceres Promoter YP0007 | DNA | *Arabidopsis thaliana* | 139 | 1024 | | | | | | | | |
| | Ceres Promoter YP0008 | DNA | *Arabidopsis thaliana* | 140 | 1000 | | | | | | | | |
| | Ceres Promoter YP0019 | DNA | *Arabidopsis thaliana* | 141 | 999 | | | | | | | | |
| | Ceres Promoter YP0028 | DNA | *Arabidopsis thaliana* | 142 | 1024 | | | | | | | | |
| | Ceres Promoter YP0039 | DNA | *Arabidopsis thaliana* | 143 | 1024 | | | | | | | | |
| | Ceres Promoter YP0050 | DNA | *Arabidopsis thaliana* | 144 | 1024 | | | | | | | | |
| | Ceres Promoter YP0086 | DNA | *Arabidopsis thaliana* | 145 | 999 | | | | | | | | |
| | Ceres Promoter YP0088 | DNA | *Arabidopsis thaliana* | 146 | 1024 | | | | | | | | |
| | Ceres Promoter YP0092 | DNA | *Arabidopsis thaliana* | 147 | 1024 | | | | | | | | |
| | Ceres Promoter YP0096 | DNA | *Arabidopsis thaliana* | 148 | 1020 | | | | | | | | |
| | Ceres Promoter YP0097 | DNA | *Arabidopsis thaliana* | 149 | 1000 | | | | | | | | |
| | Ceres Promoter YP0101 | DNA | *Arabidopsis thaliana* | 150 | 1004 | | | | | | | | |
| | Ceres Promoter YP0102 | DNA | *Arabidopsis thaliana* | 151 | 1000 | | | | | | | | |
| | Ceres Promoter YP0103 | DNA | *Arabidopsis thaliana* | 152 | 1004 | | | | | | | | |
| | Ceres Promoter YP0107 | DNA | *Arabidopsis thaliana* | 153 | 1003 | | | | | | | | |
| | Ceres Promoter YP0110 | DNA | *Arabidopsis thaliana* | 154 | 1024 | | | | | | | | |
| | Ceres Promoter YP0111 | DNA | *Arabidopsis thaliana* | 155 | 1024 | | | | | | | | |
| | Ceres Promoter YP0115 | DNA | *Arabidopsis thaliana* | 156 | 996 | | | | | | | | |
| | Ceres Promoter YP0117 | DNA | *Arabidopsis thaliana* | 157 | 1024 | | | | | | | | |

TABLE 7-continued

| Query Identifier | Functional Homolog | Sequence Type | Species | Seq Id No | Length | Pfam | Pfam Description | Start | End | Profile | HMM Bit Score | FL_Profile | FL_Score |
|---|---|---|---|---|---|---|---|---|---|---|---|---|---|
| | Ceres Promoter YP0119 | DNA | *Arabidopsis thaliana* | 158 | 1000 | | | | | | | | |
| | Ceres Promoter YP0120 | DNA | *Arabidopsis thaliana* | 159 | 999 | | | | | | | | |
| | Ceres Promoter YP0121 | DNA | *Arabidopsis thaliana* | 160 | 999 | | | | | | | | |
| | Ceres Promoter YP0128 | DNA | *Arabidopsis thaliana* | 161 | 1004 | | | | | | | | |
| | Ceres Promoter YP0137 | DNA | *Arabidopsis thaliana* | 162 | 1001 | | | | | | | | |
| | Ceres Promoter YP0143 | DNA | *Arabidopsis thaliana* | 163 | 1001 | | | | | | | | |
| | Ceres Promoter YP0144 | DNA | *Arabidopsis thaliana* | 164 | 1003 | | | | | | | | |
| | Ceres Promoter YP0156 | DNA | *Arabidopsis thaliana* | 165 | 1004 | | | | | | | | |
| | Ceres Promoter YP0158 | DNA | *Arabidopsis thaliana* | 166 | 1000 | | | | | | | | |
| | Ceres Promoter YP0188 | DNA | *Arabidopsis thaliana* | 167 | 1005 | | | | | | | | |
| | Ceres Promoter YP0190 | DNA | *Arabidopsis thaliana* | 168 | 1002 | | | | | | | | |
| | Ceres Promoter YP0212 | DNA | *Arabidopsis thaliana* | 169 | 995 | | | | | | | | |
| | Ceres Promoter YP0214 | DNA | *Arabidopsis thaliana* | 170 | 1024 | | | | | | | | |
| | Ceres Promoter YP0263 | DNA | *Arabidopsis thaliana* | 171 | 911 | | | | | | | | |
| | Ceres Promoter YP0275 | DNA | *Arabidopsis thaliana* | 172 | 999 | | | | | | | | |
| | Ceres Promoter YP0285 | DNA | *Arabidopsis thaliana* | 173 | 981 | | | | | | | | |
| | Ceres Promoter YP0286 | DNA | *Arabidopsis thaliana* | 174 | 996 | | | | | | | | |
| | Ceres Promoter YP0337 | DNA | *Arabidopsis thaliana* | 175 | 1000 | | | | | | | | |
| | Ceres Promoter YP0356 | DNA | *Arabidopsis thaliana* | 176 | 1000 | | | | | | | | |
| | Ceres Promoter YP0374 | DNA | *Arabidopsis thaliana* | 177 | 1000 | | | | | | | | |
| | Ceres Promoter YP0377 | DNA | *Arabidopsis thaliana* | 178 | 998 | | | | | | | | |
| | Ceres Promoter YP0380 | DNA | *Arabidopsis thaliana* | 179 | 999 | | | | | | | | |
| | Ceres Promoter YP0381 | DNA | *Arabidopsis thaliana* | 180 | 1000 | | | | | | | | |
| | Ceres Promoter YP0384 | DNA | *Arabidopsis thaliana* | 181 | 999 | | | | | | | | |
| | Ceres Promoter YP0385 | DNA | *Arabidopsis thaliana* | 182 | 998 | | | | | | | | |
| | Ceres Promoter YP0396 | DNA | *Arabidopsis thaliana* | 183 | 1000 | | | | | | | | |
| | Ceres Promoter p13879 | DNA | *Arabidopsis thaliana* | 184 | 1514 | | | | | | | | |
| | Ceres Promoter p326 | DNA | *Arabidopsis thaliana* | 185 | 1954 | | | | | | | | |
| | Ceres Promoter p32449 | DNA | *Arabidopsis thaliana* | 186 | 2016 | | | | | | | | |
| | Ceres Promoter PD1367 | DNA | *Arabidopsis thaliana* | 187 | 667 | | | | | | | | |
| | Ceres Promoter p530c10 | DNA | *Oryza sativa* | 188 | 1836 | | | | | | | | |

TABLE 7-continued

| Query Identifier | Functional Homolog | Sequence Type | Species | Seq Id No | Length | Pfam | Pfam Description | Start | End | Profile | HMM Bit Score | FL_Profile | FL_Score |
|---|---|---|---|---|---|---|---|---|---|---|---|---|---|
| | Ceres Promoter pOsFIE2-2 | DNA | *Oryza sativa* | 189 | 3000 | | | | | | | | |
| | Ceres Promoter pOsMEA | DNA | *Oryza sativa* | 190 | 2023 | | | | | | | | |
| | Ceres Promoter pOsYp102 | DNA | *Oryza sativa* | 191 | 2034 | | | | | | | | |
| | Ceres Promoter pOsYp285 | DNA | *Orgyza sativa* | 192 | 1877 | | | | | | | | |
| | Ceres Promoter PT0565 | DNA | *Arabidopsis thaliana* | 193 | 1000 | | | | | | | | |
| | Ceres Promoter YP0015 | DNA | *Arabidopsis thaliana* | 194 | 999 | | | | | | | | |
| | Ceres Promoter YP0087 | DNA | *Arabidopsis thaliana* | 195 | 999 | | | | | | | | |
| | Ceres Promoter YP0093 | DNA | *Arabidopsis thaliana* | 196 | 1000 | | | | | | | | |
| | Ceres Promoter YP0108 | DNA | *Arabidopsis thaliana* | 197 | 999 | | | | | | | | |
| | Ceres Promoter YP0022 | DNA | *Arabidopsis thaliana* | 198 | 999 | | | | | | | | |
| | Ceres Promoter YP0080 | DNA | *Arabidopsis thaliana* | 199 | 999 | | | | | | | | |
| | Ceres Promoter PR0924 | DNA | *Arabidopsis thaliana* | 200 | 3000 | | | | | | | | |
| | Ceres Promoter YP0388 | DNA | *Arabidopsis thaliana* | 201 | 1000 | | | | | | | | |
| | Ceres Promoter PD0901 | DNA | *Arabidopsis thaliana* | 202 | 283 | | | | | | | | |
| | Ceres Promoter PT0623 | DNA | *Arabidopsis thaliana* | 203 | 1000 | | | | | | | | |
| Ceres Clone ID no. 2403 | Truncated version of Ceres CLONE ID no. 100021733 | PRT | Artificial Sequence | 204 | 33 | ubiquitin | Ubiquitin family | 1 | 33 | | 87.6 | | −83.1 |
| Ceres Clone ID no. 2403 | Truncated version of Ceres CLONE ID no. 1036726 | PRT | Artificial Sequence | 205 | 33 | ubiquitin | Ubiquitin family | 1 | 33 | Y | 87.6 | | −83.1 |
| Ceres Clone ID no. 2403 | Truncated version of Ceres CLONE ID no. 1482731 | PRT | Artificial Sequence | 206 | 33 | ubiquitin | Ubiquitin family | 1 | 33 | Y | 87.1 | | −85 |
| Ceres Clone ID no. 30469 | Truncated Version of Ceres CLONE ID no. 1554560 | PRT | Artificial Sequence | 207 | 80 | Globin | Globin | 17 | 78 | Y | 185.7 | | 61.3 |
| Ceres Clone ID no. 30469 | Truncated Version of Ceres CLONE ID no. 1802327 | PRT | Artificial Sequence | 208 | 77 | Globin | Globin | 14 | 75 | Y | 191.4 | | 67.2 |
| Ceres Clone ID no. 30469 | Truncated Version of Ceres CLONE ID no. 1876458 | PRT | Artificial Sequence | 209 | 77 | Globin | Globin | 14 | 75 | | 191.9 | | 67.7 |
| Ceres Clone ID no. 30469 | Truncated Version of Ceres CLONE ID no. 1879148 | PRT | Artificial Sequence | 210 | 79 | Globin | Globin | 16 | 77 | | 185.7 | | 61.3 |
| Ceres Clone ID no. 2403 | Truncated version of Ceres CLONE ID no. 1884696 | PRT | Artificial Sequence | 211 | 33 | ubiquitin | Ubiquitin family | 1 | 33 | Y | 87.6 | | 65 |
| Ceres Clone ID no. 30469 | Truncated Version of Ceres CLONE ID no. 1916866 | PRT | Artificial Sequence | 212 | 76 | Globin | Globin | 13 | 74 | Y | 188.3 | | 65 |
| Ceres Clone ID no. 2403 | Truncated version of Ceres CLONE ID no. 1950105 | PRT | Artificial Sequence | 213 | 33 | ubiquitin | Ubiquitin family | 1 | 33 | Y | 87.6 | | 60.7 |

TABLE 7-continued

| Query Identifier | Functional Homolog | Sequence Type | Species | Seq Id No | Length | Pfam | Pfam Description | Start | End | Profile | HMM Bit Score | FL_Profile | FL_Score |
|---|---|---|---|---|---|---|---|---|---|---|---|---|---|
| Ceres Clone ID no. 30469 | Truncated Version of Ceres CLONE ID no. 1990746 | PRT | Artificial Sequence | 214 | 79 | Globin | Globin | 16 | 77 | | 184.9 | | 60.7 |
| Ceres Clone ID no. 30469 | Truncated Version of Ceres CLONE ID no. 2033803 | PRT | Artificial Sequence | 215 | 79 | Globin | Globin | 16 | 77 | | 184.9 | | 60.7 |
| Ceres Clone ID no. 2403 | Truncated version of Ceres CLONE ID no. 2034916 | PRT | Artificial Sequence | 216 | 33 | ubiquitin | Ubiquitin family | 1 | 33 | | 87.6 | | 63.3 |
| Ceres Clone ID no. 2403 | Truncated version of Ceres CLONE ID no. 513071 | PRT | Artificial Sequence | 217 | 33 | ubiquitin | Ubiquitin family | 1 | 33 | | 85.9 | | 14.7 |
| Ceres Clone ID no. 2403 | Truncated version of Ceres CLONE ID no. 522921 | PRT | Artificial Sequence | 218 | 33 | ubiquitin | Ubiquitin family | 1 | 33 | Y | 87.6 | | 22.4 |
| Ceres Clone ID no. 30469 | Truncated Version of Ceres CLONE ID no. 546001 | PRT | Artificial Sequence | 219 | 76 | Globin | Globin | 13 | 74 | Y | 182.8 | | 59.6 |
| Ceres Clone ID no. 30469 | Truncated Version of Ceres CLONE ID no. 651581 | PRT | Artificial Sequence | 220 | 76 | Globin | Globin | 13 | 74 | | 185.7 | | 63.9 |
| Ceres Clone ID no. 30469 | Truncated Version of Ceres CLONE ID no. 839727 | PRT | Artificial Sequence | 221 | 77 | Globin | Globin | 14 | 75 | Y | 187.8 | | 63.3 |
| Ceres Clone ID no. 30469 | Truncated Version of Public GI ID no. 11095158 | PRT | Artificial Sequence | 222 | 76 | Globin | Globin | 13 | 76 | | 167.8 | | 44.7 |
| Ceres Clone ID no. 30469 | Truncated Version of Public GI ID no. 12963875 | PRT | Artificial Sequence | 223 | 71 | Globin | Globin | 8 | 69 | | 145.8 | | 22.4 |
| Ceres Clone ID no. 30469 | Truncated Version of Public GI ID no. 14701800 | PRT | Artificial Sequence | 224 | 84 | Globin | Globin | 21 | 82 | | 170.1 | | 45.8 |
| Ceres Clone ID no. 30469 | Truncated Version of Public GI ID no. 15226675 | PRT | Artificial Sequence | 225 | 76 | Globin | Globin | 13 | 74 | | 184.6 | | 63 |
| Ceres Clone ID no. 30469 | Truncated Version of Public GI ID no. 15824736 | PRT | Artificial Sequence | 226 | 76 | Globin | Globin | 13 | 74 | | 184.2 | | 60.9 |
| Ceres Clone ID no. 30469 | Truncated Version of Public GI ID no. 30909306 | PRT | Artificial Sequence | 227 | 76 | Globin | Globin | 13 | 74 | Y | 185.7 | | 63.9 |
| Ceres Clone ID no. 30469 | Truncated Version of Public GI ID no. 37903656 | PRT | Artificial Sequence | 228 | 73 | Globin | Globin | 10 | 71 | | 172.6 | | 49.6 |
| Ceres Clone ID no. 30469 | Truncated Version of Public GI ID no. 62548111 | PRT | Artificial Sequence | 229 | 76 | Globin | Globin | 13 | 74 | | 188.3 | | 65 |

The invention claimed is:

1. A method of producing a plant, said method comprising growing plant cells transformed with an exogenous nucleic acid, said exogenous nucleic acid comprising a polynucleotide operably linked to a heterologous promoter, said polynucleotide comprising a nucleotide sequence encoding a polypeptide comprising an amino acid sequence having 95 percent or greater amino acid sequence identity to the amino acid sequence of SEQ ID NO: 7, and producing transformed plants from said transformed plant cells; and selecting for a transformed plant from said transformed plants that overexpresses said polypeptide and exhibits an increased level of cold tolerance as compared to the corresponding level in a control plant of the same species that does not comprise said exogenous nucleic acid.

2. The method of claim 1, wherein said polypeptide comprises the amino acid sequence of SEQ ID NO:7.

3. The method of claim 1, wherein said nucleotide sequence has 95 percent or greater nucleotide sequence identity to the nucleotide sequence of SEQ ID NO:6.

4. The method of claim 1, wherein said polypeptide comprises an amino acid sequence that has 97 percent or greater amino acid sequence identity to the amino acid sequence of SEQ ID NO:7.

5. The method of claim 1, wherein said polypeptide comprises an amino acid sequence that has 99 percent or greater amino acid sequence identity to the amino acid sequence of SEQ ID NO:7.

6. The method of claim 1, wherein said plant is a member of a species selected from the group consisting of *Panicum virgatum, Sorghum bicolor, Miscanthus giganteus, Saccha-*

*rum* sp., *Populus balsamifera, Zea mays, Glycine max, Brassica napus, Triticum aestivum, Gossypium hirsutum, Oryza sativa, Helianthus annuus, Medicago sativa, Beta vulgaris*, and *Pennisetum glaucum.*

* * * * *

SEQUENCE LISTING

<160> NUMBER OF SEQ ID NOS: 229

<210> SEQ ID NO 1
<211> LENGTH: 828
<212> TYPE: DNA
<213> ORGANISM: Arabidopsis thaliana
<220> FEATURE:
<221> NAME/KEY: misc_feature
<223> OTHER INFORMATION: Ceres CLONE ID no. 30087
<220> FEATURE:
<221> NAME/KEY: misc_feature
<223> OTHER INFORMATION: Ceres SEED LINE ID no. ME01451
<220> FEATURE:
<221> NAME/KEY: misc_feature
<223> OTHER INFORMATION: Encodes the protein at SEQ ID NO: 2

<400> SEQUENCE: 1

```
aacttttctc tcccactctt tcttttacta ctctcacaca tatctctgtc tatatatcac      60

tttacataaa ccactattcc acacacaaac acacatagcc atggcctctt ctttctcttc     120

acaagccttc ttcttgctca cattgtctat ggttttaatt cctttctctt tagctcaagc     180

tcccatgatg gctccttctg gctcaatgtc catgccgcct atgtctagcg gcggtggaag     240

ctcggttcct cctccagtga tgtctccgat gccaatgatg actccaccac ctatgcctat     300

gactccatca cccatgccca tgactccacc acctatgcct atggctccac caccaatgcc     360

catggcttca ccaccaatga tgccaatgac tccatctaca agcccaagcc cattaacagt     420

tccggatatg ccttcgccgc cgatgccatc cggaatggaa tcttcacctt ctccaggacc     480

catgccaccg gcaatggcgg cttcgccgga ttcgggagct ttcaatgtta gaaacaacgt     540

cgtaacactt tcatgcgttg ttggagttgt tgcagctcat ttctcctcg tttgaaatga      600

ttattgaatt ggtcagcctc gatcgttttc ttgtaattta ctttcatatt tttttccct      660

caaattatta gtggtcatca ttttataata tttgagtttg tgtttgatgt acgattcaga     720

catttgtttg cattatgtgc ttaataagtt tatcgttgac tctacttgaa gagagacttt     780

gtgtgtgatg taaatttctt ctatctatgg aacattgcat tcgtagcc                  828
```

<210> SEQ ID NO 2
<211> LENGTH: 164
<212> TYPE: PRT
<213> ORGANISM: Arabidopsis thaliana
<220> FEATURE:
<221> NAME/KEY: misc_feature
<223> OTHER INFORMATION: Ceres CLONE ID no. 30087
<220> FEATURE:
<221> NAME/KEY: misc_feature
<223> OTHER INFORMATION: Ceres SEED LINE ID no. ME01451

<400> SEQUENCE: 2

```
Met Ala Ser Ser Phe Ser Ser Gln Ala Phe Phe Leu Leu Thr Leu Ser
1               5                   10                  15

Met Val Leu Ile Pro Phe Ser Leu Ala Gln Ala Pro Met Met Ala Pro
            20                  25                  30

Ser Gly Ser Met Ser Met Pro Pro Met Ser Ser Gly Gly Gly Ser Ser
        35                  40                  45

Val Pro Pro Pro Val Met Ser Pro Met Pro Met Met Thr Pro Pro Pro
    50                  55                  60

Met Pro Met Thr Pro Ser Pro Met Pro Met Thr Pro Pro Pro Met Pro
65                  70                  75                  80

Met Ala Pro Pro Pro Met Pro Met Ala Ser Pro Pro Met Met Pro Met
                85                  90                  95
```

```
Thr Pro Ser Thr Ser Pro Ser Pro Leu Thr Val Pro Asp Met Pro Ser
            100                 105                 110

Pro Pro Met Pro Ser Gly Met Glu Ser Ser Pro Ser Pro Gly Pro Met
        115                 120                 125

Pro Pro Ala Met Ala Ala Ser Pro Asp Ser Gly Ala Phe Asn Val Arg
    130                 135                 140

Asn Asn Val Val Thr Leu Ser Cys Val Val Gly Val Val Ala Ala His
145                 150                 155                 160

Phe Leu Leu Val


<210> SEQ ID NO 3
<211> LENGTH: 155
<212> TYPE: PRT
<213> ORGANISM: Brassica napus
<220> FEATURE:
<221> NAME/KEY: misc_feature
<223> OTHER INFORMATION: Ceres CLONE ID no. 947579
<220> FEATURE:
<221> NAME/KEY: misc_feature
<223> OTHER INFORMATION: Functional homolog of Ceres Clone ID no. 30087
      given in SEQ ID NO: 2

<400> SEQUENCE: 3

Met Ala Ala Ser Gln Ala Phe Leu Leu Leu Thr Leu Ser Met Ala Leu
1               5                   10                  15

Val His Phe Ser Leu Ala Gln Ser Pro Met Met Ala Pro Ser Gly Ser
            20                  25                  30

Met Ser Met Pro Pro Met Pro Ser Gly Gly Ser Pro Met Pro Met Met
        35                  40                  45

Thr Pro Pro Pro Met Pro Met Met Thr Pro Pro Pro Met Ala Met Ala
    50                  55                  60

Pro Pro Pro Met Pro Met Thr Pro Pro Pro Met Pro Met Ala Pro Met
65                  70                  75                  80

Pro Met Thr Pro Ser Ser Ser Pro Met Ser Pro Pro Thr Thr Met Ala
                85                  90                  95

Pro Ser Pro Glu Thr Val Pro Asp Met Ala Ser Pro Pro Met Met Pro
            100                 105                 110

Gly Met Glu Ser Ser Pro Ser Pro Gly Pro Met Pro Pro Ala Met Ala
        115                 120                 125

Ser Pro Asp Ser Gly Ala Phe Asn Val Arg Asn Asp Val Val Ala Ile
    130                 135                 140

Ser Phe Leu Val Ala Ala His Leu Leu Leu Val
145                 150                 155


<210> SEQ ID NO 4
<211> LENGTH: 152
<212> TYPE: PRT
<213> ORGANISM: Brassica napus
<220> FEATURE:
<221> NAME/KEY: misc_feature
<223> OTHER INFORMATION: Public GI no. 62526422
<220> FEATURE:
<221> NAME/KEY: misc_feature
<223> OTHER INFORMATION: Functional homolog of Ceres Clone ID no. 30087
      given in SEQ ID NO: 2

<400> SEQUENCE: 4

Met Ala Leu Ser His Pro Met Thr Ile Phe Ser Leu Phe Leu Thr Phe
1               5                   10                  15

Leu Ala Leu Thr Ala Ala Gln Ser Pro Met Met Ala Pro Thr Met Pro
            20                  25                  30
```

```
Pro Ser Thr Met Ser Met Pro Pro Thr Thr Ser Thr Thr Thr Pro Pro
        35                  40                  45

Pro Met Ser Ser Met Ser Pro Pro Pro Ser Ala Met Ser Pro Thr Pro
    50                  55                  60

Ser Thr Met Ser Pro Pro Pro Met Ser Pro Met Thr Pro Ser Met Ser
65                  70                  75                  80

Pro Met Gly Pro Met Thr Pro Thr Met Ser Pro Met Asp Ser Pro Pro
                85                  90                  95

Ala Pro Ala Gly Pro Gly Met Ala Pro Gly Met Ser Thr Pro Gly Pro
            100                 105                 110

Ala Pro Gly Pro Met Gly Gly Glu Ser Met Ala Ser Pro Pro Pro Ser
        115                 120                 125

Ser Gly Phe Val His Gly Ile Ser Ile Ser Met Ala Met Val Ala Ile
    130                 135                 140

Ile Gly Ser Val Ala Leu Phe Phe
145                 150
```

<210> SEQ ID NO 5
<211> LENGTH: 150
<212> TYPE: PRT
<213> ORGANISM: Parthenium argentatum
<220> FEATURE:
<221> NAME/KEY: misc_feature
<223> OTHER INFORMATION: Ceres CLONE ID no. 1606506
<220> FEATURE:
<221> NAME/KEY: misc_feature
<223> OTHER INFORMATION: Functional homolog of Ceres Clone ID no. 30087 given in SEQ ID NO: 2

<400> SEQUENCE: 5

```
Met Ala Val Ser Arg Tyr Ile Ile Leu Leu Leu Ser Phe Thr Tyr Leu
1               5                   10                  15

Ala Ala Phe Ser Thr Ala Gln Ala Pro Ser Met Ser Pro Met Met Met
            20                  25                  30

Pro Met Ala Pro Pro Pro Ser Thr Met Pro Met Thr Pro Pro Pro Ser
        35                  40                  45

Thr Met Pro Met Thr Pro Pro Pro Thr Pro Met Thr Met Thr Pro Pro
    50                  55                  60

Pro Met Met Met Pro Met Thr Pro Pro Pro Met Pro Met Gly Thr Pro
65                  70                  75                  80

Pro Met Thr Met Pro Met Gly Pro Pro Pro Met Met Met Pro Met Ser
                85                  90                  95

Pro Gly Pro Ser Met Met Pro Ala Ser Pro Pro Ser Pro Met Gly Pro
            100                 105                 110

Ser Met Ala Pro Glu Pro Ala Thr Met Ser Pro Gly Pro Ser Met Thr
        115                 120                 125

Pro Ala Glu Thr Pro Ala Ser Gly Ala Ile Met Gln Tyr Ser Ser Ile
    130                 135                 140

Thr Met Leu Gly Ile Val
145                 150
```

<210> SEQ ID NO 6
<211> LENGTH: 586
<212> TYPE: DNA
<213> ORGANISM: Artificial Sequence
<220> FEATURE:
<223> OTHER INFORMATION: Ceres CLONE ID no. 30469
<220> FEATURE:
<221> NAME/KEY: misc_feature

```
<223> OTHER INFORMATION: Ceres SEED LINE ID no. ME02779
<220> FEATURE:
<221> NAME/KEY: misc_feature
<223> OTHER INFORMATION: Encodes the protein at SEQ ID NO: 7

<400> SEQUENCE: 6

aaaagatcta caaaacagag agttgtatac tttaaatcat ttagaggttg tgaaatatta      60

tggagagtga aggaaagatt gtgttcacag aagagcaaga ggctcttgta gtgaagtctt     120

ggagtgtcat gaagaaaaac tcagctgaat taggtctcaa actcttcatc aagatctttg     180

agattgcacc aacaacgaag aagatgttct ctttcttgag agactcacca attcctgctg     240

agcaaaatcc aaagctcaag cctcacgcaa tgtctgtttt tgtcatgtac aactgaggaa     300

aacagggaaa gttacggtga gggagactac tttgaagaga cttggagcca gccattctaa     360

atacggtgtc gttgacgaac actttgaggt ggccaagtat gcattgttgg agacgataaa     420

ggaggcagtg ccggagatgt ggtcaccgga gatgaaggtg gcttggggtc aggcttatga     480

tcaccttgtt gctgccatta aagctgaaat gaatctttcc aactaaaaaa tcatatacta     540

ttatatagtt gtaaacttgt aataaatatt tcattttgaa ttgttc                   586


<210> SEQ ID NO 7
<211> LENGTH: 78
<212> TYPE: PRT
<213> ORGANISM: Artificial Sequence
<220> FEATURE:
<223> OTHER INFORMATION: Ceres CLONE ID no. 30469
<220> FEATURE:
<221> NAME/KEY: misc_feature
<223> OTHER INFORMATION: Ceres SEED LINE ID no. ME02779
<220> FEATURE:
<221> NAME/KEY: misc_feature
<222> LOCATION: (13)..(74)
<223> OTHER INFORMATION: Pfam Name: Globin
      Pfam Description: Globin

<400> SEQUENCE: 7

Met Glu Ser Glu Gly Lys Ile Val Phe Thr Glu Glu Gln Glu Ala Leu
1               5                   10                  15

Val Val Lys Ser Trp Ser Val Met Lys Lys Asn Ser Ala Glu Leu Gly
            20                  25                  30

Leu Lys Leu Phe Ile Lys Ile Phe Glu Ile Ala Pro Thr Thr Lys Lys
        35                  40                  45

Met Phe Ser Phe Leu Arg Asp Ser Pro Ile Pro Ala Glu Gln Asn Pro
    50                  55                  60

Lys Leu Lys Pro His Ala Met Ser Val Phe Val Met Tyr Asn
65                  70                  75


<210> SEQ ID NO 8
<211> LENGTH: 483
<212> TYPE: DNA
<213> ORGANISM: Arabidopsis thaliana
<220> FEATURE:
<221> NAME/KEY: misc_feature
<223> OTHER INFORMATION: Ceres CLONE ID no. 30469_FL
<220> FEATURE:
<221> NAME/KEY: misc_feature
<223> OTHER INFORMATION: Encodes the protein at SEQ ID NO: 9

<400> SEQUENCE: 8

atggagagtg aaggaaagat tgtgttcaca gaagagcaag aggctcttgt agtgaagtct      60

tggagtgtca tgaagaaaaa ctcagctgaa ttaggtctca aactcttcat caagatcttt     120

gagattgcac caacaacgaa gaagatgttc tctttcttga gagactcacc aattcctgct     180
```

```
gagcaaaatc caaagctcaa gcctcacgca atgtctgttt ttgtcatgtg ttgtgaatca    240

gcagtacaac tgaggaaaac agggaaagtt acggtgaggg agactacttt gaagagactt    300

ggagccagcc attctaaata cggtgtcgtt gacgaacact ttgaggtggc caagtatgca    360

ttgttggaga cgataaagga ggcagtgccg gagatgtggt caccggagat gaaggtggct    420

tggggtcagg cttatgatca ccttgttgct gccattaaag ctgaaatgaa tctttccaac    480

taa                                                                  483


<210> SEQ ID NO 9
<211> LENGTH: 160
<212> TYPE: PRT
<213> ORGANISM: Arabidopsis thaliana
<220> FEATURE:
<221> NAME/KEY: misc_feature
<223> OTHER INFORMATION: Ceres CLONE ID no. 30469_FL
<220> FEATURE:
<221> NAME/KEY: misc_feature
<222> LOCATION: (13)..(152)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 9

Met Glu Ser Glu Gly Lys Ile Val Phe Thr Glu Glu Gln Glu Ala Leu
1               5                   10                  15

Val Val Lys Ser Trp Ser Val Met Lys Lys Asn Ser Ala Glu Leu Gly
            20                  25                  30

Leu Lys Leu Phe Ile Lys Ile Phe Glu Ile Ala Pro Thr Thr Lys Lys
        35                  40                  45

Met Phe Ser Phe Leu Arg Asp Ser Pro Ile Pro Ala Glu Gln Asn Pro
    50                  55                  60

Lys Leu Lys Pro His Ala Met Ser Val Phe Val Met Cys Cys Glu Ser
65                  70                  75                  80

Ala Val Gln Leu Arg Lys Thr Gly Lys Val Thr Val Arg Glu Thr Thr
                85                  90                  95

Leu Lys Arg Leu Gly Ala Ser His Ser Lys Tyr Gly Val Val Asp Glu
            100                 105                 110

His Phe Glu Val Ala Lys Tyr Ala Leu Leu Glu Thr Ile Lys Glu Ala
        115                 120                 125

Val Pro Glu Met Trp Ser Pro Glu Met Lys Val Ala Trp Gly Gln Ala
    130                 135                 140

Tyr Asp His Leu Val Ala Ala Ile Lys Ala Glu Met Asn Leu Ser Asn
145                 150                 155                 160


<210> SEQ ID NO 10
<211> LENGTH: 160
<212> TYPE: PRT
<213> ORGANISM: Raphanus sativus
<220> FEATURE:
<221> NAME/KEY: misc_feature
<223> OTHER INFORMATION: Public GI no. 30909306
<220> FEATURE:
<221> NAME/KEY: misc_feature
<222> LOCATION: (13)..(152)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
```

```
      given in SEQ ID NO: 7

<400> SEQUENCE: 10

Met Glu Ser Glu Gly Lys Ile Val Phe Thr Glu Glu Gln Glu Ala Leu
1               5                   10                  15

Val Val Lys Ser Trp Ser Val Met Lys Lys Asn Ser Ala Asp Leu Gly
            20                  25                  30

Leu Lys Leu Phe Ile Lys Ile Phe Glu Ile Ala Pro Thr Ala Lys Lys
        35                  40                  45

Leu Phe Ser Phe Leu Arg Asp Ser Pro Ile Pro Ala Glu Gln Asn Pro
    50                  55                  60

Lys Leu Lys Pro His Ala Met Ser Val Phe Val Met Cys Cys Glu Ser
65                  70                  75                  80

Ala Ala Gln Leu Arg Lys Thr Gly Lys Val Thr Val Lys Glu Thr Thr
                85                  90                  95

Leu Lys Arg Leu Gly Ala Asn His Ser Lys Tyr Gly Val Val Asp Glu
            100                 105                 110

His Phe Glu Val Thr Lys Tyr Ala Leu Leu Glu Thr Ile Lys Glu Ala
        115                 120                 125

Val Pro Glu Met Trp Ser Pro Glu Met Lys Ser Ala Trp Gly Gln Ala
    130                 135                 140

Tyr Asp His Leu Val Ala Ala Ile Lys Ala Glu Met Lys Pro Ser His
145                 150                 155                 160


<210> SEQ ID NO 11
<211> LENGTH: 158
<212> TYPE: PRT
<213> ORGANISM: Arabidopsis thaliana
<220> FEATURE:
<221> NAME/KEY: misc_feature
<223> OTHER INFORMATION: Public GI no. 37903656
<220> FEATURE:
<221> NAME/KEY: misc_feature
<222> LOCATION: (10)..(149)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 11

Met Glu Gly Lys Val Phe Thr Glu Glu Gln Glu Thr Leu Val Val Lys
1               5                   10                  15

Ser Trp Gly Val Met Lys Lys Asn Ala Ala Glu Leu Gly Leu Lys Phe
            20                  25                  30

Phe Leu Lys Ile Phe Glu Ile Ala Pro Ser Ala Gln Lys Leu Phe Ser
        35                  40                  45

Phe Leu Arg Asp Ser Asp Ile Pro Leu Glu Lys Asn Pro Lys Leu Lys
    50                  55                  60

Pro His Ala Met Ser Val Phe Val Met Thr Cys Glu Ser Ala Val Gln
65                  70                  75                  80

Leu Arg Lys Ala Gly Lys Val Thr Val Arg Glu Ser Thr Leu Lys Arg
                85                  90                  95

Leu Gly Gly Val His Phe Lys Ser Gly Val Val Asp Glu His Tyr Glu
            100                 105                 110

Val Thr Lys Phe Ala Leu Leu Glu Thr Ile Lys Glu Ala Leu Pro Glu
        115                 120                 125

Met Trp Ser Pro Glu Met Lys Asn Ala Trp Gly Glu Ala Tyr Asp Gln
```

```
    130                 135                 140

Leu Val Ala Ala Ile Lys Ser Glu Met Lys Pro Pro Leu Asn
145                 150                 155


<210> SEQ ID NO 12
<211> LENGTH: 163
<212> TYPE: PRT
<213> ORGANISM: Arabidopsis thaliana
<220> FEATURE:
<221> NAME/KEY: misc_feature
<223> OTHER INFORMATION: Public GI no. 15824736
<220> FEATURE:
<221> NAME/KEY: misc_feature
<222> LOCATION: (13)..(152)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 12

Met Ala Thr Tyr Glu Gly Lys Val Phe Thr Glu Glu Gln Glu Ala Leu
1               5                   10                  15

Val Val Lys Ser Trp Thr Val Met Lys Lys Lys Thr Ala Glu Leu Gly
            20                  25                  30

Leu Lys Phe Phe Leu Lys Ile Phe Glu Ile Ala Pro Ser Ala Lys Lys
        35                  40                  45

Leu Phe Ser Phe Leu Arg Asp Ser Asn Val Pro Leu Glu Gln Asn Thr
    50                  55                  60

Lys Leu Lys Pro His Ala Met Ser Val Phe Val Met Thr Cys Glu Ser
65                  70                  75                  80

Ala Val Gln Leu Arg Lys Ala Gly Lys Val Thr Val Arg Glu Ser Asn
                85                  90                  95

Leu Lys Lys Leu Gly Ala Thr His Phe Lys Tyr Gly Val Val Asp Glu
            100                 105                 110

His Phe Glu Val Thr Lys Phe Ala Leu Leu Glu Thr Ile Lys Glu Ala
        115                 120                 125

Val Pro Asp Met Trp Ser Asp Glu Met Lys Asn Ala Trp Gly Glu Ala
    130                 135                 140

Tyr Asp Arg Leu Val Ala Ala Ile Lys Ile Glu Met Lys Ala Cys Ser
145                 150                 155                 160

Gln Ala Ala


<210> SEQ ID NO 13
<211> LENGTH: 161
<212> TYPE: PRT
<213> ORGANISM: Glycine max
<220> FEATURE:
<221> NAME/KEY: misc_feature
<223> OTHER INFORMATION: Ceres CLONE ID no. 546001
<220> FEATURE:
<221> NAME/KEY: misc_feature
<222> LOCATION: (13)..(152)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 13

Met Thr Thr Thr Leu Glu Arg Gly Phe Ser Glu Glu Gln Glu Ala Leu
1               5                   10                  15
```

```
Val Val Lys Ser Trp Asn Val Met Lys Lys Asn Ser Gly Glu Leu Gly
            20                  25                  30

Leu Lys Phe Phe Leu Lys Ile Phe Glu Ile Ala Pro Ser Ala Gln Lys
        35                  40                  45

Leu Phe Ser Phe Leu Arg Asp Ser Thr Val Pro Leu Glu Gln Asn Pro
    50                  55                  60

Lys Leu Lys Pro His Ala Val Ser Val Phe Val Met Thr Cys Asp Ser
65                  70                  75                  80

Ala Val Gln Leu Arg Lys Ala Gly Lys Val Thr Val Arg Glu Ser Asn
                85                  90                  95

Leu Lys Lys Leu Gly Ala Thr His Phe Arg Thr Gly Val Ala Asn Glu
            100                 105                 110

His Phe Glu Val Thr Lys Phe Ala Leu Leu Glu Thr Ile Lys Glu Ala
        115                 120                 125

Val Pro Glu Met Trp Ser Pro Ala Met Lys Asn Ala Trp Gly Glu Ala
    130                 135                 140

Tyr Asp Gln Leu Val Asp Ala Ile Lys Ser Glu Met Lys Pro Pro Ser
145                 150                 155                 160

Ser


<210> SEQ ID NO 14
<211> LENGTH: 160
<212> TYPE: PRT
<213> ORGANISM: Glycine max
<220> FEATURE:
<221> NAME/KEY: misc_feature
<223> OTHER INFORMATION: Public GI no. 11095158
<220> FEATURE:
<221> NAME/KEY: misc_feature
<222> LOCATION: (13)..(152)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 14

Met Gly Thr Leu Asp Thr Lys Gly Phe Thr Glu Glu Gln Glu Ala Leu
1               5                   10                  15

Val Val Lys Ser Trp Asn Ala Met Lys Lys Asn Ser Ala Glu Leu Gly
            20                  25                  30

Leu Lys Leu Phe Leu Lys Ile Phe Glu Ile Ala Pro Ser Ala Gln Lys
        35                  40                  45

Leu Phe Ser Phe Leu Lys Asp Ser Lys Val Pro Leu Glu Gln Asn Thr
    50                  55                  60

Lys Leu Lys Pro His Ala Met Ser Val Phe Leu Met Thr Cys Glu Ser
65                  70                  75                  80

Ala Val Gln Leu Arg Lys Ser Gly Lys Val Thr Val Arg Glu Ser Ser
                85                  90                  95

Leu Lys Lys Leu Gly Ala Asn His Phe Lys Tyr Gly Val Val Asp Glu
            100                 105                 110

His Phe Glu Val Thr Lys Phe Ala Leu Leu Glu Thr Ile Lys Glu Ala
        115                 120                 125

Val Pro Glu Met Trp Ser Pro Ala Met Lys Asn Ala Trp Gly Glu Ala
    130                 135                 140

Tyr Asp Gln Leu Val Asn Ala Ile Lys Ser Glu Met Lys Pro Ser Ser
145                 150                 155                 160
```

```
<210> SEQ ID NO 15
<211> LENGTH: 152
<212> TYPE: PRT
<213> ORGANISM: Glycine max
<220> FEATURE:
<221> NAME/KEY: misc_feature
<223> OTHER INFORMATION: Public GI no. 12963875
<220> FEATURE:
<221> NAME/KEY: misc_feature
<222> LOCATION: (8)..(147)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 15

Met Ser Ser Phe Ser Glu Glu Gln Glu Ala Leu Val Val Lys Ser Trp
1               5                   10                  15

Gly Ser Met Lys Lys Asp Ala Gly Glu Trp Gly Leu Lys Phe Phe Leu
            20                  25                  30

Lys Ile Phe Glu Ile Ala Pro Ser Ala Lys Lys Met Phe Ser Phe Leu
        35                  40                  45

Lys Asp Ser Asn Val Pro Leu Asp Gln Asn Pro Lys Leu Lys Ile His
    50                  55                  60

Ala Lys Ser Val Leu Val Met Thr Cys Glu Ala Ala Val Gln Leu Arg
65                  70                  75                  80

Lys Ala Gly Lys Val Val Val Arg Asp Ser Thr Leu Lys Lys Ile Gly
                85                  90                  95

Ala Thr His Phe Lys Tyr Gly Val Val Asp Glu His Phe Glu Val Thr
            100                 105                 110

Lys Tyr Ala Leu Leu Glu Thr Ile Lys Glu Ala Ser Gln Glu Met Trp
        115                 120                 125

Ser Val Glu Met Lys Asn Ala Trp Gly Glu Ala Tyr Asp Gln Leu Val
    130                 135                 140

Ser Ala Ile Lys Thr Glu Met Lys
145                 150


<210> SEQ ID NO 16
<211> LENGTH: 165
<212> TYPE: PRT
<213> ORGANISM: Zea mays
<220> FEATURE:
<221> NAME/KEY: misc_feature
<223> OTHER INFORMATION: Ceres CLONE ID no. 1554560
<220> FEATURE:
<221> NAME/KEY: misc_feature
<222> LOCATION: (17)..(157)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 16

Met Ala Leu Ala Glu Ala Asp Asp Gly Ala Val Val Phe Gly Glu Glu
1               5                   10                  15

Gln Glu Ala Leu Val Leu Lys Ser Trp Ala Val Met Lys Lys Asp Ala
            20                  25                  30

Ala Asn Leu Gly Leu Arg Phe Phe Leu Lys Val Phe Glu Ile Ala Pro
        35                  40                  45
```

```
Ser Ala Lys Gln Met Phe Ser Phe Leu Arg Asp Ser Asp Val Pro Leu
    50                  55                  60

Glu Lys Asn Pro Lys Leu Lys Thr His Ala Met Ser Val Phe Val Met
65                  70                  75                  80

Thr Cys Glu Ala Ala Ala Gln Leu Arg Lys Ala Gly Lys Val Thr Val
                85                  90                  95

Arg Glu Thr Thr Leu Lys Arg Leu Gly Ala Thr His Leu Arg Tyr Gly
            100                 105                 110

Val Ala Asp Gly His Phe Glu Val Thr Gly Phe Ala Leu Leu Glu Thr
        115                 120                 125

Ile Lys Glu Ala Leu Pro Ala Asp Met Trp Ser Leu Glu Met Lys Lys
    130                 135                 140

Ala Trp Ala Glu Ala Tyr Ser Gln Leu Val Ala Ala Ile Lys Arg Glu
145                 150                 155                 160

Met Lys Pro Asp Ala
                165


<210> SEQ ID NO 17
<211> LENGTH: 162
<212> TYPE: PRT
<213> ORGANISM: Triticum aestivum
<220> FEATURE:
<221> NAME/KEY: misc_feature
<223> OTHER INFORMATION: Ceres CLONE ID no. 839727
<220> FEATURE:
<221> NAME/KEY: misc_feature
<222> LOCATION: (14)..(154)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 17

Met Ser Ala Ala Glu Gly Ala Val Val Phe Ser Glu Glu Lys Glu Ala
1               5                   10                  15

Leu Val Leu Lys Ser Trp Ala Ile Met Lys Lys Asp Ser Ala Asn Leu
            20                  25                  30

Gly Leu Arg Phe Phe Leu Lys Ile Phe Glu Ile Ala Pro Ser Ala Arg
        35                  40                  45

Gln Met Phe Pro Phe Leu Arg Asp Ser Asp Val Pro Leu Glu Thr Asn
    50                  55                  60

Pro Lys Leu Lys Thr His Ala Val Ser Val Phe Val Met Thr Cys Glu
65                  70                  75                  80

Ala Ala Ala Gln Leu Arg Lys Ala Gly Lys Ile Thr Val Arg Glu Thr
                85                  90                  95

Thr Leu Lys Arg Leu Gly Gly Thr His Leu Lys Tyr Gly Val Ala Asp
            100                 105                 110

Gly His Phe Glu Val Thr Arg Phe Ala Leu Leu Glu Thr Ile Lys Glu
        115                 120                 125

Ala Leu Pro Ala Asp Met Trp Gly Pro Glu Met Arg Asn Ala Trp Gly
    130                 135                 140

Glu Ala Tyr Asp Gln Leu Val Ala Ala Ile Lys Gln Glu Met Lys Pro
145                 150                 155                 160

Ser Glu


<210> SEQ ID NO 18
```

<211> LENGTH: 169
<212> TYPE: PRT
<213> ORGANISM: Triticum aestivum
<220> FEATURE:
<221> NAME/KEY: misc_feature
<223> OTHER INFORMATION: Public GI no. 14701800
<220> FEATURE:
<221> NAME/KEY: misc_feature
<222> LOCATION: (21)..(161)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 18

```
Met Ala Leu Val Glu Gly Asn Asn Gly Val Ser Gly Gly Ala Val Ser
1               5                   10                  15

Phe Ser Glu Glu Gln Glu Ala Leu Val Leu Lys Ser Trp Ala Ile Met
            20                  25                  30

Lys Lys Asp Ser Ala Asn Ile Gly Leu Arg Phe Phe Leu Lys Ile Phe
        35                  40                  45

Glu Val Ala Pro Ser Ala Ser Gln Met Phe Ser Phe Leu Arg Asn Ser
    50                  55                  60

Asp Val Pro Leu Glu Lys Asn Pro Lys Leu Lys Thr His Ala Met Ser
65                  70                  75                  80

Val Phe Val Met Thr Cys Glu Ala Ala Ala Gln Leu Arg Lys Ala Gly
                85                  90                  95

Lys Val Thr Val Arg Asp Thr Thr Leu Lys Arg Leu Gly Ala Thr His
            100                 105                 110

Phe Lys Tyr Gly Val Gly Asp Ala His Phe Glu Val Thr Arg Phe Ala
        115                 120                 125

Leu Leu Glu Thr Ile Lys Glu Ala Val Pro Val Asp Met Trp Ser Pro
    130                 135                 140

Ala Met Lys Ser Ala Trp Ser Glu Ala Tyr Asn Gln Leu Val Ala Ala
145                 150                 155                 160

Ile Lys Gln Glu Met Lys Pro Ala Glu
                165
```

<210> SEQ ID NO 19
<211> LENGTH: 416
<212> TYPE: DNA
<213> ORGANISM: Arabidopsis thaliana
<220> FEATURE:
<221> NAME/KEY: misc_feature
<223> OTHER INFORMATION: Ceres CLONE ID no. 271922
<220> FEATURE:
<221> NAME/KEY: misc_feature
<223> OTHER INFORMATION: Ceres SEED LINE ID no. ME03944
<220> FEATURE:
<221> NAME/KEY: misc_feature
<223> OTHER INFORMATION: Encodes the protein at SEQ ID NO: 20

<400> SEQUENCE: 19

```
gctcattagg gtttctcatc tacgacggcg tggtgttcct ccttcctgct ctgaaaaatg     60

gcgaagagaa cgaagaaggt tggaatcgtc ggcaaatacg gaacacgtta tggtgcgagt    120

atcaggaagc agattaagaa gatggaggtc agccagcaca gcaagtactt ctgtgagttc    180

tgtggcaagt acggagtgaa gcgaaaggct gttggtatct ggggttgcaa ggattgtggc    240

aaggtcaagg caggtggtgc ttacacaatg aacaccgcca gtgcggtcac tgttagaagc    300

acgatcagaa ggttgaggga gcagatcgag ggttaaaagt ctgctggctt tttatatttg    360
```

gtttccttgt tttgacaatt taagttttgc atcaacagtg agaacatgtt ttgatt 416

<210> SEQ ID NO 20
<211> LENGTH: 92
<212> TYPE: PRT
<213> ORGANISM: Arabidopsis thaliana
<220> FEATURE:
<221> NAME/KEY: misc_feature
<223> OTHER INFORMATION: Ceres CLONE ID no. 271922
<220> FEATURE:
<221> NAME/KEY: misc_feature
<223> OTHER INFORMATION: Ceres SEED LINE ID no. ME03944
<220> FEATURE:
<221> NAME/KEY: misc_feature
<222> LOCATION: (2)..(91)
<223> OTHER INFORMATION: Pfam Name: Ribosomal_L37ae;
Pfam Description: Ribosomal L37ae protein family

<400> SEQUENCE: 20

Met Ala Lys Arg Thr Lys Lys Val Gly Ile Val Gly Lys Tyr Gly Thr
1 5 10 15

Arg Tyr Gly Ala Ser Ile Arg Lys Gln Ile Lys Lys Met Glu Val Ser
20 25 30

Gln His Ser Lys Tyr Phe Cys Glu Phe Cys Gly Lys Tyr Gly Val Lys
35 40 45

Arg Lys Ala Val Gly Ile Trp Gly Cys Lys Asp Cys Gly Lys Val Lys
50 55 60

Ala Gly Gly Ala Tyr Thr Met Asn Thr Ala Ser Ala Val Thr Val Arg
65 70 75 80

Ser Thr Ile Arg Arg Leu Arg Glu Gln Ile Glu Gly
85 90

<210> SEQ ID NO 21
<211> LENGTH: 92
<212> TYPE: PRT
<213> ORGANISM: Arabidopsis thaliana
<220> FEATURE:
<221> NAME/KEY: misc_feature
<223> OTHER INFORMATION: Public GI no. 4090257
<220> FEATURE:
<221> NAME/KEY: misc_feature
<222> LOCATION: (2)..(91)
<223> OTHER INFORMATION: Pfam Name: Ribosomal_L37ae
Pfam Description: Ribosomal L37ae protein family
<220> FEATURE:
<221> NAME/KEY: misc_feature
<223> OTHER INFORMATION: Functional homolog of Ceres Clone ID no. 271922
given in SEQ ID NO: 20

<400> SEQUENCE: 21

Met Thr Lys Arg Thr Lys Lys Ala Gly Ile Val Gly Lys Tyr Gly Thr
1 5 10 15

Arg Tyr Gly Ala Ser Leu Arg Lys Gln Ile Lys Lys Met Glu Val Ser
20 25 30

Gln His Ser Lys Phe Phe Cys Glu Phe Cys Gly Lys Phe Ala Val Lys
35 40 45

Arg Lys Ala Val Gly Ile Trp Gly Cys Lys Asp Cys Gly Lys Val Lys
50 55 60

Ala Gly Gly Ala Tyr Thr Leu Asn Thr Pro Ser Ala Val Thr Val Arg
65 70 75 80

Ser Thr Ile Arg Arg Leu Arg Glu Gln Thr Glu Gly
85 90

```
<210> SEQ ID NO 22
<211> LENGTH: 92
<212> TYPE: PRT
<213> ORGANISM: Arabidopsis thaliana
<220> FEATURE:
<221> NAME/KEY: misc_feature
<223> OTHER INFORMATION: Public GI no. 4741896
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional homolog of Ceres Clone ID no. 271922
      given in SEQ ID NO: 20

<400> SEQUENCE: 22

Met Thr Lys Arg Thr Lys Lys Ala Gly Ile Val Gly Lys Tyr Gly Thr
1               5                   10                  15

Arg Tyr Gly Ala Ser Leu Arg Lys Gln Ile Lys Lys Met Glu Val Ser
            20                  25                  30

Gln His Ser Lys Tyr Phe Cys Glu Phe Cys Gly Lys Tyr Ala Val Lys
        35                  40                  45

Arg Lys Ala Val Gly Ile Trp Gly Cys Lys Ala Cys Gly Lys Val Lys
    50                  55                  60

Ala Gly Gly Ala Tyr Thr Leu Asn Thr Ala Ser Ala Val Thr Val Arg
65                  70                  75                  80

Ser Thr Ile Arg Arg Leu Arg Glu Gln Thr Glu Ser
                85                  90


<210> SEQ ID NO 23
<211> LENGTH: 92
<212> TYPE: PRT
<213> ORGANISM: Arabidopsis thaliana
<220> FEATURE:
<221> NAME/KEY: misc_feature
<223> OTHER INFORMATION: Ceres CLONE ID no. 36046
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<222> LOCATION: (45)..(45)
<223> OTHER INFORMATION: Xaa is any aa, unknown, or other
<220> FEATURE:
<221> NAME/KEY: misc_feature
<222> LOCATION: (49)..(49)
<223> OTHER INFORMATION: Xaa is any aa, unknown, or other
<220> FEATURE:
<221> NAME/KEY: misc_feature
<223> OTHER INFORMATION: Functional homolog of Ceres Clone ID no. 271922
      given in SEQ ID NO: 20

<400> SEQUENCE: 23

Met Ala Lys Arg Thr Lys Lys Val Gly Ile Val Gly Lys Tyr Gly Thr
1               5                   10                  15

Arg Tyr Gly Ala Ser Ile Arg Lys Gln Ile Lys Lys Met Glu Val Ser
            20                  25                  30

Gln His Ser Lys Tyr Phe Cys Glu Phe Cys Gly Lys Xaa Gly Val Lys
        35                  40                  45

Xaa Lys Ala Val Gly Ile Trp Gly Cys Lys Asp Cys Gly Lys Val Lys
    50                  55                  60

Ala Gly Gly Ala Tyr Thr Met Asn Thr Ala Ser Ala Val Thr Val Arg
65                  70                  75                  80
```

```
Ser Thr Ile Arg Arg Leu Arg Glu Gln Ile Glu Gly
                85                  90


<210> SEQ ID NO 24
<211> LENGTH: 92
<212> TYPE: PRT
<213> ORGANISM: Arabidopsis thaliana
<220> FEATURE:
<221> NAME/KEY: misc_feature
<223> OTHER INFORMATION: Public GI no. 6016699
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional homolog of Ceres Clone ID no. 271922
      given in SEQ ID NO: 20

<400> SEQUENCE: 24

Met Thr Lys Arg Thr Lys Lys Ala Arg Ile Val Gly Lys Tyr Gly Thr
1               5                   10                  15

Arg Tyr Gly Ala Ser Leu Arg Lys Gln Ile Lys Lys Met Glu Val Ser
            20                  25                  30

Gln His Asn Lys Tyr Phe Cys Glu Phe Cys Gly Lys Tyr Ser Val Lys
        35                  40                  45

Arg Lys Val Val Gly Ile Trp Gly Cys Lys Asp Cys Gly Lys Val Lys
    50                  55                  60

Ala Gly Gly Ala Tyr Thr Met Asn Thr Ala Ser Ala Val Thr Val Arg
65                  70                  75                  80

Ser Thr Ile Arg Arg Leu Arg Glu Gln Thr Glu Ser
                85                  90


<210> SEQ ID NO 25
<211> LENGTH: 92
<212> TYPE: PRT
<213> ORGANISM: Glycine max
<220> FEATURE:
<221> NAME/KEY: misc_feature
<223> OTHER INFORMATION: Ceres CLONE ID no. 664936
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional homolog of Ceres Clone ID no. 271922
      given in SEQ ID NO: 20

<400> SEQUENCE: 25

Met Thr Lys Arg Thr Lys Lys Ala Gly Ile Val Gly Lys Tyr Gly Thr
1               5                   10                  15

Arg Tyr Gly Ala Ser Leu Arg Lys Gln Ile Lys Lys Met Glu Val Ser
            20                  25                  30

Gln His Ser Lys Phe Phe Cys Glu Phe Cys Gly Lys Tyr Ala Val Lys
        35                  40                  45

Arg Lys Ala Val Gly Ile Trp Gly Cys Lys Asp Cys Gly Lys Val Lys
    50                  55                  60

Ala Gly Gly Ala Tyr Thr Leu Asn Thr Ala Ser Ala Val Thr Val Arg
65                  70                  75                  80

Ser Thr Ile Arg Arg Leu Arg Glu Gln Thr Glu Gly
                85                  90
```

```
<210> SEQ ID NO 26
<211> LENGTH: 92
<212> TYPE: PRT
<213> ORGANISM: Glycine max
<220> FEATURE:
<221> NAME/KEY: misc_feature
<223> OTHER INFORMATION: Ceres CLONE ID no. 658438
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional homolog of Ceres Clone ID no. 271922
      given in SEQ ID NO: 20

<400> SEQUENCE: 26

Met Thr Lys Arg Thr Lys Lys Ala Gly Ile Val Gly Lys Tyr Gly Thr
1               5                   10                  15

Arg Tyr Gly Ala Ser Leu Arg Lys Gln Ile Lys Lys Met Glu Val Ser
            20                  25                  30

Gln His Ser Lys Tyr Phe Cys Glu Phe Cys Gly Lys Phe Ala Val Lys
        35                  40                  45

Arg Lys Ala Val Gly Ile Trp Gly Cys Lys Asp Cys Gly Lys Val Lys
    50                  55                  60

Ala Gly Gly Ala Tyr Thr Met Asn Thr Ala Ser Ala Val Thr Val Arg
65                  70                  75                  80

Ser Thr Ile Arg Arg Leu Arg Glu Gln Thr Glu Ala
                85                  90


<210> SEQ ID NO 27
<211> LENGTH: 92
<212> TYPE: PRT
<213> ORGANISM: Glycine max
<220> FEATURE:
<221> NAME/KEY: misc_feature
<223> OTHER INFORMATION: Ceres CLONE ID no. 1049262
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional homolog of Ceres Clone ID no. 271922
      given in SEQ ID NO: 20

<400> SEQUENCE: 27

Met Thr Lys Arg Thr Lys Lys Ala Gly Ile Val Gly Lys Tyr Gly Thr
1               5                   10                  15

Arg Tyr Gly Ala Ser Leu Arg Lys Gln Ile Lys Lys Met Glu Val Ser
            20                  25                  30

Gln His Ser Lys Phe Phe Cys Glu Phe Cys Gly Lys Tyr Ala Val Lys
        35                  40                  45

Arg Lys Ala Val Gly Ile Trp Gly Cys Lys Asp Cys Gly Lys Val Lys
    50                  55                  60

Ala Gly Gly Ala Tyr Thr Leu Asn Thr Ala Ser Ala Val Thr Val Arg
65                  70                  75                  80

Ser Thr Ile Arg Arg Leu Arg Glu Gln Thr Glu Ser
                85                  90


<210> SEQ ID NO 28
```

```
<211> LENGTH: 92
<212> TYPE: PRT
<213> ORGANISM: Triticum aestivum
<220> FEATURE:
<221> NAME/KEY: misc_feature
<223> OTHER INFORMATION: Ceres CLONE ID no. 632613
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional homolog of Ceres Clone ID no. 271922
      given in SEQ ID NO: 20

<400> SEQUENCE: 28

Met Thr Lys Arg Thr Lys Lys Ala Gly Ile Val Gly Lys Tyr Gly Thr
1               5                   10                  15

Arg Tyr Gly Ala Ser Leu Arg Lys Gln Ile Lys Lys Met Glu Val Ser
            20                  25                  30

Gln His Ser Lys Tyr Phe Cys Glu Phe Cys Gly Lys Phe Ala Val Lys
        35                  40                  45

Arg Lys Ala Val Gly Ile Trp Gly Cys Lys Asp Cys Gly Lys Val Lys
    50                  55                  60

Ala Gly Gly Ala Tyr Thr Met Asn Thr Ala Ser Ala Val Thr Val Arg
65                  70                  75                  80

Ser Thr Ile Arg Arg Leu Arg Glu Gln Thr Glu Ala
                85                  90


<210> SEQ ID NO 29
<211> LENGTH: 92
<212> TYPE: PRT
<213> ORGANISM: Zea mays
<220> FEATURE:
<221> NAME/KEY: misc_feature
<223> OTHER INFORMATION: Ceres CLONE ID no. 1390976
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional homolog of Ceres Clone ID no. 271922
      given in SEQ ID NO: 20

<400> SEQUENCE: 29

Met Thr Lys Arg Thr Lys Lys Ala Gly Ile Val Gly Lys Tyr Gly Thr
1               5                   10                  15

Arg Tyr Gly Ala Ser Leu Arg Lys Gln Ile Lys Lys Met Glu Val Ser
            20                  25                  30

Gln His Ser Lys Tyr Phe Cys Glu Phe Cys Gly Lys Phe Ala Val Lys
        35                  40                  45

Arg Lys Ala Val Gly Ile Trp Gly Cys Lys Asp Cys Gly Lys Val Lys
    50                  55                  60

Ala Gly Gly Ala Tyr Thr Met Asn Thr Ala Ser Ala Val Thr Val Arg
65                  70                  75                  80

Ser Thr Ile Arg Arg Leu Arg Glu Gln Thr Glu Ala
                85                  90


<210> SEQ ID NO 30
<211> LENGTH: 92
<212> TYPE: PRT
<213> ORGANISM: Zea mays
```

```
<220> FEATURE:
<221> NAME/KEY: misc_feature
<223> OTHER INFORMATION: Ceres CLONE ID no. 1457185
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional homolog of Ceres Clone ID no. 271922
      given in SEQ ID NO: 20

<400> SEQUENCE: 30

Met Thr Lys Arg Thr Lys Lys Ala Gly Ile Val Gly Lys Tyr Gly Thr
1               5                   10                  15

Arg Tyr Gly Ala Ser Leu Arg Lys Gln Ile Lys Lys Met Glu Val Ser
            20                  25                  30

Gln His Ser Lys Tyr Phe Cys Glu Phe Cys Gly Lys Phe Ala Val Lys
        35                  40                  45

Arg Lys Ala Val Gly Ile Trp Gly Cys Lys Asp Cys Gly Lys Val Lys
    50                  55                  60

Ala Gly Gly Ala Tyr Thr Met Asn Thr Ala Ser Ala Val Thr Val Arg
65                  70                  75                  80

Ser Thr Ile Arg Arg Leu Arg Glu Gln Thr Glu Ala
                85                  90


<210> SEQ ID NO 31
<211> LENGTH: 92
<212> TYPE: PRT
<213> ORGANISM: Zea mays
<220> FEATURE:
<221> NAME/KEY: misc_feature
<223> OTHER INFORMATION: Public GI no. 56202147
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional homolog of Ceres Clone ID no. 271922
      given in SEQ ID NO: 20

<400> SEQUENCE: 31

Met Thr Lys Arg Thr Lys Lys Ala Gly Ile Val Gly Lys Tyr Gly Thr
1               5                   10                  15

Arg Tyr Gly Ala Ser Leu Arg Lys Gln Ile Lys Lys Met Glu Val Ser
            20                  25                  30

Gln His Ser Lys Tyr Phe Cys Glu Phe Cys Gly Lys Phe Ala Val Lys
        35                  40                  45

Arg Lys Ala Val Gly Ile Trp Gly Cys Lys Asp Cys Gly Lys Val Lys
    50                  55                  60

Ala Gly Gly Ala Tyr Thr Met Asn Thr Ala Ser Ala Val Thr Val Arg
65                  70                  75                  80

Ser Thr Ile Arg Arg Leu Arg Glu Gln Thr Glu Ala
                85                  90


<210> SEQ ID NO 32
<211> LENGTH: 92
<212> TYPE: PRT
<213> ORGANISM: Zea mays
<220> FEATURE:
<221> NAME/KEY: misc_feature
<223> OTHER INFORMATION: Public GI no. 58578274
```

<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional homolog of Ceres Clone ID no. 271922
      given in SEQ ID NO: 20

<400> SEQUENCE: 32

```
Met Thr Lys Arg Thr Lys Lys Ala Gly Ile Val Gly Lys Tyr Gly Thr
1               5                   10                  15

Arg Tyr Gly Ala Ser Leu Arg Lys Gln Ile Lys Lys Met Glu Val Ser
            20                  25                  30

Gln His Ser Glu Tyr Phe Cys Glu Phe Cys Gly Lys Tyr Ala Val Lys
        35                  40                  45

Arg Lys Ala Val Gly Ile Trp Gly Cys Lys Asp Cys Gly Lys Val Lys
    50                  55                  60

Ala Gly Gly Ala Tyr Thr Leu Asn Thr Ala Ser Ala Val Thr Val Arg
65                  70                  75                  80

Ser Thr Ile Arg Arg Leu Arg Glu Gln Thr Glu Ser
                85                  90
```

<210> SEQ ID NO 33
<211> LENGTH: 632
<212> TYPE: DNA
<213> ORGANISM: Arabidopsis thaliana
<220> FEATURE:
<221> NAME/KEY: misc_feature
<223> OTHER INFORMATION: Ceres CLONE ID no. 2403_FL
<220> FEATURE:
<221> NAME/KEY: misc_feature
<223> OTHER INFORMATION: Encodes the protein at SEQ ID NO: 34

<400> SEQUENCE: 33

```
attccccatc gcacagaccc gcctaagaat ccgagagaga agaagagata atgcagatct     60

tcgtcaaaac cctcaccggc aaaactataa ccctagaggt tgagagcagc gacaccatcg    120

acaatgttaa agccaaaatc caggacaaat agggcatacc acctgatcaa cagaggctga    180

tttttgctgg taagcaattg gaagatggcc ggaccttagc tgactacaac atccagaaag    240

agtctactct tcatcttgtc ctcaggctca gaggtggaac catgatcaag gtgaagacac    300

tcactggaaa agaaatcgag attgatatcg aaccaaccga cactattgat cggatcaaag    360

aacgtgttga agagaaagaa ggcatccctc ctgttcaaca aaggctcatc tatgccggaa    420

aacagcttgc tgatgacaaa acggccaaag attatgcgat agagggaggc tctgttcttc    480

atttggttct tgctcttagg ggtggtcttc tctgatctga ataaataagc ttttcaacaa    540

acatctttcc cctcactatt gtcctccttt tgtggaattc atgacacaca aaaattgcta    600

tgggaaattg gaatattatg atgtttttc tc                                  632
```

<210> SEQ ID NO 34
<211> LENGTH: 154
<212> TYPE: PRT
<213> ORGANISM: Arabidopsis thaliana
      220>
<221> NAME/KEY: misc_feature
<223> OTHER INFORMATION: Ceres CLONE ID no. 2403_FL
<220> FEATURE:
<221> NAME/KEY: misc_feature
<222> LOCATION: (1)..(74)
<223> OTHER INFORMATION: Pfam Name: ubiquitin
      Pfam Description: Ubiquitin family

```
<220> FEATURE:
<221> NAME/KEY: misc_feature
<222> LOCATION: (77)..(150)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 34

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Arg Gly Gly Thr Met Ile Lys
65                  70                  75                  80

Val Lys Thr Leu Thr Gly Lys Glu Ile Glu Ile Asp Ile Glu Pro Thr
                85                  90                  95

Asp Thr Ile Asp Arg Ile Lys Glu Arg Val Glu Glu Lys Glu Gly Ile
            100                 105                 110

Pro Pro Val Gln Gln Arg Leu Ile Tyr Ala Gly Lys Gln Leu Ala Asp
        115                 120                 125

Asp Lys Thr Ala Lys Asp Tyr Ala Ile Glu Gly Gly Ser Val Leu His
    130                 135                 140

Leu Val Leu Ala Leu Arg Gly Gly Leu Leu
145                 150


<210> SEQ ID NO 35
<211> LENGTH: 154
<212> TYPE: PRT
<213> ORGANISM: Zea mays
<220> FEATURE:
<221> NAME/KEY: misc_feature
<223> OTHER INFORMATION: Ceres CLONE ID no. 1482731
<220> FEATURE:
<221> NAME/KEY: misc_feature
<222> LOCATION: (1)..(74)
<223> OTHER INFORMATION: Pfam Name: ubiquitin
      Pfam Description: Ubiquitin family
<220> FEATURE:
<221> NAME/KEY: misc_feature
<222> LOCATION: (77)..(150)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 35

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ser Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60
```

```
Ser Thr Leu His Leu Val Leu Arg Leu Arg Gly Gly Thr Met Ile Lys
65                  70                  75                  80

Val Lys Thr Leu Thr Gly Lys Glu Ile Glu Ile Asp Ile Glu Pro Thr
                85                  90                  95

Asp Thr Ile Asp Arg Ile Lys Glu Arg Val Glu Glu Lys Glu Gly Ile
            100                 105                 110

Pro Pro Val Gln Gln Arg Leu Ile Tyr Ala Gly Lys Gln Leu Ala Asp
        115                 120                 125

Asp Lys Thr Ala Lys Asp Tyr Asn Ile Glu Gly Gly Ser Val Leu His
    130                 135                 140

Leu Val Leu Ala Leu Arg Gly Gly Ser Asp
145                 150


<210> SEQ ID NO 36
<211> LENGTH: 154
<212> TYPE: PRT
<213> ORGANISM: Glycine max
<220> FEATURE:
<221> NAME/KEY: misc_feature
<223> OTHER INFORMATION: Ceres CLONE ID no. 522921
<220> FEATURE:
<221> NAME/KEY: misc_feature
<222> LOCATION: (1)..(74)
<223> OTHER INFORMATION: Pfam Name: ubiquitin
      Pfam Description: Ubiquitin family
<220> FEATURE:
<221> NAME/KEY: misc_feature
<222> LOCATION: (77)..(150)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 36

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Arg Gly Gly Thr Met Ile Lys
65                  70                  75                  80

Val Lys Thr Leu Thr Gly Lys Glu Ile Glu Ile Asp Ile Glu Pro Thr
                85                  90                  95

Asp Thr Ile Asp Arg Ile Lys Glu Arg Val Glu Glu Lys Glu Gly Ile
            100                 105                 110

Pro Pro Val Gln Gln Arg Leu Ile Tyr Ala Gly Lys Gln Leu Ala Asp
        115                 120                 125

Asp Lys Thr Ala Lys Glu Tyr Asn Ile Glu Gly Gly Ser Val Leu His
    130                 135                 140

Leu Val Leu Ala Leu Arg Gly Gly Thr Tyr
145                 150


<210> SEQ ID NO 37
<211> LENGTH: 147
<212> TYPE: PRT
<213> ORGANISM: Brassica napus
<220> FEATURE:
```

```
<221> NAME/KEY: misc_feature
<223> OTHER INFORMATION: Ceres CLONE ID no. 1036726
<220> FEATURE:
<221> NAME/KEY: misc_feature
<222> LOCATION: (1)..(74)
<223> OTHER INFORMATION: Pfam Name: ubiquitin
      Pfam Description: Ubiquitin family
<220> FEATURE:
<221> NAME/KEY: misc_feature
<222> LOCATION: (77)..(142)
<223> OTHER INFORMATION: Pfam Name: ubiquitin
      Pfam Description: Ubiquitin family
<220> FEATURE:
<221> NAME/KEY: misc_feature
<222> LOCATION: (132)..(132)
<223> OTHER INFORMATION: Xaa can be any naturally occurring amino acid
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 37

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Arg Gly Gly Thr Met Ile Lys
65                  70                  75                  80

Val Lys Thr Leu Thr Gly Lys Glu Ile Glu Ile Asp Ile Glu Pro Thr
                85                  90                  95

Asp Thr Ile Asp Arg Ile Lys Glu Arg Val Glu Glu Lys Glu Gly Ile
            100                 105                 110

Pro Pro Val Gln Gln Arg Leu Ile Tyr Ala Gly Lys Gln Leu Ala Asp
        115                 120                 125

Asp Lys Thr Xaa Lys Asp Tyr Asn Ile Glu Gly Gly Ser Val Ser Ala
    130                 135                 140

Ser Gly Ser
145


<210> SEQ ID NO 38
<211> LENGTH: 153
<212> TYPE: PRT
<213> ORGANISM: Glycine max
<220> FEATURE:
<221> NAME/KEY: misc_feature
<223> OTHER INFORMATION: Ceres CLONE ID no. 513071
<220> FEATURE:
<221> NAME/KEY: misc_feature
<222> LOCATION: (1)..(74)
<223> OTHER INFORMATION: Pfam Name: ubiquitin
      Pfam Description: Ubiquitin family
<220> FEATURE:
<221> NAME/KEY: misc_feature
<222> LOCATION: (77)..(150)
<223> OTHER INFORMATION: Pfam Name: ubiquitin
      Pfam Description: Ubiquitin family
<220> FEATURE:
<221> NAME/KEY: misc_feature
<222> LOCATION: (146)..(146)
<223> OTHER INFORMATION: Xaa can be any naturally occurring amino acid
<220> FEATURE:
<221> NAME/KEY: misc_feature
<223> OTHER INFORMATION: Functional homolog of Ceres Clone ID no. 2403
      given in SEQ ID NO: 40
```

<400> SEQUENCE: 38

```
Met Gln Ile Phe Val Lys Thr Leu Thr Gly Lys Thr Ile Thr Leu Glu
1               5                   10                  15

Val Glu Ser Ser Asp Thr Val Asp Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Arg Gly Gly Thr Met Ile Lys
65                  70                  75                  80

Val Lys Thr Leu Thr Gly Lys Glu Ile Glu Ile Asp Ile Glu Pro Thr
                85                  90                  95

Asp Ser Ile Asp Arg Ile Lys Glu Arg Val Glu Glu Lys Glu Gly Ile
            100                 105                 110

Pro Pro Val Gln Gln Arg Leu Ile Tyr Ala Gly Lys Gln Leu Ala Asp
        115                 120                 125

Asp Lys Thr Ala Lys Asp Tyr Asn Ile Glu Gly Gly Ser Val Leu His
    130                 135                 140

Leu Xaa Leu Ala Leu Arg Gly Gly Tyr
145                 150
```

<210> SEQ ID NO 39
<211> LENGTH: 620
<212> TYPE: DNA
<213> ORGANISM: Artificial Sequence
<220> FEATURE:
<223> OTHER INFORMATION: Ceres CLONE ID no. 2403
<220> FEATURE:
<221> NAME/KEY: misc_feature
<223> OTHER INFORMATION: Ceres SEED LINE ID no. ME05304
<220> FEATURE:
<221> NAME/KEY: misc_feature
<223> OTHER INFORMATION: Encodes the protein at SEQ ID NO: 40

<400> SEQUENCE: 39

```
attccccatc gcacagaccc ccctaagaat ccgagagaga agaagagata atgcagatct     60

tcgtcaaaac cctcaccggc aaaactataa ccctagaagt tgagagcagc gacaccatcg    120

acaatgttaa agccaaaatc caggacaaag agggcatacc acctgatcaa cagaggctga    180

tttttgctgg taagcaattg gaagatggcc ggaccttagc tgattacaac atccagaaag    240

agtctactct tcatcttgtc ctcaggctca gaggtggaac catgatcaag gtgaagacac    300

tcactggaaa agaaatcgag attgatatcg aaccaaccga cactattgat cggatcaaag    360

aacgtgttga agagaaagaa ggcatccctc ctgttcaaca aaggctcata tatgccggaa    420

aacagcttgc tgatgacaaa acggccaaag attatgcgat agagggaggc tctgttcttc    480

atttggttct tgctcttagg ggtggtcttc tctgatctta ataaataagc ttttcaacaa    540

acatcttttc cctcactatt gtcctcctta tgtggaattc atgacacacc aaaattgcta    600

tgggaaattg gaatattatg                                                620
```

<210> SEQ ID NO 40
<211> LENGTH: 33
<212> TYPE: PRT
<213> ORGANISM: Artificial Sequence
<220> FEATURE:
<223> OTHER INFORMATION: Ceres CLONE ID no. 2403
<220> FEATURE:

<221> NAME/KEY: misc_feature
<223> OTHER INFORMATION: Ceres SEED LINE ID no. ME05304
<220> FEATURE:
<221> NAME/KEY: misc_feature
<222> LOCATION: (1)..(33)
<223> OTHER INFORMATION: Pfam Name: ubiquitin
Pfam Description: Ubiquitin family

<400> SEQUENCE: 40

```
Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys
```

<210> SEQ ID NO 41
<211> LENGTH: 1106
<212> TYPE: DNA
<213> ORGANISM: Glycine max
<220> FEATURE:
<221> NAME/KEY: misc_feature
<223> OTHER INFORMATION: Ceres CLONE ID no. 674166
<220> FEATURE:
<221> NAME/KEY: misc_feature
<223> OTHER INFORMATION: Ceres SEED LINE ID no. ME03186
<220> FEATURE:
<221> NAME/KEY: misc_feature
<223> OTHER INFORMATION: Encodes the protein at SEQ ID NO: 42

<400> SEQUENCE: 41

```
atatttttgt gtagatgaag atcaacaaga gaaggtgttg ttgtgagttg tgttgttatg     60

gtaccttcct tcaaccacaa aacctctctc cctctaccac ccattctctt ctctctctct    120

ctctcccgtc ctccatctct caccttctca atctcttcac caccaccatc atcatcatta    180

tcttctccaa tctctataac ctcgaaatcc ctcaaaacct ctccctcaaa ccaaatgaaa    240

tgaccctttt gtgagaacat tttttccccc ttaagaaaag gtcaaaggct gcaacttttt    300

cttaaccaat ctcacatttt tttatttttc aacgtatttt ggccaggttt ggttttctgg    360

gttgtcttgg aattcaaaaa agattccaac tttgaagatg ggtaggggtg gaaccgccgc    420

ggcggcggcg gaggtcgccg aacccggttt aaggccggtt tatttcaaag aacagcgata    480

taggggcgtc agaaaaagac cgtggggccg gttcgctgcc gaaatcagag accctttgaa    540

gaaagccagg gtttggctcg gaacctttga caccgccgag gaggcggcgc gtgcctacga    600

cacggcggcg agaaccctcc ggggaccaaa ggcgaagacc aatttccctc tttctccgcc    660

gttctaccat cccgatccat tttccgatca ccggcacttc gccaacaccg gcgaagattt    720

ccacgatcac cggcgaccaa catccagtgg catgagcagc accgtagagt ccttcagcgg    780

cccccgtgct gccgtgccgg cgacagcgcc ggtggccacc ggccggagat atccccggac    840

gccacccgtt atccccgagg actgccgcag cgactgcgat tcgtcgtcct ccgtcgttga    900

cgacggcgaa ggcgacaacg tggcgtcgtc gttcccgcga gaaccgttgc cgtttgatct    960

aaacgcgttg ccgttagacg atgctgacgt ggcaaccgat gatctgttct gcaccgttct   1020

ttgcctctga tgagaaaaaa tgaaaaaacg gaacgaaatg atgtatttgg ttcgttgacg   1080

gaattattat tattttttc tttctt                                        1106
```

<210> SEQ ID NO 42
<211> LENGTH: 210
<212> TYPE: PRT
<213> ORGANISM: Glycine max
<220> FEATURE:

```
<221> NAME/KEY: misc_feature
<223> OTHER INFORMATION: Ceres CLONE ID no. 674166
<220> FEATURE:
<221> NAME/KEY: misc_feature
<223> OTHER INFORMATION: Ceres SEED LINE ID no. ME03186
<220> FEATURE:
<221> NAME/KEY: misc_feature
<222> LOCATION: (26)..(89)
<223> OTHER INFORMATION: Pfam Name: AP2
      Pfam Description: AP2 domain
<220> FEATURE:
<221> NAME/KEY: misc_feature
<222> LOCATION: (26)..(89)
<223> OTHER INFORMATION: Pfam Name: AP2;
      Pfam Description: AP2 domain

<400> SEQUENCE: 42

Met Gly Arg Gly Gly Thr Ala Ala Ala Ala Ala Glu Val Ala Glu Pro
1               5                   10                  15

Gly Leu Arg Pro Val Tyr Phe Lys Glu Gln Arg Tyr Arg Gly Val Arg
            20                  25                  30

Lys Arg Pro Trp Gly Arg Phe Ala Ala Glu Ile Arg Asp Pro Leu Lys
        35                  40                  45

Lys Ala Arg Val Trp Leu Gly Thr Phe Asp Thr Ala Glu Glu Ala Ala
    50                  55                  60

Arg Ala Tyr Asp Thr Ala Ala Arg Thr Leu Arg Gly Pro Lys Ala Lys
65                  70                  75                  80

Thr Asn Phe Pro Leu Ser Pro Pro Phe Tyr His Pro Asp Pro Phe Ser
                85                  90                  95

Asp His Arg His Phe Ala Asn Thr Gly Glu Asp Phe His Asp His Arg
            100                 105                 110

Arg Pro Thr Ser Ser Gly Met Ser Ser Thr Val Glu Ser Phe Ser Gly
        115                 120                 125

Pro Arg Ala Ala Val Pro Ala Thr Ala Pro Val Ala Thr Gly Arg Arg
    130                 135                 140

Tyr Pro Arg Thr Pro Pro Val Ile Pro Glu Asp Cys Arg Ser Asp Cys
145                 150                 155                 160

Asp Ser Ser Ser Ser Val Val Asp Asp Gly Glu Gly Asp Asn Val Ala
                165                 170                 175

Ser Ser Phe Pro Arg Glu Pro Leu Pro Phe Asp Leu Asn Ala Leu Pro
            180                 185                 190

Leu Asp Asp Ala Asp Val Ala Thr Asp Asp Leu Phe Cys Thr Val Leu
        195                 200                 205

Cys Leu
    210


<210> SEQ ID NO 43
<211> LENGTH: 225
<212> TYPE: PRT
<213> ORGANISM: Glycine max
<220> FEATURE:
<221> NAME/KEY: misc_feature
<223> OTHER INFORMATION: Public GI no. 12322345
<220> FEATURE:
<221> NAME/KEY: misc_feature
<222> LOCATION: (26)..(89)
<223> OTHER INFORMATION: Pfam Name: AP2
      Pfam Description: AP2 domain
<220> FEATURE:
<221> NAME/KEY: misc_feature
<223> OTHER INFORMATION: Functional homolog of Ceres Clone ID no. 674166
      given in SEQ ID NO: 42

<400> SEQUENCE: 43
```

```
Met Arg Arg Gly Arg Gly Ser Ser Ala Val Ala Gly Pro Thr Val Val
1               5                   10                  15

Ala Ala Ile Asn Gly Ser Val Lys Glu Ile Arg Phe Arg Gly Val Arg
            20                  25                  30

Lys Arg Pro Trp Gly Arg Phe Ala Ala Glu Ile Arg Asp Pro Trp Lys
        35                  40                  45

Lys Ala Arg Val Trp Leu Gly Thr Phe Asp Ser Ala Glu Glu Ala Ala
    50                  55                  60

Arg Ala Tyr Asp Ser Ala Ala Arg Asn Leu Arg Gly Pro Lys Ala Lys
65                  70                  75                  80

Thr Asn Phe Pro Ile Asp Ser Ser Ser Pro Pro Pro Pro Asn Leu Arg
                85                  90                  95

Phe Asn Gln Ile Arg Asn Gln Asn Gln Asn Gln Val Asp Pro Phe Met
            100                 105                 110

Asp His Arg Leu Phe Thr Asp His Gln Gln Gln Phe Pro Ile Val Asn
        115                 120                 125

Arg Pro Thr Ser Ser Ser Met Ser Ser Thr Val Glu Ser Phe Ser Gly
    130                 135                 140

Pro Arg Pro Thr Thr Met Lys Pro Ala Thr Thr Lys Arg Tyr Pro Arg
145                 150                 155                 160

Thr Pro Pro Val Val Pro Glu Asp Cys His Ser Asp Cys Asp Ser Ser
                165                 170                 175

Ser Ser Val Ile Asp Asp Asp Asp Asp Ile Ala Ser Ser Ser Arg Arg
            180                 185                 190

Arg Asn Pro Pro Phe Gln Phe Asp Leu Asn Phe Pro Pro Leu Asp Cys
        195                 200                 205

Val Asp Leu Phe Asn Gly Ala Asp Asp Leu His Cys Thr Asp Leu Arg
    210                 215                 220

Leu
225
```

<210> SEQ ID NO 44
<211> LENGTH: 215
<212> TYPE: PRT
<213> ORGANISM: Brassica napus
<220> FEATURE:
<221> NAME/KEY: misc_feature
<223> OTHER INFORMATION: Ceres CLONE ID no. 975672
<220> FEATURE:
<221> NAME/KEY: misc_feature
<222> LOCATION: (21)..(84)
<223> OTHER INFORMATION: Pfam Name: AP2
      Pfam Description: AP2 domain
<220> FEATURE:
<221> NAME/KEY: misc_feature
<222> LOCATION: (174)..(174)
<223> OTHER INFORMATION: Xaa is any aa, unknown, or other
<220> FEATURE:
<221> NAME/KEY: misc_feature
<222> LOCATION: (194)..(194)
<223> OTHER INFORMATION: Xaa is any aa, unknown, or other
<220> FEATURE:
<221> NAME/KEY: misc_feature
<222> LOCATION: (208)..(208)
<223> OTHER INFORMATION: Xaa is any aa, unknown, or other
<220> FEATURE:
<221> NAME/KEY: misc_feature
<222> LOCATION: (209)..(209)
<223> OTHER INFORMATION: Xaa is any aa, unknown, or other
<220> FEATURE:
<221> NAME/KEY: misc_feature
<222> LOCATION: (214)..(214)
<223> OTHER INFORMATION: Xaa is any aa, unknown, or other
<220> FEATURE:
<221> NAME/KEY: misc_feature
<223> OTHER INFORMATION: Functional homolog of Ceres Clone ID no. 674166
      given in SEQ ID NO: 42

<400> SEQUENCE: 44

```
Met Arg Lys Gly Arg Gly Ser Ser Ala Val Pro Pro Ala Leu Pro Gly
1               5                   10                  15

Ser Val Lys Glu Pro Arg Tyr Arg Gly Val Arg Lys Arg Pro Trp Gly
            20                  25                  30

Arg Phe Ala Ala Glu Ile Arg Asp Pro Leu Lys Lys Ser Arg Val Trp
        35                  40                  45

Leu Gly Thr Phe Asp Ser Ala Glu Glu Ala Ala Arg Ala Tyr Asp Ala
    50                  55                  60

Ala Ala Arg Asn Leu Arg Gly Pro Lys Ala Lys Thr Asn Phe Gln Ile
65                  70                  75                  80

Asp Cys Ser Pro Ser Ser Pro Leu Gln Pro Leu His His Arg Asn Gln
                85                  90                  95

Ile Asp Pro Phe Met Asp His Arg Leu Tyr Gly Gly Glu Gln Glu Val
            100                 105                 110

Val Ile Ile Ser Arg Pro Ala Ser Ser Ser Met Ser Ser Thr Val Lys
        115                 120                 125

Ser Cys Ser Gly Val Arg Pro Ala Ser Ser Ser Val Ala Lys Ala Ala
    130                 135                 140

Thr Lys Arg Tyr Pro Arg Thr Pro Pro Val Ala Pro Glu Asp Cys Arg
145                 150                 155                 160

Ser Asp Cys Asp Ser Ser Ser Ser Val Val Glu Asp Gly Xaa Asp Ile
                165                 170                 175

Ala Ser Ser Ser Ser Arg Arg Lys Pro Pro Phe Glu Phe Asp Leu Asn
            180                 185                 190

Phe Xaa Pro Leu Asp Gly Val Asp Leu Phe Val Gly Ala Asp Asp Xaa
        195                 200                 205

Xaa Cys Thr Asp Leu Xaa Leu
    210                 215
```

<210> SEQ ID NO 45
<211> LENGTH: 211
<212> TYPE: PRT
<213> ORGANISM: Zea mays
<220> FEATURE:
<221> NAME/KEY: misc_feature
<223> OTHER INFORMATION: Ceres CLONE ID no. 273307
<220> FEATURE:
<221> NAME/KEY: misc_feature
<222> LOCATION: (17)..(80)
<223> OTHER INFORMATION: Pfam Name: AP2
      Pfam Description: AP2 domain
<220> FEATURE:
<221> NAME/KEY: misc_feature
<223> OTHER INFORMATION: Functional homolog of Ceres Clone ID no. 674166
      given in SEQ ID NO: 42

<400> SEQUENCE: 45

```
Met Arg Arg Arg Gly Val Ala Ala Ala Asp Ala Asp Gly Asp Val Glu
1               5                   10                  15

Leu Arg Phe Arg Gly Val Arg Lys Arg Pro Trp Gly Arg Tyr Ala Ala
            20                  25                  30

Glu Ile Arg Asp Pro Ala Lys Lys Ala Arg Val Trp Leu Gly Thr Phe
        35                  40                  45

Asp Ser Ala Glu Asp Ala Ala Arg Ala Tyr Asp Ala Ala Ala Arg Met
```

```
    50                  55                  60

Leu Arg Gly Pro Lys Ala Arg Thr Asn Phe Pro Leu Pro Ala Ala Ala
65                  70                  75                  80

Ala Leu His His Pro His Met Pro Ala Ala Ala Ala Ala Ala Ala Pro
                85                  90                  95

Pro Tyr Thr Thr Tyr Pro Thr Ala Thr Gly Val Val Ser Thr Pro Pro
            100                 105                 110

Val Ala Arg Pro Ala Cys Ser Ser Leu Ser Ser Thr Val Glu Ser Phe
        115                 120                 125

Ser Gly Ala Arg Pro Arg Pro Val Leu Pro Pro Arg Phe Pro Pro Pro
    130                 135                 140

Ser Ile Pro Asp Gly Asp Cys Arg Ser Asp Cys Gly Ser Ser Ala Ser
145                 150                 155                 160

Val Val Asp Asp Asp Cys Thr Asp Ala Ala Ala Ser Ala Ser Cys Pro
                165                 170                 175

Phe Pro Leu Pro Phe Asp Leu Asn Leu Pro Pro Gly Gly Gly Gly Ala
            180                 185                 190

Gly Val Gly Phe Tyr Ala Asp Glu Glu Asp Glu Leu Arg Leu Thr Ala
        195                 200                 205

Leu Arg Leu
    210


<210> SEQ ID NO 46
<211> LENGTH: 194
<212> TYPE: PRT
<213> ORGANISM: Triticum aestivum
<220> FEATURE:
<221> NAME/KEY: misc_feature
<223> OTHER INFORMATION: Ceres CLONE ID no. 1055099
<220> FEATURE:
<221> NAME/KEY: misc_feature
<222> LOCATION: (20)..(83)
<223> OTHER INFORMATION: Pfam Name: AP2
      Pfam Description: AP2 domain
<220> FEATURE:
<221> NAME/KEY: misc_feature
<223> OTHER INFORMATION: Functional homolog of Ceres Clone ID no. 674166
      given in SEQ ID NO: 42

<400> SEQUENCE: 46

Met Arg Lys Ala Arg Pro Pro Gln Pro Gln Pro Gln Pro Ser Gln Gln
1               5                   10                  15

Ser Pro Glu Ile Arg Tyr Arg Gly Val Arg Lys Arg Pro Ser Gly Arg
            20                  25                  30

Tyr Ala Ala Glu Ile Arg Asp Pro Ala Lys Lys Thr Pro Ile Trp Leu
        35                  40                  45

Gly Thr Phe Asp Cys Ala Glu Asp Ala Ala Arg Ala Tyr Asp Ser Ala
    50                  55                  60

Ala Arg Ser Leu Arg Gly Pro Thr Ala Arg Thr Asn Phe Pro Pro Ser
65                  70                  75                  80

Ser Ala Thr Gln Pro Pro Pro Arg Pro Pro Pro Pro Ala Ala Ala Ala
                85                  90                  95

Ala Ala Ala Thr Ser Ser Gln Ser Ser Thr Val Glu Ser Trp Ser Gly
            100                 105                 110

Gly Gly Pro Arg Ala Pro Ala Arg Ala Arg Ser Ala Ala Arg Ala Gly
        115                 120                 125

Thr Ala Lys Glu Gly Glu Glu Asp Cys Arg Ser Tyr Cys Gly Ser Ser
    130                 135                 140
```

```
Ser Ser Val Leu Leu Glu Glu Gly Ala Asp Asp Ala Ala Ala Ser Arg
145                 150                 155                 160

Ser Pro Leu Pro Phe Asp Leu Asn Met Pro Pro Pro Gln Glu Gly Ala
                165                 170                 175

Leu Asp Ala Glu Ala Asp Gln Met Thr Cys Arg Tyr Asp Thr Leu Leu
            180                 185                 190

Arg Leu


<210> SEQ ID NO 47
<211> LENGTH: 660
<212> TYPE: DNA
<213> ORGANISM: Populus balsamifera subsp. trichocarpa
<220> FEATURE:
<221> NAME/KEY: misc_feature
<223> OTHER INFORMATION: Ceres ANNOT ID no.1441430
<220> FEATURE:
<221> NAME/KEY: misc_feature
<223> OTHER INFORMATION: Encodes the protein at SEQ ID NO: 48

<400> SEQUENCE: 47

atggggagaa caagaacaac aacaaaacag gctgttgacc caaatggatc tgcaacccaa     60

aatatgttag taattgcaaa agagcccaga tacagaggag tacgaaagag accatgggga    120

agattcgctg cggagattag agatccctgg aaaaagacca gagtttggct gggcaccttc    180

gactctgcag aggatgcagc gcgtgcctac gatgcggctg ctcgcaccct ccgcggagca    240

aaggccaaga caaactttcc tatctccaca acgaaccagt tattcaatca tcaaaatcaa    300

aaccaaagcc caaccgatcc cttcttggat caccacagta taaatcccca aagacccaca    360

tctagcagtt tgagcagtac agtggagtct ttcagcggtc ctaggcctcc gcagccaaca    420

acaacaacaa aatcgggaaa tgggccgagg agatctcatc cacggatccc accggttgtt    480

ccagaagatt gtcatagcga ttgcgattca tcttcttcgg tggttgatga cagagatgtc    540

gcatccgctg cttcttcttt gtgccgcaag cctttgcctt tcgatctaaa tttcccaccg    600

ttggaccagg ttgacttggg ctctggtgat gatctccact gcactgcttt atgcctttga    660


<210> SEQ ID NO 48
<211> LENGTH: 219
<212> TYPE: PRT
<213> ORGANISM: Populus balsamifera subsp. trichocarpa
<220> FEATURE:
<221> NAME/KEY: misc_feature
<223> OTHER INFORMATION: Ceres ANNOT ID no. 1441430
<220> FEATURE:
<221> NAME/KEY: misc_feature
<222> LOCATION: (29)..(92)
<223> OTHER INFORMATION: Pfam Name: AP2
      Pfam Description: AP2 domain
<220> FEATURE:
<221> NAME/KEY: misc_feature
<223> OTHER INFORMATION: Functional Homolog of Ceres CLONE ID no. 674166
      Given in SEQ ID NO: 42

<400> SEQUENCE: 48

Met Gly Arg Thr Arg Thr Thr Thr Lys Gln Ala Val Asp Pro Asn Gly
1               5                   10                  15

Ser Ala Thr Gln Asn Met Leu Val Ile Ala Lys Glu Pro Arg Tyr Arg
            20                  25                  30

Gly Val Arg Lys Arg Pro Trp Gly Arg Phe Ala Ala Glu Ile Arg Asp
        35                  40                  45

Pro Trp Lys Lys Thr Arg Val Trp Leu Gly Thr Phe Asp Ser Ala Glu
    50                  55                  60
```

```
Asp Ala Ala Arg Ala Tyr Asp Ala Ala Ala Arg Thr Leu Arg Gly Ala
65                  70                  75                  80

Lys Ala Lys Thr Asn Phe Pro Ile Ser Thr Thr Asn Gln Leu Phe Asn
                85                  90                  95

His Gln Asn Gln Asn Gln Ser Pro Thr Asp Pro Phe Leu Asp His His
            100                 105                 110

Ser Ile Asn Pro Gln Arg Pro Thr Ser Ser Ser Leu Ser Ser Thr Val
        115                 120                 125

Glu Ser Phe Ser Gly Pro Arg Pro Pro Gln Pro Thr Thr Thr Thr Lys
    130                 135                 140

Ser Gly Asn Gly Pro Arg Arg Ser His Pro Arg Ile Pro Pro Val Val
145                 150                 155                 160

Pro Glu Asp Cys His Ser Asp Cys Asp Ser Ser Ser Ser Val Val Asp
                165                 170                 175

Asp Arg Asp Val Ala Ser Ala Ala Ser Ser Leu Cys Arg Lys Pro Leu
            180                 185                 190

Pro Phe Asp Leu Asn Phe Pro Pro Leu Asp Gln Val Asp Leu Gly Ser
        195                 200                 205

Gly Asp Asp Leu His Cys Thr Ala Leu Cys Leu
    210                 215
```

```
<210> SEQ ID NO 49
<211> LENGTH: 985
<212> TYPE: DNA
<213> ORGANISM: Glycine max
<220> FEATURE:
<221> NAME/KEY: misc_feature
<223> OTHER INFORMATION: Ceres CLONE ID no.1240330
<220> FEATURE:
<221> NAME/KEY: misc_feature
<223> OTHER INFORMATION: Encodes the protein at SEQ ID NO: 50

<400> SEQUENCE: 49

attattcctc ttccatctct attctccata acacccacca caccacttgt gaaaaacctc     60

attaatatca cacactgaca tgtatctctg agctccaatc caatacaaga ccacaccttg    120

tcgtgtcgga cgaaccttgg tgtctgtttt tttttttttt tcattatttt ctccgaagag    180

atgaggaagg gcagaggtgg aggcgcctcg gcggcggcgg tggatgtgaa cggatccatt    240

ttaaaggagc ctcggtaccg gggcgtgagg aagagaccgt gggggagatt cgccgcggag    300

atcagagacc cgttgaagaa agccagggtt tggttgggaa ccttcgattc tgccgaggat    360

gctgctcgtg cctacgacgc cgccgctcgg actctccgag gtcccaaggc caaaacaaat    420

ttccccccctc tctcaccttt ttgctatcca caccccacca ccgatccttt cttctacact    480

ggtttccacg atcaacacca ccaccacaac aacaacaacc ttaacaaccc tcaaagaccc    540

acttcaagtg gcatgagtag caccgttgag tccttcagtg ggccccgccc tcccaccacc    600

accactacca ccacaaccac aactgcgacg ccgtttttga ctgctacgcg gagatacccg    660

cgcactcccc ctcttgtccc tgaagactgc cacagtgact gcgactcttc ctcctccgtc    720

gttgacgacg gcgacgacaa catcgtttcg tcgtcgtttc gacctccctt gccgtttgat    780

ctcaacgcgc tgccgtttga tgatgctgcc gcggatgatg atctacgccg caccgcgctt    840

tgtctctgat gatgattatc gtgcgatgat gatttttaat ttctcatttt tttacttgat    900

ttttttgtta ttgctatgca gaagaaatat atatttaaaa tgatgatcag atgtaagatt    960

atggtaatat gatcttaatt ctgtg                                          985
```

```
<210> SEQ ID NO 50
<211> LENGTH: 222
<212> TYPE: PRT
<213> ORGANISM: Glycine max
<220> FEATURE:
<221> NAME/KEY: misc_feature
<223> OTHER INFORMATION: Ceres CLONE ID no. 1240330
<220> FEATURE:
<221> NAME/KEY: misc_feature
<222> LOCATION: (24)..(87)
<223> OTHER INFORMATION: Pfam Name: AP2
      Pfam Description: AP2 domain
<220> FEATURE:
<221> NAME/KEY: misc_feature
<223> OTHER INFORMATION: Functional Homolog of Ceres CLONE ID no. 674166
      Given in SEQ ID NO: 42

<400> SEQUENCE: 50

Met Arg Lys Gly Arg Gly Gly Gly Ala Ser Ala Ala Ala Val Asp Val
1               5                   10                  15

Asn Gly Ser Ile Leu Lys Glu Pro Arg Tyr Arg Gly Val Arg Lys Arg
            20                  25                  30

Pro Trp Gly Arg Phe Ala Ala Glu Ile Arg Asp Pro Leu Lys Lys Ala
        35                  40                  45

Arg Val Trp Leu Gly Thr Phe Asp Ser Ala Glu Asp Ala Ala Arg Ala
    50                  55                  60

Tyr Asp Ala Ala Ala Arg Thr Leu Arg Gly Pro Lys Ala Lys Thr Asn
65                  70                  75                  80

Phe Pro Pro Leu Ser Pro Phe Cys Tyr Pro His Pro Thr Thr Asp Pro
                85                  90                  95

Phe Phe Tyr Thr Gly Phe His Asp Gln His His His His Asn Asn Asn
            100                 105                 110

Asn Leu Asn Asn Pro Gln Arg Pro Thr Ser Ser Gly Met Ser Ser Thr
        115                 120                 125

Val Glu Ser Phe Ser Gly Pro Arg Pro Pro Thr Thr Thr Thr Thr Thr
    130                 135                 140

Thr Thr Thr Thr Ala Thr Pro Phe Leu Thr Ala Thr Arg Arg Tyr Pro
145                 150                 155                 160

Arg Thr Pro Pro Leu Val Pro Glu Asp Cys His Ser Asp Cys Asp Ser
                165                 170                 175

Ser Ser Ser Val Val Asp Asp Gly Asp Asp Asn Ile Val Ser Ser Ser
            180                 185                 190

Phe Arg Pro Pro Leu Pro Phe Asp Leu Asn Ala Leu Pro Phe Asp Asp
        195                 200                 205

Ala Ala Ala Asp Asp Asp Leu Arg Arg Thr Ala Leu Cys Leu
    210                 215                 220


<210> SEQ ID NO 51
<211> LENGTH: 726
<212> TYPE: DNA
<213> ORGANISM: Zea mays
<220> FEATURE:
<221> NAME/KEY: misc_feature
<223> OTHER INFORMATION: Ceres CLONE ID no.1382611
<220> FEATURE:
<221> NAME/KEY: misc_feature
<223> OTHER INFORMATION: Encodes the protein at SEQ ID NO: 52

<400> SEQUENCE: 51

acttttctct cccattcttt tacaactcac gttgcacagc ctttttctct atatattact     60

tgacataaac tactattcac aacacaaaca cacacataac catggcctct tcttcacaag    120
```

```
ctttcctttt gctcacattg tctatggttt tagttcattt ctctttagct caatctccca    180

tgatggctcc ttctggctcc atgtccatgc cgccaatgcc tagcggcggc tctccaatgc    240

caatgatgac tccaccacct atgccaatga tgactccacc acctatggct atggctccac    300

cacctatgcc tatgactcca ccaccaatgc ccatggctcc gatgccaatg actccatctt    360

caagtccaat gagcccacca actactatgg ccccaagtcc agaaacagtc cctgatatgg    420

cttcgccacc gatgatgcca ggaatggatt cttctccttc tccgggaccc atgccaccgg    480

caatggcctc tccagattcc ggagcattca atgtaagaaa cgacgtcgta gcaatttcgt    540

tccttgttgc agctcatttg ctcctagttt gagattatta ttaaattggc cagcgtcgtg    600

tttgtgtaat ttactttcat ttttttctcg agccattaat tttcatgttt tatcatatat    660

ttgggtttgt gtttgatatg gtacgattca gacatttgtt tgcttaataa gtttatcgtt    720

gactct                                                                726
```

```
<210> SEQ ID NO 52
<211> LENGTH: 156
<212> TYPE: PRT
<213> ORGANISM: Zea mays
<220> FEATURE:
<221> NAME/KEY: misc_feature
<223> OTHER INFORMATION: Ceres CLONE ID no. 1382611
<220> FEATURE:
<221> NAME/KEY: misc_feature
<223> OTHER INFORMATION: Functional Homolog of Ceres CLONE ID no. 30087
      Given in SEQ ID NO: 2

<400> SEQUENCE: 52

Met Ala Ser Ser Ser Gln Ala Phe Leu Leu Leu Thr Leu Ser Met Val
1               5                   10                  15

Leu Val His Phe Ser Leu Ala Gln Ser Pro Met Met Ala Pro Ser Gly
            20                  25                  30

Ser Met Ser Met Pro Pro Met Pro Ser Gly Gly Ser Pro Met Pro Met
        35                  40                  45

Met Thr Pro Pro Pro Met Pro Met Met Thr Pro Pro Pro Met Ala Met
    50                  55                  60

Ala Pro Pro Pro Met Pro Met Thr Pro Pro Pro Met Pro Met Ala Pro
65                  70                  75                  80

Met Pro Met Thr Pro Ser Ser Ser Pro Met Ser Pro Pro Thr Thr Met
                85                  90                  95

Ala Pro Ser Pro Glu Thr Val Pro Asp Met Ala Ser Pro Pro Met Met
            100                 105                 110

Pro Gly Met Asp Ser Ser Pro Ser Pro Gly Pro Met Pro Pro Ala Met
        115                 120                 125

Ala Ser Pro Asp Ser Gly Ala Phe Asn Val Arg Asn Asp Val Val Ala
    130                 135                 140

Ile Ser Phe Leu Val Ala Ala His Leu Leu Leu Val
145                 150                 155
```

```
<210> SEQ ID NO 53
<211> LENGTH: 580
<212> TYPE: DNA
<213> ORGANISM: Papaver somniferum
<220> FEATURE:
<221> NAME/KEY: misc_feature
<223> OTHER INFORMATION: Ceres CLONE ID no.1627907
<220> FEATURE:
<221> NAME/KEY: misc_feature
<223> OTHER INFORMATION: Encodes the protein at SEQ ID NO: 54
```

```
<400> SEQUENCE: 53

gcagaagcac aaggtaagat tgaaggagga gaccggaact cttcttcgcc aaaaccctag     60

ttcgagctca ccaacaacaa tctttcgcaa tgactaagcg taccaagaag gccggaattg    120

tgggtaaata tggtaccaga tatggagctt cattaaggaa acagattaag aagatggaag    180

tgagtcagca tgcaaagtac ttctgtgagt tctgcggaaa gtacgctgtg aagagacagg    240

ctgttggaat ctggggatgc aaggattgtg gcaaagttaa agctggtggt gcttacactt    300

tgaacaccgc cagtgccgtg acagttagaa gcaccattag aaggttgagg gagcaaactg    360

aatcttagat tgatctcgtt atctatattt tgtattttgg tactgggtga gaggtaccat    420

cagagctaat ttagtgttta tcaccttttc tggtcttcaa gaactagtta gtcattttgt    480

tattcagaga tttttgataa tgtctagtat cttacatttg tgagcagact atttctttgt    540

ttcaaattat ggagttctga tgaatcttat atttattctc                          580


<210> SEQ ID NO 54
<211> LENGTH: 92
<212> TYPE: PRT
<213> ORGANISM: Papaver somniferum
<220> FEATURE:
<221> NAME/KEY: misc_feature
<223> OTHER INFORMATION: Ceres CLONE ID no. 1627907
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional Homolog of Ceres CLONE ID no. 271922
      Given in SEQ ID NO: 20

<400> SEQUENCE: 54

Met Thr Lys Arg Thr Lys Lys Ala Gly Ile Val Gly Lys Tyr Gly Thr
1               5                   10                  15

Arg Tyr Gly Ala Ser Leu Arg Lys Gln Ile Lys Lys Met Glu Val Ser
            20                  25                  30

Gln His Ala Lys Tyr Phe Cys Glu Phe Cys Gly Lys Tyr Ala Val Lys
        35                  40                  45

Arg Gln Ala Val Gly Ile Trp Gly Cys Lys Asp Cys Gly Lys Val Lys
    50                  55                  60

Ala Gly Gly Ala Tyr Thr Leu Asn Thr Ala Ser Ala Val Thr Val Arg
65                  70                  75                  80

Ser Thr Ile Arg Arg Leu Arg Glu Gln Thr Glu Ser
                85                  90


<210> SEQ ID NO 55
<211> LENGTH: 983
<212> TYPE: DNA
<213> ORGANISM: Panicum virgatum
<220> FEATURE:
<221> NAME/KEY: misc_feature
<223> OTHER INFORMATION: Ceres CLONE ID no.1761125
<220> FEATURE:
<221> NAME/KEY: misc_feature
<223> OTHER INFORMATION: Encodes the protein at SEQ ID NO: 56

<400> SEQUENCE: 55

accagaccac accacaccac accgcgtcca catcctcccg cgcttctccg ctcagcccgc     60

gcgtttccgc tgaggaggga tagccgcgcg gcgcgtcgag ggtttgtctt ttgatcgggt    120

agctgaggct gagcgggcgg ggcaggatga tgcgcgacac ggcggccgtg gccgtggcgg    180
```

```
cgccgcggta caggggcgtg cggaagcggc cgtggggccg gttcgcggcg gagatccgcg    240

acccggcgaa gcgcgcgcgc gtctggctcg gcaccttcga ctccgccgag gccgcggcgc    300

gcgcctacga cgtcgccgcg cggaccctgc gcggcccgct cgccaggacc aacttcccct    360

gcgcctcctc ccgcctcccg ctgccctccc gccaccaagg cggctgtggc ggcggcctcg    420

tcgcgccgcc gcccgccgcg ccgacgtgca gctccagctc caccgtcgag tcctccagcg    480

gaccccgagg ggcgcccagg gctgctgcgg cggcggcgcc tcgaattcgg aggcggtcgg    540

tgaaaaagcc gcggccggca gcgcccgaca tcgactgcca cagcgactgc gcctcgtcgg    600

cctccgtcgt ggacgacggc gacgacgcct ccacggtccg gtcgcgcgcg ccgttcgacc    660

tcaacgtccc ggctccggtg gacggtgacc acgccctcga cctctgcacg gagctgcggc    720

tctgagcaat atgatcctcg aacaacaaca acagcaaaac attgaaggcg atttttcccc    780

ggtcttcttt tcctgactaa attctgatat gatcaatatg ctcgagagtt ctcgttttct    840

ttaacgcctc ttgtatttgg atctgctacc atcttctctg cccattctat ttgtacacca    900

gataacatgt aagatgttca cgaattaaca catatctttt cttaaaaaaa tgaattaaca    960

cggaaaaaaa aaaaaaaaaa aaa                                            983
```

<210> SEQ ID NO 56
<211> LENGTH: 192
<212> TYPE: PRT
<213> ORGANISM: Panicum virgatum
<220> FEATURE:
<221> NAME/KEY: misc_feature
<223> OTHER INFORMATION: Ceres CLONE ID no. 1761125
<220> FEATURE:
<221> NAME/KEY: misc_feature
<222> LOCATION: (13)..(76)
<223> OTHER INFORMATION: Pfam Name: AP2
      Pfam Description: AP2 domain
<220> FEATURE:
<221> NAME/KEY: misc_feature
<223> OTHER INFORMATION: Functional Homolog of Ceres CLONE ID no. 674166
      Given in SEQ ID NO: 42

<400> SEQUENCE: 56

```
Met Met Arg Asp Thr Ala Ala Val Ala Val Ala Ala Pro Arg Tyr Arg
1               5                   10                  15

Gly Val Arg Lys Arg Pro Trp Gly Arg Phe Ala Ala Glu Ile Arg Asp
            20                  25                  30

Pro Ala Lys Arg Ala Arg Val Trp Leu Gly Thr Phe Asp Ser Ala Glu
        35                  40                  45

Ala Ala Ala Arg Ala Tyr Asp Val Ala Ala Arg Thr Leu Arg Gly Pro
    50                  55                  60

Leu Ala Arg Thr Asn Phe Pro Cys Ala Ser Ser Arg Leu Pro Leu Pro
65                  70                  75                  80

Ser Arg His Gln Gly Gly Cys Gly Gly Gly Leu Val Ala Pro Pro Pro
                85                  90                  95

Ala Ala Pro Thr Cys Ser Ser Ser Ser Thr Val Glu Ser Ser Ser Gly
            100                 105                 110

Pro Arg Gly Ala Pro Arg Ala Ala Ala Ala Ala Ala Pro Arg Ile Arg
        115                 120                 125

Arg Arg Ser Val Lys Lys Pro Arg Pro Ala Ala Pro Asp Ile Asp Cys
    130                 135                 140

His Ser Asp Cys Ala Ser Ser Ala Ser Val Val Asp Asp Gly Asp Asp
145                 150                 155                 160
```

```
Ala Ser Thr Val Arg Ser Arg Ala Pro Phe Asp Leu Asn Val Pro Ala
                165                 170                 175

Pro Val Asp Gly Asp His Ala Leu Asp Leu Cys Thr Glu Leu Arg Leu
            180                 185                 190


<210> SEQ ID NO 57
<211> LENGTH: 594
<212> TYPE: DNA
<213> ORGANISM: Panicum virgatum
<220> FEATURE:
<221> NAME/KEY: misc_feature
<223> OTHER INFORMATION: Ceres CLONE ID no.1783890
<220> FEATURE:
<221> NAME/KEY: misc_feature
<223> OTHER INFORMATION: Encodes the protein at SEQ ID NO: 58

<400> SEQUENCE: 57

gagccctacc cgcacccgcg ccgccgccgc cccgcgcccc gtcgccgcag acgactccgc      60

cccgtcgccg cgatgacgaa gcgcaccaag aaggccggaa tcgtcggcaa atatggaact     120

aggtatggtg ctagcttgcg taagcaaatc aagaagatgg aggtgtctca gcactccaag     180

tacttctgcg agttctgtgg aaagtttgct gtgaaaagga aagcagttgg aatctgggga     240

tgcaaggact gcgggaaggt taaggctggt ggtgcttaca ccatgaacac tgctagtgca     300

gtcaccgtca ggagcacaat ccgtcgcttg agggagcaga ctgaagcata atcggagctc     360

ttctctgcag tagtcctgtg ctttttgtac cgtctaagac atatggctgt ttggcctaag     420

aacattcatg aatattctgg ttatgcttaa ggatatcaaa aattatggtg ctaaaatttg     480

tacttcgttg ctgttgcaaa gttgacctgt cttgatccat tcataatgta gaatttcctc     540

atggttctta tctccagttt gctactcttt ggccaaaaaa aaaaaaaaaa aaaa           594


<210> SEQ ID NO 58
<211> LENGTH: 92
<212> TYPE: PRT
<213> ORGANISM: Panicum virgatum
<220> FEATURE:
<221> NAME/KEY: misc_feature
<223> OTHER INFORMATION: Ceres CLONE ID no. 1783890
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional Homolog of Ceres CLONE ID no. 271922
      Given in SEQ ID NO: 20

<400> SEQUENCE: 58

Met Thr Lys Arg Thr Lys Lys Ala Gly Ile Val Gly Lys Tyr Gly Thr
1               5                   10                  15

Arg Tyr Gly Ala Ser Leu Arg Lys Gln Ile Lys Lys Met Glu Val Ser
            20                  25                  30

Gln His Ser Lys Tyr Phe Cys Glu Phe Cys Gly Lys Phe Ala Val Lys
        35                  40                  45

Arg Lys Ala Val Gly Ile Trp Gly Cys Lys Asp Cys Gly Lys Val Lys
    50                  55                  60

Ala Gly Gly Ala Tyr Thr Met Asn Thr Ala Ser Ala Val Thr Val Arg
65                  70                  75                  80

Ser Thr Ile Arg Arg Leu Arg Glu Gln Thr Glu Ala
                85                  90
```

```
<210> SEQ ID NO 59
<211> LENGTH: 880
<212> TYPE: DNA
<213> ORGANISM: Panicum virgatum
<220> FEATURE:
<221> NAME/KEY: misc_feature
<223> OTHER INFORMATION: Ceres CLONE ID no.1802327
<220> FEATURE:
<221> NAME/KEY: misc_feature
<223> OTHER INFORMATION: Encodes the protein at SEQ ID NO: 60

<400> SEQUENCE: 59

acacagatac attcgtcgat ccaccactgt ccagtgcttg gcggttacgc acgcacgcac      60

acagatagga ttatctttta ctacaccaac tcaccaagat actagcaagc cgaatcgaca     120

aacaagcagc aggaagagga ggcatggcgc tcgcggaggg gaacgtcatc ttcggcgagg     180

agcaggaggc gctggtgctc aagtcgtggg ccctcatgaa gaaggactcg gccgacctcg     240

gcctccgctt cttcctcaag atcttcgaga tcgcgccgtc ggcgaagcag atgttctcgt     300

tcctgcgcga ctccgacgtg ccgctcgaga agaaccccaa gctcaagaac cacgccatgt     360

ccgtcttcgt catgacctgc gaggcggcgg cgcagctacg gaaggccggg aaggtcaccg     420

tcagggagac gacgctcaag cggctgggcg ccacgcactt caagtacggc gtcgccgacg     480

gccacttcga ggtgacgagg ttcgcgctgc tggagacgat aaaggaggcg cttcccgccg     540

acatgtggag cctggagatg aagaacgcct ggagcgaggc ttacaaccag ctggtggcgg     600

ccatcaagca ggagatgaag cctgccgcat gatgctgctg ctgctactga gatgaagcct     660

gcccgcatga tgctgctgct gctactcggc ctccgcgctg agttccccct acgatgcacc     720

accatctcca aattcttcat cgctgttttt tttttttgc tgttttgact tgtattgtgc      780

attttccaaa tctctcgatg gagacaagtg tgatgactaa tttttgagag catgtatata     840

tgttgtgatg agcattgaat aaaaaaaaaa aaaaaaaaaa                           880


<210> SEQ ID NO 60
<211> LENGTH: 162
<212> TYPE: PRT
<213> ORGANISM: Panicum virgatum
<220> FEATURE:
<221> NAME/KEY: misc_feature
<223> OTHER INFORMATION: Ceres CLONE ID no. 1802327
<220> FEATURE:
<221> NAME/KEY: misc_feature
<222> LOCATION: (14)..(154)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 60

Met Ala Leu Ala Glu Gly Asn Val Ile Phe Gly Glu Glu Gln Glu Ala
1               5                   10                  15

Leu Val Leu Lys Ser Trp Ala Leu Met Lys Lys Asp Ser Ala Asp Leu
            20                  25                  30

Gly Leu Arg Phe Phe Leu Lys Ile Phe Glu Ile Ala Pro Ser Ala Lys
        35                  40                  45

Gln Met Phe Ser Phe Leu Arg Asp Ser Asp Val Pro Leu Glu Lys Asn
    50                  55                  60

Pro Lys Leu Lys Asn His Ala Met Ser Val Phe Val Met Thr Cys Glu
65                  70                  75                  80

Ala Ala Ala Gln Leu Arg Lys Ala Gly Lys Val Thr Val Arg Glu Thr
```

```
                85                  90                  95

Thr Leu Lys Arg Leu Gly Ala Thr His Phe Lys Tyr Gly Val Ala Asp
            100                 105                 110

Gly His Phe Glu Val Thr Arg Phe Ala Leu Leu Glu Thr Ile Lys Glu
        115                 120                 125

Ala Leu Pro Ala Asp Met Trp Ser Leu Glu Met Lys Asn Ala Trp Ser
    130                 135                 140

Glu Ala Tyr Asn Gln Leu Val Ala Ala Ile Lys Gln Glu Met Lys Pro
145                 150                 155                 160

Ala Ala


<210> SEQ ID NO 61
<211> LENGTH: 1017
<212> TYPE: DNA
<213> ORGANISM: Gossypium hirsutum
<220> FEATURE:
<221> NAME/KEY: misc_feature
<223> OTHER INFORMATION: Ceres CLONE ID no.1838364
<220> FEATURE:
<221> NAME/KEY: misc_feature
<223> OTHER INFORMATION: Encodes the protein at SEQ ID NO: 62

<400> SEQUENCE: 61

cctgcccatt tccatcttcc ttctttcctt cctctttcct ttgtcttctt gctttatctt      60

ccctttatct tcaatctttt ctgttctgtt tttttcttag attcataggt aagttcgttt     120

tggttggctt gattatttcc tcacttccct tcttttttgg ttcatcgtga tcttttcatc     180

aaccccttttt gattgttata tagattgtta ctattctttt aatcttttaa atattttttt    240

tccatgagga gagggagagg tgccgcagct gcaaacgccg tagctaggag accggcactg     300

caacccagcg gatctattaa agagccgaga tacagaggtg ttagaaaaag gccatggggc     360

agattcgcgg ccgagattcg agacccttgg aagaagacca gggtctggtt agggacgttc     420

gactcggccg aagaagccgc tcgagcctac gatacggcgg cgaggacgct ccgtggaccc     480

aaagctaaaa caaatttccc cataaattct tcaaatatcc cggcttttcc tttcgaaacc     540

aatcatcacc acaacgaagg gttcatcgac caacgccggt tatatccgat gggcgaattt     600

catgaccccg aagtgaatcc acagagaccc acgaggagta gcatgagtag cacggtggag     660

tcgtttagtg gacccagacc ggcccaacca ccgcaaaagt cggcggactt cgcggtggtt     720

tcgactagga agtactatcc gaggccgccg ccagtagagc cagaggattg tcatagtgac     780

tgtgattcat catcgtcggt ggttgatgat ggggatatcg cgttgtcttc ttgtcggaaa     840

actttgcctt tcgatctcaa ttttccaccc ttggatgaag atggaagatc tccagtgtac     900

tgctttatgt ctttgatcgc gatgccggtg atgaatgatg atgatcgatt attggatctc     960

tttttctttt ttaaaaaatg ttagcttttt taagcggaaa aaaaaaaaaa aaaaaaa       1017


<210> SEQ ID NO 62
<211> LENGTH: 246
<212> TYPE: PRT
<213> ORGANISM: Gossypium hirsutum
<220> FEATURE:
<221> NAME/KEY: misc_feature
<223> OTHER INFORMATION: Ceres CLONE ID no. 1838364
<220> FEATURE:
<221> NAME/KEY: misc_feature
<222> LOCATION: (28)..(91)
<223> OTHER INFORMATION: Pfam Name: AP2
      Pfam Description: AP2 domain
<220> FEATURE:
<221> NAME/KEY: misc_feature
```

```
<223> OTHER INFORMATION: Functional Homolog of Ceres CLONE ID no. 674166
      Given in SEQ ID NO: 42

<400> SEQUENCE: 62

Met Arg Arg Gly Arg Gly Ala Ala Ala Ala Asn Ala Val Ala Arg Arg
1               5                   10                  15

Pro Ala Leu Gln Pro Ser Gly Ser Ile Lys Glu Pro Arg Tyr Arg Gly
            20                  25                  30

Val Arg Lys Arg Pro Trp Gly Arg Phe Ala Ala Glu Ile Arg Asp Pro
        35                  40                  45

Trp Lys Lys Thr Arg Val Trp Leu Gly Thr Phe Asp Ser Ala Glu Glu
    50                  55                  60

Ala Ala Arg Ala Tyr Asp Thr Ala Ala Arg Thr Leu Arg Gly Pro Lys
65                  70                  75                  80

Ala Lys Thr Asn Phe Pro Ile Asn Ser Ser Asn Ile Pro Ala Phe Pro
                85                  90                  95

Phe Glu Thr Asn His His His Asn Glu Gly Phe Ile Asp Gln Arg Arg
            100                 105                 110

Leu Tyr Pro Met Gly Glu Phe His Asp Pro Glu Val Asn Pro Gln Arg
        115                 120                 125

Pro Thr Arg Ser Ser Met Ser Ser Thr Val Glu Ser Phe Ser Gly Pro
    130                 135                 140

Arg Pro Ala Gln Pro Pro Gln Lys Ser Ala Asp Phe Ala Val Val Ser
145                 150                 155                 160

Thr Arg Lys Tyr Tyr Pro Arg Pro Pro Pro Val Glu Pro Glu Asp Cys
                165                 170                 175

His Ser Asp Cys Asp Ser Ser Ser Ser Val Val Asp Asp Gly Asp Ile
            180                 185                 190

Ala Leu Ser Ser Cys Arg Lys Thr Leu Pro Phe Asp Leu Asn Phe Pro
        195                 200                 205

Pro Leu Asp Glu Asp Gly Arg Ser Pro Val Tyr Cys Phe Met Ser Leu
    210                 215                 220

Ile Ala Met Pro Val Met Asn Asp Asp Asp Arg Leu Leu Asp Leu Phe
225                 230                 235                 240

Phe Phe Phe Lys Lys Cys
                245


<210> SEQ ID NO 63
<211> LENGTH: 708
<212> TYPE: DNA
<213> ORGANISM: Panicum virgatum
<220> FEATURE:
<221> NAME/KEY: misc_feature
<223> OTHER INFORMATION: Ceres CLONE ID no.1876458
<220> FEATURE:
<221> NAME/KEY: misc_feature
<223> OTHER INFORMATION: Encodes the protein at SEQ ID NO: 64

<400> SEQUENCE: 63

acacagatac attcgtcgat ccaccactgt ccagtgcttg gcggttacgc acgcacgcac      60

acagatagga ttatctttta ctacaccaac tcaccaagat actagcaagc cgaatcgaca     120

aacaagcagc aggaagagga ggcatggcgc tcgcggaggg gaacgtcatc ttcggcgagg     180

agcaggaggc gctggtgctc aagtcgtggg ccctcatgaa gaaggactcg gccgacctcg     240

gcctccgctt cttcctcaag atcttcgaga tcgcgccgtc ggcgaagcag atgttctcgt     300

tcctgcgcga ctccgacgtg ccgctcgaga agaaccccaa gctcaagacc cacgccatgt     360
```

```
ccgtcttcgt catgacctgc gaggcggcgg cgcagctacg gaaggccggg aaggtcaccg    420

tcagggagac gacgctcaag cggctgggcg ccacgcactt caagtacggc gtcgccgacg    480

gccacttcga ggtgacgagg ttcgcgctgc tggagacgat aaaggaggcg cttcccgccg    540

acatgtggag cctggagatg aagtacgcct ggagcgaggc ttacaaccag cttgtggcgg    600

ccatcaagca ggagatgaag cctgccgcat gatgctgctg ctgctactcg gcctccgcgc    660

tgagttcccc ctacgatgca ccaccatctc caaattcttc atcgctgt                708
```

```
<210> SEQ ID NO 64
<211> LENGTH: 162
<212> TYPE: PRT
<213> ORGANISM: Panicum virgatum
<220> FEATURE:
<221> NAME/KEY: misc_feature
<223> OTHER INFORMATION: Ceres CLONE ID no. 1876458
<220> FEATURE:
<221> NAME/KEY: misc_feature
<222> LOCATION: (14)..(154)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 64

Met Ala Leu Ala Glu Gly Asn Val Ile Phe Gly Glu Glu Gln Glu Ala
1               5                   10                  15

Leu Val Leu Lys Ser Trp Ala Leu Met Lys Lys Asp Ser Ala Asp Leu
            20                  25                  30

Gly Leu Arg Phe Phe Leu Lys Ile Phe Glu Ile Ala Pro Ser Ala Lys
        35                  40                  45

Gln Met Phe Ser Phe Leu Arg Asp Ser Asp Val Pro Leu Glu Lys Asn
    50                  55                  60

Pro Lys Leu Lys Thr His Ala Met Ser Val Phe Val Met Thr Cys Glu
65                  70                  75                  80

Ala Ala Ala Gln Leu Arg Lys Ala Gly Lys Val Thr Val Arg Glu Thr
                85                  90                  95

Thr Leu Lys Arg Leu Gly Ala Thr His Phe Lys Tyr Gly Val Ala Asp
            100                 105                 110

Gly His Phe Glu Val Thr Arg Phe Ala Leu Leu Glu Thr Ile Lys Glu
        115                 120                 125

Ala Leu Pro Ala Asp Met Trp Ser Leu Glu Met Lys Tyr Ala Trp Ser
    130                 135                 140

Glu Ala Tyr Asn Gln Leu Val Ala Ala Ile Lys Gln Glu Met Lys Pro
145                 150                 155                 160

Ala Ala
```

```
<210> SEQ ID NO 65
<211> LENGTH: 712
<212> TYPE: DNA
<213> ORGANISM: Panicum virgatum
<220> FEATURE:
<221> NAME/KEY: misc_feature
<223> OTHER INFORMATION: Ceres CLONE ID no.1879148
<220> FEATURE:
<221> NAME/KEY: misc_feature
<223> OTHER INFORMATION: Encodes the protein at SEQ ID NO: 66

<400> SEQUENCE: 65

acacagatac attcgtcgat ccaccactgt ccagtgctcg gctcggttac gcacgcacgc     60
```

```
acacaaattg tagtacctgt gttttacacc accaaagata ctagcaagcc gagtcgacaa    120

acaaagcagc aggaagaggc atggcgctcg ctgacgggaa cggcgcggcc atcttcggcg    180

aggagcagga ggcgctggtg ctcaagtcgt gggccctcat gaagaaggac tcggccgacc    240

tcggcctccg cttcttcctc aagatcttcg agatcgcgcc gtcggcgaag cagatgttct    300

cgttcctgcg cgactccgac gtgccgctgg agaagaaccc caagctcaag acccacgcca    360

tgtccgtctt cgtcatgacc tgcgaggcgg cagcgcagct acggaaggcc gggaaggtca    420

ccgtcaggga gacgacgctc aagcggctgg gcgcaacgca cttcaagtac ggcgtcgccg    480

acggccactt cgaggtgaca aggttcgcgc tgctggagac gataaaggag gcgcttcccg    540

ccgacatgtg gagcctggag atgaagaacg cctggagcga ggcttacaac cagctcgtgg    600

cggccatcaa gcaggagatg aagcctgctg catgatgctg catgctgcta catactcggc    660

ctccgagttc cccctacgat gcaccaccat ctccaagttc ttcatcgcta tt            712


<210> SEQ ID NO 66
<211> LENGTH: 164
<212> TYPE: PRT
<213> ORGANISM: Panicum virgatum
<220> FEATURE:
<221> NAME/KEY: misc_feature
<223> OTHER INFORMATION: Ceres CLONE ID no. 1879148
<220> FEATURE:
<221> NAME/KEY: misc_feature
<222> LOCATION: (16)..(156)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 66

Met Ala Leu Ala Asp Gly Asn Gly Ala Ala Ile Phe Gly Glu Glu Gln
1               5                   10                  15

Glu Ala Leu Val Leu Lys Ser Trp Ala Leu Met Lys Lys Asp Ser Ala
            20                  25                  30

Asp Leu Gly Leu Arg Phe Phe Leu Lys Ile Phe Glu Ile Ala Pro Ser
        35                  40                  45

Ala Lys Gln Met Phe Ser Phe Leu Arg Asp Ser Asp Val Pro Leu Glu
    50                  55                  60

Lys Asn Pro Lys Leu Lys Thr His Ala Met Ser Val Phe Val Met Thr
65                  70                  75                  80

Cys Glu Ala Ala Ala Gln Leu Arg Lys Ala Gly Lys Val Thr Val Arg
                85                  90                  95

Glu Thr Thr Leu Lys Arg Leu Gly Ala Thr His Phe Lys Tyr Gly Val
            100                 105                 110

Ala Asp Gly His Phe Glu Val Thr Arg Phe Ala Leu Leu Glu Thr Ile
        115                 120                 125

Lys Glu Ala Leu Pro Ala Asp Met Trp Ser Leu Glu Met Lys Asn Ala
    130                 135                 140

Trp Ser Glu Ala Tyr Asn Gln Leu Val Ala Ala Ile Lys Gln Glu Met
145                 150                 155                 160

Lys Pro Ala Ala


<210> SEQ ID NO 67
<211> LENGTH: 1129
<212> TYPE: DNA
```

<213> ORGANISM: Gossypium hirsutum
<220> FEATURE:
<221> NAME/KEY: misc_feature
<223> OTHER INFORMATION: Ceres CLONE ID no.1884696
<220> FEATURE:
<221> NAME/KEY: misc_feature
<223> OTHER INFORMATION: Encodes the protein at SEQ ID NO: 68

<400> SEQUENCE: 67

```
atccgccccc atttgttcgc tctgtatatt gaacttttct ttctcgattt tctctttgaa     60

caaaaatgat gaagatcttc aaccagactc tcaccggcaa gactatcacg ctcgaggtcg    120

agagctccga caccatcgaa ggcgccaaca ccattctcca agatggaggg agcctccctc    180

cttaccgaac ccgactgatc ttcgccggac aacagcttga ggacggactg accttgtgcg    240

attacaacat cttaaaggag gtcaactctc cacctcttcc tccggttgcg cggtgggatg    300

cttaccttcc ggaggacctt gaccggcaat accatcactc tccaggtcta aagcgccgac    360

tcgatcaagt tcgttcacgc taacatccaa gactaggaag gcgtccccccc ataccaacta    420

cgactctgct tcgaccgaaa acaacttgaa gacggccgta ccttggccga ctacaacatc    480

cagaaggagt caacgctcca tcttgtcctt cgtttgcgtg gcgggatgca aatcttcgtt    540

aagacgctta cgggaaagac gatcactctc gaggtcgaga gctctgacac gatcgacaac    600

gtgaaagcca aaatccaaga caaggaaggc atcccgccag accagcaacg tctcatcttc    660

gccggaaagc aactcgagga cgggcggact ttagccgatt acaatatcca gaaggaatcg    720

actcttcatc tggtcctgcg tcttggaggt gggatgcaga tcttcgtcaa gactttgacc    780

ggtaagacga ttactttaga agtggagagc tcggatacga ttgataacgt gaaagcgaag    840

attcaggaca aagaaggaat tccaccagat cagcaaaggt tgatttttgc tgggaaacaa    900

ctggaagacg gaaggacttt ggctgattac aatattcaaa aggattccac tcttcacctt    960

gttcttcgtc ttcgtggtgg gttctaagcc ttaaggtctc ccttaatgtg ggtttctgg   1020

ttttacgtga aggactgtgc cctgtaatgg ccttttaaat aatttctagt ctttgtttac   1080

cggttgcatc tatgtatggt ttctcttaga atggaattag catatttac              1129
```

<210> SEQ ID NO 68
<211> LENGTH: 153
<212> TYPE: PRT
<213> ORGANISM: Gossypium hirsutum
<220> FEATURE:
<221> NAME/KEY: misc_feature
<223> OTHER INFORMATION: Ceres CLONE ID no. 1884696
<220> FEATURE:
<221> NAME/KEY: misc_feature
<222> LOCATION: (1)..(74)
<223> OTHER INFORMATION: Pfam Name: ubiquitin
Pfam Description: Ubiquitin family
<220> FEATURE:
<221> NAME/KEY: misc_feature
<222> LOCATION: (77)..(150)
<223> OTHER INFORMATION: Pfam Name: ubiquitin
Pfam Description: Ubiquitin family
<220> FEATURE:
<221> NAME/KEY: misc_feature
<223> OTHER INFORMATION: Functional Homolog of Ceres CLONE ID no. 2403
Given in SEQ ID NO: 40

<400> SEQUENCE: 68

```
Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30
```

```
Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Gly Gly Gly Met Gln Ile Phe
65                  70                  75                  80

Val Lys Thr Leu Thr Gly Lys Thr Ile Thr Leu Glu Val Glu Ser Ser
                85                  90                  95

Asp Thr Ile Asp Asn Val Lys Ala Lys Ile Gln Asp Lys Glu Gly Ile
            100                 105                 110

Pro Pro Asp Gln Gln Arg Leu Ile Phe Ala Gly Lys Gln Leu Glu Asp
        115                 120                 125

Gly Arg Thr Leu Ala Asp Tyr Asn Ile Gln Lys Asp Ser Thr Leu His
    130                 135                 140

Leu Val Leu Arg Leu Arg Gly Gly Phe
145                 150
```

```
<210> SEQ ID NO 69
<211> LENGTH: 679
<212> TYPE: DNA
<213> ORGANISM: Gossypium hirsutum
<220> FEATURE:
<221> NAME/KEY: misc_feature
<223> OTHER INFORMATION: Ceres CLONE ID no.1916866
<220> FEATURE:
<221> NAME/KEY: misc_feature
<223> OTHER INFORMATION: Encodes the protein at SEQ ID NO: 70

<400> SEQUENCE: 69

aaatcaaata cctactgcaa ttaaaatccc ggaattactt aaacaacaat ggctacctat      60

gaaggtaaag ttttcactga agaacaagaa gctttggtgg tcaagtcatg gactgtaatg     120

aagaagaacg cagctgaatt gggtcttaaa ttcttcttga agatatttga gattgcacca     180

tcagccaaga aactattctc attcttgaga gactccaatg ttccattgga gcaaaacaca     240

aagctgaagc cccatgccat gtctgtcttt gtcatgacat gtgaatctgc agtgcaactg     300

cgtaaagcag gcaaagttac agtgagggaa tcaaatttga agaaattagg agctacccat     360

tttaagtatg ggtagttga tgaacatttt gaggtaacaa aatttgctct tttggagacc      420

ataaaagaag cagtaccaga tatgtggtca gatgagatga agaatgcatg gggtgaagcc     480

tatgatcgtt tggtcgcagc cattaaaata gaaatgaagg catgctcaca agctgcatga     540

tttcacaagt tccctacatt attgcttgtt aattttgggt ccaataagat tgaaagtttt     600

caatcattta aacatgtaat gtaacatagc tattgctcat cactactgtt tttttcccct     660

agtttgtttg ctcctgttc                                                  679
```

```
<210> SEQ ID NO 70
<211> LENGTH: 163
<212> TYPE: PRT
<213> ORGANISM: Gossypium hirsutum
<220> FEATURE:
<221> NAME/KEY: misc_feature
<223> OTHER INFORMATION: Ceres CLONE ID no. 1916866
<220> FEATURE:
<221> NAME/KEY: misc_feature
<222> LOCATION: (13)..(152)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7
```

<400> SEQUENCE: 70

```
Met Ala Thr Tyr Glu Gly Lys Val Phe Thr Glu Glu Gln Glu Ala Leu
1               5                   10                  15

Val Val Lys Ser Trp Thr Val Met Lys Lys Asn Ala Ala Glu Leu Gly
            20                  25                  30

Leu Lys Phe Phe Leu Lys Ile Phe Glu Ile Ala Pro Ser Ala Lys Lys
        35                  40                  45

Leu Phe Ser Phe Leu Arg Asp Ser Asn Val Pro Leu Glu Gln Asn Thr
    50                  55                  60

Lys Leu Lys Pro His Ala Met Ser Val Phe Val Met Thr Cys Glu Ser
65                  70                  75                  80

Ala Val Gln Leu Arg Lys Ala Gly Lys Val Thr Val Arg Glu Ser Asn
                85                  90                  95

Leu Lys Lys Leu Gly Ala Thr His Phe Lys Tyr Gly Val Val Asp Glu
            100                 105                 110

His Phe Glu Val Thr Lys Phe Ala Leu Leu Glu Thr Ile Lys Glu Ala
        115                 120                 125

Val Pro Asp Met Trp Ser Asp Glu Met Lys Asn Ala Trp Gly Glu Ala
    130                 135                 140

Tyr Asp Arg Leu Val Ala Ala Ile Lys Ile Glu Met Lys Ala Cys Ser
145                 150                 155                 160

Gln Ala Ala
```

<210> SEQ ID NO 71
<211> LENGTH: 1003
<212> TYPE: DNA
<213> ORGANISM: Panicum virgatum
<220> FEATURE:
<221> NAME/KEY: misc_feature
<223> OTHER INFORMATION: Ceres CLONE ID no.1950105
<220> FEATURE:
<221> NAME/KEY: misc_feature
<223> OTHER INFORMATION: Encodes the protein at SEQ ID NO: 72

<400> SEQUENCE: 71

```
atcgccacaa gttcgcgatc tctcgatttc acaaatcgcc gagaagaccc gagcagagaa     60

gttccctccg atcgccttgc caagatgcag atctttgtga agacactcac tggcaagact    120

atcacccttg aggtggagtc ttctgacaca attgacaatg tcaaggcaaa gatccaggac    180

aaggaaggga ttcctccaga ccagcagcgc cttatcttcg ctggcaagca gcttgaggat    240

ggccgtacac ttgcagatta caacattcag aaggagtcca cactgcacct tgtcctcagg    300

ctgcgtggag gcatgcagat tttcgtgaag accctcactg gcaagacgat caccctggag    360

gtggagtcat ctgacaccat cgacaatgtg aaggcaaaga tccaggacaa ggagggcatc    420

ccccctgacc agcagcgcct catctttgca ggcaagcagt tggaggatgg gcgaactctg    480

gctgactaya atatccagaa agaatcmacc ctgcacctsg tsctccgcct gcgtggtgga    540

atgcagatct ttgtgaagac gcttaccggc aagaccatca ccttggaggt ggagtcttcg    600

gacaccatcg acaatgtgaa ggcgaagatt caggacaagg agggcattcc tccggaccag    660

crgcgcctca tctttgctgg caagcagcta gaggacgggc gtaccctggc ggattacaac    720

atccagaagg agtccaccct ccaccttgtc ctgcgcctcc gtggtggttt ctgagcctag    780

tgctcctgag ttgccttttg tcgttatggt caacctctgg tttaagtcgt gtgaactctc    840

tgcattgcgt tgctagtgtc tggttgtggt tgtaataaga acatgaagaa catgttgctg    900
```

```
tggatcacat gacttttttt ttttgaaccg gaagatcaca tgactttcat ggctttaagt    960

tcctgaactc tgaaatctgg accccctttt aagctctgaa ctc                     1003


<210> SEQ ID NO 72
<211> LENGTH: 229
<212> TYPE: PRT
<213> ORGANISM: Panicum virgatum
<220> FEATURE:
<221> NAME/KEY: misc_feature
<223> OTHER INFORMATION: Ceres CLONE ID no. 1950105
<220> FEATURE:
<221> NAME/KEY: misc_feature
<222> LOCATION: (1)..(74)
<223> OTHER INFORMATION: Pfam Name: ubiquitin
      Pfam Description: Ubiquitin family
<220> FEATURE:
<221> NAME/KEY: misc_feature
<222> LOCATION: (77)..(150)
<223> OTHER INFORMATION: Pfam Name: ubiquitin
      Pfam Description: Ubiquitin family
<220> FEATURE:
<221> NAME/KEY: misc_feature
<222> LOCATION: (153)..(226)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional Homolog of Ceres CLONE ID no. 2403
      Given in SEQ ID NO: 40
<220> FEATURE:
<221> NAME/KEY: misc_feature
<222> LOCATION: (135)..(135)
<223> OTHER INFORMATION: Xaa is any aa, unknown, or other
<220> FEATURE:
<221> NAME/KEY: misc_feature
<222> LOCATION: (141)..(141)
<223> OTHER INFORMATION: Xaa is any aa, unknown, or other
<220> FEATURE:
<221> NAME/KEY: misc_feature
<222> LOCATION: (145)..(145)
<223> OTHER INFORMATION: Xaa is any aa, unknown, or other
<220> FEATURE:
<221> NAME/KEY: misc_feature
<222> LOCATION: (146)..(146)
<223> OTHER INFORMATION: Xaa is any aa, unknown, or other
<220> FEATURE:
<221> NAME/KEY: misc_feature
<222> LOCATION: (193)..(193)
<223> OTHER INFORMATION: Xaa is any aa, unknown, or other

<400> SEQUENCE: 72

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Arg Gly Gly Met Gln Ile Phe
65                  70                  75                  80

Val Lys Thr Leu Thr Gly Lys Thr Ile Thr Leu Glu Val Glu Ser Ser
                85                  90                  95

Asp Thr Ile Asp Asn Val Lys Ala Lys Ile Gln Asp Lys Glu Gly Ile
            100                 105                 110

Pro Pro Asp Gln Gln Arg Leu Ile Phe Ala Gly Lys Gln Leu Glu Asp
        115                 120                 125

Gly Arg Thr Leu Ala Asp Xaa Asn Ile Gln Lys Glu Xaa Thr Leu His
```

```
    130                 135                 140

Xaa Xaa Leu Arg Leu Arg Gly Gly Met Gln Ile Phe Val Lys Thr Leu
145                 150                 155                 160

Thr Gly Lys Thr Ile Thr Leu Glu Val Glu Ser Ser Asp Thr Ile Asp
                165                 170                 175

Asn Val Lys Ala Lys Ile Gln Asp Lys Glu Gly Ile Pro Pro Asp Gln
            180                 185                 190

Xaa Arg Leu Ile Phe Ala Gly Lys Gln Leu Glu Asp Gly Arg Thr Leu
        195                 200                 205

Ala Asp Tyr Asn Ile Gln Lys Glu Ser Thr Leu His Leu Val Leu Arg
    210                 215                 220

Leu Arg Gly Gly Phe
225
```

<210> SEQ ID NO 73
<211> LENGTH: 724
<212> TYPE: DNA
<213> ORGANISM: Panicum virgatum
<220> FEATURE:
<221> NAME/KEY: misc_feature
<223> OTHER INFORMATION: Ceres CLONE ID no.1990746
<220> FEATURE:
<221> NAME/KEY: misc_feature
<222> LOCATION: (623)..(623)
<223> OTHER INFORMATION: n is a, c, t, g, unknown, or other
<220> FEATURE:
<221> NAME/KEY: misc_feature
<222> LOCATION: (624)..(624)
<223> OTHER INFORMATION: n is a, c, t, g, unknown, or other
<220> FEATURE:
<221> NAME/KEY: misc_feature
<222> LOCATION: (625)..(625)
<223> OTHER INFORMATION: n is a, c, t, g, unknown, or other
<220> FEATURE:
<221> NAME/KEY: misc_feature
<223> OTHER INFORMATION: Encodes the protein at SEQ ID NO: 74

<400> SEQUENCE: 73

```
acacagatac actcgtcgat ccaccagacc accactgtcc agtgctcggc tcggttacgc     60

acgcacgcac acaaatagga gtacctgttt tacaccacca agatactagc aagcccaagc    120

cgagtcgaca aacaagcagc aggaagaggc atggcgctcg cggaggggaa cggcgcggcc    180

atcttcggcg aggaacagga ggcgctggtg ctcaagtcgt gggccctcat gaagaaggac    240

tcggccgacc tcggcctccg cttcttcctc aagatcttcg agatcgcgcc gtcggcgaag    300

cagatgttct cgttcctgcg cgactccgac gtgccgctgg agaagaaccc caagctcaag    360

acccacgcca tgtccgtctt cgtcatgacc tgcgaggcgg cagtgcagct acggaaggcc    420

gggaaggtca ccgtcaggga gacgacgctc aagcggctgg gcgcaacgca cttcaagtac    480

ggcgtcgccg acggccactt cgaggtgaca aggttcgcgc tgctggagac gataaaggag    540

gcgcttcccg ccgacatgtg gagcctggag atgaagaacg cctggagcga ggcttacaac    600

cagctcgtgg cggccatcaa gcnnnagatg aagcctgccg catgatgctg catgctgcta    660

catactcggc ctccgagtcc cccctacgat gcaccaccat ctcccagttc ttcatcgcta    720

tttt                                                                 724
```

<210> SEQ ID NO 74
<211> LENGTH: 164
<212> TYPE: PRT
<213> ORGANISM: Panicum virgatum
<220> FEATURE:
<221> NAME/KEY: misc_feature
<223> OTHER INFORMATION: Ceres CLONE ID no. 1990746
<220> FEATURE:
<221> NAME/KEY: misc_feature
<222> LOCATION: (16)..(156)
<223> OTHER INFORMATION: Pfam Name: Globin
Pfam Description: Globin
<220> FEATURE:
<221> NAME/KEY: misc_feature
<223> OTHER INFORMATION: Functional homolog of Ceres Clone ID no. 30469
given in SEQ ID NO: 7
<220> FEATURE:
<221> NAME/KEY: misc_feature
<222> LOCATION: (158)..(158)
<223> OTHER INFORMATION: Xaa is any aa, unknown, or other
<220> FEATURE:
<221> NAME/KEY: misc_feature
<222> LOCATION: (159)..(159)
<223> OTHER INFORMATION: Xaa is any aa, unknown, or other

<400> SEQUENCE: 74

```
Met Ala Leu Ala Glu Gly Asn Gly Ala Ala Ile Phe Gly Glu Glu Gln
1               5                   10                  15

Glu Ala Leu Val Leu Lys Ser Trp Ala Leu Met Lys Lys Asp Ser Ala
            20                  25                  30

Asp Leu Gly Leu Arg Phe Phe Leu Lys Ile Phe Glu Ile Ala Pro Ser
        35                  40                  45

Ala Lys Gln Met Phe Ser Phe Leu Arg Asp Ser Asp Val Pro Leu Glu
    50                  55                  60

Lys Asn Pro Lys Leu Lys Thr His Ala Met Ser Val Phe Val Met Thr
65                  70                  75                  80

Cys Glu Ala Ala Val Gln Leu Arg Lys Ala Gly Lys Val Thr Val Arg
                85                  90                  95

Glu Thr Thr Leu Lys Arg Leu Gly Ala Thr His Phe Lys Tyr Gly Val
            100                 105                 110

Ala Asp Gly His Phe Glu Val Thr Arg Phe Ala Leu Leu Glu Thr Ile
        115                 120                 125

Lys Glu Ala Leu Pro Ala Asp Met Trp Ser Leu Glu Met Lys Asn Ala
    130                 135                 140

Trp Ser Glu Ala Tyr Asn Gln Leu Val Ala Ala Ile Lys Xaa Xaa Met
145                 150                 155                 160

Lys Pro Ala Ala
```

<210> SEQ ID NO 75
<211> LENGTH: 696
<212> TYPE: DNA
<213> ORGANISM: Panicum virgatum
<220> FEATURE:
<221> NAME/KEY: misc_feature
<223> OTHER INFORMATION: Ceres CLONE ID no.2007485
<220> FEATURE:
<221> NAME/KEY: misc_feature
<223> OTHER INFORMATION: Encodes the protein at SEQ ID NO: 76

<400> SEQUENCE: 75

```
agagcagggg gatggaagaa aataaactac tggccaaacc ctagccgagc cccgggtccg     60

ctcaccgcct tcccaccccc ccacccaccc acctgccccc cccccccccc cgccctcgcc    120

gtccgcgatg cgccgggcga agccgccgca gccgcagccg tcgccgtcgc cggagatccg    180

gtaccgcggc gtgcggaggc ggccatcggg gcgctacgcc gccgagatcc gggacccggc    240

caagaagacc ccgatctggc tcggcacctt cgactccgcc gaggccgccg cgcgcgccta    300

cgacgccgcc gcccgatccc tccgcgggcc caccgcccgc accaacttcc ccagcgccgc    360
```

```
ggcccccgcg ccgcggcaca gcaggccccc cgccccctcc gccgccgcgc aggcggctgc    420

cgcggcggca gcggccacgt ccagccacag cagcaccata gagtcgtgga gcgacggcgc    480

gacccgcgcc gcgctggcgc gtagcgctgc ctccgtcctg gcgcgcagcg ccgctccgac    540

ggaggaggaa gacgaggact gccgcagcta ctgcggatcc tcgtcgtccg tcctctgcga    600

agacactggg ggcgacgatg cggccgcctc ccgcgcgccc ctgccgttcg atctgaacct    660

gccgccgcct catgacgcgg cctccgagac cgatca                              696
```

```
<210> SEQ ID NO 76
<211> LENGTH: 201
<212> TYPE: PRT
<213> ORGANISM: Panicum virgatum
<220> FEATURE:
<221> NAME/KEY: misc_feature
<223> OTHER INFORMATION: Ceres CLONE ID no. 2007485
<220> FEATURE:
<221> NAME/KEY: misc_feature
<222> LOCATION: (17)..(80)
<223> OTHER INFORMATION: Pfam Name: AP2
      Pfam Description: AP2 domain
<220> FEATURE:
<221> NAME/KEY: misc_feature
<223> OTHER INFORMATION: Functional Homolog of Ceres CLONE ID no. 674166
      Given in SEQ ID NO: 42

<400> SEQUENCE: 76

Met Arg Arg Ala Lys Pro Pro Gln Pro Gln Pro Ser Pro Ser Pro Glu
1               5                   10                  15

Ile Arg Tyr Arg Gly Val Arg Arg Arg Pro Ser Gly Arg Tyr Ala Ala
            20                  25                  30

Glu Ile Arg Asp Pro Ala Lys Lys Thr Pro Ile Trp Leu Gly Thr Phe
        35                  40                  45

Asp Ser Ala Glu Ala Ala Ala Arg Ala Tyr Asp Ala Ala Ala Arg Ser
    50                  55                  60

Leu Arg Gly Pro Thr Ala Arg Thr Asn Phe Pro Ser Ala Ala Ala Pro
65                  70                  75                  80

Ala Pro Arg His Ser Arg Pro Pro Ala Pro Ser Ala Ala Ala Gln Ala
                85                  90                  95

Ala Ala Ala Ala Ala Ala Ala Thr Ser Ser His Ser Ser Thr Ile Glu
            100                 105                 110

Ser Trp Ser Asp Gly Ala Thr Arg Ala Ala Leu Ala Arg Ser Ala Ala
        115                 120                 125

Ser Val Leu Ala Arg Ser Ala Ala Pro Thr Glu Glu Glu Asp Glu Asp
    130                 135                 140

Cys Arg Ser Tyr Cys Gly Ser Ser Ser Ser Val Leu Cys Glu Asp Thr
145                 150                 155                 160

Gly Gly Asp Asp Ala Ala Ala Ser Arg Ala Pro Leu Pro Phe Asp Leu
                165                 170                 175

Asn Leu Pro Pro Pro His Asp Ala Ala Ser Glu Thr Asp Gln Met Gly
            180                 185                 190

Ala Arg Tyr Asp Thr Leu Leu Arg Leu
        195                 200
```

```
<210> SEQ ID NO 77
<211> LENGTH: 698
<212> TYPE: DNA
<213> ORGANISM: Panicum virgatum
<220> FEATURE:
<221> NAME/KEY: misc_feature
<223> OTHER INFORMATION: Ceres CLONE ID no.2033803
```

```
<220> FEATURE:
<221> NAME/KEY: misc_feature
<223> OTHER INFORMATION: Encodes the protein at SEQ ID NO: 78

<400> SEQUENCE: 77

acacagatac attcgtcgat ccaccagacc accactgtcc agtgctcggc tcggttacgc      60

acgcacgcac acaaatagga gtacctgttt tacaccaaga tactagcaag cccaagccga     120

gtcgacaaac aagcagcagg aagaggcatg gcgctcgcgg aggggaacgg cgcggccatc     180

ttcggcgagg agcaggaggc gctggtgctc aagtcgtggg ccctcatgaa gaaggactcg     240

gccgacctcg gcctccgctt cttcctcaag atcttcgaga tcgcgccgtc ggcgaagcag     300

atgttctcgt tcctgcgcga ctccgacgtg ccgctggaga agaaccccaa gctcaagacc     360

cacgccatgt ccgtcttcgt catgacctgc gaggcggcag cgcagctacg gaaggccggg     420

aaggtcaccg tcagggagac gacgctcaag cggctgggcg caacgcactt caagtacggc     480

gtcgccgacg gccacttcga ggtgacaagg ttcgcgcttc ccgccgactt gtggagcctg     540

gagatgaaga acgcctggag cgaggcttac aaccagctcg tggcggccat caagcaggag     600

atgaagcctg ccgcatgatg ctgcatgctg ctacatactc ggcctccgag ttccccctac     660

gatgcaccac catctccaag ttctttcatt gtcttgtg                             698


<210> SEQ ID NO 78
<211> LENGTH: 156
<212> TYPE: PRT
<213> ORGANISM: Panicum virgatum
<220> FEATURE:
<221> NAME/KEY: misc_feature
<223> OTHER INFORMATION: Ceres CLONE ID no. 2033803
<220> FEATURE:
<221> NAME/KEY: misc_feature
<222> LOCATION: (16)..(148)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 78

Met Ala Leu Ala Glu Gly Asn Gly Ala Ala Ile Phe Gly Glu Glu Gln
1               5                   10                  15

Glu Ala Leu Val Leu Lys Ser Trp Ala Leu Met Lys Lys Asp Ser Ala
            20                  25                  30

Asp Leu Gly Leu Arg Phe Phe Leu Lys Ile Phe Glu Ile Ala Pro Ser
        35                  40                  45

Ala Lys Gln Met Phe Ser Phe Leu Arg Asp Ser Asp Val Pro Leu Glu
    50                  55                  60

Lys Asn Pro Lys Leu Lys Thr His Ala Met Ser Val Phe Val Met Thr
65                  70                  75                  80

Cys Glu Ala Ala Ala Gln Leu Arg Lys Ala Gly Lys Val Thr Val Arg
                85                  90                  95

Glu Thr Thr Leu Lys Arg Leu Gly Ala Thr His Phe Lys Tyr Gly Val
            100                 105                 110

Ala Asp Gly His Phe Glu Val Thr Arg Phe Ala Leu Pro Ala Asp Leu
        115                 120                 125

Trp Ser Leu Glu Met Lys Asn Ala Trp Ser Glu Ala Tyr Asn Gln Leu
    130                 135                 140

Val Ala Ala Ile Lys Gln Glu Met Lys Pro Ala Ala
145                 150                 155
```

```
<210> SEQ ID NO 79
<211> LENGTH: 724
<212> TYPE: DNA
<213> ORGANISM: Panicum virgatum
<220> FEATURE:
<221> NAME/KEY: misc_feature
<223> OTHER INFORMATION: Ceres CLONE ID no.2034916
<220> FEATURE:
<221> NAME/KEY: misc_feature
<223> OTHER INFORMATION: Encodes the protein at SEQ ID NO: 80

<400> SEQUENCE: 79

aatccaatct cccccgatcc ccaatcgcga attcccctct ccggcaggcg aagcaatcga      60

ggggcaccct ttcatctcgt caagatgcag atctttgtga agaccctcac tggtaagacc     120

atcaccctcg aggttgagtc ctcggatacc attgacaacg tcaaggctaa aatccaggac     180

aaggagggga tccctccgga ccagcagcgc ctcatctttg ccggcaagca gctcgaagat     240

gggaggacgc ttgctgacta caacatccag aaggagtcca ccctccacct cgtgctcagg     300

ctcaggggtg gtatgcagat ctttgtcaag actctcaccg gcaagacgat tactcttgag     360

gttgagtcct cggacacgat cgacaatgta aaggtgaaga tccaagacaa ggaggggatc     420

ccaccggacc agcagcgcct catctttgcc ggcaagcagc tcgaggatgg ccgcactctg     480

gctgactaca acattcagaa agagtcgacc cttcaccttg tgctcaggct gaggggaggc     540

atgcaaatat ttgtcaagac tctgactggc aagaccatca cgcttgaggt ggagtcgtct     600

gacaccattg ataatgtgaa ggcgaagatc caagacaagg agggcatccc gccggaccag     660

cagcgcctga tctttgccgg taagcagctg gaggatggtc gtaccctggc agactataat     720

attc                                                                  724

<210> SEQ ID NO 80
<211> LENGTH: 213
<212> TYPE: PRT
<213> ORGANISM: Panicum virgatum
<220> FEATURE:
<221> NAME/KEY: misc_feature
<223> OTHER INFORMATION: Ceres CLONE ID no. 2034916
<220> FEATURE:
<221> NAME/KEY: misc_feature
<222> LOCATION: (1)..(74)
<223> OTHER INFORMATION: Pfam Name: ubiquitin
      Pfam Description: Ubiquitin family
<220> FEATURE:
<221> NAME/KEY: misc_feature
<222> LOCATION: (77)..(150)
<223> OTHER INFORMATION: Pfam Name: ubiquitin
      Pfam Description: Ubiquitin family
<220> FEATURE:
<221> NAME/KEY: misc_feature
<222> LOCATION: (153)..(213)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional Homolog of Ceres CLONE ID no. 2403
      Given in SEQ ID NO: 40

<400> SEQUENCE: 80

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45
```

```
Gln Leu Glu Asp Gly Arg Thr Leu Ala Asp Tyr Asn Ile Gln Lys Glu
    50                  55                  60

Ser Thr Leu His Leu Val Leu Arg Leu Arg Gly Gly Met Gln Ile Phe
65                  70                  75                  80

Val Lys Thr Leu Thr Gly Lys Thr Ile Thr Leu Glu Val Glu Ser Ser
                85                  90                  95

Asp Thr Ile Asp Asn Val Lys Val Lys Ile Gln Asp Lys Glu Gly Ile
            100                 105                 110

Pro Pro Asp Gln Gln Arg Leu Ile Phe Ala Gly Lys Gln Leu Glu Asp
        115                 120                 125

Gly Arg Thr Leu Ala Asp Tyr Asn Ile Gln Lys Glu Ser Thr Leu His
    130                 135                 140

Leu Val Leu Arg Leu Arg Gly Gly Met Gln Ile Phe Val Lys Thr Leu
145                 150                 155                 160

Thr Gly Lys Thr Ile Thr Leu Glu Val Glu Ser Ser Asp Thr Ile Asp
                165                 170                 175

Asn Val Lys Ala Lys Ile Gln Asp Lys Glu Gly Ile Pro Pro Asp Gln
            180                 185                 190

Gln Arg Leu Ile Phe Ala Gly Lys Gln Leu Glu Asp Gly Arg Thr Leu
        195                 200                 205

Ala Asp Tyr Asn Ile
    210
```

<210> SEQ ID NO 81
<211> LENGTH: 1194
<212> TYPE: DNA
<213> ORGANISM: Glycine max
<220> FEATURE:
<221> NAME/KEY: misc_feature
<223> OTHER INFORMATION: Ceres CLONE ID no.651581
<220> FEATURE:
<221> NAME/KEY: misc_feature
<222> LOCATION: (678)..(678)
<223> OTHER INFORMATION: n is a, c, t, g, unknown, or other
<220> FEATURE:
<221> NAME/KEY: misc_feature
<222> LOCATION: (679)..(679)
<223> OTHER INFORMATION: n is a, c, t, g, unknown, or other
<220> FEATURE:
<221> NAME/KEY: misc_feature
<223> OTHER INFORMATION: Encodes the protein at SEQ ID NO: 82

<400> SEQUENCE: 81

```
gtgtagttga aggagcagaa gaagaagaag agaaggtggt accgccttca attctctttt     60

tctctctcca tttctcatcc tcatcatctt attattcctc ttccatctct attctccata    120

acacccacca caccacttgt gaaaaacctc attaatatca cacactgaca tgtatctctg    180

agctccaatc caatacaaga ccacaccttg tcgtgtcgga cgaaccttgg tgtctgtttt    240

tttttttttt tttcattatt ttctccgaag agatgaggaa gggcaraggt ggaggcgcct    300

cggcggcggc ggtggatgtg aacggatcca ttttaaagga gcctcggtac cggggcgtga    360

ggaagagacc gtgggggaga ttcgccgcgg agatcagaga cccgttgaag aaagccaggg    420

tttggttggg aaccttcaat tctgccgagg atgctgctcg tgcctacrac gccgccgctc    480

ggactctccg aggtcccaag gccaaaacaa atttcccccc tctctcacct ttttgctatc    540

cacaccccac caccgatcct ttcttstaca ctggtttcca cgatcaacac caccaccaca    600

acaacaacaa ccttaacaac cctcaaagac ccacttcaag tggcatgagt agcmccgttg    660

agtccttcag tgggcccnnc ccttttttccc ccaccaccac cmctaccacc acaaccacaa    720
```

```
ctgcgacgcc gtttttgact gctacgcgga gatacccgcg cactcccccct cttgtccctg    780

aagactgcca cagtgactgc gactcttcct cctccgtcgt tgacgacggc gacgacaaca    840

tcgtttcgtc gtcgtttcga cctcccttgc cgtttgatct caacgcgctg ccgtttgatg    900

atgctgccgc ggatgatgat ctacgccgca ccgcgctttg tctctgatga tgattatcgt    960

gcgatgatga tttttaattt ctcatttttt tacttgattt ttttgttatt gctatgcaga   1020

agaaatatat atttaaaatg atgatcagat gtaagattat ggtaatatga tcttaattct   1080

gtgagaggaa gattccgtgt tggttatatt ttcttctttt tattattttt ttaaacattt   1140

ttatttagaa ggaaatattg aatgaaaaga aaaaagagaa agtaattatg atcg         1194


<210> SEQ ID NO 82
<211> LENGTH: 224
<212> TYPE: PRT
<213> ORGANISM: Glycine max
<220> FEATURE:
<221> NAME/KEY: misc_feature
<223> OTHER INFORMATION: Ceres CLONE ID no. 651581
<220> FEATURE:
<221> NAME/KEY: misc_feature
<222> LOCATION: (24)..(87)
<223> OTHER INFORMATION: Pfam Name: AP2
      Pfam Description: AP2 domain
<220> FEATURE:
<221> NAME/KEY: misc_feature
<223> OTHER INFORMATION: Functional Homolog of Ceres CLONE ID no. 674166
      Given in SEQ ID NO: 42
<220> FEATURE:
<221> NAME/KEY: misc_feature
<222> LOCATION: (137)..(137)
<223> OTHER INFORMATION: Xaa is any aa, unknown, or other

<400> SEQUENCE: 82

Met Arg Lys Gly Arg Gly Gly Gly Ala Ser Ala Ala Ala Val Asp Val
1               5                   10                  15

Asn Gly Ser Ile Leu Lys Glu Pro Arg Tyr Arg Gly Val Arg Lys Arg
            20                  25                  30

Pro Trp Gly Arg Phe Ala Ala Glu Ile Arg Asp Pro Leu Lys Lys Ala
        35                  40                  45

Arg Val Trp Leu Gly Thr Phe Asn Ser Ala Glu Asp Ala Ala Arg Ala
    50                  55                  60

Tyr Asp Ala Ala Ala Arg Thr Leu Arg Gly Pro Lys Ala Lys Thr Asn
65                  70                  75                  80

Phe Pro Pro Leu Ser Pro Phe Cys Tyr Pro His Pro Thr Thr Asp Pro
                85                  90                  95

Phe Phe Tyr Thr Gly Phe His Asp Gln His His His His Asn Asn Asn
            100                 105                 110

Asn Leu Asn Asn Pro Gln Arg Pro Thr Ser Ser Gly Met Ser Ser Thr
        115                 120                 125

Val Glu Ser Phe Ser Gly Pro Arg Xaa Phe Ser Pro Thr Thr Thr Thr
    130                 135                 140

Thr Thr Thr Thr Thr Thr Ala Thr Pro Phe Leu Thr Ala Thr Arg Arg
145                 150                 155                 160

Tyr Pro Arg Thr Pro Pro Leu Val Pro Glu Asp Cys His Ser Asp Cys
                165                 170                 175

Asp Ser Ser Ser Ser Val Val Asp Asp Gly Asp Asp Asn Ile Val Ser
            180                 185                 190

Ser Ser Phe Arg Pro Pro Leu Pro Phe Asp Leu Asn Ala Leu Pro Phe
        195                 200                 205
```

```
Asp Asp Ala Ala Ala Asp Asp Asp Leu Arg Arg Thr Ala Leu Cys Leu
    210                 215                 220


<210> SEQ ID NO 83
<211> LENGTH: 184
<212> TYPE: PRT
<213> ORGANISM: Oryza sativa subsp. indica
<220> FEATURE:
<221> NAME/KEY: misc_feature
<223> OTHER INFORMATION: Public GI ID no. 125550159
<220> FEATURE:
<221> NAME/KEY: misc_feature
<222> LOCATION: (7)..(70)
<223> OTHER INFORMATION: Pfam Name: AP2
      Pfam Description: AP2 domain
<220> FEATURE:
<221> NAME/KEY: misc_feature
<223> OTHER INFORMATION: Functional Homolog of Ceres CLONE ID no. 674166
      Given in SEQ ID NO: 42

<400> SEQUENCE: 83

Met Cys Glu Ala Ala Ala Pro Arg Tyr Arg Gly Val Arg Lys Arg Pro
1               5                   10                  15

Trp Gly Arg Phe Ala Ala Glu Ile Arg Asp Pro Ala Lys Arg Ala Arg
            20                  25                  30

Val Trp Leu Gly Thr Tyr Asp Ser Ala Glu Ala Ala Ala Arg Ala Tyr
        35                  40                  45

Asp Val Ala Ala Arg Asn Leu Arg Gly Pro Leu Ala Arg Thr Asn Phe
    50                  55                  60

Pro Leu Val Ser Ser Leu Pro Leu Pro Ser Pro His Tyr His Leu Pro
65                  70                  75                  80

Gly Lys Ala Ala Ala Ala Ala Pro Pro Val Ala Gly Pro Ala Cys Ser
                85                  90                  95

Ala Ser Ser Thr Val Glu Ser Ser Ser Gly Pro Arg Gly Pro Arg Pro
            100                 105                 110

Ala Ala Thr Ala Ala Ala Val Pro Arg Arg Arg Val Pro Arg Pro Ala
        115                 120                 125

Pro Pro Ala Pro Asp Ala Gly Cys His Ser Asp Cys Ala Ser Ser Ala
    130                 135                 140

Ser Val Val Asp Asp Ala Asp Asp Ala Ser Thr Val Arg Ser Arg Val
145                 150                 155                 160

Ala Ala Phe Asp Leu Asn Leu Pro Pro Pro Leu Asp Arg Asp His Val
                165                 170                 175

Asp Leu Cys Thr Asp Leu Arg Leu
            180


<210> SEQ ID NO 84
<211> LENGTH: 225
<212> TYPE: PRT
<213> ORGANISM: Arabidopsis thaliana
<220> FEATURE:
<221> NAME/KEY: misc_feature
<223> OTHER INFORMATION: Public GI ID no. 15223609
<220> FEATURE:
<221> NAME/KEY: misc_feature
<222> LOCATION: (26)..(89)
<223> OTHER INFORMATION: Pfam Name: AP2
      Pfam Description: AP2 domain
<220> FEATURE:
<221> NAME/KEY: misc_feature
<223> OTHER INFORMATION: Functional Homolog of Ceres CLONE ID no. 674166
      Given in SEQ ID NO: 42

<400> SEQUENCE: 84
```

```
Met Arg Arg Gly Arg Gly Ser Ser Ala Val Ala Gly Pro Thr Val Val
1               5                   10                  15

Ala Ala Ile Asn Gly Ser Val Lys Glu Ile Arg Phe Arg Gly Val Arg
            20                  25                  30

Lys Arg Pro Trp Gly Arg Phe Ala Ala Glu Ile Arg Asp Pro Trp Lys
        35                  40                  45

Lys Ala Arg Val Trp Leu Gly Thr Phe Asp Ser Ala Glu Glu Ala Ala
    50                  55                  60

Arg Ala Tyr Asp Ser Ala Ala Arg Asn Leu Arg Gly Pro Lys Ala Lys
65                  70                  75                  80

Thr Asn Phe Pro Ile Asp Ser Ser Ser Pro Pro Pro Pro Asn Leu Arg
                85                  90                  95

Phe Asn Gln Ile Arg Asn Gln Asn Gln Asn Gln Val Asp Pro Phe Met
            100                 105                 110

Asp His Arg Leu Phe Thr Asp His Gln Gln Gln Phe Pro Ile Val Asn
        115                 120                 125

Arg Pro Thr Ser Ser Ser Met Ser Ser Thr Val Glu Ser Phe Ser Gly
    130                 135                 140

Pro Arg Pro Thr Thr Met Lys Pro Ala Thr Thr Lys Arg Tyr Pro Arg
145                 150                 155                 160

Thr Pro Pro Val Val Pro Glu Asp Cys His Ser Asp Cys Asp Ser Ser
                165                 170                 175

Ser Ser Val Ile Asp Asp Asp Asp Asp Ile Ala Ser Ser Ser Arg Arg
            180                 185                 190

Arg Asn Pro Pro Phe Gln Phe Asp Leu Asn Phe Pro Pro Leu Asp Cys
        195                 200                 205

Val Asp Leu Phe Asn Gly Ala Asp Asp Leu His Cys Thr Asp Leu Arg
    210                 215                 220

Leu
225
```

<210> SEQ ID NO 85
<211> LENGTH: 164
<212> TYPE: PRT
<213> ORGANISM: Arabidopsis thaliana
<220> FEATURE:
<221> NAME/KEY: misc_feature
<223> OTHER INFORMATION: Public GI ID no. 30683885
<220> FEATURE:
<221> NAME/KEY: misc_feature
<223> OTHER INFORMATION: Functional Homolog of Ceres CLONE ID no. 30087 Given in SEQ ID NO: 2

<400> SEQUENCE: 85

```
Met Ala Ser Ser Phe Ser Ser Gln Ala Phe Phe Leu Leu Thr Leu Ser
1               5                   10                  15

Met Val Leu Ile Pro Phe Ser Leu Ala Gln Ala Pro Met Met Ala Pro
            20                  25                  30

Ser Gly Ser Met Ser Met Pro Pro Met Ser Ser Gly Gly Gly Ser Ser
        35                  40                  45

Val Pro Pro Pro Val Met Ser Pro Met Pro Met Met Thr Pro Pro Pro
    50                  55                  60

Met Pro Met Thr Pro Pro Pro Met Pro Met Thr Pro Pro Pro Met Pro
65                  70                  75                  80

Met Ala Pro Pro Pro Met Pro Met Ala Ser Pro Pro Met Met Pro Met
                85                  90                  95
```

```
Thr Pro Ser Thr Ser Pro Ser Pro Leu Thr Val Pro Asp Met Pro Ser
            100                 105                 110

Pro Pro Met Pro Ser Gly Met Glu Ser Ser Pro Ser Pro Gly Pro Met
        115                 120                 125

Pro Pro Ala Met Ala Ala Ser Pro Asp Ser Gly Ala Phe Asn Val Arg
    130                 135                 140

Asn Asn Val Val Thr Leu Ser Cys Val Val Gly Val Val Ala Ala His
145                 150                 155                 160

Phe Leu Leu Val


<210> SEQ ID NO 86
<211> LENGTH: 218
<212> TYPE: PRT
<213> ORGANISM: Pisum sativum
<220> FEATURE:
<221> NAME/KEY: misc_feature
<223> OTHER INFORMATION: Public GI ID no. 56384582
<220> FEATURE:
<221> NAME/KEY: misc_feature
<222> LOCATION: (21)..(84)
<223> OTHER INFORMATION: Pfam Name: AP2
      Pfam Description: AP2 domain
<220> FEATURE:
<221> NAME/KEY: misc_feature
<223> OTHER INFORMATION: Functional Homolog of Ceres CLONE ID no. 674166
      Given in SEQ ID NO: 42

<400> SEQUENCE: 86

Met Gly Arg Gly Gly Ala Thr Thr Ala Ala Ala Ala Val Glu Pro Val
1               5                   10                  15

Phe Phe Lys Glu Pro Arg Tyr Arg Gly Val Arg Lys Arg Pro Trp Gly
            20                  25                  30

Arg Phe Ala Ala Glu Ile Arg Asp Pro Leu Lys Lys Ala Arg Val Trp
        35                  40                  45

Leu Gly Thr Phe Asp Thr Ala Glu Glu Ala Ala Arg Ala Tyr Asp Thr
    50                  55                  60

Ala Ala Arg Asn Leu Arg Gly Pro Lys Ala Lys Thr Asn Phe Pro Leu
65                  70                  75                  80

Ala Gln Pro Phe Tyr Gln Asn Pro Glu Ala Gly Asn Pro Phe Gly Glu
                85                  90                  95

Leu Arg Phe Tyr Ala Gly Gly Ala Gly Glu Gly Phe Gln Asp His Arg
            100                 105                 110

Arg Pro Thr Ser Ser Gly Met Ser Ser Thr Val Glu Ser Phe Gly Gly
        115                 120                 125

Pro Arg Pro Val Arg Pro Pro Met Pro Pro Ser Ala Val Thr Gly Arg
    130                 135                 140

Arg Tyr Pro Arg Thr Pro Pro Val Ala Pro Gly Asp Cys Arg Ser Asp
145                 150                 155                 160

Cys Asp Ser Ser Ser Ser Val Val Asp Asp Ala Asp Asn Asp Asn Ala
                165                 170                 175

Ala Ser Ser Thr Met Leu Ser Phe Lys Arg Gln Pro Leu Pro Phe Asp
            180                 185                 190

Leu Asn Ala Pro Pro Leu Glu Glu Gly Asp Val Ala Asn Gly Leu Gly
        195                 200                 205

Glu Asp Leu His Cys Thr Leu Leu Cys Leu
    210                 215


<210> SEQ ID NO 87
<211> LENGTH: 225
```

```
<212> TYPE: PRT
<213> ORGANISM: Nicotiana tabacum
<220> FEATURE:
<221> NAME/KEY: misc_feature
<223> OTHER INFORMATION: Public GI ID no. 57012880
<220> FEATURE:
<221> NAME/KEY: misc_feature
<222> LOCATION: (26)..(89)
<223> OTHER INFORMATION: Pfam Name: AP2
      Pfam Description: AP2 domain
<220> FEATURE:
<221> NAME/KEY: misc_feature
<223> OTHER INFORMATION: Functional Homolog of Ceres CLONE ID no. 674166
      Given in SEQ ID NO: 42

<400> SEQUENCE: 87

Met Arg Arg Gly Arg Ala Ala Ala Ala Pro Ala Pro Val Thr Gly Glu
1               5                   10                  15

Pro Asn Gly Ser Gly Gly Ser Lys Glu Ile Arg Phe Arg Gly Val Arg
            20                  25                  30

Lys Arg Pro Trp Gly Arg Phe Ala Ala Glu Ile Arg Asp Pro Trp Lys
        35                  40                  45

Lys Thr Arg Val Trp Leu Gly Thr Phe Asp Ser Ala Glu Asp Ala Ala
    50                  55                  60

Arg Ala Tyr Asp Ala Ala Ala Arg Ala Leu Arg Gly Pro Lys Ala Lys
65                  70                  75                  80

Thr Asn Phe Pro Leu Pro Tyr Ala His His His Gln Phe Asn Gln Gly
                85                  90                  95

His Asn Pro Asn Asn Asp Pro Phe Val Asp Ser Arg Phe Tyr Pro Gln
            100                 105                 110

Asp Asn Pro Ile Ile Ser Gln Arg Pro Thr Ser Ser Ser Met Ser Ser
        115                 120                 125

Thr Val Glu Ser Phe Ser Gly Pro Arg Pro Pro Pro Ala Pro Arg Gln
    130                 135                 140

Gln Thr Thr Ala Ser Ser Arg Lys Tyr Thr Arg Ser Pro Pro Val Val
145                 150                 155                 160

Pro Asp Asp Cys His Ser Asp Cys Asp Ser Ser Ser Ser Val Val Asp
                165                 170                 175

His Gly Asp Cys Glu Lys Glu Asn Asp Asn Asp Asn Asp Asn Ile Ala
            180                 185                 190

Ser Ser Ser Phe Arg Lys Pro Leu Leu Phe Asp Leu Asn Leu Pro Pro
        195                 200                 205

Pro Met Asp Asp Ala Gly Ala Asp Asp Leu His Cys Thr Ala Leu Cys
    210                 215                 220

Leu
225


<210> SEQ ID NO 88
<211> LENGTH: 163
<212> TYPE: PRT
<213> ORGANISM: Gossypium hirsutum
<220> FEATURE:
<221> NAME/KEY: misc_feature
<223> OTHER INFORMATION: Public GI ID no. 62548111
<220> FEATURE:
<221> NAME/KEY: misc_feature
<222> LOCATION: (13)..(152)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7
```

<400> SEQUENCE: 88

```
Met Ala Thr Tyr Glu Gly Lys Val Phe Thr Glu Glu Gln Glu Ala Leu
1               5                   10                  15

Val Val Lys Ser Trp Thr Val Met Lys Lys Asn Ala Ala Glu Leu Gly
            20                  25                  30

Leu Lys Phe Phe Leu Lys Ile Phe Glu Ile Ala Pro Ser Ala Lys Lys
        35                  40                  45

Leu Phe Ser Phe Leu Arg Asp Ser Asn Val Pro Leu Glu Gln Asn Thr
    50                  55                  60

Lys Leu Lys Pro His Ala Met Ser Val Phe Val Met Thr Cys Glu Ser
65                  70                  75                  80

Ala Val Gln Leu Arg Lys Ala Gly Lys Val Thr Val Arg Glu Ser Asn
                85                  90                  95

Leu Lys Lys Leu Gly Ala Thr His Phe Lys Tyr Gly Val Val Asp Glu
            100                 105                 110

His Phe Glu Val Thr Lys Phe Ala Leu Leu Glu Thr Ile Lys Glu Ala
        115                 120                 125

Val Pro Asp Met Trp Ser Asp Glu Met Lys Asn Ala Trp Gly Glu Ala
    130                 135                 140

Tyr Asp Arg Leu Val Ala Ala Ile Lys Ile Glu Met Lys Ala Cys Ser
145                 150                 155                 160

Leu Ala Ala
```

<210> SEQ ID NO 89
<211> LENGTH: 153
<212> TYPE: PRT
<213> ORGANISM: Gossypium hirsutum
<220> FEATURE:
<221> NAME/KEY: misc_feature
<223> OTHER INFORMATION: Ceres CLONE ID no. 100021733
<220> FEATURE:
<221> NAME/KEY: misc_feature
<222> LOCATION: (1)..(74)
<223> OTHER INFORMATION: Pfam Name: ubiquitin
      Pfam Description: Ubiquitin family
<220> FEATURE:
<221> NAME/KEY: misc_feature
<222> LOCATION: (77)..(150)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional Homolog of Ceres CLONE ID no. 2403
      Given in SEQ ID NO: 40

<400> SEQUENCE: 89

```
Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Arg Gly Gly Met Gln Ile Phe
65                  70                  75                  80

Val Lys Thr Leu Thr Gly Lys Thr Ile Thr Leu Glu Val Glu Ser Ser
                85                  90                  95

Asp Thr Ile Asp Asn Val Lys Ala Lys Ile Gln Asp Lys Glu Gly Ile
```

```
            100                 105                 110

Pro Pro Asp Gln Gln Arg Leu Ile Phe Ala Gly Lys Gln Leu Glu Asp
        115                 120                 125

Gly Arg Thr Leu Ala Asp Tyr Asn Ile Gln Lys Glu Ser Thr Leu His
    130                 135                 140

Leu Val Leu Arg Leu Arg Gly Gly Phe
145                 150
```

```
<210> SEQ ID NO 90
<211> LENGTH: 775
<212> TYPE: DNA
<213> ORGANISM: Brassica napus
<220> FEATURE:
<221> NAME/KEY: misc_feature
<223> OTHER INFORMATION: Ceres CLONE ID no. 947579
<220> FEATURE:
<221> NAME/KEY: misc_feature
<223> OTHER INFORMATION: Encodes the protein at SEQ ID NO: 3

<400> SEQUENCE: 90

ctctctagat cttggatcac tcggacgaca tgtgttggat cccagtgcac tggccctgcc      60

agcctactca aaaaaacswt samttttckc tcccattstt tkacractca tcgttggcac     120

wtcctwcttt ctstatatat tacttgacat wawcyrctmt ycacmwcaca wacacacacw     180

taaccatggc cagcttcaca wgctttcctt ttgctcacat tgyctatggc tttagytcat     240

ytctctttag ctcwatctcc catgatggct ccttctggct ccatgtccat gscgckchat     300

gccatagcgg cggctctcca atgccaatga tgactccacc acctatgcca atgatgactc     360

cmccgcctat ggctatggct ccaccaccta tgcctatgac tccaccacca atgcccatgg     420

ctccgatgcc aatgactcca tcttcaagtc caatgagccc accaactact atggccccaa     480

gtccagaaac agtccctgat atggcttcgc caccgatgat gccgggaatg gagtcttctc     540

cttctccggg acccatgcca ccggcaatgg cctctccaga ttccggagca ttcaatgtaa     600

gaaacgacgt cgtagcaatt tcgttccttg ttgcagctca tttgctccta gtttgagatt     660

attattaaat tggccagcgt cgtgttgtgt aatttacttt catttttct cgagccatta      720

gttttcatgt tttatcatat atttgggttt gtgtttgata tggtacgatt cagmc          775
```

```
<210> SEQ ID NO 91
<211> LENGTH: 1032
<212> TYPE: DNA
<213> ORGANISM: Arabidopsis thaliana
<220> FEATURE:
<221> NAME/KEY: misc_feature
<223> OTHER INFORMATION: Ceres CLONE ID no. 36046
<220> FEATURE:
<221> NAME/KEY: misc_feature
<223> OTHER INFORMATION: Encodes the protein at SEQ ID NO: 23

<400> SEQUENCE: 91

gctcattagg gtttctcatc tacggcgtgg tgttcctcct tcctgctctg aaaaatggcg      60

aagagaacga agaaggttgg aatcgtcggc aaatacggaa cacgttatgg tgcgagtatc     120

aggaagcaga ttaagaagat ggaggtcagc cagcacagca agtacttctg tgagttctgt     180

ggcaagtacg gagtgaagcg aaaggctgtt ggtatctggg gttgcaagga ttgtggcaag     240

gtcaaggcag gtggtgctta cacaatgaac accgccagtg cggtcactgt tagaagcacg     300

atcagaaggt tgagggagca gatcgagggt taaaagtctg ctgaggaaga tgctgagaca     360

gtatacgctt gtatcgactt ggtatcaacg ataatacaga ggaagctgag gaagatcaag     420
```

```
gagaaggact cagaccatgg aaggcacatg aaaggtttca acagattgaa ggtaagggaa    480

ccagtgattg agccggttgt ggaggatgtt gaggacagta ctgactcgag cgtaggagaa    540

gaagaagaag aggatgattt gatcaaggag attgtccgta ccaagacttt cgagatgcca    600

ccattgactg tcgctgaggc agtcgagcag ctggaactag tcagtcacga cttctatggc    660

ttccaaaatg aaaactggtg agataaacat agtgtacaag agaaaagaag gaggttacgg    720

tctgataatc ccaaagaaag acgggaaggc cgagaaggtt gagccgcttc caaccgagca    780

attgaatgaa cactctttcg ccgagtagac tgcctctgca cacaccaaaa ccgataagct    840

catctctcct tacagtttac ctgtgtagga gttagggttc ttgaataaac aatgcaacaa    900

agattgtaga agtcagtgta cataaaaaaa tggccaacca ctctttgtta cttttgtggt    960

gaaaaggaag atcttaattc tctttccatc agatgatagc aatacatttt ttcataaaca   1020

agaatgttac at                                                       1032
```

<210> SEQ ID NO 92
<211> LENGTH: 492
<212> TYPE: DNA
<213> ORGANISM: Parthenium argentatum
<220> FEATURE:
<221> NAME/KEY: misc_feature
<223> OTHER INFORMATION: Ceres CLONE ID no. 1606506
<220> FEATURE:
<221> NAME/KEY: misc_feature
<223> OTHER INFORMATION: Encodes the protein at SEQ ID NO: 5

<400> SEQUENCE: 92

```
atctagcttc aacctttttt tcctctcact actcaattca atatggctgt ctcacgttac     60

attatcctac tcttatcctt cacctacttg gctgccttct ccaccgctca agctccatca    120

atgtcaccaa tgatgatgcc catggcacca ccaccatcga cgatgcccat gacaccacca    180

ccatcgacga tgcccatgac accaccacca acgcccatga ccatgacacc accaccaatg    240

atgatgccca tgacaccacc accaatgccc atggggacac caccaatgac aatgcccatg    300

ggaccgccac caatgatgat gcccatgagc ccaggaccat ccatgatgcc agcctccccg    360

ccatcaccca tgggaccgtc catggcacct gaaccagcta ccatgtcgcc tggaccctcc    420

atgacgcctg ctgagacacc agccagtggc gctatcatgc agtattctag catcactatg    480

ttgggcattg tg                                                        492
```

<210> SEQ ID NO 93
<211> LENGTH: 970
<212> TYPE: DNA
<213> ORGANISM: Glycine max
<220> FEATURE:
<221> NAME/KEY: misc_feature
<223> OTHER INFORMATION: Ceres CLONE ID no. 546001
<220> FEATURE:
<221> NAME/KEY: misc_feature
<223> OTHER INFORMATION: Encodes the protein at SEQ ID NO: 13

<400> SEQUENCE: 93

```
agatataatc gaaaaaaatt actgtttgga tatattccac tatttagaaa gcaaaatgga     60

ctacgaaaac ttgagtaaca aggtaagcca cacaaatggg aatgactccc cattacaatg    120

aagggccaac ttcattttca atgaatccca ctataaaaac tttagcaatg caaaagctaa    180

aacatcaacc atttcctcat ccactttcac tggaatcaca atcctgaaac aaaaacatct    240

tagcatttaa catactacta gacaacatga ccaccacatt ggaaagaggt ttctcggaag    300

agcaagaagc tctggtggtg aagtcatgga atgtcatgaa gaagaattct ggagagttgg    360
```

```
gtctcaagtt tttcttgaaa atatttgaga ttgctccatc agctcagaaa ttgttctcat    420

tcttgagaga ttcaacggtt cctttggagc aaaatcccaa gctcaagccc catgccgtgt    480

ctgtctttgt aatgacctgt gattcagcag ttcagctgcg gaaggccggg aaagtcactg    540

tcagagaatc aaacttgaaa aaattaggtg ctacccattt tagaaccggc gtagcaaacg    600

agcatttcga ggtgacaaag tttgcactgt tggagaccat aaaagaagct gtaccagaaa    660

tgtggtcacc ggctatgaag aatgcatggg gagaagctta tgatcagctg gtcgatgcca    720

ttaaatctga aatgaaacca ccctcctctt agactccagt ttaagcagtt cctttccttc    780

cctctcaatt ctcaaattgt tatattaata aaagtgagaa agtttaggct tgtgctttta    840

ttttgtgtga atgtaatata ctttgtgtac gtagacttgg ctattgggag ttgctaggtt    900

gggaagtgtt tcgcattcaa caattctgta gttgaaggtg attaaatgaa ttatagctat    960

ttgtttcttc                                                            970
```

<210> SEQ ID NO 94
<211> LENGTH: 604
<212> TYPE: DNA
<213> ORGANISM: Zea mays
<220> FEATURE:
<221> NAME/KEY: misc_feature
<223> OTHER INFORMATION: Ceres CLONE ID no. 1554560
<220> FEATURE:
<221> NAME/KEY: misc_feature
<223> OTHER INFORMATION: Encodes the protein at SEQ ID NO: 16

<400> SEQUENCE: 94

```
tcgtatccac ccaacctccc actgtaaaaa agagcagcgg aacgtgcgtg catccatcca     60

attccaatcc cagtcccaat cccaccagtg tccagtgctc ggggaaccga cacagctcct    120

cagcagagaa gccagcccga tcagcagaca gcaggcatgg cgctcgcgga ggccgacgac    180

ggcgcggtgg tcttcggcga ggagcaggag gcgctggtgc tcaagtcgtg ggccgtcatg    240

aagaaggacg ccgccaacct gggcctccgc ttcttcctca aggtcttcga gatcgcgccg    300

tcggcgaagc agatgttctc gttcctgcgc gactccgacg tgccgctaga gaagaacccc    360

aagctcaaga cgcacgccat gtccgtcttc gtcatgacct gcgaggcggc ggcgcagctc    420

cgcaaggccg ggaaggtcac cgtgagggag accacgctca agaggctggg cgccacgcac    480

ttgaggtacg gcgtcgcaga tggacacttc gaggtgacgg ggttcgcgct gcttgagacg    540

atcaaggagg cgctccccgc tgacatgtgg agcctcgaga tgaagaaagc ctgggccgag    600

gcct                                                                  604
```

<210> SEQ ID NO 95
<211> LENGTH: 846
<212> TYPE: DNA
<213> ORGANISM: Triticum aestivum
<220> FEATURE:
<221> NAME/KEY: misc_feature
<223> OTHER INFORMATION: Ceres CLONE ID no. 839727
<220> FEATURE:
<221> NAME/KEY: misc_feature
<223> OTHER INFORMATION: Encodes the protein at SEQ ID NO: 17

<400> SEQUENCE: 95

```
acgccgtccg tttctggctc atcaggaggt ccaaaggccg cgcaagtcga cctatataag     60

cgcctccgct ccagcttggg atcaaatcac gaccaacacg taccggatct tgaccgaccg    120

aaccattcag tgctcgcgct cactcacgca tcatagccaa gttaagcggg aaggaaggaa    180
```

```
ggaaggaagc catgtctgcc gcggagggag ccgtcgtgtt cagcgaggag aaggaggcgc    240

tggtgctcaa gtcatgggcc atcatgaaga aggattccgc caaccttggg ctccgcttct    300

tcctcaagat cttcgagatc gcgccgtcgg cgaggcagat gttcccgttc ctgcgcgact    360

ccgacgtgcc gctggagacc aaccccaagc tcaagaccca cgccgtgtcc gtcttcgtca    420

tgacgtgcga ggctgctgcg cagctgcgga aagccgggaa gatcaccgtc agggagacca    480

ccctgaagag gctgggcggc acgcacttga aatacggcgt ggcagatggc cactttgagg    540

tgacgcggtt cgctctgctc gagacgatca aggaggcgct tccggcggac atgtgggggc    600

cggagatgag gaacgcgtgg ggcgaggcct acgaccaact ggtcgcggcc atcaagcaag    660

agatgaagcc ctctgagtag ctcatccatt gtactcatat catatgccac gcaacttccg    720

tccatatccg tccaactttc gttgcttgac cggttcactc atgtcaccat attgtgtttg    780

tattgtgtgt ttacgtgtac taacgcatat tgtaaaatgg gcattcaata aaggaacaaa    840

ttgtgc                                                               846


<210> SEQ ID NO 96
<211> LENGTH: 440
<212> TYPE: DNA
<213> ORGANISM: Glycine max
<220> FEATURE:
<221> NAME/KEY: misc_feature
<223> OTHER INFORMATION: Ceres CLONE ID no. 664936
<220> FEATURE:
<221> NAME/KEY: misc_feature
<223> OTHER INFORMATION: Encodes the protein at SEQ ID NO: 25

<400> SEQUENCE: 96

ctcttgtctt agtctaataa acaacacgga cgcagagcct tcgatccaga aaccatgact     60

aagagaacga agaaggcagg cattgtcgga aaatatggta cccgatatgg tgctagtttg    120

cggaagcaga ttaagaagat ggaagttagt cagcatagca aattcttttg tgaattttgt    180

gggaagtatg ctgtgaagag gaaggctgtg ggaatatggg gatgcaagga ttgtggtaaa    240

gtgaaagctg gcggtgccta cactttgaat actgcaagtg ctgtcactgt gcgcagcacc    300

atccggaggt tgagggaaca aaccgagggt tgagcttttt ggttgatgtt agattttgag    360

caaattaact ggagaaatga ttcgtttttg tttaggaagc tgtattgttt caacttacaa    420

tgcagtgtga attgctttcg                                                440


<210> SEQ ID NO 97
<211> LENGTH: 463
<212> TYPE: DNA
<213> ORGANISM: Glycine max
<220> FEATURE:
<221> NAME/KEY: misc_feature
<223> OTHER INFORMATION: Ceres CLONE ID no. 658438
<220> FEATURE:
<221> NAME/KEY: misc_feature
<223> OTHER INFORMATION: Encodes the protein at SEQ ID NO: 26

<400> SEQUENCE: 97

atatawcttg actctccgca attccctgtc tcckccgccg cagcttccgt ctcccggatt     60

tcgccgcctg ccgcakccgc agcagctcgc cgsccacgcs tcctayccgt cgacgagatg    120

acgaascgca ccaagaaggc tggaattgtc ggcaaatatg gtacccgtta tggtgccagt    180

ttgcgtaagc agatcargaa gatggaggtg tctcagcact ccaagtactt ckgtgagttc    240

tgtgggaagt ttgctgtgaa gaggaaagsa gttggaattt ggggatgcaa tggactgtgg    300

gaaggwsaag gaaaccttcg ccwkaaaccg tgagctcgaa gtgmggtcca ctccaggwgg    360
```

gccatgctcg gggccttggg swgcagtctt ccccgaagct attgtyccgc aacggggtca 420
agtttggaga agctgtgtgg ttcaaggccg ggtcccagat ctt 463

<210> SEQ ID NO 98
<211> LENGTH: 458
<212> TYPE: DNA
<213> ORGANISM: Glycine max
<220> FEATURE:
<221> NAME/KEY: misc_feature
<223> OTHER INFORMATION: Ceres CLONE ID no. 1049262
<220> FEATURE:
<221> NAME/KEY: misc_feature
<223> OTHER INFORMATION: Encodes the protein at SEQ ID NO: 27
<220> FEATURE:
<221> NAME/KEY: misc_feature
<222> LOCATION: (224)..(224)
<223> OTHER INFORMATION: n is a, c, t, g, unknown, or other

<400> SEQUENCE: 98
aacaaaccct cgttcacggt tcaacttcag cagccgcgcc tctaacttgt agcagcgata 60
cctcttctct tatcactaaa aaatgaccaa gagaaccaag aaggccggta ttgttggaaa 120
atacggcacc cgatatggtg ctagtttaag gaagcaaatc aagaagatgg aagttagtca 180
gcacagtaaa ttcttttgtg agttctgtgg aaagtacgct gttnagagga aggccgtggg 240
tatttggggc tgcaaagatt gtggaaaagt gaaggctgga ggtgcttaca cattgaatac 300
tgcgagtgct gtcactgtcc ggagcaccat tcggaggctg agagagcaga ctgagagttg 360
aaagcagttt acacttttca tttgtttcca aagcttattt taaaattatc atacaatttt 420
ggcaggtcta tgttaggaat attagtaatg tgctactt 458

<210> SEQ ID NO 99
<211> LENGTH: 600
<212> TYPE: DNA
<213> ORGANISM: Triticum aestivum
<220> FEATURE:
<221> NAME/KEY: misc_feature
<223> OTHER INFORMATION: Ceres CLONE ID no. 632613
<220> FEATURE:
<221> NAME/KEY: misc_feature
<223> OTHER INFORMATION: Encodes the protein at SEQ ID NO: 28

<400> SEQUENCE: 99
ctcaaaaccc taggcttcca tatataactt gactctccac aattccctgt ctccgccgcc 60
gcagctttcg tctcccggat ttcgccgccg cagccgctca ccgcccacgc ctcctacccg 120
tcgacgagat gacgaagcgc accaagaagg ctggtattgt cggcaaatat ggtacccgtt 180
atggtgccag tttgcgtaag cagatcaaga agatggaggt gtctcagcac tccaagtact 240
tctgtgagtt ctgtgggaag tttgctgtga agaggaaagc agttggaatt tggggatgca 300
aggactgtgg gaaggtgaag gctggcggtg cttacactat gaacactgcc agtgcggtca 360
ctgtcaggag cactatccgt cgtttgaggg agcagactga agcataagtt gctactagtg 420
ttttgtccta gtgaatcatc tgggatttcg cagtttagac gatactttgg attcagttcc 480
attggctgtt tagtcaagga ttatctttgt acttggtgcg atgatgttct gttatgttat 540
tctcccaccc ttttgttgcc tgattccact ctgatttact gtggattctg atttgccttc 600

<210> SEQ ID NO 100
<211> LENGTH: 546
<212> TYPE: DNA
<213> ORGANISM: Zea mays
<220> FEATURE:

<221> NAME/KEY: misc_feature
<223> OTHER INFORMATION: Ceres CLONE ID no. 1390976
<220> FEATURE:
<221> NAME/KEY: misc_feature
<223> OTHER INFORMATION: Encodes the protein at SEQ ID NO: 29

<400> SEQUENCE: 100
aagcatccac aattccacat aacctcgccc gcgccgcctc ccccacgaga cgccttcttg 60
ctctcgcttc cggtgacgcc cgccacttcc tccccgacga gatgacgaaa cgcaccaaga 120
aggcaggaat cgttggcaaa tatggtacca ggtatggtgc cagtttacgt aaacagatca 180
agaagatgga ggtctcgcag cactccaaat acttctgtga gttctgtggc aagtttgccg 240
tgaagaggaa agcagttggt atctggggat gcaaggactg tgggaaggtt aaggccggtg 300
gcgcctacac aatgaacact gctagtgcgg tcactgtgag aagcacaatc cggcgcctgc 360
gggagcagac cgaagcatga ttgcgggcag cttgaaaagg agtacctgga tttttgtagt 420
tcagccaaga gccgtgaacc attttgcctt tttagctaaa tgaacaagaa atgtttatct 480
atctgtagtg accactttgt actcatggtt tgtcatgcta aattgatggt atgcactatg 540
caatgc 546

<210> SEQ ID NO 101
<211> LENGTH: 550
<212> TYPE: DNA
<213> ORGANISM: Zea mays
<220> FEATURE:
<221> NAME/KEY: misc_feature
<223> OTHER INFORMATION: Ceres CLONE ID no. 1457185
<220> FEATURE:
<221> NAME/KEY: misc_feature
<223> OTHER INFORMATION: Encodes the protein at SEQ ID NO: 30

<400> SEQUENCE: 101
atatataact tgactctccg caattccctg tctccgccgc cgcagcttcc gtctcccgga 60
tttcgccgcc gccgcagccg cagcagctcg ccgcccacgc ctcctacccg tcgacgagat 120
gacgaagcgc accaagaagg ctggaattgt cggcaaatat ggtacccgtt atggtgccag 180
tttgcgtaag cagatcaaga agatggaggt gtctcagcac tccaagtact tctgtgagtt 240
ctgtgggaag tttgctgtga agaggaaagc agttggaatt tggggatgca aggactgtgg 300
gaaggtgaag gctggcggtg cttacaccat gaacactgcc agtgcggtca ctgtcaggag 360
cactatccgt cgcttgaggg agcagactga agcataagtt gctactagtg ttttgtccta 420
gtgaatcatc tgggattttg cagtttagac gatactttgg attcagttct gttggctgtt 480
tagtcaagga ttatctttgt acttggtgcg atgatgttct gttatgttat tctctcaccc 540
tttttttgcc 550

<210> SEQ ID NO 102
<211> LENGTH: 668
<212> TYPE: DNA
<213> ORGANISM: Zea mays
<220> FEATURE:
<221> NAME/KEY: misc_feature
<223> OTHER INFORMATION: Ceres CLONE ID no. 1482731
<220> FEATURE:
<221> NAME/KEY: misc_feature
<223> OTHER INFORMATION: Encodes the protein at SEQ ID NO: 35

<400> SEQUENCE: 102
aaaaattcat tgatcgaaaa aaagaaaaaa gaaagaaaag aaaagatgca gatcttcgtg 60
aaaaccttga ccggcaaaac cataacccta gaggttgaaa gcagcgacac catcgacaat 120

```
gtcaaatcca aaatccagga caaagagggg ataccacctg atcaacagag gctcatcttt    180

gctgggaaac aacttgagga tggtcgaacg ctagctgact acaacattca gaaagagtcc    240

actcttcact tggttctgag gcttaggggt gggaccatga tcaaggtcaa gactctcact    300

ggtaaagaaa tcgaaattga tatcgaacct accgatacta ttgaccggat caaggaacgt    360

gttgaggaga aagaaggcat ccctcctgtt caacaaaggc tcatctatgc tgggaaacag    420

ctagctgatg acaaaacggc aaaggactac aacatagagg gaggctctgt tcttcatctg    480

gtccttgctc tcaggggtgg ttctgactaa ataactattt gctctagagt tcctttcaat    540

ggctttggtt ggttgaatcc atgagacaaa gtgaatacaa tttggatttc gtgctttggt    600

tactatgatg ctatttcagc tggtttggat caatttacca aaaaaaaaaa aaaaaaaaaa    660

aaaaaaag                                                             668
```

<210> SEQ ID NO 103
<211> LENGTH: 752
<212> TYPE: DNA
<213> ORGANISM: Glycine max
<220> FEATURE:
<221> NAME/KEY: misc_feature
<223> OTHER INFORMATION: Ceres CLONE ID no. 522921
<220> FEATURE:
<221> NAME/KEY: misc_feature
<223> OTHER INFORMATION: Encodes the protein at SEQ ID NO: 36
<220> FEATURE:
<221> NAME/KEY: misc_feature
<222> LOCATION: (639)..(639)
<223> OTHER INFORMATION: n is a, c, t, g, unknown, or other
<220> FEATURE:
<221> NAME/KEY: misc_feature
<222> LOCATION: (674)..(674)
<223> OTHER INFORMATION: n is a, c, t, g, unknown, or other
<220> FEATURE:
<221> NAME/KEY: misc_feature
<222> LOCATION: (690)..(690)
<223> OTHER INFORMATION: n is a, c, t, g, unknown, or other
<220> FEATURE:
<221> NAME/KEY: misc_feature
<222> LOCATION: (697)..(697)
<223> OTHER INFORMATION: n is a, c, t, g, unknown, or other
<220> FEATURE:
<221> NAME/KEY: misc_feature
<222> LOCATION: (700)..(700)
<223> OTHER INFORMATION: n is a, c, t, g, unknown, or other
<220> FEATURE:
<221> NAME/KEY: misc_feature
<222> LOCATION: (714)..(714)
<223> OTHER INFORMATION: n is a, c, t, g, unknown, or other

<400> SEQUENCE: 103

```
aattacaaat acaaatacga atacccttct ctctcacaca aaacactagt ccctcccttc     60

ttccttgtct ctttctcttc tcaacaacat gcagatcttc gtcaagactt tgactggcaa    120

gaccatcacc ctcgaggtcg agagtagcga caccatcgac aacgtcaagg ccaagatcca    180

ggacaaggaa ggtatccctc ctgaccagca gagtttgatt tttgctggta agcagctgga    240

agatggtcgc actcttgctg attataacat acaaaaggaa tcaacacttc acttggtctt    300

gaggctcagg ggaggaacca tgattaaagt gaagactcta actggaaaag aaattgaaat    360

tgacattgag ccaactgata caatcgaccg gatcaaggaa cgcgttgaag aaaaagaggg    420

aattccacct gtgcagcaga gactcatata tgcaggtaaa cagcttgctg atgacaaaac    480

agctaaagag tacaacattg agggtggttc tgtacttcac ttggtgcttg cattgagggg    540

tggtacttat tagtgtagat gccatatcag aacccaaaga catgaaagga agctctattc    600
```

```
ctgccccgtc tctctgaaga catcattgtt cttttatgng cttggttttt gtaattgtgg    660

ctactattgg tggncagtaa ctcagtatcn ttttagntgn atgctattta aaanccctaa    720

ggtgggcctt tatatgaata tctgaaccaa tg                                  752


<210> SEQ ID NO 104
<211> LENGTH: 484
<212> TYPE: DNA
<213> ORGANISM: Brassica napus
<220> FEATURE:
<221> NAME/KEY: misc_feature
<223> OTHER INFORMATION: Ceres CLONE ID no. 1036726
<220> FEATURE:
<221> NAME/KEY: misc_feature
<223> OTHER INFORMATION: Encodes the protein at SEQ ID NO: 37

<400> SEQUENCE: 104

gaaatcaaat aaaaaaatct ttaagcaaga aaagaaagaa aatgcagatc ttcgtcaaaa     60

ccctgacggg gaaaaccata accctggagg ttgaaagcag cgacaccatc gacaatgtca    120

aagccaaaat ccaggacaaa gaaggaatac cgccggatca gcagaggctg atcttcgctg    180

ggaagcaact agaagacggt agaacccttg cggactacaa catccagaaa gagtccactc    240

ttcacttggt cttgaggctt aggggtggca ccatgatcaa ggtcaagact ctcactggca    300

aagaaatcga gattgacatc gaacctaccg acaccattga tcgcatcaag gagcgtgttg    360

aggagaaaga aggcatccct cctgttcaac agaggctcat ctacgctgga aaacagctag    420

ctgatgacaa gacggcmaaa gactacaaca tcgagggagg ctctgtttct gcatctggtt    480

cttg                                                                 484


<210> SEQ ID NO 105
<211> LENGTH: 580
<212> TYPE: DNA
<213> ORGANISM: Glycine max
<220> FEATURE:
<221> NAME/KEY: misc_feature
<223> OTHER INFORMATION: Ceres CLONE ID no. 513071
<220> FEATURE:
<221> NAME/KEY: misc_feature
<223> OTHER INFORMATION: Encodes the protein at SEQ ID NO: 38
<220> FEATURE:
<221> NAME/KEY: misc_feature
<222> LOCATION: (543)..(543)
<223> OTHER INFORMATION: n is a, c, t, g, unknown, or other

<400> SEQUENCE: 105

aagaaaaagg aaattttctt gggcgttctt cggcttcgtt gtcacaaggt tcgagttcgt     60

caccgtctag tacgactgtg cgagggagga agaggcgagg agaagatgca gatcttcgtg    120

aagaccctga cggggaagac catcaccctc gaggtggaga gcagcgacac cgtcgacaac    180

gtcaaagcca aaatccagga caaggaaggg attcccccag atcaacagcg actgatattc    240

gctggcaagc agctggagga tggacgcacg ctggctgact acaacatcca aaaggagtca    300

actcttcatt tggtcctcag gcttaggggt ggaaccatga tcaaggtcaa aactctcact    360

gggaaagaga tcgagatcga cattgaaccc actgactcga ttgacaggat caaggagcgt    420

gttgaagaga aagaaggcat tcctcccgtg cagcaaaggc tcatctatgc tggtaagcag    480

cttgctgatg acaagaccgc aaaggactac aacatcgagg gtggatctgt cctccatctt    540

gtncttgctc tgaggggtgg ttactagtct aaacctgatg                          580


<210> SEQ ID NO 106
<211> LENGTH: 987
```

<212> TYPE: DNA
<213> ORGANISM: Brassica napus
<220> FEATURE:
<221> NAME/KEY: misc_feature
<223> OTHER INFORMATION: Ceres CLONE ID no. 975672
<220> FEATURE:
<221> NAME/KEY: misc_feature
<223> OTHER INFORMATION: Encodes the protein at SEQ ID NO: 44

<400> SEQUENCE: 106

```
attccatcaa cttcagacac acagatctct tctcaatcac attacttctg gttctcccac     60
catgaggaaa gggagaggct cttccgccgt tccacccgcc cttcccggat ctgtgaagga    120
gccgaggtac agaggcgtta ggaagagacc ttggggccgt ttcgccgccg agatccgtga    180
ccccttgaaa aaatcccgag tctggctcgg cacgttcgac tccgcggagg aagccgcacg    240
cgcctacgac gcagccgctc gtaacctccg cggtccaaag gccaagacca acttccaaat    300
cgactgttct ccttcctctc ctctccaacc actccatcat cggaaccaga tcgatccctt    360
tatggaccac cggttatacg gcggagagca ggaggttgtt atcatcagcc ggccggcgag    420
tagcagcatg agcagcaccg ttaagtcgtg cagcggagtg agaccagcgt cttcttccgt    480
ggcgaaggcg gcgacgaaga gatatccacg gactccgccg gtggcgccgg aggattgccg    540
cagcgactgc gattcgtcgt cgtcggtggt tgaagacgga sacgacatag cttcgtcgtc    600
ttcgcggcgg aaaccgccgt ttgagtttga tcttaatttt ccsccgttgg atggcgttga    660
cttattcgta ggcgcggacg atctccactg caccgatctg cgtctttgat ctttgagcac    720
aatgacaaca aagatgatga agaagtgata gggagagaga gtttgtgtta agatctgttg    780
ttgtaagaac cagatctgtg tttcattcac ttgtctgttt cttataaaga tcaaaccttt    840
gttacatgta acacttatat agctgctgat gattcttaat tattcaaaat ccaaagtctg    900
tagaatttat acagtatcta tcactgatgt gcttatggat ggtttggagt atgaggctac    960
attttcataa atacattcaa tgtgtgt                                        987
```

<210> SEQ ID NO 107
<211> LENGTH: 1034
<212> TYPE: DNA
<213> ORGANISM: Zea mays
<220> FEATURE:
<221> NAME/KEY: misc_feature
<223> OTHER INFORMATION: Ceres CLONE ID no. 273307
<220> FEATURE:
<221> NAME/KEY: misc_feature
<223> OTHER INFORMATION: Encodes the protein at SEQ ID NO: 45

<400> SEQUENCE: 107

```
ctctccttcc ttcacggatt cccaaatact cgcttccaat accaattctc cgatccacgt     60
tcgttcccgc accctcgcgc tccgctgatc cggcggcatg cggcgccgcg gcgtggcggc    120
ggctgatgcg gacggtgacg tggagttgcg gttccgcggg gtgcggaaga ggccgtgggg    180
ccggtacgca gcggagatcc gggacccggc gaagaaggcg cgcgtctggc tcggcacatt    240
cgactccgcc gaggacgccg cccgcgccta cgacgccgca gcgcggatgc tgcgcgggcc    300
caaggccagg accaacttcc cgctccccgc cgcagccgcc ctccaccacc cccacatgcc    360
cgctgctgcc gccgcagcag ctccaccata cacaacatat cccaccgcca cgggcgtcgt    420
ctcgacgccg ccggtcgcca gaccggcttg cagcagcctc agctccaccg tggagtcctt    480
cagcggcgcg cggccgcggc ctgtgctccc gccgcggttc cctccgccgt cgattcctga    540
tggcgactgc cgcagcgact gtggttcctc ggcctcggtc gtggacgacg actgcacgga    600
```

```
cgcggccgcc tctgcgtcgt gccccttccc gctcccgttc gacctcaacc tgcccccagg    660

cggcggcgga gccggcgtcg ggttttacgc cgatgaggag gatgagctca ggctcacggc    720

gctgcggctg tgacgtcgag ctcaatcgag ccgctgctta gaaagaggaa aaggagaaaa    780

atatttggtt cttcccttct cttgtagccg acacgaactc tccatccact acgatgttgt    840

tgtttacttg atctgattat gatatttgcc tgaatcctag tcaacttacc tgcatgcatg    900

cctgcttgtt ttctggcgat tgaggattat cgccaaacgc caaatcttgc agcagctgtt    960

gtactgtaat atatcaacat tttacttcct tcctcttatg aggaaagaga cagataaagt   1020

aacttatttc aatc                                                     1034
```

```
<210> SEQ ID NO 108
<211> LENGTH: 911
<212> TYPE: DNA
<213> ORGANISM: Triticum aestivum
<220> FEATURE:
<221> NAME/KEY: misc_feature
<223> OTHER INFORMATION: Ceres CLONE ID no. 1055099
<220> FEATURE:
<221> NAME/KEY: misc_feature
<223> OTHER INFORMATION: Encodes the protein at SEQ ID NO: 46

<400> SEQUENCE: 108

aaacaaaaaa ccaccagggg aagaagggaa agacacacgc cactgtgacc aaaccctagg     60

ccggccgcga tgcgcaaggc gaggccgccg cagccccagc cgcagccgtc gcagcagtcg    120

ccggagatcc ggtaccgcgg cgtgcggaag cgcccctcgg gccgctacgc cgccgagatc    180

cgggaccccg ccaagaagac gccgatctgg ctcggcacct tcgactgcgc cgaggacgcc    240

gcccgcgcct acgactccgc cgcccgatcc ctccgcgggc ccaccgcccg caccaacttc    300

ccgccctcct ccgccacgca gccgccgccg aggccccctc cccccgcggc cgcggccgcg    360

gccgccacgt ccagccagag cagcaccgtc gagtcctgga gcggcggcgg gccccgcgcc    420

cccgccaggg cccgcagcgc cgcccgagcg ggcacggcca aggaggggga ggaggactgc    480

cgcagctact gcggctcctc gtcctccgtc ctcctcgagg agggcgcgga cgacgcggcc    540

gcctcccgct ccccgctgcc cttcgatctg aacatgccgc ccccgcagga gggggcgctt    600

gacgccgagg ccgatcagat gacctgccgg tacgacacgc tgctccgcct ctagctccac    660

gacgacgaga gcaaggattc gtgggagggg aactgggaaa aggaacgaga aaagcgcttg    720

cccccgctcc gctccggtcc gtcttccgat gatctcgtgg tgttctctct ttgttagaaa    780

tggataattc ttgccatttt tttttcttac tttctttcct tcttcttttt tttttcttct    840

taccactttg attcgatatg tgaataattg agtcatgtaa gctgcgagca aggaaatctg    900

agcttttcct t                                                         911
```

```
<210> SEQ ID NO 109
<211> LENGTH: 160
<212> TYPE: PRT
<213> ORGANISM: Arabidopsis thaliana
<220> FEATURE:
<221> NAME/KEY: misc_feature
<223> OTHER INFORMATION: Ceres GI ID no. GI_15226675
<220> FEATURE:
<221> NAME/KEY: misc_feature
<222> LOCATION: (13)..(152)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7
```

<400> SEQUENCE: 109

```
Met Glu Ser Glu Gly Lys Ile Val Phe Thr Glu Glu Gln Glu Ala Leu
1               5                   10                  15

Val Val Lys Ser Trp Ser Val Met Lys Lys Asn Ser Ala Glu Leu Gly
            20                  25                  30

Leu Lys Leu Phe Ile Lys Ile Phe Glu Ile Ala Pro Thr Thr Lys Lys
        35                  40                  45

Met Phe Ser Phe Leu Arg Asp Ser Pro Ile Pro Ala Glu Gln Asn Pro
    50                  55                  60

Lys Leu Lys Pro His Ala Met Ser Val Phe Val Met Cys Cys Glu Ser
65                  70                  75                  80

Ala Val Gln Leu Arg Lys Thr Gly Lys Val Thr Val Arg Glu Thr Thr
                85                  90                  95

Leu Lys Arg Leu Gly Ala Ser His Ser Lys Tyr Gly Val Val Asp Glu
            100                 105                 110

His Phe Glu Val Ala Lys Tyr Ala Leu Leu Glu Thr Ile Lys Glu Ala
        115                 120                 125

Val Pro Glu Met Trp Ser Pro Glu Met Lys Val Ala Trp Gly Gln Ala
    130                 135                 140

Tyr Asp His Leu Val Ala Ala Ile Lys Ala Glu Met Asn Leu Ser Asn
145                 150                 155                 160
```

<210> SEQ ID NO 110
<211> LENGTH: 1823
<212> TYPE: DNA
<213> ORGANISM: Arabidopsis thaliana
<220> FEATURE:
<221> NAME/KEY: misc_feature
<223> OTHER INFORMATION: Ceres Promoter 28176

<400> SEQUENCE: 110

```
gtctcttaaa aaggatgaac aaacacgaaa ctggtggatt atacaaatgt cgccttatac     60

atatatcggt tattggccaa aagagctatt ttaccttatg gataatggtg ctactatggt    120

tggagttgga ggtgtagttc aggcttcacc ttctggttta agccctccaa tgggtaatgg    180

taaatttccg gcaaaaggtc ctttgagatc agccatgttt tccaatgttg aggtcttata    240

ttccaagtat gagaaaggta aaataaatgc gtttcctata gtggagttgc tagatagtag    300

tagatgttat gggctacgaa ttggtaagag agttcgattt tggactagtc cactcggata    360

ctttttcaat tatggtggtc ctggaggaat ctcttgtgga gtttgatatt tgcgagtata    420

atctttgaac ttgtgtagat tgtacccaaa accgaaaaca tatcctatat aaatttcatt    480

atgagagtaa aattgtttgt tttatgtatc atttctcaac tgtgattgag ttgactattg    540

aaaacatatc ttagataagt ttcgttatga gagttaatga tgattgatga catacacact    600

cctttatgat ggtgattcaa cgttttggag aaaatttatt tataatctct cataaattct    660

ccgttattag ttgaataaaa tcttaaatgt ctcctttaac catagcaaac caacttaaaa    720

atttagattt taaagttaag atggatattg tgattcaacg attaattatc gtaatgcata    780

ttgattatgt aaaataaaat ctaactaccg gaatttattc aataactcca ttgtgtgact    840

gcatttaaat atatgtttta tgtcccatta attaggctgt aatttcgatt tatcaattta    900

tatactagta ttaatttaat tccatagatt tatcaaagcc aactcatgac ggctagggtt    960

ttccgtcacc ttttcgatca tcaagagagt ttttttataa aaaaatttat acaattatac   1020

aatttcttaa ccaaacaaca cataattata agctatttaa catttcaaat tgaaaaaaaa   1080
```

aatgtatgag aattttgtgg atccattttt gtaattcttt gttgggtaaa ttcacaacca 1140
aaaaaataga aaggcccaaa acgcgtaagg gcaaattagt aaaagtagaa ccacaaagag 1200
aaagcgaaaa ccctagacac ctcgtagcta taagtaccct cgagtcgacc aggattaggg 1260
tgcgctctca tatttctcac attttcgtag ccgcaagact cctttcagat tcttacttgc 1320
aggttagata ttttctctct ttagtgtctc cgatcttcat cttcttatga ttattgtagc 1380
tgtttagggt ttagattctt agttttagct ctatattgac tgtgattatc gcttattctt 1440
tgctgttgtt atactgcttt tgattctcta gctttagatc cgtttactcg tcgatcaata 1500
ttgttcctat tgagtctgat gtataatcct ctgattaatt gatagcgttt agttttgata 1560
tcgtcttcgc atgtttttta tcatgtcgat ctgtatctgc tctggttata gttgattctg 1620
atgtatttgg ttggtgatgt tccttagatt tgatatacct gttgtctcgt ggtttgatat 1680
gatagctcaa ctggtgatat gtggttttgt ttcagtggat ctgtgtttga ttatattgtt 1740
gacgttttgg ttgttgtatg gttgatggtt gatgtatttt tgttgattct gatgtttcga 1800
tttttgtttt tgttttgaca gct 1823

<210> SEQ ID NO 111
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0668

<400> SEQUENCE: 111
atagagtttt actatgcttt tggaatcttt cttctaatgt gccaactaca gagaaataca 60
tgtattacca ctaggaatcg gaccatatca tagatatcag gattagataa ctagttctcg 120
tcgctatcac ttcgcattaa gttctagtaa ttgttaaaga ttctaatttt ttactaaaca 180
aaaactaaat caacatcaaa tatgcaaagt gtgtgttgtc cacacaagtg actcaaagta 240
tacgcaggtg ggattggacc atattattgc aaatcgtttc cgaaccactc atatttcttt 300
ttttctctcc tttttttatc cggagaatta tggaaccact tcatttcaac ttcaaaacta 360
attttttggt tcagtgatca aatacaaaaa aaaaaaaaaa gttatagata ttaaatagaa 420
aactattcca atcttaaaaa tacaaatgaa accataattt taatttatac aaaactattt 480
aattagctaa gggttgtctt aacgtttaga aaataaaaaa ttatgattgt ctgtttaaaa 540
ttacaatgaa tgaataaaaa aaatatgcaa tgaatgaaag aataaatttt gtacatccga 600
tagaatgaga aaatgaattt tgtacaaacc actcaagaat tcaaaacaat tgtcaaagtt 660
ttcttctcag ccgtgtgtcc tcctctccta gccgccacat ctcacacact aatgctaacc 720
acgcgatgta accgtaagcg ctgagttttt gcatttcaga tttcacttcc accaaacaaa 780
actcgccacg tcatcaatac gaatcattcc gtataaacgt ctagattctt tacagcctac 840
aatgttctct tctttggtcg gccattattt aacgctttga acctaaatct agcccagcca 900
acgaagaaga cgaagcaaat ccaaaccaaa gttctccatt ttcgtagctt ctttaagctt 960
tttcagtatc atagagacac tttttttttt ttgattagaa 1000

<210> SEQ ID NO 112
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0535

<400> SEQUENCE: 112

```
ttagtgaaat tatgacatta agtaaggttt tcttagttag ctaatgtatg gctattcaat     60
tgttatgtta ggctatttta gttagtatat gaatttaggc agtctatgca aatgatttcg    120
ttttcatttt ttcatatgta aacatcaaga tcaagtaacg ccattcgagt tgatattttt    180
tttttaaatt agtgtgtgta aattttggac cgcttatttg agtttgctaa tgaagttgca    240
tatatattac gttaaaccat aggcaaacta atttgaaaca tccgattcga tttcctgtaa    300
tttttcttgg ttaattgacc aaaatcaaga tcttcagaaa taaaataaaa gacgaaagaa    360
agctgtcgca aagcagattg tgttaaaaaa aagtggattg ggctcaaacg caacttgtcc    420
agcccgtgac aattacccta tacgcaagta agagtaacgt atcactggca aaagttggta    480
ttagttacga tatctttgtc atgggggcat gcatgggcat ggcttaagag ttaagcctta    540
agaagagtcc cacactcgtg actctcatga tcacttgttg tttcttacgg gcaaatacat    600
ttaactttat tcttcattta ttcacctata ttcttttgga taataacttt tctctatata    660
aaataacaaa catcgtacgt ttcatttatt tacaacaagc gatgagaatt aaaaggagac    720
cttaattgat gatactcttc ttttctctcg gttacaacgg gattattaca gataatgata    780
atctatatgg atgctgacgt ggaaaaacaa aatttggtga aacacgtcaa ttaagcacga    840
cttttccatg gctagtggct aagatcgttt catcacatgg ctatatcata taatacttgg    900
atgaattcaa aataaacgac tgagaaaatg tccacgtcac ggcgcaccgc tttggactta    960
agtctcctat aataaataca acaccaaaca ttgcattcca                        1000
```

<210> SEQ ID NO 113
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter PT0585

<400> SEQUENCE: 113

```
tgaagtcatt taatatgagt ttgacattag gtaaacctaa tctatgagat tatagaatgt     60
agcaaaacta tcaatgtttc ttttccaaaa tattttgtgg tttttctttt tggttcatta    120
tgttttgtta tttgtgaatt attttaatat gaagtaatta tattgatttt atatgatata    180
catattattt tgatataaaa tttaacactt atccattaaa atagcatggg cataatcaaa    240
atcgggacta ttacgatgaa aaagatagtt aaattgtatg ataaaataaa atgtgtaaga    300
ttaaaatttt gggttttaga aaattactaa acaaaatata gacaaagtat gttgactatt    360
atttaaaatt taaatatcat caataagata tagttaaagt cattaagtgt atagcaaaat    420
gaaaattcta agattaaaat tcgattaaaa ttttttttac taaattaaat atttaaaaat    480
agggattatc atttactatt tacaattcta atatcatggg taaaaattga taactttttt    540
taaacccgcc tatctaggtg ggcctaacct agtttactaa ttactatatg attaacttat    600
taccactttt acttcttctt ttttggtcaa attactttat tgttttttat aaagtcaaat    660
tactctttgc attgtaaata atagtagtaa ctaaaatctt aaaacaaaat attcaacctt    720
tcccattatt ggaatggtaa tgtcttcaac accattgacc aacgttaagg aatgtctttt    780
aatatttttg gaacctaaat gctaatactg tataccacaa tcacttatga gtattgaagt    840
tgagatagag gaggtacaag gagaccttat ctgcagaaga caaaaagcca tttttagcaa    900
```

aactaaagaa agaaaaaaga ttgaaacaca aatatgcgcc actcgtagtc cacccctatc 960
tctttggcaa aagccacttc actctttttc cctttttat 999

<210> SEQ ID NO 114
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0613

<400> SEQUENCE: 114
ttaatactaa cattgtagaa agccacaaaa aagaaattga aatgtgagta gatgctgagt 60
cagaggtttg gtcaatacac aacagctaat tgagataata ttatacacgt cacgatgact 120
tgttttttct cctcccaact tgttaatttc tttattctta aaattaaacc atcgcaaaaa 180
cagaagaaca cagctgtttt tctcgactcc caatttctat tttgctgcta aggacatttc 240
atttcattat ttcccaattc aggactcctt agattttcct aaatttgttt tcctaacttg 300
ctctctctca ttctaacatt ttctcatttt tttagattat cttgtacttt ttagtagatt 360
attttatcag gttttacaaa catacattga cattctaaaa agggcttcta aaaattcagt 420
gtggaatgct gatatactaa aaaaaggtca tgcaaaatta tctacgattt atctaaaatt 480
agataatttg ccatatataa ctattaacta ataatcgatc ctttgatttt ttgtttagat 540
aaaacgaaac agctatatct ttttttttg ttatcggatt ttaatcgaat aaaagctgaa 600
aaataacagt tatatcttct tctttttaa ctaatgaaac agttatatct taaacaaaca 660
acagaaacag taaaatatta atgcaaatcc gcgtcaagag ataaatttta acaaactaat 720
aacaattgag ataagattag cgcaaaagaa actctaattt tagagcgtgt aaacacaaac 780
acgtcttgaa agtaaacgtg aattacacgc ttctaaaacg agcgtgagtt ttggttataa 840
cgaagatacg gtgaagtgtg acacctttct acgttaattt cagtttgagg acacaactca 900
agttatgttt gatatctaag gacttgcact gtctccaaat ctgcaggaag gactttttga 960
ttggatcaat ataaatacca tctccattct cgtctccttc 1000

<210> SEQ ID NO 115
<211> LENGTH: 351
<212> TYPE: DNA
<213> ORGANISM: Arabidopsis thaliana
<220> FEATURE:
<221> NAME/KEY: misc_feature
<223> OTHER INFORMATION: Ceres Promoter PT0625

<400> SEQUENCE: 115
gatcatgatc agtttcaact cgctgtgccc acgtgtcgag agatcggcac gtgcctgagc 60
tctcagccgc tcataaatac acttgtttag tagcaacagt atactatagt agtcctctcc 120
tgtttggctt ttagcttgca tcgatggatg gatggatgga tcgcatgaga gggcttcgcg 180
aaggtacgga accttacaca acgcgtgtcc tttctacgtg gccatcgtgt aggcgtctcg 240
ccatgctacg tgtcccggag gatgtctcga tgccaaccct tataaatact gttccattcc 300
aatcccatcg ccacagccag tgcaaatctg atcgatcaag ataatcgagc a 351

<210> SEQ ID NO 116
<211> LENGTH: 1022
<212> TYPE: DNA
<213> ORGANISM: Arabidopsis thaliana
<220> FEATURE:
<221> NAME/KEY: misc_feature
<223> OTHER INFORMATION: Ceres Promoter PT0633

<400> SEQUENCE: 116

```
cccgatcggc cttaatctga gtcctaaaaa ctgttatact taacagttaa cgcatgattt     60
gatggaggag ccatagatgc aattcaatca aactgaaatt tctgcaagaa tctcaaacac    120
ggagatctca aagtttgaaa gaaaatttat ttcttcgact caaaacaaac ttacgaaatt    180
taggtagaac ttatatacat tatattgtaa ttttttgtaa caaaatgttt ttattattat    240
tatagaattt tactggttaa attaaaaatg aatagaaaag gtgaattaag aggagagagg    300
aggtaaacat tttcttctat tttttcatat tttcaggata aattattgta aaagtttaca    360
agatttccat ttgactagtg taaatgagga atattctcta gtaagatcat tatttcatct    420
acttctttta tcttctacca gtagaggaat aaacaatatt tagctccttt gtaaatacaa    480
attaattttc gttcttgaca tcattcaatt ttaattttac gtataaaata aaagatcata    540
cctattagaa cgattaagga gaaatacaat tcgaatgaga aggatgtgcc gtttgttata    600
ataaacagcc acacgacgta aacgtaaaat gaccacatga tgggccaata gacatggacc    660
gactactaat aatagtaagt tacattttag gatggaataa atatcatacc gacatcagtt    720
tgaaagaaaa gggaaaaaaa gaaaaaaataa ataaaagata tactaccgac atgagttcca    780
aaaagcaaaa aaaaagatca agccgacaca gacacgcgta gagagcaaaa tgactttgac    840
gtcacaccac gaaaacagac gcttcatacg tgtcccttta tctctctcag tctctctata    900
aacttagtga gaccctcctc tgttttactc acaaatatgc aaactagaaa acaatcatca    960
ggaataaagg gtttgattac ttctattgga aagaaaaaaa tctttggaaa aggcctgcag   1020
gg                                                                  1022
```

<210> SEQ ID NO 117
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0650

<400> SEQUENCE: 117

```
catacttaat tctaaaaaaa caacacttat agtttataag cagctcttat gataaaaatc     60
tttctgagtt atagctctgt taaacttgta ttcaccccaa aaacggatgt ttcatttctt    120
attttttact tggagtattt tattgtaatt tgtaaaaaaa aatgtaaagt gggggatatc    180
atgaaaaaca acgtcacttt gtttggtcac aatatacatt tgataaaata atggtcgtcg    240
cgtgatttag ttgatttttg ttttatcaac cacgtgtttc acttgatgag tagtttatat    300
agttaacatg attcggccac ttcagatttg ggtttgccca catatgacat accgacatag    360
aaggttaaat ccacgtggga aatgccaata ttcaatgttt ggttttcaaa agagaatcat    420
ttctttatat gatctcaaaa gtatggaatt gaaatgacta atgagcacat gcaattggtg    480
ctatcttaaa aaccgaacgt ctttgaattt aatttgtttt tcaccaaagg tacctaatga    540
aaccctttca ttaaaaaata aaggtaacaa acaaaatttt gtattggaaa aaacattttt    600
tggaatatat aatttggtaa tagaattatg agcaaaaaag aaaaagaaaa gaaagaataa    660
tgagcataat aaagccttta cagtattact aattgggccg agcagttttg ggctcttgat    720
catgtctagt aatcttaaac agacgataaa gttaactgca atttagttgg ttcaggtgag    780
ctaccaaatc caaaaatacg cagattaggt tcaccgtacc ggaacaaacc ggatttatca    840
```

```
aaatccttaa gttatacgaa atcacgcttt tccttcgatt tctccgctct tctccactct     900

tcttctctgt tctatcgcag acatttttgt ttatatgcat acataataat aatacactct     960

tgtcaggatt tttgattctc tctttggttt tctcggaaaa                          1000
```

<210> SEQ ID NO 118
<211> LENGTH: 998
<212> TYPE: DNA
<213> ORGANISM: Arabidopsis thaliana
<220> FEATURE:
<221> NAME/KEY: misc_feature
<223> OTHER INFORMATION: Ceres Promoter PT0660

<400> SEQUENCE: 118

```
caagtcaagt tccaatattc taaggagaaa taatagtata ctaaacatac attagagagg      60

ttaaacttct ttttggattt aagtgtgtat gcataggcta tttattctta agtataacta     120

ttaactgtag ctagatttat acaagaaata cataaaactt tatgcatgtg aggtagccat     180

gaatatacgt acatgttgca atcgattata catgttgtat ttggatttct ctatacatgt     240

tttaacttgt cattctctaa gtatatacat accattaata ctgtgggcat gagtttatga     300

taagactttt cttttggaga ccagttttgt tttcctttcc acctatattt gtctataggc     360

ttcacggtac actagtttac aagtgttttt atatgttcta aataaaattg agattttccg     420

gaacggtatg atctgtttgc aaataaggac gtatatataa cagtatcaaa tatatttgtt     480

gttataaggc aataaatatat tttctgagat attgcgtgtt acaaaaaaga aatatttgtt     540

aagaaaaaaa aagatggtcg aaaaagggga gtaggtgggg gcggtcggct tttgattagt     600

aataaaagaa accacacgag tgacctaccg attcgactca acgagtctac cgagctaaca     660

cagattcaac tcgctcgagc ttcgttttat gacaagttgg tttttttttt ttttttaat      720

tttttcatct tcttgggttt ggttgggtca ctcttcaggt caggtgtgta aaaaagaaag     780

aaagaaaaga gagattgttg tgttgtaacc cctttgacta aaatctaatg aactttttta     840

acacaacaaa actccttcag atctgaaagg gttcttcttc tctcttagtc tcttcgtcct     900

tttattctcc gtcgtcgttt catgatctga ctctctggtc ttctcttctt cttcttcttc     960

ttctattttt tcttacttcg tcactgttgt gtctgaac                             998
```

<210> SEQ ID NO 119
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0665

<400> SEQUENCE: 119

```
aaaaaggatg ggtaatggga cctattttcc ccaacatccc acatgcacac ttccctctcc      60

attctctcac atttatttct ttcattctaa tttatccatt ccgtgtgtaa catattcact     120

aataatctca tctcactaac tcattcattg attgtgatat gtttatctag aattagtgtt     180

ttaacactgt gtctacatat gatttccttt tcattgtatg tgaacatgtt aactcactaa     240

tcattttgta ttttcgagtt aacatgagtc tccacttcgg tagactaaag taaagatagg     300

tttgagtata ataaagttta aaatttgctt taaaatcaat atttataaat aagtttttat     360

cataagtgat ttttgtatgt tatattggac cttgtataaa cagactacag aagaaaatta     420

tttatgagaa cttgtaatgt tagagtggac ctcgtataaa ctaattatgt gggcttttac     480

cataaactat ttatgaaaat tattatggcc cacaccacta taactaaagc ccacatattt     540
```

agcagcccag tttcattgta agagacatgt tcgctctgga actagaattt tctggttttt 600
gggtatttgt tttcttatgt gtagagaaat gatggtaacg attaaatgtt gtgtattaca 660
atttacaatg gtaagacgat taatatattt acacacaatt ttgttgttgc tgtaacacgt 720
tagtgtgtgt gatgatagaa tttcataaag ctttaactac gaggggcaaa atgttaattc 780
taaatagttg acagcagaaa aagatatgta tacataatat aaggattaaa acgtaaataa 840
taataaataa ggcgagttaa attaaaaccc tgttaaaacc ctagcttgaa acacatgtat 900
aaaaacactt gcgagcgcag cttcatcgcc atcgccattc tctctctcat caaaagcttt 960
tctccttgat tttcgcattc tttagagtct taacgcaaag 1000

<210> SEQ ID NO 120
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter PT0672

<400> SEQUENCE: 120
cagccgtaaa tcctccataa atttattttg caagttttgc tcattatata atgagcggaa 60
tttatgatat aatcgtttgt aataatgtta tgttttgatc aaaatttgaa attaaaagta 120
ggtgagaact tgttatacag tgtagataag gtggatcttg aatataaaaa taaaatttat 180
aagatgtatt taaagcagaa aagcataaaa ctttagataa aataatgtaa aaatgtgtta 240
gcatcaatgt tgggatattg gccgacccga acttaatcaa tgtcggaagc cattacttct 300
ctcccaaaag accttttttcc ttcggagaac taggaacttc ctcactacct ttcgcttaac 360
gtgaaagcca taaatttcat atattcataa aaatcagaaa atctaaaact gtttagtatc 420
acctgttttt ggtatagact attggttttg tgttacttcc taaactatat gatttcgtac 480
ttcattggat cttatagaga tgaatattcg taaaaagata agttatctgg tgaaacgtta 540
cttcagtcat gttgggtcta gatttacata ctactatgaa acattttaag ataataatta 600
tcctagccaa ctatatgttc tatattatgg gccaagaaga tatagaacta aaagttcaga 660
atttaacgat ataaattact agtatattct aatacttgaa tgattactgt tttagttgtt 720
tagaataaat agtagcgtgt tggttaagat accatctatc cacatctata tttgtgtggg 780
ttacataaaa tgtacataat attatataca tatatatgta tatttttgat aaagccatat 840
attactcctt gacctctgcc cccatttcct tttactataa ataggaatac tcatgatcct 900
ctaattcagc aatcaacacc aacgaacaca accttttcca aagccaataa taaaagaaca 960
aaagctttta gtttcatcaa agacgaagct gccttagaa 999

<210> SEQ ID NO 121
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0676

<400> SEQUENCE: 121
aagatagtac agtttcagtg ttttgagaaa aaaagctgaa ctaaaactaa aatgtttaag 60
gacacaatat ttagtttcaa ttagataatt caacagtttg aacaattttt tttttttttt 120
tttgaagtca tttatttata caatgtttta aaacgcatta agcatttagg cagccgacaa 180

```
acgcctattg tctaactgta aataggcgct tccacttagg ttcatattgc atatttacta    240

tatgtgtata gtgacaaaaa ccaatatttc tcttattttg gatgaaggta tagtagttgt    300

taaatgttca atataattaa gcattaatga caaataaaat aaaattaatt tagttgataa    360

aaagataatc ttataaaaag atcgatgaat agatataatg gtttactgaa ttctatagct    420

cttaccttgc acgactatgt cccaaggaga ggaagtacct taactataat tctgaacata    480

attttgtcta tcttggtgag tattatatga cctaaaccct ttaataagaa aaagtataat    540

actggcgtaa cgtaataaat taacacaatc ataagttgtt gacaagcaaa aaaacataca    600

taatttgttt aatgagatat attagttata gttcttatgt caaagtacaa ttatgcctac    660

caaaattaat taatgatttc aacaggaagt ctgagatgat gggccgacgt gtagttacgt    720

ttcttgaatt gtgagagatg gtatttatta tactgaagaa aacattattt actaaataaa    780

ttttcatttc acatcttctg taatcaatgc gggtagatga agaagttgtt aatacgatgg    840

ccaaccatat ggatctcttt tttggcgttt ctatatatag taacctcgac tccaaaggca    900

ttacgtgact caataaaatc aagtcttttg tttcctttta tccaaaaaaa aaaaaaagtc    960

ttgtgtttct cttaggttgg ttgagaatca tttcatttca                         1000
```

<210> SEQ ID NO 122
<211> LENGTH: 998
<212> TYPE: DNA
<213> ORGANISM: Arabidopsis thaliana
<220> FEATURE:
<221> NAME/KEY: misc_feature
<223> OTHER INFORMATION: Ceres Promoter PT0678

<400> SEQUENCE: 122

```
aattaaatga aaccgcccct aaattaggag ggatttgggt aagtggtaac acattcactg     60

gaaacatgtg aagaaaggag gatgtcaagt agctgaaaac tcagtatagt aaccaacggc    120

ttctcaccaa cctttcatta ataatttggt catccctata tttttattca acattttgtt    180

tttcaatagc ttagagcacc ttaatacctt tcagtgtttt tttataaaaa aaacaaaaat    240

tgggattaat catcaatccc caaatgtaac gtttacttag attatgttca tttttctata    300

cacacaaatc atattctttt gttttaatct tcgaaaaacg agaggacatt aaatacccct    360

aaaaaaggag gggacattac taccaacgta cattaacatg tttgatagca aacgatttat    420

tttgttcgtt ttgaaaaggg gaaagtaatg tgtaaattat gtaaagatta ataaactttt    480

atggtatagt aacattttcg aataataaga gagggaaaac actcgccatt gtcggcaatt    540

tagaaccaat attagaaggg tttttttaga gaaaaaggac ttaaaagttt agagacctta    600

acaacaactt atttagaaat agacatgctt aagttgacaa cagcgagttt attttctata    660

tcgaagaaaa atacgaactt tttcttaatt agatttcgaa tgcatgcact atcgagaatc    720

gaccgtcaca agaaaaaact aatatacata ctgtacatat ctatattcaa tattggtggg    780

gatgggttta atgtgtattt ataattcatg gataaattca cacaataagg tccatgaaac    840

tagaaggtac caaaaataag cattaatgac tctttgccac ttatatatat gattctctca    900

tagtaccatt ttattctccc aaacctatct tcttcttcct ctcttgtctc tctcgctctc    960

tctcttctac attgtttctt gaggtcaatc tattaaaa                            998
```

<210> SEQ ID NO 123
<211> LENGTH: 1000
<212> TYPE: DNA
<213> ORGANISM: Arabidopsis thaliana
<220> FEATURE:

<221> NAME/KEY: misc_feature
<223> OTHER INFORMATION: Ceres Promoter PT0683

<400> SEQUENCE: 123
gattgaatga tgagtgtgca cccttgtatt actaataaaa aatttagcaa cagttataag 60
ctaacgtcat ccatgagtca ttcattagat tcactatttg cgttctcaaa aatcgaattg 120
ttaaaatttg agaagctcta atatacgagt caatgagatg tggcaaaagc atgtccttga 180
ccataaaatt tcgaggggtc aactcattag ataaggacaa gaatcaacca attgaaggcg 240
tcttctataa caagtttctt tattactaat attaaagtcc aatggggtga gggggagaag 300
aacttaaata aaaggaaata attggtaagt gaataaaatc taaatacgat actagatgat 360
tgatttgtgc tagtgcatgg tattagatca gatatgtgtt actattcgaa ttcaaattgg 420
catattccat gttgttgata agaaaattgt agaagtgtaa aagctgagtt actatattca 480
aactagtggt ttacataaag tgagacaaca actgtttcac aaaaatgact ataaaatagt 540
aagtagtatt aggtcaattg attttaaaat tttaatcaaa ttcaaatttg tgatataatc 600
aaatttgttt atagaaaatg ttaagaaatc aattttggca gaactaattc agtgagaaac 660
aatcatttac aaaaacaatt ttaacattat ttaacagtaa gatttgacat ttaacccgtt 720
cgtgtgaacc catcatatct aacatggctc tacccatgac gcctccatgc catggacaat 780
tttgacagat cagaagttct gaacgtggac gaggtaagaa caccatgatg atacgattgg 840
agttagttat gtcgccaccg acatcactgc caatctcatt aataaaagtg gtactaaatc 900
tctaatctct attaactata aatataacaa agaaccaaaa gaaagtttct tatctctctt 960
atctttcata atttccaaga aacacaaacc ttttctacta 1000

<210> SEQ ID NO 124
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0688

<400> SEQUENCE: 124
acgttcagag gcatcgcttt tgtacaaatt gaagcgggtt tgttcaatat ttaaaataac 60
acaggaaaca ttcaaatgta ttattgatgt tgcttaggtt tgtgaaatga tatgaaccat 120
atcgtatata ttactagatt tttcttatat gttttaaggg tagtggggct gacctatcat 180
tctgtttggc attaccaatc agactatcag agtattcacc attcaggatt ccataactag 240
aaaaagaagg ggtttacatt ttctcatact gtataatttt ctactatcag agattttatc 300
gattacatta atctcatagt gattattctg atttataaaa aagttgacaa aataattaaa 360
accagtattt tataacaaga ttgtctctct cccatggcca ttattttgac ctctgactta 420
tttaaatctt aattaacagc ataatactgt attaagcgta tttaaatgaa acaaaataaa 480
agaaaaaaag aacaaaacga aagagtggac cacatgcgtg tcaagaaagg ccggtcgtta 540
ccgttaaggt gtgtcgaact gtgattgggc cacgttaacg gcgtatccaa aagaaagaaa 600
gggcacgtgt atagatctag gaaaaaagaa agaatggacg gtttagattg tatctaggta 660
ccaggaaatg gaacgtcaca ccaaacggta cgtgtcggat cctgcccgtt gatgctgacg 720
gtcagcaact tccccttatt catgcccccc tgcccgttaa ttacgtgtaa cccttccatg 780
cgaaaatcaa accctttttt ttttttgcgt tcttcttcaa cttttctttt taaatcaaac 840
cttttctttt taaaatcaca ttgcatttcc taacgctcaa caaaatctct ctctactaat 900
atctctctct ctctctctct attgttgaag aagactcata atcggagatt gtttgttttt 960
ggtttgctct gtaaattgga gaagttttgt tagagatcaa 1000

<210> SEQ ID NO 125
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0695

<400> SEQUENCE: 125
aacattttct ttaacttact cttaaatttt aatagtaagt tgatgcatgt tatgttgatc 60
cgtcttgatc acaaatattg ttttatggac gaattctttg acagtaaatg gctatagtga 120
ctcagcttgg agcatcccga tatgaaaaca aagtgcagta ttgtgtcgtg gtcatcacta 180
acgcactttc ctagaactat cgcgcgtgtt tgacctatgc aacacaccag atgtcatgaa 240
cgtatactta aatagaaaca atgatataga caattggcta tattctgtca tggaacgcaa 300
accggataac atgtctatta gattcatcgg acttgatcat ggttatgtct taatagacga 360
attctttgtt aacgattggt taaaacggct cacgttagag catcctacta tgacttcaaa 420
attgataaat attacatgga aatcacttta attttagtta gaaggtagtt aatttagata 480
ttcttattta ataaattaaa aaatagaaga aaaaaagatg agaagagttt ttgtttataa 540
aataagaaat atcttttatt gtaattttaa aattaaacaa atttaattta tattaaaatt 600
atctttgttt tattgttaag gcaataatta ttttttggt gggaattgtt aaaacaataa 660
ttagtatact gttaagtggt cctttaataa taagataacg tgatttaaaa aagaacgaga 720
caggctaata tagtagagag gaaaaaatac aatttaggcc caataaagcc caatatagag 780
ttgtgctcaa acacaggtct tcgccagatt tcctatgacg ccgtgtgtca atcatgacgc 840
caagtgtcat tcaagaccgt cacgtggcgt tgtttctaca cataggcgat ccatacaaat 900
cagtaacaaa cacgaaaaga gcattcatat gtacgaaagt agaaaagaag agactctttg 960
tgataaaact aagtaagaaa tagcataaaa gtaaaaggga 1000

<210> SEQ ID NO 126
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0708

<400> SEQUENCE: 126
gtttccaaaa ctagtattct ttatttgctc tattcattat atttttatat ttgtaacgtc 60
ccgaccgtct ttattaggtt tcgacaatca cttctcggaa ggtcgtccat cctgaaatta 120
ctctatccta aacatgttta actataaaat tctctcgaaa cttttgtaac gtatataacc 180
acataaattc tcttaaactt atttgcatac accattatat ttctgaaatc gatatgttac 240
aatattattt aatatttaga ttacttttac tgaatcgaat taaatatcaa atcgaaacaa 300
atctaatcta ccaaaaataa ttttgttata aacatttctt gcctagttct acctcatata 360
cattttagtt aaagaaagaa atcacaacaa ttcccataat tcaataatta aatccacaaa 420
atcttggagt aagtaagaga aataaaaaga tagtatctta acataaacaa ttcaaagatg 480
ctctctcaca caattcacac acacttacaa aacaaaagac agaaacaatg ttttcattca 540

```
aatcaaaaga agttataaca ctagtacaaa aaaagctcaa attctaatag taactctttt    600

tatttcccaa ttacccaaag attctctctc acttcacaaa actagctttg agagtcgtgt    660

tccacaaaat ccattaaagc tgaaacggtt ttgctcacca ttcaaacaaa tacaaaattg    720

caaaacccca aattataaca aaataatata aaaattaaac cgctaaaaag agtgaaccaa    780

caaaaatcgc cgaatgtgtg tgtaatgaga aaaccgaccc atcatcccaa tcatctcttc    840

ccgtgtcact ctcttcctct cccacgtttc ttctctcttc cctttatggg ttttaacttc    900

tccttcttct tcttcttcaa tcttcagttt tcaaattcaa caacaattca cattttgatt    960

tcttcatcat ctctctctct ctcgcttctc tctcaaatcg                         1000
```

<210> SEQ ID NO 127
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0710

<400> SEQUENCE: 127

```
tagtgcgcgt ggggagaggg aatggtgaaa ccttagtggt taagttatga ggaaaatgat     60

aaaaggataa aacaatcaaa tgcagcttga aacggccata acataaagta ccttatggtg    120

gtgcgaatat ttttgtgttt ctttcactct tttattgctg aaagctacga cacttgtctt    180

aatatattgt ttccgcaagt cacatgatct actttttatt taacgtctag aaacgccgag    240

atatatgatg attagtatat cacgtctatg caaattgtta gttcgtgttt ggccaaaaga    300

tatcgagaca tgtctgaaga accgagtctg gttttgagat atttcttcaa gcattactat    360

acaatagaaa aaggagacac gcgaatatga taatagcaaa aggcataaaa aggcgaaaat    420

taaagaaaaa cgtaaagtga tttggcctca atcaacggga acgtatctta attttagagg    480

ttcttctttt acttttgaga cgagagagtt tgcgtctttg cgagctgctt tggttgacta    540

aacattatca tattgaaaac caaaatacaa cggaggaata tttgtcacag tttcactttc    600

acattgtttc cttaacgttt aatcaacctt gttcaaaatt tctatagttg taatcatcat    660

tgtttacaaa attttcgttc aaagatgatt ttaaataaaa ttgtgaaaga aaaccttttc    720

tgaaataagg attggatgat agtgttaaaa gaaaaatatg aactgaggca aaaagaggag    780

tggtccccgg aagattgtga aatgtgtcat ctaaaccagc cagacgtagt cacgtgttct    840

ctctagcttt atgaacttcc ttagccagca ccatcattgt gattgtagta tatatgtaac    900

cctaccttca tctctcccat tttccattct ccatatagac tcctttacaa tatacaaaac    960

ctatccaaaa gcgaagaagc caagcaaaca tattataaaa                         1000
```

<210> SEQ ID NO 128
<211> LENGTH: 1002
<212> TYPE: DNA
<213> ORGANISM: Arabidopsis thaliana
<220> FEATURE:
<221> NAME/KEY: misc_feature
<223> OTHER INFORMATION: Ceres Promoter PT0723

<400> SEQUENCE: 128

```
gtcatatctt atcaacacgt caacgatcaa aacctttagc ctattaaatt caacggctta     60

gatcaaaacg aaactaggtg ggtcccactt ttaatatcgt ggctgcataa catttcctcg    120

ataactgaag ccgttgtggt ctttctcaga atctggtgct taaacactct ggtgagttct    180

agtacttctg ctatgatcga tctcattacc atttcttaaa tttctctccc taaatattcc    240
```

```
gagttcttga tttttgataa cttcaggttt tctctttttg ataaatctgg tctttccatt    300
ttttttttt tgtggttaat ttagtttcct atgttcttcg attgtattat gcatgatctg    360
tgtttggatt ctgttagatt atgttattgg tgaatatgta tgtgtttttg catgtctggt    420
tttggtctta aaaatgttca aatctgatga tttgattgaa gctttttttag tgttggtttg    480
attcttctca aaactactgt taatttacta tcatgttttc caactttgat tcatgatgac    540
acttttgttc tgctttgtta taaaattttg gttggtttga ttttgtaatt atagtgtaat    600
tttgttagga atgaacatgt tttaatactc tgttttrcga tttgtcacac attcgaatta    660
ttaatcgata atttaactga aaattcatgg ttctagatct tgttgtcatc agattatttg    720
tttcgataat tcatcaaata tgtagtcctt ttgctgattt gcgactgttt cattttttct    780
caaaattgtt ttttgttaag tttatctaac agttatcgtt gtcaaaagtc tctttcattt    840
tgcaaaatct tcttttttt tttgtttgta actttgtttt ttaagctaca catttagtct    900
gtaaaatagc atcgaggaac agttgtctta gtagacttgc atgttcttgt aacttctatt    960
tgtttcagtt tgttgatgac tgctttgatt ttgtaggtca aa                      1002
```

<210> SEQ ID NO 129
<211> LENGTH: 1001
<212> TYPE: DNA
<213> ORGANISM: Arabidopsis thaliana
<220> FEATURE:
<221> NAME/KEY: misc_feature
<223> OTHER INFORMATION: Ceres Promoter PT0740

<400> SEQUENCE: 129

```
tgtggccact aaagatttac ccttaaccgg gcccatataa gcccacgtca agtggcgctt     60
atacgctctc cgtaagagag ccaacatttg gtatgtaatg ttgcaaatta ttcttcaaga    120
caataaattc aaatataatt caatattgtc caaatatagt gatgtacttc agttgtgcac    180
atagaaactc cactaaacca acttttagat agatgcattc acaaattttc aacaatgtcg    240
cgaaagtcta atccatcacc agattctaac attttaatta ttatatttaa ctatacatac    300
tctaatcagc atgagtcaaa cgtgtacaat agcccaagca tataataaga ccaaagtcaa    360
actcaaataa atgtctccaa actcaaaact tgaaaaagac ctaattatta catggtagat    420
atgactttgt cgacaagtaa accaactaat cctcgaagct accttctctt cccagttatt    480
atgtgtgatc gatttataaa tctcttcttc taataacacc tatatttttc ttatgatgtg    540
aataaatata aaactttaa ctttaaaaca tatttatccg aaatattgca cttagatttc    600
aaatagataa ataatagtac tatctaactg atattgaaaa gacctaacac ggaaaacagt    660
tttataaaaa atcccaaatg tgggtaatta tcttgatttc ttgggggaaa cagaaaatgg    720
attaagatta atcggagtcg tgtcaagcag ctcgttaata actgtagcaa gttgactgag    780
taagcatcaa cgtgtcatct ccgtaaagcc cattatttct agtctcgccg cgtcttctct    840
tccacgtagc acttcacttt ttctctcctt ttgtttcctt tggaacacaa acgtttctat    900
ttataggaat aattacgtcg tccgtatctg tgtcggaaca tagatccaaa ttaaaagcga    960
cttacttaat tacatatcgt tcgtgttttt ttcttcaaaa a                       1001
```

<210> SEQ ID NO 130
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter PT0743

<400> SEQUENCE: 130

```
tcgattggcc cgatcggccc caaaatcaag ctgagccgct tcaaacttca gcttttgaaa     60
tcacccccaa actcatgtcc tcttatcatt ataactaaag gatctttcat tttatttaac    120
tcatcgtctt gcactaccca acccaaaggt tccaactata cccgaagctt tctaaaggtc    180
caaagacttt ttttttcgag ccagactatt caagccaaga aaagccaaac cccacaagcc    240
agtacttttc aattccatat tataaactta tctgtcttgt tttagtccca ctaaaaacaa    300
cagaatttaa tttaggttga gctaaaaccc ttgacaaaag tgtatagtcg tcgattcagt    360
agcacactca tcactcatca gatttgatag ttgacctaaa gtatgactac tccatttcaa    420
ctaacaaatg aaaataaaag agacctaagg gttagaggat tgaaactata ctctcaagtc    480
ttttatcact aggctactac cagctagtta acttgatgga tttaagcaag aaaacgtaga    540
atttatattc gagcagattg tttagctaaa aaagcttggg tttgaaattg ccttttctcc    600
catataagca cgtcggttcc taaataactc tttctagcgg agagtgtctt tccaataatt    660
taataaaaat ggtgtttgta tatcaaaaaa aaaagaaaaa agaaactgat cgagatagaa    720
cgtttgcagt tttataaaca atttaaaaaa caaaaaaaat taaactcaat gtatttttta    780
ttaattcaca aacaataata aatcatagga tcgaatattt acacggtatc aaaacctact    840
cgccgctact atataaaaat tgaagtcaaa tatcaaccgc aattattaaa ccagcaagac    900
aataattcat aaacttaata taaacataaa taaattaatg ttacacaacg atatatggtg    960
agggttatta ctatcttctt cctctcaaaa cacatctcct aaccttaagc tttagacggc   1020
ctgc                                                                1024
```

<210> SEQ ID NO 131
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0758

<400> SEQUENCE: 131

```
agctagccac atcagtgacc aaaaaagata attaacaaac caaataaaat aacaaatttt     60
gatcatttgg aataaaattt ataaaaggaa cgaaagcgcc ttctcacggg tcccatccat    120
tgaaatatat tctctctttt tgctctatat aataataacg cgtactaatt tgtagtatat    180
attattacaa agtcgatatt tgattgtttt gtgaacgttg atatattaat tttcttggat    240
gatgacaaaa aaagtcatag aaagtaacgt gtgaacatag cattaacaaa atacaaacat    300
aatatataac caaatatatg aaaataggat aaaatctcat tgaatagatc ttcttctatt    360
caaatatata aatatttgtt tgtctataaa attaacagag cattcacatt atctaaaata    420
atagtaaaat caaaataaaa ctaaataaaa ataactctgg ttttataacg attgatttta    480
aatattagtt tttgttgtaa agagatcatt atatatgtct gtaatatttt tatactgagt    540
tacatgatat ttagttatta tagcgtaatt aactaagata agaaattaac taaagtgata    600
ttctgattat tattattttt gttaggacac gtacgtggaa aaactaaaca ctataggtta    660
caaaacggta taataaactc accattactg gaaaatgttt gcatttgact caataagtaa    720
cttattataa gttactgata taatgcatag ttttgaaatt cttaaataaa ttattttggt    780
ttcgcatgaa aatatgaaag gagagaaatt tattattgtc acttatatat atatacatcg    840
```

```
taatcatttt ttcgtgaata attctctctc ccattccatt atttctcagt atctctcttt    900

ctttccctta ctttattgtt gcttttaaac cttcaatttg ctcataaacc aaatatataa    960

tatcaaaaca aacaaacaaa aaatcagaat tcccctaata                         1000
```

<210> SEQ ID NO 132
<211> LENGTH: 921
<212> TYPE: DNA
<213> ORGANISM: Arabidopsis thaliana
<220> FEATURE:
<221> NAME/KEY: misc_feature
<223> OTHER INFORMATION: Ceres Promoter PT0829

<400> SEQUENCE: 132

```
aaagttttga attattggga atcaatttcg aagttttgta attctttggg ggctaatagg     60

atattttatt ttcttggttt cgtctattgt tgtttttcta tttatggttg ggcttttaga    120

actctggaca ggcccatgtc atatgttttc ccttctcctt atatttttca tttttcattt    180

tgttaaatta atgcataata tccaaaaaca atttaaattt ttgaaggaac cctttagtta    240

cggctccgaa gctttcacaa gtgagaatgt gagatcaaag aaggcaaatg gaggatttta    300

aaagttaaaa tcatctttta tctgcaaaag ttgacaattt ttttgtatca aatctaaatc    360

atcaaactct cttaaactac aagagcataa caacctctat gtaatccatg aaataatctg    420

cttgaaggac ataacataaa tcattatggc tagagtgact aacttcaatc aaatcctctt    480

aactctagct cccttacaat ggtatcgtaa aacattatgc attagggatt gttgtcctag    540

gaaaataaaa taaaaatccc cacagaccaa ctaccatttt aacttaaaaa taagcttcgt    600

ccgcgacgaa ttgttttcca tcctaaaaat agaatggtgt aatctgctaa tggtttagtt    660

ccattaactt gcaagttcta ttgaaagcct aaatgtcaat aaagatatta aaattcggag    720

tcaaaagaca aatgaatcaa aagcaacaag acaagtcagc tccattcttc actacccatc    780

ttttacaata aatcatctct cttttcacaa atttcaaact actctcattg ccctttagct    840

ttgttataga gccaacacta cagagagact cacacacttg tttcaataat taaatctgaa    900

tttggctctt cttataaact a                                              921
```

<210> SEQ ID NO 133
<211> LENGTH: 763
<212> TYPE: DNA
<213> ORGANISM: Arabidopsis thaliana
<220> FEATURE:
<221> NAME/KEY: misc_feature
<223> OTHER INFORMATION: Ceres Promoter PT0837

<400> SEQUENCE: 133

```
aactacaagg gagacataat atcaccatct ggttcctgtt atcatctgaa gatttcttgt     60

tttaccttcc agtgataaaa tgatccttat aatacatata gatatattaa attgctgtat    120

tttaagatta tagatatata aggtacatga gagtgtttat ttaaaaaaat tcacttggaa    180

ttcatgtttt gtgatacgtt agattggaat ccatttggga aaagaagaat catctgttct    240

tatgtctcaa attttgactt cattcacttt tcttcttgtc ttttaagaaa gcttccacaa    300

tctaactgtt cgatgtgaaa actgagattc gagtaagaaa atgtgaactg tgttatactg    360

ttttttaatt agataattta gattgcactc agataaatta ataacattcc tcgaatactt    420

ttatgtgatt ggatatatta ggtatatctg ccaaccaacc aataaactgc tatgtttaaa    480

caaattaaat aaattagtat atgtttactc aagaataaag aagatagaaa agaaaattct    540

atatgagcta aatttgctgg aggaggcatc ggacgtgggt accagacctt tccaagcaca    600
```

cgagtagtgc ttagccatgt catgctaaca tacaccattt ggttcataca aaatccaaat 660
caaaatctat ttttaaaatc ttttgcacac gtctttgaaa aacacctctc atactatagc 720
tacggaagct tcaatttcaa ggtttgtcta aaagctaacg att 763

<210> SEQ ID NO 134
<211> LENGTH: 751
<212> TYPE: DNA
<213> ORGANISM: Arabidopsis thaliana
<220> FEATURE:
<221> NAME/KEY: misc_feature
<223> OTHER INFORMATION: Ceres Promoter PT0838

<400> SEQUENCE: 134
atactggtat gcttaaggtt gaagccaaga tctctgtctt acccaagtaa ccactttcta 60
ttagaaggga tcaacactaa gaatatggag atttaagcct aagggctaag gcggttctca 120
acaatacatg atgtgaatac aatcacagac gatttactga ggtttgttga taagatcttg 180
atcagtctct gcatcatctg ttcaacaatc tcaatctttg actgtttgct ttcggagcca 240
taaacagagg aatcccttat tccctgttat aggagcaata caccaagtat tatttccatg 300
gctgaaattc tcttatggaa acctaattgt tccattgaag ctgtaaaatc gaatctggtg 360
aatattctcg agcaaagccg catgctaatt atgtcaattc agaagagttt gattaggaga 420
ctcgaagcga gtttgatgat ctttcttgat gttcaactcc gattgtaagg gtataattga 480
cttttcatgt attacggctc caccacctga cactaaggca ctctttgtcc atctcgttgg 540
tatcatcgga ttcggatggt aaaaataaaa agagcagagg aaacttgtta ctcatgcaag 600
cttctcaggt gccacgtcac tccattacgt gtcatcttca cacaccatct cgctcaaaac 660
cgatctcatt tttcaaacct taaaggcaga agcaactgat taagttaaca ctcttgagaa 720
gctctcgatt aagcttgaac ttggaggatc a 751

<210> SEQ ID NO 135
<211> LENGTH: 669
<212> TYPE: DNA
<213> ORGANISM: Arabidopsis thaliana
<220> FEATURE:
<221> NAME/KEY: misc_feature
<223> OTHER INFORMATION: Ceres Promoter PT0848

<400> SEQUENCE: 135
tctctttaaa tcagttaact aaccgtttat atatttacga taaggtttga agagattatt 60
gataaaataa tacatttcat aatcccgcgt tcaaccgttt aaagtaacat ttaagttgac 120
tatatctaat ttttttcca ttaaatatgg agctggtaaa ctttatcaac ttctaaaaag 180
tgtaacaaca aaaattaggt caatcacaat tctgtttttt ttattatttt ggattgactt 240
ccaattgcaa atagtcttag tgatcaccat tatcatacat atatacatca agtaggtttc 300
atcatgatat accacaaagt atttgacaag ccatatggtt ttggatcaaa aagtcggtcc 360
aaaattaatg ttttatgtgc aagaaccgac ccattgtaca cacgtgttaa catcttcaag 420
actttcatct ctatttttct tttggtcatt aagataccca ttgatccgaa tctgttacat 480
tcccacctac tttttaatt tttactatcc actccaaatt aaacacaacc gatgatttta 540
ataattggaa gcttttaaaa atatttcaaa acaagcctct ttgtgtttgt ctatatatat 600
acacgtaata agaaggtgaa tgaatctcac agcttacttg ttctaaggct tccaataacg 660
aaaacagta 669

<210> SEQ ID NO 136
<211> LENGTH: 702
<212> TYPE: DNA
<213> ORGANISM: Arabidopsis thaliana
<220> FEATURE:
<221> NAME/KEY: misc_feature
<223> OTHER INFORMATION: Ceres Promoter PT0863

<400> SEQUENCE: 136
cgggaaacga caatctgatc tctagtccag tcgattggcc cgatcggccg attataaact 60
tacatgagac aagtataaat aattattata aacttattaa gtttaagatc aaggcttttg 120
tgcaatgtat caatgaatgt tagatgtgat atgatgaaag caatgtttta aacacataca 180
tagtcattga tcggaatgtg tgttattaga aatgcatgcc taagccgata gggttatcta 240
tgtttggtct tggacattat agccaaattt cgaatctaat tcttccaata tatatttttt 300
tttttttgct tagggccact actagtattg cttatcaatt ttaagagctc atgaaaatgc 360
aacaatatag tagttgcaaa tccttgtttc aagagaaatc aaagggccac ttgtgaattg 420
aataataata atatttgcaa ataacctttc actaaaccat accaacaaaa ccacacagat 480
ttggcaaaga cataaccttt gggagacgtg aaaaggctca aaatttgaca attgtcctta 540
caaattcgct cattagtgca attgtgagat ttgtttgcat ccaaatccaa ttcataactc 600
acactcgtct caaattcgaa aaggcctgca gggccagtgc actgggatcc aacaatgtcc 660
tccgactcgt ccaagatcaa gaggaagcgg aaccgcaccg cg 702

<210> SEQ ID NO 137
<211> LENGTH: 435
<212> TYPE: DNA
<213> ORGANISM: Arabidopsis thaliana
<220> FEATURE:
<221> NAME/KEY: misc_feature
<223> OTHER INFORMATION: Ceres Promoter PT0879

<400> SEQUENCE: 137
ttctaggaag actggtcaag ctaagctgtt tctgtttttt gtttttgtac tttacttttt 60
gtttgctagt gggaactggg tttattgggc cttgaagttg ataaaagatg aataaaagac 120
atatcgccta aagcccatat gagaagcaga agacaaaaac ctccaacttt gggcataaat 180
tttgattata gttaaaagtc cagacccaat ttggcacctg gcttagttac gattctaagg 240
catgacacct gcctaatatg tttattacag aaaataaaga gaatcagcta ggtgtccctt 300
attgaacaca ttaacaaact ccaacgacac tacgtgtctt cgtgactctt actatatcca 360
aaaacctata gctaaagctg aattttccat gattagtata gtcccaacca aaaaaatact 420
gaagaaggca taagc 435

<210> SEQ ID NO 138
<211> LENGTH: 397
<212> TYPE: DNA
<213> ORGANISM: Arabidopsis thaliana
<220> FEATURE:
<221> NAME/KEY: misc_feature
<223> OTHER INFORMATION: Ceres Promoter PT0886

<400> SEQUENCE: 138
agtgtatttg aaaacgacat tgaagaatta atatattttt ttttaatttt agttttttat 60
agtacaaata ttaaaacaaa caatcctacc atatcataac atttgtaaat aacattttaa 120
gttttgtttt gagttttaat taattttcta tgacaaaaaa atgaagtcaa tagactaagt 180

```
gaatcatata gtataaataa acacaattta aatagtttca aataaattta gaaagaataa    240

aacaaataga aatcagaagg tgtctgtttc ctcctcgcaa catacgatca aagagaaaca    300

acttgaccct ttacattgct caagagctca tctcttccct ctacaaaaat ggccgcacgt    360

ctccaacctt ctcccaactc cttcttccgc catcatc                             397


<210> SEQ ID NO 139
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0007

<400> SEQUENCE: 139

agcagaacaa ctatatttat tgtgtcacat aaatctgaga tcatttataa ccaccaaaga     60

acctatacac agtaaatgac aaatgtatct ccctctatct ctattgccca tatgtagatg    120

ctaaagtaag atttctcttt tttttaatgt actttttttt gtataaagta tattccataa    180

gaaaaaggaa aagcttgttt atggatcaat tgaccccaaa aaaagttttt agatcaaagc    240

ccaatataaa aaaaaaacac agtagtgaca caaaggaact taaataaacc atgaattgat    300

ctataaacag tagagatcga taaggcgaac attttccatg tgaagtgtct tctttcatct    360

ataatatttt tgacatccaa taatttcctc tataatatca ttcacataat tgatagaaac    420

attatgttag aattgtccac atcatttgag ctgtaatata ttctgtttta acaaattata    480

tggtagttgc ttaatcttat gtccatcttc ttctatgcat cgttttcgcg cctagttgtc    540

cagtccattt caactaccta cctctaattc ttatcttaaa acaacatttt ttaatttaag    600

tattatgctc aaagactaac tagatagaaa accgttatta aacattaaac gaattaaaag    660

tcttacatgg aaaatgtagg tttataaacc acgagttatg attgacaata aaaaaaatgc    720

aaatcatcaa tcaaaagaga cttgagtgcg actctatatc aaccattgca attaaaatta    780

tctatcacaa aaattttaga cagattaagt taatttagtc taaattcact aatttatttt    840

ctataattag taattaacta tatttattta tttacacatt ttctgataat ttagaaattt    900

gcatgaataa caaatataag attttggaaa ttagtagcaa atttaattaa taattatttt    960

tgcctaaatg aaccaaacta taaaacctcc acatacacca gtcatcaaat ttacagagac   1020

aaca                                                                1024


<210> SEQ ID NO 140
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0008

<400> SEQUENCE: 140

ctcgagagat gaagtcttag taatgtttga acaaacaata atcacgtttt ccatcaaatt     60

cgagcattta aagtttatat tactacatgc cccaagatga taccgtccat ctcatccgaa    120

aatatttctg aaattgcgct aagacaacaa tgtttgctca aattcgatca tttaaagttt    180

acaaatctct catcaatctt acaaacttct cacactaaac agaggtacat attttcttat    240

aaagacaaaa ggttcgaaca gctggcttct caactcgagt tgtttgtcag ggcctctctt    300

cactaactac aagttggtac ttcaaatatt ggtggctagc ttcacgtgat attgtctaca    360

aattaaaccc atgaaaaagc tgcattaatt gttccaagtg aaccctgagg agtgtcaata    420
```

```
gtctttgctt tagtgtgatc attaaaccaa atctctaaat tcctaatttg tactaacatt    480

tggaacgtat ttcctactct tctccctgct ccaactccca aaaataagat tagttagatt    540

tctataacta atatacatgt atactcccaa aaacagtaaa accatattaa taaagctaat    600

tttgcataga tttatttcgg taaaccggcg gttcaagttg ggaaaaaaa agacaaacgg    660

tctaaagtca tccaaagaca aaaaaccaaa gacaagttga gagagacgag accaatcaca    720

acattgcttc gtagattgcg tgacatcatc cttgacggct actttcattt gtgtcttatt    780

tggataaaac gcacgtgttt aattcacgaa ccttcatagc aataagaaat ttccattact    840

ttcatatttt caacttttt tattacccat tacatgctta aaatattaat tcacaagtct    900

ttgtcaaaat tcaatatttt ccaggttcat gaaccctttt tatctcaatc tactctataa    960

tatctcccta taaattacaa caaaacctct ttatttttca                        1000
```

<210> SEQ ID NO 141
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0019

<400> SEQUENCE: 141

```
gatataagta gaatcatttt ttgccgccgt ttctcgctaa cacaccgaaa actgaatcaa     60

atctcctagc tcttctacgc aaaatcgagt gcatcgacaa tggcggaacg tggtgtcgaa    120

cgtggtggag atcgcggcga tttcggacgt ggattcggtg gtcgcggcgg tggaagaggt    180

ggtccgagag gtcgtggtcg ccgtgcaggt cgtgctccag aggaggagaa atgggtgcca    240

gtgactaagc ttggtcgtct cgtaaaggaa ggtaagatca caaagattga gcagatctac    300

ctccattctc tcccagtcaa ggagtaccag atcatagatt tactcgtcgg tccttcattg    360

aaagacgaag tgatgaaaat catgccggtt caaaaacaaa ccagagccgg tcagagaacg    420

agattcaagg ccttcatcgt cgtcggagat agtaacggtc acgtcggatt aggagtcaaa    480

tgctccaagg aagttgcgac ggcgatcaga ggcgcgatca ttctcgcgaa attgtctgtg    540

gttccgatac gaagaggtta ttggggtaac aagattggaa aaccacatac ggttccgtgt    600

aaggtaaccg ggaaatgtgg atctgttact gtacgtatgg ttccagctcc gagaggttct    660

ggtattgtgg cggctagagt tcctaagaag gttcttcaat tcgctggaat tgatgatgtc    720

tttacttctt ctagaggatc caccaaaact cttggaaact tcgtcaaggt atgtactttc    780

acaatggctg ttttggtttg atgaactctg aattaggcag tgaaaaagta atcattacca    840

gttaagtgaa tttatattga agattaggat ttagctgatt gtattggttt gagcatgtga    900

gtttgtgttt aagattgctt gaattgaaat gctttaggtt gtttgattac gctaaattct    960

gactaatgta attcaaattg ttgttgtttt tttttggtc                          999
```

<210> SEQ ID NO 142
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0028

<400> SEQUENCE: 142

```
gtcagtgaag tcgattggta gtacttgaaa cacttggttg gtttcatgta tttggcctat     60
```

```
atataaacaa acatcgtaat tatatacgga tttttttcgg aattttacgc catatctgta    120

agtatatata acatgcatgt cgttttcaaa ttcatatgat gaacgatcca cgtaagtgct    180

actactccta caatattgca tgagagagat atgtatttat aaattttatt ttgaagaaga    240

aataagaggg aaggttactt gggtggatcg atgtgaaaac aaaagaagaa aaagcgaaac    300

ccactaagcc attacatgat atcgaccttc ttatcttttt cctctttatt ttatttttct    360

catcttcttt ttgtcaggac ttttttctac ttaatgaaac ctccaaacta tctaactaat    420

acactcccat gtagaataaa gaaaattata taagatattg ttgatatttt gtaactagaa    480

aatatatttg ctctgtaatt tttcgtaagt taaatcaaca ttttaaagta gaaacaaata    540

ttactgcaaa aagtaggatc attatttttg tccaaaatct cagttagcta tagggttgta    600

gtaaaaacaa aacacattct tgatttgccc caaaaaataa agagagagaa gaatattgtt    660

caaaagtggt ctcttctctc tctaattatg ttttcactaa acccaattag attcaaacag    720

tctacaaagt ccaaaagata aacatgggac aacaattcga tgcaaaaaat cctcttttca    780

tgctcttttt ttattctcta gtcttttaaa ttactaataa aaactcacaa atccaccaaa    840

cccattctct acaactcacc ttcatctaga tttacccact cccaccgaga aacacaagaa    900

aaaaaatata catatataaa tatacaagac aacacatgat gctgatgcaa tatacacaac    960

aaagtattaa atcttagata ttgtgggtct ccctttcttc tattcatttt cttattcatt   1020

aaaa                                                                1024
```

<210> SEQ ID NO 143
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0039

<400> SEQUENCE: 143

```
ccgttcgagt atttgaaaat ttcgggtaca cccgcctaaa taggcggacc ttatctagta     60

tatatataca tttgaactat attgtttact ttttagttga tttaggctat gtcatgacat    120

tgacataaat ctacctgtta tttatcacgt gtaattcgtg taaagtgtaa actagaaagt    180

tcaaatacgt atttgttttt gttctgttat ataggattgt catagttgta aatctacaat    240

ttattacaac atgaataagt acacaagcaa tgtaattgga tttaattgct aaactcttta    300

catggtcaat ctaaatttga taagaaatac gtcacatatt actaagactg atagtttttt    360

tgttgtcacc aattattttt gttaaattga cgaaaacaat tccaaaaact caaatgtaca    420

aaatcataca gtctcacaaa catctcatag agaaagatat aaatctccca tatgggaacg    480

ataacacgag gtcgaaatac tattcgtaaa actaaaacgc cttagttata aatcgttagt    540

tgtaaccgcg gtcgagaata catacagatc cacgaaacta ctactacaca tgctgctgaa    600

ttggaatttg gaaaagacca tcttctttag gaagagctca cccaatgagt gacaaaggtg    660

tcggtggctt gttttctacc catatgtata catcaaatgg tagtttcatt aacgtttggt    720

tttgagaaaa gtaagacttt ggctagtagc taggttcgta tataataaac tcttttgaga    780

aagttcatca ctggtggaaa atgttaaacc ggtttttttct cattttttcc gccatgttaa    840

ccaccggttt aaaaagaccg taacacattg aaagattaat aagggtatat ttgtaattac    900

ggtttgctgg caatttttaa ttattatttt aattagagaa aatagagaag ccctatcaat    960

gtacatggta tatatataaa aggcaaaacc ctagaaaacg atactattcg actcagccgt   1020
```

cctt 1024

<210> SEQ ID NO 144
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0050

<400> SEQUENCE: 144
aatctgatct ctagtccagt cgattggtac ttgagggaaa catcatattt ttaaaccttg 60
tctcagtaag ctaacacaca ccccttgtga ttacttatcc atgtttatcc acaagaatgc 120
agttggattg agatattttc ttctttgttg aaatcaggcc tcaaggtgtt catgtggtct 180
gcaaaaaaat tcccaaaaat aaagatagtg acatctgaaa tcgataatgg attagacgaa 240
gagtttcgtg ttattccttg gtatgggcgg gtttggggac agatattttg gcacagacga 300
ggactaggcc actgtggtcc tgcagcatta ggtgtccctt ccatgtcctg cattacattt 360
tattgatgga ttcatcaccc tatctactac aacggctaca caaactatga agagttttgt 420
ttactaataa atgcccaagt gaggggtcga tcgaacccgg gacacgtttt tcagtttacc 480
atatagaatt atccttggaa cccttgatac tccatagaac atcaccacct ctgttgtcat 540
ctcaggaatc caggttcaaa cctagtctct ctctccctag tgggaggtat atggccactg 600
ggccaatgat gacaaaatgc aaaaaaaata aaatacattt gggttcatta tctaaaatat 660
ctcttgtgtt tgtaagtttt ggttgcacac tcgtgtggtt gaagtgtgtg tgagaggtac 720
tatacaatac actctgcttt tgttttgtac ctatctcttt ctcttctcca catatccaag 780
actttgggga taaagctgag atcattggtt gccatttggt tgtgtagaag caatcaccca 840
tttgctttat ccgaggttga taaatttcct cgggttctcc ttctgacacg tatgacaaat 900
tctaatagta tattcctcgt agatattacc tatatattct caatagttgc aggtacttaa 960
ggctttgtct tggcatcctc gtcctcttca gcaaaactcg tctctcttgc actccaaaaa 1020
gcaa 1024

<210> SEQ ID NO 145
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0086

<400> SEQUENCE: 145
cttatccttt aacaatgaac aggtttttag aggtagcttg atgattcctg cacatgtgat 60
cttggcttca ggcttaattt tccaggtaaa gcattatgag atactcttat atctcttaca 120
tacttttgag ataatgcaca agaacttcat aactatatgc tttagtttct gcatttgaca 180
ctgccaaatt cattaatctc taatatcttt gttgttgatc tttggtagac atgggtacta 240
gaaaaagcaa actacaccaa ggtaaaatac ttttgtacaa acataaactc gttatcacgg 300
aacatcaatg gagtgtatat ctaacggagt gtagaaacat ttgattattg caggaagcta 360
tctcaggata ttatcggttt atatggaatc tcttctacgc agagtatctg ttattcccct 420
tcctctagct ttcaatttca tggtgaggat atgcagtttt ctttgtatat cattcttctt 480
cttctttgta gcttggagtc aaaatcggtt ccttcatgta catacatcaa ggatatgtcc 540
ttctgaattt ttatatcttg caataaaaat gcttgtacca attgaaacac cagcttttg 600 agttctatga tcactgactt ggttctaacc aaaaaaaaaa aaatgtttaa tttacatatc 660
taaaagtagg tttagggaaa cctaaacagt aaaatatttg tatattattc gaatttcact 720
catcataaaa acttaaattg caccataaaa ttttgtttta ctattaatga tgtaatttgt 780
gtaacttaag ataaaaataa tattccgtaa gttaaccggc taaaaccacg tataaaccag 840
ggaacctgtt aaaccggttc tttactggat aaagaaatga aagcccatgt agacagctcc 900
attagagccc aaaccctaaa tttctcatct atataaaagg agtgacatta gggtttttgt 960
tcgtcctctt aaagcttctc gttttctctg ccgtctctc 999

<210> SEQ ID NO 146
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0088

<400> SEQUENCE: 146
tcgattggga ttactacttc atctagtaag gttctgaaaa cgtttgttgt tgataaggaa 60
gattcgtctc aggttattac tgttgatctt caaggtttgt gattgtgacg cttatacatg 120
tgctgaaact gtggtgttta tttattgaaa acaaaaaaaa agtctctctt gtagtttcat 180
tgtactaaat agaaaacaag aaacgttttt ttctttaatc ttctacattg ataatattgg 240
atcaaaggat tgtttctgca agacacaaca caaacatact tatactagtt tacttctact 300
aagtactaac tacataccca tacacacact tgcacctaga ctttacttct agacatcatt 360
accctaaggt agaaccaagc ttacaagcaa gttttaccga caactcttac attacaactc 420
tagtctgtag tctttaacgt agacttacta actagtcatt agtggtttaa ttttttaaat 480
tttcatccat atgtttttgt tgtagatata aactaaagtc ggtcacattt aataattgtc 540
attatgtccg cgtaaaagtc aattcagcta ttggacattt atgaaatgta agattttctc 600
tctcatttcc ccgtgcgtga agacatgcat tggtttttct gtaataatca acaaatccaa 660
accccttttc gatctttatt tggacattgt tagagacaaa atttctctat agtctttttc 720
ctaatttgat accatgtttt tgtttctgca caaatttact cactggttta actaactatc 780
cacttattta tgattttacc attaggcgtc agctagccct agtcaaattt gtaaacaagc 840
caagctatct acataaatcg agatgtcatt aacgttaatc gtcgttaatt cgaatttgaa 900
aacatagata gctttagcag tacaatgggc aatggtaaga agaatagcaa aaggcccaat 960
atttggtttg cagaaattaa agccttaaaa aaaagcccac agatatttgt caaagaaccc 1020
taat 1024

<210> SEQ ID NO 147
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0092

<400> SEQUENCE: 147
aaagattgag ttgagagaga tggtggagac gcagaacaga caaagggagt ttaccatata 60
gtgctctaaa gggcaatgag attgcagtga tgtggctatc cggggaatca tcgcaggtta 120
ttccttccca tgagcaacaa tcaatggatg ggttccaatt cagaggagaa acagaagaag 180

```
aaacgtttcc agagaaccac agtagggatt ctcgatcttg cgagttgcag agagcctctg    240

aaactgcaat agaaaggaca ctgatgaaaa gaacacactg aaggagtatg ccaatcatgt    300

gaaaactcag agcttgtatt ggtcttgtgg ttgatgaagt tctcacaaaa cctttggctt    360

tgaatctccc ctcattagtc atggtgagaa caagaacaag acgagaaaca gacaaagaag    420

atgaaaaaac ttgttggcca gtgttgacta agggggaata gccccagaca taacaaaatt    480

agacttgtcg tacatcttta atattttttt atctgtttct ttgtcctgac gctttcatta    540

ttcctgtgat caattttctc ataccattgg tccatcgtta atcctttctt aatttcattt    600

tctacgtaac atgagaggag accaagtcct atgagaacag ttgacgtaac agtggttgtt    660

aagttaagtt aaaaagagga agctagtgag agtgaccgtt aggtagagaa gtgagatctt    720

taaccactct tctttctctc tctctctgct tttttcgtcg tctttcacat ctactgttcg    780

caaactctct tatgcttcca ataatggtga taccaattga gacttgcagg agaatctcct    840

cttctccaca ctctatcaac tggtcagcca tggaatggtc gtttcagttt caatattcct    900

ggattctttt taaggattcc tgtttctctt ctgttcctgg tatattctta acgacgaaat    960

tagtatcgga tcctggtaat acattttgaa gcttttaagt accattgcac tgggatccaa   1020

caat                                                                1024


<210> SEQ ID NO 148
<211> LENGTH: 1020
<212> TYPE: DNA
<213> ORGANISM: Arabidopsis thaliana
<220> FEATURE:
<221> NAME/KEY: misc_feature
<223> OTHER INFORMATION: Ceres Promoter YP0096

<400> SEQUENCE: 148

gaggtcagtg agtcgattgg tgcaaaattg aaaaattgaa gggtgaaaca aatttaaaga     60

taatatctat taaatcctct aattttaaaa atttagcaaa aattgtattt tcttatggat    120

ctgttagttc acacgtatct taattagtac caaatcatat ctaatgatta gtgataaaac    180

tagttagata tctatatgtg tctttaccat ttaacttgaa tccttcttct ttttttttacg   240

taaacaactt gaatccttcg ttaatacata aatttaaagc atttttttctt taattctatt   300

gatcggtata tatttactat aagttttagc tcatatgcaa tttcaaatga tatgctttta    360

aattttgtct aggtgtgata gttgtatctt taacataaat cttatagcaa aattatactt    420

gatattctaa atttatctat ttgctcttgt gaacctcata ttagtctaga gaaactttga    480

aatcctttca attagttgta tgtccaatac atttttacta acatttatta gtctttttaa    540

ttaagattat tgttagaaaa aaaaagattt tttaaaaata aataatatgt tttagataca    600

atgtgagtta ggcttcttat attttaaaaa ataaatttat ttcatactta aaaatagttt    660

ggaatttcaa tttatttggc tgaataccat aaaatatgtc aatttgaacc ttatacccat    720

tgactatttg gtgttagaaa ccctttaaca aaaaaaaact atttggtgtt agatatcaaa    780

ataaaaaaag tttaaccatt ggtttcttat attgaattgg atattgttac atgtattaaa    840

gttttttgg tttaatttttg aaacgttgat agaaactatt aagtttaagt ttggtagtat    900

atttatttgt ggaaaattta attgccatta aatataacgt caactttttt tggttttttt    960

tgagaagtta cgttgtgatt ttgatttcct atataaaagt tagattacgt catttttttaa  1020


<210> SEQ ID NO 149
<211> LENGTH: 1000
<212> TYPE: DNA
```

<213> ORGANISM: Arabidopsis thaliana
<220> FEATURE:
<221> NAME/KEY: misc_feature
<223> OTHER INFORMATION: Ceres Promoter YP0097

<400> SEQUENCE: 149
ttcatcttta tatttaagag tttaaaaact gcaacttttg tttttctttc actaagtctt 60
atggccacag ttaattaaaa gcagatgaaa ggtggtccaa tggaaaagga gaatgtgatt 120
gggctagttg ggagagttct gatgtctagt gttgggtaca cgtgtccgtc agttacacat 180
agcattaaat cagacggcat gtcattattc aaatctagtt cacatagtac gactaatagc 240
tgataaatta atgattatac agcatatgaa ttatgaattc aaaaaaaaaa aaaaattgaa 300
aatgttaagg agatgctata ttttacaaaa ttcatcgcaa tgctttctac taatttgcta 360
agtggtcttc tccagttagt cttgtcgatt ccaagcgata ttattaaatc ttgaagcatc 420
gctcaaagca ttatagctta agataaccaa attgttatta aaaacaccta gtgaaatttt 480
taaattaaaa caattttgat atctttgtaa tatctaatac tactctttct gtgtctaaaa 540
ggattaattt tcaaaaattt cacacatatt aaaaaaaaaa aaaaattact agctaaacaa 600
ttttcaataa tcataaaaca atagtaactt aataattttt ttttatttc aaaatagtcc 660 ttcaagttta caattcattt tagtattata atcaacaaaa tttgtattaa aaagttggaa 720
aattaatctt tgtggaacaa aaaaatctag aaatcatttt ttagaattag agagaggttt 780
gataaaaaaa aataaaaaaa aatagagaga ggtagtacat actaaacgat gtgatactac 840
tattgacaaa atcttaattc tcagtttagt agaataaact agaaggaatg aatgaagtaa 900
atgcgaatcc aactactaac aaaccctact tagtcatcat attttcccat atgaaatccc 960
tatataaacc catcatcatc tcccactttt ttcatatcca 1000

<210> SEQ ID NO 150
<211> LENGTH: 1004
<212> TYPE: DNA
<213> ORGANISM: Arabidopsis thaliana
<220> FEATURE:
<221> NAME/KEY: misc_feature
<223> OTHER INFORMATION: Ceres Promoter YP0101

<400> SEQUENCE: 150
ttctcgttct ctagaatatt gctggaccgg attaggtcaa tattattggg ccagattaga 60
tattgaattg tcgacgttgc ttacgttacg ttatatcttg tttaagaatt aaacctatcg 120
acttagtctt aattaagaaa acattgcctt aaattctctg gtctgcgacc gtttttttga 180
ccgttaaccc ctaattaaag aaacaaaata attatagaaa gagcactgaa atgtgattat 240
tttaacagta ctcttatgag aaaattcgta ctttttagtt ttttttttgt acaaatctct 300
aagaaaaaca ctactactaa ttaagaaacg tttcaaacaa ttttattttc gttggctcat 360
aatctttctt tctcggtccg ggactaaccg ttggcaaaaa aaaaaaaaaa gttgacaata 420
attattaaag cgtaaatcat acctctcaaa taaaaacttg aatttggaaa caaagacaac 480
taaaaaactc gaatttaaga gaattcctaa aatcaagtga agtatcatca cttggtaaaa 540
tttcataacc gttggcttct atttctatgt gtgccttggt ttgcaggaga taatatttca 600
tttccaacca atgatattcg tacacatagt caaacaaatg tttgtctttg ttattatatt 660
gagaaagaaa caagaaagag agagagagat agataagacg aaggaagtga agcttccaag 720
cgcccaccgt taaaaatctc gtgtgcaagt ttcaaataca agtggccggt ggtctccata 780
atttgatcgt catccaatta aaaaggaaga aaaagcgtgt tttatacaag aaaactcatt 840
aaaatagcaa gtctagaaat atctcaacac taatctacca cgtctattac acacacacac 900
acacacactt gatcttaatt tattttcaag attcaagaaa atacccattc cattaccaca 960
acttgaccac acgcctatat ataaaacata aaagcccttt cccc 1004

<210> SEQ ID NO 151
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0102

<400> SEQUENCE: 151
atttggttga taacgttttc actcgactaa ttatatactt cagaaggata gtaatagaat 60
accaaaataa ttaaatgatt ggttagtgcc ttagtggaga ctttttaacc gattctaata 120
gactaatgat gtagctaagc atttatttgg gatcatcact gtttgaaaac gtgaaatgtg 180
ataaaagtta tgaaacgatt aaaatataaa ataaccgtac aaaacattat gtaccgtttt 240
tttctctgtt cttttggcga tttggtttag ttcgttacac tctaaatgtt attgcagata 300
tatatataat gatgcatttg catctgagga acatataatt ccggttaaca cttccaaatc 360
ttatatccgt ctaggtaggg attttataaa tcatttgtgt catcatgcgt tatgcttgtc 420
ggctttgacc ataacgcaga gatatagaac tagcttttac ttaactttta gatttattat 480
ttgatctaga gttaagtgga gatatatagt gtttttgtta gattattggt ggatgtgaga 540
gtttgtcttt agtttcaagt tgagaatata aggcaagagg agactctgag gcaatcagag 600
gttttgattg gcaaaatatc caaaaggccc aaaccaagtc gaagcccatc tcgtacaaaa 660
aaagaaagag atctgtaaga aaaaatattc tttgatattc ttacaaaaat aagtgtaaaa 720
cttttattag tcaaaatctt caatctttaa aaactctcat cactcctacg aaagcgcgtg 780
agagttatga gacattcctt aatagcatta ctcacaagtc acaagttcaa aacgtctgac 840
tgaaacagaa acaagccttt gttgaagtct tgaagaagag acattagtac tcgtcgtata 900
gccataaaag gtaatatacg aaatttcttc gctaatctct tcaccttcct ctacgcgttt 960
cactttcact ttataaatcc aaatctccct tcgaaaacat 1000

<210> SEQ ID NO 152
<211> LENGTH: 1004
<212> TYPE: DNA
<213> ORGANISM: Arabidopsis thaliana
<220> FEATURE:
<221> NAME/KEY: misc_feature
<223> OTHER INFORMATION: Ceres Promoter YP0103

<400> SEQUENCE: 152
gttttgaaga acaatctgga tcgaaatcta acataaggtc atcgtattca agttacgcag 60
tcaaggactt gacatcatcc tactctggtc tgaggttacc acttccaaag atgggatttt 120
tcgactcggt atgcttccta agaaattcgt tttattgaac ctagcaaata tcttgtaatg 180
taagattcct gagatgatga agaaaaaaca aacttttgtt acagcaggag aacggagaga 240
aagaaaacag agaaccaaat gctcttgaag caaacagaag aagaagacac aaatccaaac 300
ttgagacttc ttctacacca gaaaaccgca gcattctggg acaacgcaaa acacgaaagt 360
gaaacgggca atgatatata tgtcttgggt gcgttacaag gcatcgtttg caactgttga 420
gttggataag tcaactgtct tcttttcctt tggttgtagt agctgccttt tttttccttt 480

```
gttgctttaa gaaatagccc gaaaaaaaga atgttctaca tttcggagca gaaaactaac    540

cgaatgagtt tttggtcgga tcatcggatc gatcagatat attttgagtt acgaactgtt    600

ataaaaaaag ccataatttt gtgttgagtt tgcaaaatac cttataactt gttatttgag    660

attgcacctc catatatatt aattcgtaag agtatttatt aagtaagctt tagtataaat    720

cctttttcc tttaaagtaa gttaatgttc tactaaataa tagtaaagtt gaagaaccgc    780

tccgttttta caccatgcac gtgttatcta acaaagaaaa tatggtacac ctaatggcta    840

atgcaaagga caacacaatg aaactaactt gactctgtgt tatagaaacc catagacatc    900

tgcatacatc ctagtatttg tataaattgg actcaaattc ctgaggacaa tcatagcaaa    960

caatcacatc atcgcaatat acataaacaa aagaggaaga aaaa                   1004
```

<210> SEQ ID NO 153
<211> LENGTH: 1003
<212> TYPE: DNA
<213> ORGANISM: Arabidopsis thaliana
<220> FEATURE:
<221> NAME/KEY: misc_feature
<223> OTHER INFORMATION: Ceres Promoter YP0107

<400> SEQUENCE: 153

```
taacaatcct tgggaacatt gcatccatag atatccggtt aagatcgatc tttgaactca     60

taaaaactag tagattggtt ggttggtttc catgtaccag aaggcttacc ctattagttg    120

aaagttgaaa ctttgttccc tactcaattc ctagttgtgt aaatgtatgt atatgtaatg    180

tgtataaaac gtagtactta aatgactagg agtggttctt gagaccgatg agagatggga    240

gcagaactaa agatgatgac ataattaaga acgaatttga aaggctctta ggtttgaatc    300

ctattcgaga atgtttttgt caaagatagt ggcgattttg aaccaaagaa aacatttaaa    360

aaatcagtat ccggttacgt tcatgcaaat agaaagtggt ctaggatctg attgtaattt    420

tagacttaaa gagtctctta agattcaatc ctggctgtgt acaaaactac aaataatcta    480

ttttagacta tttgggcctt aactaaactt ccactccatt atttactgag gttagagaat    540

agacttgcga ataaacacat tccccgagaa atactcatga tcccataatt agtcggaggg    600

tatgccaatc agatctaaga acacacattc cctcaaattt taatgcacat gtaatcatag    660

tttagcacaa ttcaaaaata atgtagtatt aaagacagaa atttgtagac tttttttgg    720

cgttaaaaga agactaagtt tatacgtaca ttttatttta agtggaaaac cgaaattttc    780

catcgaaata tatgaattta gtatatatat ttctgcaatg tactattttg ctattttggc    840

aactttcagt ggactactac tttattacaa tgtgtatgga tgcatgagtt tgagtataca    900

catgtctaaa tgcatgcttt gtaaaacgta acggaccaca aaagaggatc catacaaata    960

catctcatag cttcctccat tattttccga cacaaacaga gca                    1003
```

<210> SEQ ID NO 154
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0110

<400> SEQUENCE: 154

```
gggatgcggt tccgcttcct cttgatcttg gacgagtcgg aggacattgt tggatcccag     60

tgcaatggta atataaaaca agaaaacaag agattttata ggacaatcac taaatgacat    120

ttaattgatt aaacatttat tcattaataa ttgtatgtta ctaacttcaa catttaataa    180
```

```
ttttgtttaa gatacgttta catcagagac tattaatatt tttacaggtt gtaactttaa    240

actttgtctt gaatcgaaca tgactataga ttttgggcaa acttaaagat aacaacattt    300

ccgttttttt tcaaattatt acaaatcaaa ctgatatatt agacacaaca cgattacacg    360

taatgaaaaa agaaaaagat aaaaagataa aagaagggat cgattctgtt tggtctggtt    420

tagtgagatt caaagttaag ctcttccttt caagacatgc cttcttaaac cgggaatgtg    480

aacgtttgta atgtagtccg tccagttaat gcttccaaca tcaaatccaa attctctctt    540

ctcgtcctct gacatattct ccattaatct ctggggtatt gctgttatca aatctgtaaa    600

agaaaccaaa aaaaaaagat gaaaactttg cgggtaccgg ttttgtctgc tctaagaatt    660

agaatgttaa tgagttctgt cttaccttcc accatagaaa gtgtatggct cataaatagt    720

agcaaggtgt ttggcttgtt caacagattt cttgcatata aactttagct tctgcatcat    780

cttactatcc actgaactca taccactcat caacccactc cgttcttgag catctctcca    840

caaatgatcc gagaaatcat caacggaatt gaaaagtttc atcaaacgca ccataatagg    900

atcaccttta gagtccatgc atggagatgt tttgtagtgg ttataaagaa gctccgctaa    960

gtcttcgaaa accagcgggt ttatcgccga agaagcgatc tgatacacgt ttatttcagg   1020

ttcc                                                                1024
```

```
<210> SEQ ID NO 155
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0111

<400> SEQUENCE: 155

cgattggatt tagtctatac attatagggc gcaagtttgt ggatttaaga attatataaa     60

aacttgaaat atatagtttt tatgcattct cctcttgtgt aatacataaa ccaaatatga    120

gataggttaa tctgtatttc agataatatt aaattccaaa caatattttt acttgttata    180

agaaggcaat taatatctct ctgttaatgg caagtggtac caagtagtat taaactatta    240

atgcaatgga agagtactgt tggaaattat aatcctctat cacacattca aacagatctc    300

ctgaaatctt ctcttccaaa cttgtacttc tctgatccaa atgtaggctc caaaatatag    360

acatttacca tttactaagt ccacaactcc tttcttgtct ccttcaaaaa tgactcttgt    420

gtaaccacca tatgactccg acagttcggc attgccatga tgagagctta aaaattcacc    480

ttcctgagca tttcaagtct tcactccctt agcttgacct gaaccaagat aaaatgcctt    540

tgtcgtcccg taatatccat cctgctttgg acggcatcat agttacattc gatccatcct    600

atttacaatg ttattttagt attaaaaaca tgacaataaa tttgttgtta aacatattca    660

aatacaatat gattggattt ataagtaatt gtaatatgaa atgtccttag taatatgtta    720

aaaaatacat agatacacac acgtactaaa agaggcaacg cgggagatgt cattagagga    780

agaactagga agcagagcgt tcatgcaaaa tgctaccaaa aacgttaatg caatatctca    840

actaatcagc acagtccatt tcatactgag aatgtaaaaa ccaatcagca tcgtccattt    900

tttcatctaa ttatttgtta actcttaatt ggccacaact tccaaccaca tgacgctctt    960

tctattccct ttatatattc ccatctcaaa tgttcttgga gacacaaaat atcataaaca   1020

tata                                                                1024
```

<210> SEQ ID NO 156
<211> LENGTH: 996
<212> TYPE: DNA
<213> ORGANISM: Arabidopsis thaliana
<220> FEATURE:
<221> NAME/KEY: misc_feature
<223> OTHER INFORMATION: Ceres Promoter YP0115

<400> SEQUENCE: 156
gtcgattgga tgatgaacat tctacatata taattattat gtttaagcac ttagacagca 60
taaattcttt ctaattatat aaatctaacc ttgttacatt gtacatctat aaattacttg 120
aagaaataac gagttctatt tctttttaaa aattaaaaat actataccat atctcagtga 180
ttaagttgaa ccaaaaggta cggaggagaa acaagcattt gattcttcct tattttattt 240
tattcatctc tcactaatga tggtggagaa aaaaagaaaa tacctaacaa acaaatatat 300
attgtcatac aaaaatattt ctatattttt agttaattag tttatattcc tcacttttca 360
gggcttatat aagaaagtga gcaaacacaa atcaaaatgc agcagcaaat actatcatca 420
cccatctcct tagttctatt ttataattcc tcttcttttt gttcatagct ttgtaattat 480
agtcttattt ctctttaagg ctcaataaga ggaggtacta ttactacact tctctctact 540
tttacttgta ttttagcatt aaaatcctaa aatccgtttt aaattcaaaa ataaacttag 600
agatgtttaa tctcgattcg gtttttcggc tttaggagaa taattatatg aaattagtat 660
ggatatcttt actagtttcc attcaaatga ttctgatttc aatctaatac tctcactctt 720
taattaaact atatgtagtg taatttcaca ctgttaaatt tctaccatgt catgtatatt 780
agagttgcat agaaaattgt aaaacatcca tttgaattcg aatgaaacaa aatgttttaa 840
aataaaattt tggtttttaa aagaaaaatc taaaactgaa ttatatcgtt taaccaagtt 900
gtaaaagtca taaaacgtag tatcttgtaa atcgctcttc cacggtccaa atagacttct 960
agtaataaac aagtaaaact aattttggtt tcttac 996

<210> SEQ ID NO 157
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0117

<400> SEQUENCE: 157
gtcagtgagt cgattggatc acagtccttt atgataaaac aaactcataa ttattccacc 60
gacaacatgc gttttaaatt atttttcttt aaattatatt atattatatt gatatcaacc 120
tagctaaaat aattcggatg gcgaaatcgg acaattttta atagaaaaaa tgggtatgaa 180
gatagtctat gattccgttc ttagcgacta gagggacctg ctcaaatctc ccgggtgata 240
cgcgatgtca agctcaatag aaccccacaa ccgacgagac cgagaaatcc ttgatttggg 300
ctagaagatt ttgaaataaa tttaatatat tctaagtaac ttgcttaaat ttttttcaa 360 actctaaaga cataactaac ataaagtaaa aaaaaaaaag ttaatacatg ggaagaaaaa 420
aattaaacta atgattagct ctctaacgtg tttaatctcg tatcaagttt ttttttaaaa 480
attatattgc tattaaaaca ttgtactatt gtttctattt tgtttagcta ttattcttgt 540
gaaatgaaaa gttgtgttta ttcaattact aaatggcaat atttatcttg gaaaactata 600
cctctaattg gattaggccc tagacatcct ctttagctta ttgacgttaa aattattccc 660
aaaactatta aagtttagta gtttgaaaga tgcatcaaga cctactcaga taggtaaaag 720

```
tagaaaacta cagttagtgt gattatattt taaaatatat aaaacaatct tattaaacta    780

aatattcaag atatatactc aaatggaaga taaaaacatt tagtctgtta ccactaccag    840

cctagctagt cactaatagt cactttggaa ctgagtagat atttgcatct tgagttacca    900

tggactcaaa agtccaaaaa gagaccccga gtgaaaatgc taccaactta ataacaaaga    960

agcatttaca gcggtcaaaa agtatctata aatgtttaca caacagtagt cataagcacc   1020

attg                                                                1024
```

<210> SEQ ID NO 158
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0119

<400> SEQUENCE: 158

```
taccaaaaat aaggagtttc caaaagatgg ttctgatgag aaacagagcc catccctctc     60

cttttcccct tcccatgaaa gaaatcggat ggtcctcctt caatgtcctc cacctactct    120

tctcttcttt cttttttct ttcttattat taaccattta attaatttcc ccttcaattt    180

cagtttctag ttctgtaaaa agaaaataca catctcactt atagatatcc atatctattt    240

atatgcatgt atagagaata aaaaagtgtg agtttctagg tatgttgagt atgtgctgtt    300

tggacaattg ttagatgatc tgtccatttt tttcttttt cttctgtgta taaatatatt    360

tgagcacaaa gaaaaactaa taaccttctg ttttcagcaa gtagggtctt ataaccttca    420

aagaaatatt ccttcaattg aaaacccata aaccaaaata gatattacaa aaggaaagag    480

agatattttc aagaacaaca taattagaaa agcagaagca gcagttaagt ggtactgaga    540

taaatgatat agtttctctt caagaacagt ttctcattac ccaccttctc ctttttgctg    600

atctatcgta atcttgagaa ctcaggtaag gttgtgaata ttatgcacca ttcattaacc    660

ctaaaaataa gagatttaaa ataaatgttt cttctttctc tgattcttgt gtaaccaatt    720

catgggtttg atatgtttct tggttattgc ttatcaacaa agagatttga tcattataaa    780

gtagattaat aactcttaaa cacacaaagt ttctttattt tttagttaca tccctaattc    840

tagaccagaa catggatttg atctatttct tggttatgta ttcttgatca ggaaaaggga    900

tttgatcatc aagattagcc ttctctctct ctctctagat atctttcttg aatttagaaa    960

tctttattta attatttggt gatgtcatat ataggatcaa                         1000
```

<210> SEQ ID NO 159
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0120

<400> SEQUENCE: 159

```
tagtttttga tttaatctac gtttttctta atcataaatg ggtaattatt agtttttgca     60

aaatcaaaat ccaaaaattg ttctaaacac tgcaaccatt taaggcctat atcactcaga    120

aaatttctgg tgggagaact aatcgtttgt cctttctaaa tctcacatat tagaatttag    180

aattagtgtg ctacataaga atattagttc agctcggaac aactattttt tggtaaaaca    240

gagaacttaa acaaatgcat tattttatca acatgcattt tgaattgaat ataaaatttc    300

ataattgtaa agacataaat tacataaaat tttacatgaa aaaatagata tagaaagaaa    360
```

atgaaactaa ctgatgatat gctctctaaa ttttttaatc tcataacaag aattcaaatt 420
aattagttca tatttttggt taatataaca tttacctgtc taagttggaa ctttcatttt 480
tttctgtttt gtttagtcag tattcttaat gtgaaacgga aagttgaatt tattcaaact 540
taaattcaat agcattaatt aaaggcgaaa gctattatct ctacatgtgg ttcaaactag 600
acatccaatt taattagctt attgacgttg aaatgttttc caaaactact atagtttggc 660
aatttgaaag atgcatcaga actactcaga caggtaaaag tagaacctct agctgtgtga 720
attgtatgtt agtccataaa gaacatcttg taaacttcat acttaagata tatattacaa 780
tatatacttg aatggtagat aaaaacgatt agtctgattg ctagcatact cacaactatt 840
tggaaatgag taagatattg gcattctaga gttactacta tggagacaaa agtcgaataa 900
aagagacctc acgtgaaaat gttacgagct agtaaaaaaa gcatttacac taacggtaaa 960
aaaagtatct ataaatgttt acacaaggta gtagtcatt 999

<210> SEQ ID NO 160
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0121

<400> SEQUENCE: 160
ttggattttt tttttgttga gtcagcagac catctaatct ctctttttcc accacagcct 60
gctttctatg aagcatttgg gcttacggtt gtggaatcaa tgacttgtgc actcccaacg 120
tttgctacct gtcatggtgg acccgcagag attatcgaaa acggagtttc tgggttccac 180
attgacccat atcatccaga ccaggttgca gctaccttgg tcagcttctt tgagacctgt 240
aacaccaatc caaatcattg ggttaaaatc tctgaaggag ggctcaagcg aatctatgaa 300
aggttggccc attctccttg acaggcttaa caatacaact tgtatcgctt caacaagatg 360
atggcttaat aaggattttt gcatgtatag gtacacatgg aagaagtact cagagagact 420
gcttaccctg gctggagtct atgcattctg gaaacatgtg tctaagctcg aaaggagaga 480
aacacgacgt tacctagaga tgttttactc attgaaattt cgtgatttgg ttagtgtaac 540
ccactgttat tcttttgatg tctacatcta ctttacttac attattcttt tcttcggttt 600
gcaggccaat tcaatcccgc tggcaacaga tgagaactga tcatgacagg gtaggatttt 660
atttcctgca ctttctttag atcttttgtt tgtgttatct tgaataaaaa ttgttgggtt 720
ttgtttcctt cagtggtttg attttggact tatttgtgtt aatgttgttt tggctgttct 780
cttaatatca ataacaaata aatttactgg ttggtatcta agatctaaca atagttacta 840
tttttagagg taaagacacc aaccttgtta tattggtcag agagctaaaa ccttgacttg 900
ttgggaaaac aaaactctaa tgacagaaaa tctgacatga tgccttataa ttcacagcct 960
catgttctac ataaatccta acaatagcac tttgtttct 999

<210> SEQ ID NO 161
<211> LENGTH: 1004
<212> TYPE: DNA
<213> ORGANISM: Arabidopsis thaliana
<220> FEATURE:
<221> NAME/KEY: misc_feature
<223> OTHER INFORMATION: Ceres Promoter YP0128

<400> SEQUENCE: 161

```
gataaactga taatggaaaa gaacaaagaa accagttttt aactatttgc atatgtaatt      60

tatttgttgc aaattatatt tagttaaaat gtttcctcta tttatatata tatatatcag     120

tcaagcacta tgtataagaa atgtcaattt ataaattttt acatgtcctt taacagaaag     180

aaaatgaatt tttacatgtc attcatagag agtcactcgt ttatttctta tatagagaat     240

aacacactca catgcatatg catgcaatat gatacatttt atgacaaaga taatcaacgg     300

aaacggtcaa gacataattt gataaacaac ttgcacgatg cacagatctg atcaaatata     360

taactcttta acatatccaa aatattcaaa aagaaaaact cgatccaaac tagcaacatc     420

acgctcacgc ggtaggctaa aaatttatta atctccaaaa gtctttctta tgaacactgc     480

aaacacaaca acttgaaaag tcatataggt ttagatgatg acgcgtattg gctatcgctt     540

accggagtgg ctcataaata caataaacaa tacgtaaaag tcaaagtcaa atatatttag     600

tcaactataa ccattaatcg ggcaaaacct ttagctgtca aaacaacgtg aaaacgatat     660

ttgtatatat catcaagaat cagtagataa gagaatgatt taatcccctg actattacaa     720

ttttggtgta ataaacagtc tctattggtt tttattcttt gttttaattt ctcatgacct     780

atagagagaa ttaggtagtt tcgaaaattg gctaatcaac ttttgaaaac tactgtctac     840

tttgcttaaa ttctctacac ttagtttcgg ataagataat tgtcggacta atagttaatc     900

ccttgacaat ctttgatatt ataaaaggtt tagttaatct cttctctata taaatattca     960

tacaccagct ttcaaaaata tataatccaa acaccaaaaa caaa                     1004
```

```
<210> SEQ ID NO 162
<211> LENGTH: 1001
<212> TYPE: DNA
<213> ORGANISM: Arabidopsis thaliana
<220> FEATURE:
<221> NAME/KEY: misc_feature
<223> OTHER INFORMATION: Ceres Promoter YP0137

<400> SEQUENCE: 162

gtggcacatg ctgaaacccc gagcatctct ccggaagaca cgcgtcgttc gctccaaaga      60

aaacagtcac agctgccgga gaatctccgc cgtcttcttc tgccaccgga aaaactctct     120

ccaccacttt cagtgcccac ctcgtgttat atccactgta tcctcgtagc accatatcag     180

cctaataaaa ttttatgtat caaattttaa gacatagccg aaactacact atactagaca     240

ataataatat gatttgtttc ctgaaaaatt atggtttcat gagaaacatt aatcatctat     300

aaaacaaatt agctatggca tcgaagagtt atcaatcaaa actgatgaat ctttacttaa     360

tatatacaac atatctttac cttgcggcgg agaagatcgg cgagagaagc accccagcca     420

ccgtcactaa aggattcttc agtgatggaa tcaccaaaga gaaaaacctt ccgtctcatc     480

atcttccaca caatcttctt gagaaaatct gagagataag aaaggtgtag tggttttgct     540

gaagtgatcg tgtttgattt agtaaagaaa tgctttattt attgttgggg gaaacataaa     600

taaataaagt aaaagtggat gcactaaatg ctttcaccca ctaatcaccg acctttcatg     660

gtttattgtg aaatacactc atagatagac atacaatacc ttatgtacgt aaataacatt     720

ttatttgtcg acacttatgt aagtaacgca tagattattt tctatgtgat tgccactctc     780

agactctcag tttcaaccaa taataacaat aactacaaca acattaatca taaacatatg     840

ctctggttta caattaaagc ttagattaag aaactgtaac aacgttacag aaaaaaaatg     900

ttatttacgt tttgtaagat tagtctctag aatcatcacc gttttttata tattaatgat     960

tctttcttat atataaaacc tttctcgaaa tacccatgaa a                       1001
```

<210> SEQ ID NO 163
<211> LENGTH: 1001
<212> TYPE: DNA
<213> ORGANISM: Arabidopsis thaliana
<220> FEATURE:
<221> NAME/KEY: misc_feature
<223> OTHER INFORMATION: Ceres Promoter YP0143

<400> SEQUENCE: 163
atacaacaga tggcagatat cgagttaaat acgtgaatca gccgttacga tattttaaaa 60
ctagaaaatt atttaaaaat attgcaaaat accatttaat ttcattgttc ataaaaaaaa 120
gaaattcaaa aacttaaaaa ctgattcaaa aatttggatt aattctcatt aacagtcttc 180
aacactacaa caacatgttt ctaatttatt ttatatttta ataattaaac aatatatacg 240
tctgcacatt gttgctccga cataatctag tataaaaata gttgcagcat atgtgaaaag 300
caagcagcat ttatcactca atacttttaa ttttatctgt tgtatgtatt aaggttttgt 360
agctttaaga aaacgcttat aatataaaat aacttctaaa agatatttca tgcgtataca 420
ataaatattt gtgaaaaaac atttcgaaaa cgtgtacaat atataaacta ttgtgttatc 480
ttttgacatt caaacaaatg ttgacaatgt aattttatcc atgatatgat tggccaatta 540
gctgcgaggt aaaaatccgt atacgagtaa aagtaagata aaatttcgca agaagatttt 600
tagcaggaaa tctaagacaa gtgtcatgaa cgtgtcaatc aacaaacgaa aaggagaatt 660
atagaatcca gattcgacgt accacattaa taaatatcaa aacattttat gttattttat 720
ttttgctctg gcagttacac tctttttcat tgctccaata aaaaaatcac tcgcatgcat 780
gcatatatat acaccatagt aaactccgcc tcttcttcat tttaaaagta tcagtttaca 840
ctgacacaat ccttaactat tttcctttgt tcttcttcat ctttattaca catttttttc 900
aaggtaacaa ataatctttt taagtcactt ttatactctt taaatcttag attgatatat 960
gaatgcatgt taatatttca agatttatag gtctaccaaa c 1001

<210> SEQ ID NO 164
<211> LENGTH: 1003
<212> TYPE: DNA
<213> ORGANISM: Arabidopsis thaliana
<220> FEATURE:
<221> NAME/KEY: misc_feature
<223> OTHER INFORMATION: Ceres Promoter YP0144

<400> SEQUENCE: 164
aaacgttgca agattattga ttgtgagaaa gagtgctcaa ggtagtactg atttctgtaa 60
agctcacggt ggtgggaaac gatgttcttg gggagatggg aaatgtgaga aaatttgcta 120
gaggaaagaa gcggtttatg cgctgcgcat aacactatta tgtctcggga gaacaaagat 180
ggaagcaaga gcggtttgat tggaccggga ctctttagtg gccttgtttt tggctctact 240
tctgatcatt ctcagtctgg agctagcgct gtctctgatt gtactgattc tgttgaacga 300
atacagtttg agaataggca gaagaacaag aagatgatga taccgatgca ggttctagta 360
ccttcatcaa tgaaatctcc aagtaattca catgaaggag aaacaaacat ctatgacttc 420
atggttccgg aggagagagt tcacggcggt gggctagtaa tgtctttact tggtggctcc 480
attgatcgaa actgaaagcc atttatggta aaagtgtcac attctcagca aaaacctgtg 540
taaagctgta aaatgtgtgg gaatctccga atctgtttgt agccggttac gttatgctgg 600
atcaaaaact caagatttgt tggatattgt tatgctggat cggtggtgaa accacttccc 660
ggttgctaaa taaataaacg tttttgtttt ataatctttt tcactaaacg gcagtatggg 720

```
cctttagtgg gcttccttta agcgaccaat acaatcgtcg caccggaatc tactaccatt     780

tataggttta ttcatgtaaa acctcggaaa atttgagagc cacaacggtc aagagacaaa     840

aacaacttga agataaaggg ataaggaagg cttcctacat gatggacaac atttctttcc     900

acacaaattc tcataataaa aatcttataa tacaaatact tacgtcataa tcattcaatc     960

tagtccccat gttttaaggt cctgtttctt gtctgataca aat                     1003
```

<210> SEQ ID NO 165
<211> LENGTH: 1004
<212> TYPE: DNA
<213> ORGANISM: Arabidopsis thaliana
<220> FEATURE:
<221> NAME/KEY: misc_feature
<223> OTHER INFORMATION: Ceres Promoter YP0156

<400> SEQUENCE: 165

```
ttggtttgca ttgtgaagat ttgtattaac tatagaacat tgaattgatg gtgttaagtt      60

cttacacaag cgtgcttctc ggtttgaact gtttcttttg tatgttgaat cagagcttag     120

tttataggaa ccagagtatc tacttagtca ttctctgatg ctaagtgcta aggttctacc     180

tagttgccct ctaggccctt atgttattga taacttatga agctatttga acacttgatt     240

cttaggagac ctaagttggt acagccagat agagtgtatg ttcttgttct ctatgtgaca     300

ggatcaagct gccacacata gttcaagggt atgctctgtg tgggtttgct cagattgagg     360

acaaatctat acaaggaagt agagtctttg acattttgat gttgtatgat aagaagaaga     420

aaggagagta ataaagaaag agaaaaggga aacagaaaca cgtgggagaa catcccaaag     480

aggaagcaca cgcggatctt catgcaaagc tccccgattc tcccatgtgg tccctttctc     540

cctttgtccc cctcctcttt cttcttttct cattttactc cttttttttac cattatacaa     600

cgaatctttt ttatcataat tttttggttt tggtttattt tccaataaca ctttcttggt     660

tacttcccat tctcactttt tcatataaga aactcacttt gggaaactta tgtttgagaa     720

tgacaagtct ttttagagaa agtgatgtaa caaatctaaa gtgattatat aataaccttg     780

cacaatgttt ttgatttttt gtaagattcg aatattaggt ttattattcg tagggaataa     840

acttactttc aaaagcgttc ataagttaat actttcatat atgatcataa gtacggacac     900

tattgttttt tgtttgtttg tgtttattct aaaagaaagt agcttttaat tgaaatgtcc     960

tcggaggcac agtttaaagt tcgagtgtaa cagtttctaa ggca                    1004
```

<210> SEQ ID NO 166
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0158

<400> SEQUENCE: 166

```
ttattagatt aatagattgc attgcattgc ttgtgctttc aatttacaaa ttgtctccca      60

actccatcga cacatctctt tttgtgtata taagattcag acttgttata ttttttttat     120

aaatatgtta ttagcatctt aagttaaatt gattttttat atctgcatta aggattacac     180

gactatattt gcgattgtgt gttggttaaa atataattta ggattgtctt taactacatt     240

taggattata tgactatatt tggttaaata taaaatctag ctgtgattat tagtattcaa     300

aaataagtag cctaaccaat taaaacaacg gctattgggg caaattagaa cattttagtg     360
```

```
tgtccaaaat ataatggtca ttaggtcata ttcctcctag cttcatcgca gcataattga    420
atgattgcct tatttagaag agcttttcca ctttcccaaa atctaggtgg gatctttttg    480
ttttgacctt catttttctt gtttaccatt tttagctaaa ttatttacga ttacaaaaga    540
tatcaaaagt tggatcataa tacaatttat agacttactg tagaaaattc gtatgtacaa    600
gtacaacaaa ttcttcataa taaattttga aaattctatt acaaatgttg taagaaatag    660
aatttgaaat atatataaac taaggagaaa aaaaaagaga acatgcattg ctctagtcag    720
agtggaccaa catcaacgag ataagataac ataaaaacca actcaccata actaaaaaca    780
tcccaagaga tccaacgatt catatcaaac acaaaaacat cgaacgatca gatttaaacc    840
atctctggta tctccaaaac acaaacactt tttttttct tttgtctgaa tggaacaaaa    900
gcatgcgaca tctctgtgtc tttatcttct ctctcctctt cttgaaaaac tgaaccttta    960
attctttctt cacatctcct ttagctttct gaagctgcta                          1000
```

<210> SEQ ID NO 167
<211> LENGTH: 1005
<212> TYPE: DNA
<213> ORGANISM: Arabidopsis thaliana
<220> FEATURE:
<221> NAME/KEY: misc_feature
<223> OTHER INFORMATION: Ceres Promoter YP0188

<400> SEQUENCE: 167

```
gattggtatg aaatttcgga gaccaacaaa aaaaacttta ttgagcttgg agtgaagcta     60
tatatatggg gcaagatcat aatatgttta tatcggcctt ttcgttaact gaaaataata    120
gttttgagaa atatatcaaa tggtaaacag acatcatctt tgaaaaatac catcaatgaa    180
gttaatattg ttattggcat atggtttacc catcttaatt ttaatgcaac caaacaaaca    240
agaaacaaaa actgtataag atacaaggtg ttttacgatt ttccgtctta aaaccgaaat    300
atttttgttc ctacgacttt aaacggactt tgcttaagtt gtgtgcatgt aagctcgtcg    360
tccctcgatt gtcatcaaca ttcaccaata tcagcctcta tcacacgagt gaaggtggtg    420
attcggctta atgaaaacag agaaatattt caatatgatt cctattaaat tttaaatctt    480
ttttctcaat ctctagattt tcattaaaag catcatgatt tttttccact atgttcatat    540
atctctatca cagttttagg tacattgtag aaattggata agatacgtca tacgtctaac    600
atgaatttgg tctagcaagg aaggtttgag ataataagtg aaaagaaaac acaagataat    660
aaattataat ttataaatgc tttatagtat tgaaaaataa gatgattttt ttttttttta    720
ataccggatt ggctgatcca cttatgatga ctcaaatgtt attaagtttc aagacaattt    780
atgatgacac aaatcacaat gagtcaatag tagccacgaa gccagaaaaa aaaaatgtac    840
tacaaaaaga taatgatagt acaaaatgat acgtcgtact gccacatgta cgacacaact    900
cgattaccaa aaagcagagc catccaacca taaaactcaa aacacacaga ttccactggc    960
gtgtgctctc ctcacttcac tcgtccttga aacttgaggt actga                    1005
```

<210> SEQ ID NO 168
<211> LENGTH: 1002
<212> TYPE: DNA
<213> ORGANISM: Arabidopsis thaliana
<220> FEATURE:
<221> NAME/KEY: misc_feature
<223> OTHER INFORMATION: Ceres Promoter YP0190

<400> SEQUENCE: 168

```
taaatagtga cattggtaag aagaaaaaaa acactattaa atagtgaaaa aatggtttat     60
```

```
aactctctta attaacatta cttattattg ctagcaccta aaatctccca caaaatattt    120

gttgtaaaac acaaatttac aaaatgattt tgtttttaaa ttagtaacac atgttcatat    180

atacgttaat aagaacatac cctatatgat tttatataaa aaaatttctt tgagacgtct    240

tattcttttt tctttaataa tatgcaattg tgagagtttg gatttgaatg gtagcattag    300

aagcaaactt gaaccaaaca tatttcatga agtcaaactt gaaccaatgt gatcactaat    360

cacagtgttc gcagtgtaag gcatcagaaa atagaagaag ggacatagct atgaatcata    420

taatcttgac acatgtttta taggttttag gtgtgtatgc taacaaaaaa tgagacagct    480

ttcttctaat agacttaata tttgggctaa atgtaccaca gttgtgaatt tcttacaaaa    540

atgggccgag ctacaaaaaa ctacaggccc actctcaact cttatcaaac gacagcgttt    600

tacttttta aaagcacaca ctttttgttt ggtgtcggtg acggtgagtt tcgtccgctc    660

ttcctttaaa ttgaagcaac ggttttgatc cgatcaaatc caacggtgct gattacacaa    720

agcccgagac gaaaacgttg actattaagt taggttttaa tctcagccgt taatctacaa    780

atcaacggtt ccctgtaaaa cgaatcttcc ttccttcttc acttccgcgt cttctctctc    840

aatcacctca aaaaaatcga tttcatcaaa atattcaccc gcccgaattt gactctccga    900

tcatcgtctc cgaatctaga tcgacgagat caaaacccta gaaatctaaa tcggaatgag    960

aaattgattt tgatacgaat tagggatctg tgtgttgagg ac                      1002
```

<210> SEQ ID NO 169
<211> LENGTH: 995
<212> TYPE: DNA
<213> ORGANISM: Arabidopsis thaliana
<220> FEATURE:
<221> NAME/KEY: misc_feature
<223> OTHER INFORMATION: Ceres Promoter YP0212

<400> SEQUENCE: 169

```
agtcgattgg tacactctta atttaattag agtaagagat caacaaaaat atagaatttt     60

ctttatatcg aagtgctacg accttatata tatagaaaaa aaagcatagg tgaatctcta    120

aattgagatt gtgctgtagt aaacatatta agtttttagt ttttttaaga aatgaatctt    180

tttgttgatt aattcaaact agtagtcatt aagattccgg agattccaat ttagaaaagt    240

caaagattca aagaacaagt ccaggtccac atgttgaatc cgattcatca tccactcatc    300

cttcatatct tcctccaccg tctccgccca aaaaatcaat aacaataaaa aatcctaaaa    360

aaacatattt gattttgaaa aaactttatc atatattata ttaattaaat agttatccga    420

tgactcatcc tatggtcagg gccttgctgt ctctgacgtc cttaattatc attattttta    480

aatttgtctc tctcagaaaa ttacgccaca atcttcctct ttccctttc cgaaaacagc    540

taatatttgt ggacctaaac taaataacgt agcctctaga ttttatataa ttactaatac    600

tatatgctac tacttgttat tatttactcc aatcatatat gataccaatc aagaatcact    660

acataagtag aaaactttgc aatgagtcca ttaattaaaa ttaagaataa acttaaaatt    720

ttatggtatt ttaagattcc ctttggattg taatgacaag aaatcagcaa attagtcgta    780

actcgtaaga ataaacaaga tcaattttta ctttctttac aaagattccg ttgtaatttt    840

agaaattttt ttttgtcact gtttttttat agattaattt atctgcatca atccgattaa    900

gaagtgtaca catgggcatc tatatatatc taacaggtaa aacgtgtatg tacatgcata    960

aggttttacg tgcttctata aatatatgtg gcagt                               995
```

<210> SEQ ID NO 170
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0214

<400> SEQUENCE: 170

```
ccagtcgatt ggcgcctcgc atgcctatca tatttaaccg tcaataatgg atttggcggt     60

tttggtaggc cgggtcaacc ggattaaaag aaaacggttt ggagtccttc cttgcaattg    120

aattttcaca cattcgggtt ttgtgatttc tctgtcataa tgggcccggc acatatggtt    180

cataacccat gtgggcctat ggtataattt ttccaattaa aactattgtt aggtcgataa    240

aacaaaaaac aataaaaacg agtggaatac acataccaaa aagaatgtga tgaacattag    300

taattttatt ttgatggtta atgaaaaaca aaataaatgc atcttggcat cttccgttgg    360

aaagcgcaaa tagggcagat tttcagacag atatcactat gatggggggt gagagaaaga    420

aaacgaggcg tacctaatgt aacactactt aattagtcgt tagttatagg acttttttt     480

tgtttgggcc tagttatagg atcataaggt aaaaatgaag aatgaatatt agattagtag    540

gagctaatga tggagttaag tatgcacgtg taagaactgg gaagtgaaac ctcctgtatg    600

gtgaagaaac tatacaacaa agccctttgt tggtgtatac gtattaattt ttattctttt    660

atcacaagcg atacgtatct taagacataa taaatatata tcttactcat aataaatatc    720

ttaagatata tatacagtat acacctgtat atatataata aataggcata tagtagaaat    780

taatatgagt tgttgttgtt gcaaatatat aaatcaatca aaagatttaa aacccaccat    840

tcaatcttgg taagtaacga aaaaaaaggg aagcaagaag aaccacagaa aaggggggcta    900

acaactagac acgtagatct tcatctgccc gtccatctaa cctaccacac tctcatcttc    960

tttttcccgt gtcagtttgt tatataagct ctcactctcc ggtatatttc cccattgcac   1020

tgga                                                                1024
```

<210> SEQ ID NO 171
<211> LENGTH: 911
<212> TYPE: DNA
<213> ORGANISM: Arabidopsis thaliana
<220> FEATURE:
<221> NAME/KEY: misc_feature
<223> OTHER INFORMATION: Ceres Promoter YP0263

<400> SEQUENCE: 171

```
atctagctgt ggattccacc aaaattctgg cagggccatg atctaaaaac tgagactgcg     60

cgtgttgttt tgcagtgatt tgtatttcat atttgcacca tcctacacag tccacttggt    120

atcgtaacca aacataagga gaacctaatt acattattgt tttaatttcg tcaaactggt    180

ttttaccttt tagttacata gttgattctt catttgtttt agtagttatg gagcacaata    240

atgtgcaaca aagaaagatc atagtggatt aatatgttga gaggtcagaa attcttggtt    300

aacaaaaaaa agttacaagg actgagattt tgggtgggag aaagccatag cttttaaaac    360

atgattgaac ttaaaagtga tgttatggtt tgaggggaaa aaggttgatg tcaactaaga    420

tagttgaagt aatgtcttaa actaaagtaa accaccggtc caaccgtggt ccggaagcat    480

ctctggtatg atttatccta aaaatcaaaa tagtagaaac atactttaaa tatatacatt    540

gatcggacga aaattgtaaa ctagtatagt ttcaaaaact agttgaacag gttatgtacc    600

ttaaacattt atttcaaact taaacactaa agaacatata tgaatagaag tttatataaa    660
```

```
ttactatata tctaccataa atctcttata attatgatgt cacgatgagg aagtgttgaa    720

acgttaaaat gccaaaatat aagcatgcga cggaattttg gcagaagatt gtagagttgt    780

aatctgtcgc aatcattact cgtgctagca tttttcattt tcccttcatt tgtggataac    840

gcacgatata acattctaca caccaacaag attctataaa aacgcaaagg ttgtctccat    900

agaatatcgt c                                                         911
```

<210> SEQ ID NO 172
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0275

<400> SEQUENCE: 172

```
aaacattaat atgtagtaac tatgggcgta tgctttactt tttaaaatgg gcctatgcta     60

taattgaatg acaaggatta aacaactaat aaaattgtag atgggttaag atgacttatt    120

tttttactta ccaatttata aatgggcttc gatgtactga aatatatcgc gcctattaac    180

gaggccattc aacgaatgtt ttaagggccc tatttcgaca ttttaaagaa cacctaggtc    240

atcattccag aaatggatat tataggattt agataatttc ccacgtttgg tttatttatc    300

tattttttga cgttgaccaa cataatcgtg cccaaccgtt tcacgcaacg aatttatata    360

cgaaatatat atatttttca aattaagata ccacaatcaa aacagctgtt gattaacaaa    420

gagatttttt ttttttggtt ttgagttaca ataacgttag aggataaggt ttcttgcaac    480

gattaggaaa tcgtataaaa taaaatatgt tataattaag tgttttattt tataatgagt    540

attaatataa ataaaacctg caaaaggata gggatattga ataataaaga gaaacgaaag    600

agcaatttta cttctttata attgaaatta tgtgaatgtt atgtttacaa tgaatgattc    660

atcgttctat atattgaagt aaagaatgag tttattgtgc ttgcataatg acgttaactt    720

cacatataca cttattacat aacatttatc acatgtgcgt cttttttttt ttttactttg    780

taaaatttcc tcacttttaa gacttttata acaattacta gtaaaataaa gttgcttggg    840

gctacaccct ttctccctcc aacaactcta tttatagata acattatatc aaaatcaaaa    900

catagtccct ttcttctata aaggtttttt cacaaccaaa tttccattat aaatcaaaaa    960

ataaaaactt aattagtttt tacagaagaa aagaaaaca                           999
```

<210> SEQ ID NO 173
<211> LENGTH: 981
<212> TYPE: DNA
<213> ORGANISM: Arabidopsis thaliana
<220> FEATURE:
<221> NAME/KEY: misc_feature
<223> OTHER INFORMATION: Ceres Promoter YP0285

<400> SEQUENCE: 173

```
gggattatat atgatagacg attgtatttg cgggacattg agatgtttcc gaaaatagtc     60

atcaaatatc aaaccagaat ttgatgtgaa aacactaatt aaaacatata attgacaact    120

agactatatc atttgttaag ttgagcgttg aaagaaaatg aaagagtgta gactgtagta    180

cgtatgagtt tcccaaaaga tggtgcttga atattattgg gaagagactt tggttggttc    240

ggttgaatga agatttttac ctgccatgtt gatagagaaa ggcaaataaa tgtaggggtc    300

gatgtctaac gtaaagactg gatcaaccaa gagtcctcct cctcgtcttc accaaaaaaa    360

aagagtcctc ctcgtggaaa cttatttctt ctccagccaa gatctcatct catctcttca    420
```

ctctatgaaa tataaaggaa tcttatggtt tttctaaaaa ctatagtacg tctatatacc 480
aaaggaaaca atataaaatc agttaatctg ataaattttg agtaaataat aaagttaact 540
ttgtacttac ctatatcaaa ctaattcaca aaataaagta ataataacaa agaattttta 600
gtagatccac aatatacaca cacactatga gaaatcataa tagagaattt taatgatttt 660
gtctaactca tagcaacaag tcgctttggc cgagtggtta aggcgtgtgc ctgctaagta 720
catgggctct gcccgcgaga gttcgaatct ctcaggcgac gtttcttttg ttttcggcca 780
taaaggaaaa agcccaatta acacgtctcg cttataagcc cataaagcaa acaatgggct 840
gtctctgtct cactcacaca cgcgttttcc tactttttga ctatttttat aaccggcggg 900
tctgacttaa ttagggtttt ctttaataat cagacactct ctcactcgtt tcgtcaacat 960
tgaacacaga caaaaccgcg t 981

<210> SEQ ID NO 174
<211> LENGTH: 996
<212> TYPE: DNA
<213> ORGANISM: Arabidopsis thaliana
<220> FEATURE:
<221> NAME/KEY: misc_feature
<223> OTHER INFORMATION: Ceres Promoter YP0286

<400> SEQUENCE: 174
gaaaacaatc ataggttacg ctattatcat cgaaaggtat gtgatgcata ttcccattga 60
accagatttc catatatttt atttgtaaag tgataatgaa tcacaagatg attcaatatt 120
aaaaatgggt aactcacttt gacgtgtagt acgtggaaga atagttagct atcacgcata 180
catatatcta tgaataagtg tgtatgacat aagaaactaa aatatttacc taaagtccag 240
ttactcatac tgatttcatg catatatgta ttatttattt atttttaata aagaagcgat 300
tggtgttttc atagaaatca tgatagattg ataggtattt cagttccaca aatctagatc 360
tgtgtgctat acatgcatgt attaattttt tccccttaaa tcatttcagt tgataatatt 420
gctctttgtt ccaactttag aaaaggtatg aaccaacctg acgattaaca agtaaacatt 480
aattaatctt tatatgagat aaaaccgagg atatatatga ttgtgttgct gtctattgat 540
gatgtgtcga tattatgctt gttgtaccaa tgctcgagcc gagcgtgatc gatgccttga 600
caaactatat atgtttcccg aattaattaa gttttgtatc ttaattagaa taacattttt 660
atacaatgta atttctcaag cagacaagat atgtatccta tattaattac tatatatgaa 720
ttgccgggca cctaccagga tgtttcaaat acgagagccc attagtttcc acgtaaatca 780
caatgacgcg acaaaatcta gaatcgtgtc aaaactctat caatacaata atatatattt 840
caagggcaat ttcgacttct cctcaactca atgattcaac gccatgaatc tctatataaa 900
ggctacaaca ccacaaagga tcatcagtca tcacaaccac attaactctt caccactatc 960
tctcaatctc tcgtttcatt tcttgacgcg tgaaaa 996

<210> SEQ ID NO 175
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0337

<400> SEQUENCE: 175
taattttttt atttttggaa ctaacactta ttagtttagg tttccatcac ctatttaatt 60

```
cgtaattctt atacatgcat ataatagaga tacatatata caaatttatg atcatttttg    120

cacaacatgt gatctcattc attagtatgc attatgcgaa aacctcgacg cgcaaaagac    180

acgtaatagc taataatgtt actcatttat aatgattgaa gcaagacgaa aacaacaaca    240

tatatatcaa attgtaaact agatatttct taaaagtgaa aaaaaacaaa gaaatataaa    300

ggacaatttt gagtcagtct cttaatatta aaacatatat acataaataa gcacaaacgt    360

ggttacctgt cttcatgcaa tgtggacttt agtttatcta atcaaaatca aaataaaagg    420

tgtaatagtt ctcgtcattt ttcaaatttt aaaaatcaga accaagtgat ttttgtttga    480

gtattgatcc attgtttaaa caatttaaca cagtatatac gtctcttgag atgttgacat    540

gatgataaaa tacgagatcg tctcttggtt ttcgaatttt gaactttaat agttttcttt    600

tttagggaaa ctttaatagt tgtttatcat aagattagtc acctaatggt tacgttgcag    660

taccgaacca attttttacc ctttttttcta aatgtggtcg tggcataatt tccaaaagag    720

atccaaaacc cggtttgctc aactgataag ccggtcggtt ctggtttgaa aaacaagaaa    780

taatctgaaa gtgtgaaaca gcaacgtgtc tcggtgtttc atgagccacc tgccacctca    840

ttcacgtcgg tcattttgtc gtttcacggt tcacgctcta gacacgtgct ctgtccccac    900

catgactttc gctgccgact cgcttcgctt tgcaaactca aacatgtgtg tatatgtaag    960

tttcatccta ataagcatct cttaccacat taattaaaaa                          1000
```

<210> SEQ ID NO 176
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0356

<400> SEQUENCE: 176

```
ttagttcatt gaaacgtcaa ctttttactt gcaaccactt tgtaggacca ttaactgcaa     60

aataagaatt ctctaagctt cacaaggggt tcgtttggtg ctataaaaac attgttttaa    120

gaactggttt actggttcta taaatctata aatccaaata tgaagtatgg caataataat    180

aacatgttag cacaaaaaat actcattaaa ttcctaccca aaaaaaatct ttatatgaaa    240

ctaaaactta tatacacaat aatagtgata caaagtaggt cttgatattc aactattcgg    300

gattttctgg tttcgagtaa ttcgtataaa aggtttaaga tctattatgt tcactgaaat    360

cttaactttg ttttgtttcc agttttaact agtagaaatt gaaattttta aaaattgtta    420

cttacaataa aatttgaatc aatatcctta atcaaaggat cttaagacta gcacaattaa    480

aacatataac gtagaatatc tgaaataact cgaaaatatc tgaactaagt tagtagtttt    540

aaaatataat cccggtttgg accgggcagt atgtacttca atacttgtgg gttttgacga    600

ttttggatcg gattgggcgg gccagccaga ttgatctatt acaaatttca cctgtcaacg    660

ctaactccga acttaatcaa agattttgag ctaaggaaaa ctaatcagtg atcacccaaa    720

gaaaacattc gtgaataatt gtttgctttc catggcagca aaacaaatag gacccaaata    780

ggaatgtcaa aaaaaagaaa gacacgaaac gaagtagtat aacgtaacac acaaaaataa    840

actagagata ttaaaaacac atgtccacac atggatacaa gagcatttaa ggagcagaag    900

gcacgtagtg gttagaaggt atgtgatata attaatcggc ccaaatagat tggtaagtag    960

tagccgtcta tatcatccat actcatcata acttcaacct                          1000
```

<210> SEQ ID NO 177

<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0374

<400> SEQUENCE: 177

```
aagacacccg taaatgttgt catgtagaag aaactagaaa cgttaaacgc atcaaatcaa      60
gaaattaaat tgaaggtaat ttttaacgcc gcctttcaaa tattcttcct aggagaggct     120
acaagacgcg tatttctttc gaattctcca aaccattacc attttgatat ataataccga     180
catgccgttg ataaagtttg tatgcaaatc gttcattggg tatgagcaaa tgccatccat     240
tggttcttgt aattaaatgg tccaaaaata gtttgttccc actactagtt actaatttgt     300
atcactctgc aaaataatca tgatataaac gtatgtgcta tttctaatta aaactcaaaa     360
gtaatcaatg tacaatgcag agatgaccat aaaagaacat taaaacacta cttccactaa     420
atctatgggg tgccttggca aggcaattga ataaggagaa tgcatcaaga tgatatagaa     480
aatgctattc agtttataac attaatgttt tggcggaaaa ttttctatat attagacctt     540
tctgtaaaaa aaaaaaaatg atgtagaaaa tgctattatg tttcaaaaat ttcgcactag     600
tataatacgg aacattgtag tttacactgc tcattaccat gaaaaccaag gcagtatata     660
ccaacattaa taaactaaat cgcgatttct agcacccccca ttaattaatt ttactattat     720
acattctctt tgcttctcga aataataaac ttctctatat cattctacat aataaataag     780
aaagaaatcg acaagatcta aatttagatc tattcagctt tttcgcctga gaagccaaaa     840
ttgtgaatag aagaaagcag tcgtcatctt cccacgtttg gacgaaataa aacataacaa     900
taataaaata ataaatcaaa tatataaatc cctaatttgt ctttattact ccacaatttt     960
ctatgtgtat atatataccc acctctctct tgtgtatttg                          1000
```

<210> SEQ ID NO 178
<211> LENGTH: 998
<212> TYPE: DNA
<213> ORGANISM: Arabidopsis thaliana
<220> FEATURE:
<221> NAME/KEY: misc_feature
<223> OTHER INFORMATION: Ceres Promoter YP0377

<400> SEQUENCE: 178

```
tataaaccat tcctataaca ccatatttaa acataacaat gaattgcttg gatttcaaac      60
tttattaaat ttggatttta aattttaatt tgattgaatt ataccccctt aattggataa     120
attcaaatat gtcaactttt tttttgtaag attttttttat ggaaaaaaaa attgattatt     180
cactaaaaag atgacaggtt acttataatt taatatatgt aaaccctaaa aagaagaaaa     240
tagtttctgt tttcacttta ggtcttatta tctaaacttc tttaagaaaa tcgcaataaa     300
ttggtttgag ttctaacttt aaacacatta atatttgtgt gctatttaaa aaataattta     360
caaaaaaaaa aacaaattga cagaaaatat caggttttgt aataagatat ttcctgataa     420
atatttaggg aatataacat atcaaaagat tcaaattctg aaaatcaaga atggtagaca     480
tgtgaaagtt gtcatcaata tggtccactt ttctttgctc tataacccaa aattgaccct     540
gacagtcaac ttgtacacgc ggccaaacct ttttataatc atgctattta tttccttcat     600
ttttattcta tttgctatct aactgatttt tcattaacat gataccagaa atgaatttag     660
atggattaat tcttttccat ccacgacatc tggaaacact tatctcctaa ttaaccttac     720
ttttttttta gtttgtgtgc tccttcataa aatctatatt gtttaaaaca aaggtcaata     780
```

```
aatataaata tggataagta taataaatct ttattggata tttctttttt taaaaaagaa    840

ataaatcttt tttggatatt ttcgtggcag catcataatg agagactacg tcgaaaccgc    900

tggcaaccac ttttgccgcg tttaatttct ttctgaggct tatataaata gatcaaaggg    960

gaaagtgaga tataatacag acaaaacaag agaaaaga                           998


<210> SEQ ID NO 179
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0380

<400> SEQUENCE: 179

acaagtacca ttcacttttt tacttttcaa tgtatacaat catcatgtga taaaaaaaaa     60

aatgtaacca atcaacacac tgagatacgg ccaaaaaatg gtaatacata aatgtttgta    120

ggttttgtaa tttaaatact ttagttaagt tatgatttta ttatttttgc ttatcactta    180

tacgaaatca tcaatctatt ggtatctctt aatcccgctt tttaatttcc accgcacacg    240

caaatcagca aatggttcca gccacgtgca tgtgaccaca tattgtggtc acagtactcg    300

tccttttttt ttcttttgta atcaataaat ttcaatccta aaacttcaca cattgagcac    360

gtcggcaacg ttagctccta aatcataacg agcaaaaaag ttcaaattag ggtatatgat    420

caattgatca tcactacatg tctacataat taatatgtat tcaaccggtc ggtttgttga    480

tactcatagt taagtatata tgtgctaatt agaattagga tgaatcagtt cttgcaaaca    540

actacggttt catataatat gggagtgtta tgtacaaaat gaaagaggat ggatcattct    600

gagatgttat gggctcccag tcaatcatgt tttgctcgca tatgctatct tttgagtctc    660

ttcctaaact catagaataa gcacgttggt tttttccacc gtcctcctcg tgaacaaaag    720

tacaattaca ttttagcaaa ttgaaaataa ccacgtggat ggaccatatt atatgtgatc    780

atattgcttg tcgtcttcgt tttcttttaa atgtttacac cactacttcc tgacacgtgt    840

ccctattcac atcatccttg ttatatcgtt ttacttataa aggatcacga acaccaaaac    900

atcaatgtgt acgtcttttg cataagaaga aacagagagc attatcaatt attaacaatt    960

acacaagaca gcgagattgt aaaagagtaa gagagagag                          999


<210> SEQ ID NO 180
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0381

<400> SEQUENCE: 180

cacggtcaaa gtattgctaa catggtcatt acattgaaaa agaaaattaa ttgtctttac     60

tcatgtttat tctatacaaa taaaaatatt aaccaaccat cgcactaaca aaatagaaat    120

cttattctaa tcacttaatt gttgacaatt aaatcattga aaaatacact taaatgtcaa    180

atattcgttt tgcatacttt tcaatttaaa tacatttaaa gttcgacaag ttgcgtttac    240

tatcatagaa aactaaatct cctaccaaag cgaaatgaaa ctactaaagc gacaggcagg    300

ttacataacc taacaaatct ccacgtgtca attaccaaga gaaaaaaaga gaagataagc    360

ggaacacgtg gtagcacaaa aaagataatg tgatttaaat taaaaaacaa aaacaaagac    420
```

```
acgtgacgac ctgacgctgc aacatcccac cttacaacgt aataaccact gaacataaga    480

cacgtgtacg atcttgtctt tgttttctcg atgaaaacca cgtgggtgct caaagtcctt    540

gggtcagagt cttccatgat tccacgtgtc gttaatgcac caaacaaggg tactttcggt    600

attttggctt ccgcaaatta gacaaaacag ctttttgttt gattgatttt tctcttctct    660

ttttccatct aaattctctt tgggctctta atttcttttt gagtgttcgt tcgagatttg    720

tcggagattt tttcggtaaa tgttgaaatt ttgtgggatt ttttttttatt tctttattaa    780

actttttttt attgaattta taaaaaggga aggtcgtcat taatcgaaga aatggaatct    840

tccaaaattt gatattttgc tgttttcttg ggatttgaat tgctctttat catcaagaat    900

ctgttaaaat ttctaatcta aaatctaagt tgagaaaaag agagatctct aatttaaccg    960

gaattaatat tctccgaccg aagttattat gttgcaggct                       1000
```

```
<210> SEQ ID NO 181
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0384

<400> SEQUENCE: 181

tttaaaaaat tggataaaac accgataaaa attcacattt gcaaatttta ttcagtcgga     60

atatatattt gaaacaagtt ttgaaatcca ttggacgatt aaaattcatt gttgagagga    120

taaatatgga tttgttcatc tgaaccatgt cgttgattag tgattgacta ccatgaaaaa    180

tatgttatga aaagtataac aactttttgat aaatcacatt tattaacaat aaatcaagac    240

aaaatatgtc aacaataata gtagtagaag atattaattc aaattcatcc gtaacaacaa    300

aaaatcatac cacaattaag tgtacagaaa aacctttttgg atatatttat tgtcgctttt    360

caatgatttt cgtgaaaagg atatatttgt gtaaaataag aaggatcttg acgggtgtaa    420

aaacatgcac aattcttaat ttagaccaat cagaagacaa cacgaacact tctttattat    480

aagctattaa acaaaatctt gcctattttg cttagaataa tatgaagagt gactcatcag    540

ggagtggaaa atatctcagg atttgctttt agctctaaca tgtcaaacta tctagatgcc    600

aacaacacaa agtgcaaatt cttttaatat gaaaacaaca ataatatttc taatagaaaa    660

ttaaaaaggg aaataaaata ttttttttaaa atatacaaaa gaagaaggaa tccatcatca    720

aagttttata aaattgtaat ataatacaaa cttgtttgct tccttgtctc tccctctgtc    780

tctctcatct ctcctatctt ctccatatat acttcatctt cacacccaaa actccacaca    840

aaatatctct ccctctatct gcaaattttc caaagttgca tcctttcaat ttccactcct    900

ctctaatata attcacattt tcccactatt gctgattcat tttttttttgt gaattatttc    960

aaacccacat aaaaaaatct ttgtttaaat ttaaaacca                        999
```

```
<210> SEQ ID NO 182
<211> LENGTH: 998
<212> TYPE: DNA
<213> ORGANISM: Arabidopsis thaliana
<220> FEATURE:
<221> NAME/KEY: misc_feature
<223> OTHER INFORMATION: Ceres Promoter YP0385

<400> SEQUENCE: 182

actcaacaat aggacaagcc aaaaaaattc caattattgt gttactctat tcttctaaat     60

ttgaacacta atagactatg acatatgagt atataatgtg aagtcttaag atattttcat    120
```

```
gtgggagatg aataggccaa gttggagtct gcaaacaaga agctcttgag ccacgacata    180

agccaagttg atgaccgtaa ttaatgaaac taaatgtgtg tggttatata ttagggaccc    240

atggccatat acacaatttt tgtttctgtc gatagcatgc gtttatatat atttctaaaa    300

aaactaacat atttactgga tttgagttcg aatattgaca ctaatataaa ctacgtacca    360

aactacatat gtttatctat atttgattga tcgaagaatt ctgaactgtt ttagaaaatt    420

tcaatacact taacttcatc ttacaacggt aaaagaaatc accactagac aaacaatgcc    480

tcataatgtc tcgaaccctc aaactcaaga gtatacattt tactagatta gagaatttga    540

tatcctcaag ttgccaaaga attggaagct tttgttacca aacttagaaa cagaagaagc    600

cacaaaaaaa gacaaaggga gttaaagatt gaagtgatgc atttgtctaa gtgtgaaagg    660

tctcaagtct caactttgaa ccataataac attactcaca ctcccttttt ttttcttttt    720

ttttcccaaa gtaccctttt taattccctc tataacccac tcactccatt ccctctttct    780

gtcactgatt caacacgtgg ccacactgat gggatccacc tttcctctta cccacctccc    840

ggtttatata aacccttcac aacacttcat cgctctcaaa ccaactctct cttctctctt    900

ctctcctctc ttctacaaga agaaaaaaaa cagagccttt acacatctca aaatcgaact    960

tactttaacc accaaatact gattgaacac acttgaaa                            998
```

<210> SEQ ID NO 183
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0396

<400> SEQUENCE: 183

```
catagtaaaa gtgaatttaa tcatactaag taaaataaga taaaacatgt tatttgaatt     60

tgaatatcgt gggatgcgta tttcggtatt tgattaaagg tctggaaacc ggagctccta    120

taacccgaat aaaaatgcat aacatgttct tccccaacga ggcgagcggg tcagggcact    180

agggtcattg caggcagctc ataaagtcat gatcatctag gagatcaaat tgtatgtcgg    240

ccttctcaaa attacctcta agaatctcaa acccaatcat agaacctcta aaaagacaaa    300

gtcgtcgctt tagaatgggt tcggtttttg gaaccatatt tcacgtcaat ttaatgttta    360

gtataatttc tgaacaacag aattttggat ttatttgcac gtatacaaat atctaattaa    420

taaggacgac tcgtgactat ccttacatta agtttcactg tcgaaataac atagtacaat    480

acttgtcgtt aatttccacg tctcaagtct ataccgtcat ttacggagaa agaacatctc    540

tgtttttcat ccaaactact attctcactt tgtctatata tttaaaatta agtaaaaaag    600

actcaatagt ccaataaaat gatgaccaaa tgagaagatg gttttgtgcc agattttagg    660

aaaagtgagt caaggtttca catctcaaat ttgactgcat aatcttcgcc attaacaacg    720

gcattatata tgtcaagcca attttccatg ttgcgtactt ttctattgag gtgaaaatat    780

gggtttgttg attaatcaaa gagtttgcct aactaatata actacgactt tttcagtgac    840

cattccatgt aaactctgct tagtgtttca tttgtcaaca atattgtcgt tactcattaa    900

atcaaggaaa aatatacaat tgtataattt tcttatattt taaaattaat tttgatgtat    960

taccccttta taaataggct atcgctacaa caccaataac                         1000
```

<210> SEQ ID NO 184
<211> LENGTH: 1514

<212> TYPE: DNA
<213> ORGANISM: Arabidopsis thaliana
<220> FEATURE:
<221> NAME/KEY: misc_feature
<223> OTHER INFORMATION: Ceres Promoter p13879

<400> SEQUENCE: 184

```
tttcgatcct cttcttttt aggtttcttg atttgatgat cgccgccagt agagccgtcg     60

tcggaagttt cagagattaa aaccatcacc gtgtgagttg gtagcgaatt aacggaaagt    120

ctaagtcaag attttttaaa aagaaattta tgtgtgaaaa gaagccgttg tgtatattta    180

tataatttag aaaatgtttc atcattttaa ttaaaaaatt aataatttgt agaagaaaga    240

agcatttttt atacataaat catttacctt ctttactgtg tttttcttca cttacttcat    300

ttttactttt ttacaaaaaa gtgaaaagta aattacgtaa ttggtaacat aaattcactt    360

taaatttgca tatgttttgt tttcttcgga aactatatcg aaaagcaaac ggaaagaact    420

tcacaaaaaa ccctagctaa ctaaagacgc atgtgttctt cttattcttc atatatcctc    480

tgtttcttgt gttctgtttt gagtcttaca ttttcaatat ctgactctga ttactatatc    540

taaaagggaa catgaagaac ttgagaccat gttaaactgt acaatgcctt caaacatggc    600

taactaaaga tacattagat ggctttacag tgtgtaatgc ttattatctt taggtttttt    660

aaatcccttg tattaagtta tttaccaaat tatgttcttg tactgcttat tggcttggtt    720

gttgtgtgct ttgtaaacaa cacctttggc tttatttcat cctttgtaaa cctactggtc    780

tttgttcagc tcctcttgga agtgagtttg tatgcctgga acgggtttta atggagtgtt    840

tatcgacaaa aaaaaaatgt agcttttgaa atcacagaga gtagttttat attcaaatta    900

catgcatgca actaagtagc aacaaagttg atatggccga gttggtctaa ggcgccagat    960

taaggttctg gtccgaaagg gcgtgggttc aaatcccact gtcaacattc tctttttctc   1020

aaattaatat ttttctgcct caatggttca ggcccaatta tactagacta ctatcgcgac   1080

taaaataggg actagccgaa ttgatccggc ccagtatcag ttgtgtatca ccacgttatt   1140

tcaaatttca aactaaggga taaagatgtc atttgacata tgagatattt ttttgctcca   1200

ctgagatatt tttctttgtc ccaagataaa atatcttttc tcgcatcgtc gtctttccat   1260

ttgcgcatta aaccaaaaag tgtcacgtga tatgtcccca accactacga attttaacta   1320

cagatttaac catggttaaa ccagaattca cgtaaaccga ctctaaacct agaaaatatc   1380

taaaccttgg ttaatatctc agcccccta taaataacga gacttcgtct acatcgttct   1440

acacatctca ctgctcacta ctctcactgt aatcccttag atcttctttt caaatttcac   1500

cattgcactg gatg                                                      1514
```

<210> SEQ ID NO 185
<211> LENGTH: 1954
<212> TYPE: DNA
<213> ORGANISM: Arabidopsis thaliana
<220> FEATURE:
<221> NAME/KEY: misc_feature
<223> OTHER INFORMATION: Ceres Promoter p326

<400> SEQUENCE: 185

```
gtgggtaaaa gtatccttct ttgtgcattt ggtattttta agcatgtaat aagaaaaacc     60

aaaatagacg gctggtattt aataaaagga gactaatgta tgtatagtat atgatttgtg    120

tggaatataa taaagttgta aaatatagat gtgaagcgag tatctatctt ttgactttca    180

aaggtgatcg atcgtgttct ttgtgatagt tttggtcgtc ggtctacaag tcaacaacca    240
```

```
ccttgaagtt ttcgcgtctc ggtttcctct tcgcatctgg tatccaatag catacatata    300

ccagtgcgga aaatggcgaa gactagtggg cttgaaccat aaggtttggc cccaatacgg    360

attccaaaca acaagcctag cgcagtcttt tgggatgcat aagactaaac tgtcgcagtg    420

atagacgtaa gatatatcga cttgattgga atcgtctaag ctaataagtt taccttgacc    480

gtttatagtt gcgtcaacgt ccttatggag attgatgccc atcaaataaa cctgaaaatc    540

catcaccatg accaccataa actcccttgc tgccgctgct ttggcttgag caaggtgttt    600

ccttgtaaag ctccgatctt tggataaagt gttccacttt ttgcaagtag ctctgacccc    660

tctcagagat gtcaccggaa tcttagacag aacctcctct gccaaatcac ttggaagatc    720

ggacaatgtc atcattttg caggtaattt ctccttcgtt gctgctttgg cttgagcacg    780

gtgcttcttt gtaaagctcc gatctttgga taagagcgga tcggaatcct ctaggaggtg    840

ccagtccctt gacctattaa tttatagaag gttttagtgt attttgttcc aatttcttct    900

ctaacttaac aaataacaac tgcctcatag tcatgggctt caaattttat cgcttggtgt    960

atttcgttat ttgcaaggcc ttggcccatt ttgagcccaa taactaaatc tagccttttc   1020

agaccggaca tgaacttcgc atattggcgt aactgtgcag ttttaccttt ttcggatcag   1080

acaagatcag atttagacca cccaacaata gtcagtcata tttgacaacc taagctagcc   1140

gacactacta aaaagcaaac aaaagaagaa ttctatgttg tcattttacc ggtggcaagt   1200

ggacccttct ataaaagagt aaagagacag cctgtgtgtg tataatctct aattatgttc   1260

accgacacaa tcacacaaac ccttctctaa tcacacaact tcttcatgat ttacgacatt   1320

aattatcatt aactctttaa attcacttta catgctcaaa aatatctaat ttgcagcatt   1380

aatttgagta ccgataacta ttattataat cgtcgtgatt cgcaatcttc ttcattagat   1440

gctgtcaagt tgtactcgca cgcggtggtc cagtgaagca aatccaacgg tttaaaacct   1500

tcttacattt ctagatctaa tctgaaccgt cagatatcta gatctcattg tctgaacaca   1560

gttagatgaa actgggaatg aatctggacg aaattacgat cttacaccaa ccccctcgac   1620

gagctcgtat atataaagct tatacgctcc tccttcacct tcgtactact actaccacca   1680

catttcttta gctcaacctt cattactaat ctccttttaa ggtatgttca cttttcttcg   1740

attcatactt tctcaagatt cctgcatttc tgtagaattt gaaccaagtg tcgatttttg   1800

tttgagagaa gtgttgattt atagatctgg ttattgaatc tagattccaa tttttaattg   1860

attcgagttt gttatgtgtg tttatactac ttctcattga tcttgtttga tttctctgct   1920

ctgtattagg tttctttcgt gaatcagatc ggaa                                1954
```

<210> SEQ ID NO 186
<211> LENGTH: 2016
<212> TYPE: DNA
<213> ORGANISM: Arabidopsis thaliana
<220> FEATURE:
<221> NAME/KEY: misc_feature
<223> OTHER INFORMATION: Ceres Promoter p32449

<400> SEQUENCE: 186

```
gatcggcctt cttcaggtct tctctgtagc tctgttactt ctatcacagt tatcgggtat     60

ttgagaaaaa agagttagct aaaatgaatt tctccatata atcatggttt actacaggtt    120

tacttgattc gcgttagctt tatctgcatc caaagttttt tccatgatgt tatgtcatat    180

gtgataccgt tactatgttt ataactttat acagtctggt tcactggagt ttctgtgatt    240

atgttgagta catactcatt catcctttgg taactctcaa gtttaggttg tttgaattgc    300
```

```
ctctgttgtg atacttattg tctattgcat caatcttcta atgcaccacc ctagactatt    360

tgaacaaaga gctgtttcat tcttaaacct ctgtgtctcc ttgctaaatg gtcatgcttt    420

aatgtcttca cctgtctttc tcttctatag atatgtagtc ttgctagata gttagttcta    480

cagctctctt ttgtagtctt gttagagagt tagttgagat attacctctt aaaagtatcc    540

ttgaacgctt tccggttatg accaatttgt tgtagctcct tgtaagtaga acttactggg    600

accagcgaga cagtttatgt gaatgttcat gcttaagtgt cgaacgtatc tatctctact    660

atagctctgt agtcttgtta gacagttagt tttatatctc catttttttg tagtcttgct    720

agttgagata ttacctcttc tcttcaaagt atccttgaac gctcaccggt tatgaaatct    780

ctacactata gctctgtagt cttgctagat agttagttct ttagctctct ttttgtagcc    840

tagttcttta gctctccttt tgtagccttg ctacagagta agatgggata ttacctcctt    900

gaacgctctc cggttatgac caatttgttg tagctccttg taagtagaac ttaggataga    960

gtgagtcaac tttaagaaag aacctagtat gtggcataac cagattgcag gctctgtctc   1020

ggctacagta acgtaactct atagctcttt gttttgttca gaaagaacca gtgattggat   1080

gattcgtcct tagaaactgg acctaacaac agtcattggc tttgaaatca agccacaaca   1140

atgcctatat gaaccgtcca tttcatttat ccgtttcaaa ccagcccatt acatttcgtc   1200

ccattgataa ccaaaagcgg ttcaatcaga ttatgtttta attttaccaa attctttatg   1260

aagtttaaat tatactcaca ttaaaaggat tattggataa tgtaaaaatt ctgaacaatt   1320

actgattttg gaaaattaac aaatattctt tgaaatagaa gaaaaagcct tttcctttt    1380

gacaacaaca tataaaatca tactcccatt aaaaagattt taatgtaaaa ttctgaatat   1440

aagatatttt ttacaacaac aaccaaaaat atttattttt ttcctttttt acagcaacaa   1500

gaaggaaaaa cttttttttt tgtcaagaaa aggggagatt atgtaaacag ataaaacagg   1560

gaaaataact aaccgaactc tcttaattaa catcttcaaa taaggaaaat tatgatccgc   1620

atatttagga agatcaatgc attaaaacaa cttgcacgtg gaaagagaga ctatacgctc   1680

cacacaagtt gcactaatgg tacctctcac aaaccaatca aaatactgaa taatgccaac   1740

gtgtacaaat tagggtttta cctcacaacc atcgaacatt ctcgaaacat tttaaacagc   1800

ctggcgccat agatctaaac tctcatcgac caatttttga ccgtccgatg gaaactctag   1860

cctcaaccca aaactctata taaagaaatc ttttccttcg ttattgctta ccaaatacaa   1920

accctagccg ccttattcgt cttcttcgtt ctctagtttt ttcctcagtc tctgttctta   1980

gatcccttgt agtttccaaa tcttccgata aggcct                             2016
```

<210> SEQ ID NO 187
<211> LENGTH: 667
<212> TYPE: DNA
<213> ORGANISM: Arabidopsis thaliana
<220> FEATURE:
<221> NAME/KEY: misc_feature
<223> OTHER INFORMATION: Ceres Promoter PD1367

<400> SEQUENCE: 187

```
acagttttct tttctcatct tacaacaagt ttccaggagg atagagacat aaacgaagct     60

cggattgtat cgttcttttt agcttttatt cacatccgaa agtcctgtag tttagattct    120

gttatcttgc ggttttgagt taatcagaaa cagagtaatc aatgtaatgt tgcaggctag    180

atctttcatc tttggaaatt tgttttttc tcatgcaatt tctttagctt gaccatgagt     240

gactaaaaga tcaatcagta gcaatgattt gatttggcta agagacattt gtccacttgg    300
```

```
catcttgatt tggatggtta caacttgcaa gacccaattg gatacttgct atgacaactc    360

caactcaaga gtgtcgtgta actaagaacc ttgactaatt tgtaatttca atcccaagtc    420

atgttactat atgttttttt gtttgtatta ttttctctcc tacaattaag ctctttgacg    480

tacgtaatct ccggaaccaa ctcctatatc caccatttac tccacgttgt ctccaattat    540

tggacgttga aacttgacac aacgtaaacg tatctacgtg gttgattgta tgtacatatg    600

tacaaacgta cacctttctc ctctttcact tcatcacttg gcttgtgaat tcattaattc    660

ctgcgaa                                                              667
```

<210> SEQ ID NO 188
<211> LENGTH: 1836
<212> TYPE: DNA
<213> ORGANISM: Oryza sativa
<220> FEATURE:
<221> NAME/KEY: misc_feature
<223> OTHER INFORMATION: Ceres Promoter p530c10

<400> SEQUENCE: 188

```
gcctctcgac cacgagttta gcacttgtgc aacatatatg cgtgcgatga acatctactg     60

atgcgccatg cgaattttag cgttcgttca tgacgcttcc aacggcacag aggctgagca    120

gcagcatgca tgcatggctc ttgtgaaaac aaaaaaggtt actggtaaat gacatgctgc    180

tgtagctagc tagcagaatg caaggcccat gcatatgcaa tgctatgcga caagtacagt    240

accagcatgt atggtagcca gctaactaat ctatcagcag aggcagcaag ctcgtgcatg    300

gtgtgatgca cttctctcca gtaatctagt ggtaattttc acccaaagcg ttgctcatat    360

ggacagtaat tagtaatatt accaaggttc acaatcccgt tacctgacca aatactactc    420

acgaatggta tctctggttt tcgttaaaac cgttggtaaa ccagcaaaaa tagacaaaat    480

ttgtcaaaat tttaaatttt agtttttttt ttttaactta gccgggaaac cttgaagttt    540

gtgctgtcga gctgtcctgg gaaggacggt tttggttggg attgtgaacc ctggttactg    600

cacttcattt ttgaacagat attagtgcaa cagacaaatg ccaacgcatt tttttctgtt    660

taccggcaag ctgaagcttt tacgatcccc atacagccgt tgctgcaaac ctgccaagaa    720

agagcagcag aaacaggtgt cattttgtgg tggaaagcca agtaaagtaa acagaagatg    780

gaagatagtg aggaccaggg agtgaggcag gggacacatg gcccacgcct ccctgcacat    840

tttcgtgtat aaatacaggt ggatgcatcg ctctcccagc atccatcggt tctctgctct    900

gttcatccat agagtttcct cctcttctcc tttagtgcaa ggtagagaag agcatgtgtg    960

tgtgtgtgtg tgtgtgaact gtgaagtgca gagtgcttct gtagttctgt gttatgtcca   1020

tagtgatctt gttaggattg ttgctatgga tgcatgatgt tatggttgat ctctgaatta   1080

cagtagggac ttttctgaga tctctggatt agtggggggt gctaaatttt tttctggttg   1140

catcagcttg ggtttctggt attggtgtgg gttcttgctc tgaattttgg ttcagaatgt   1200

cgatttgttt gtgtttgttc tctgaagttg agagtagcta tgatccatcc agcacagaac   1260

tgcaggtcct gcctgccggc tgcatataca ggacatgcca ttttgcaagc tctgggctta   1320

tggtttctct tttggagttc ttcttcttgc atgatctgtg ttctctaaca aaggaagcaa   1380

gatttagcaa ctttattcag agacaagaaa aggatctggc aaccttttgt ttctgtttta   1440

tcctactcgt aaagattgtt atttaagcaa aaatttccca aaagttttaa atataatttc   1500

catgatgtgc cactctcatg tccttgaacc tggcactcat tatgggctcc tcagaagtgc   1560

tgtagctaat gtcactaatc ttttgtatct ttgttcatag tcttgtattt tatgatgctt   1620
```

```
atccctttgt gctttccatg tttgatgtcc aaatgtcatg gcaatgtttt tgacttctag   1680

taggggtttt agtacctttt tgttagataa gtacatccaa attctgttta tttattcaaa   1740

aatcattctg tttattcact gaaaacattt gtccattcaa tggactcata aactgtctgt   1800

gtttttcagg cttgaggatc catctagaag atagca                              1836
```

```
<210> SEQ ID NO 189
<211> LENGTH: 3000
<212> TYPE: DNA
<213> ORGANISM: Oryza sativa
<220> FEATURE:
<221> NAME/KEY: misc_feature
<223> OTHER INFORMATION: Ceres Promoter pOsFIE2-2

<400> SEQUENCE: 189

gcttaacaca tgaactacca aaatatactg atcactttgt tctagtcata cataccttaa     60

gtcattttat tctgcagtgt ttggattgga gggagcattc tagcatccct tgggtcgttc    120

cagcaaatgt ggttctccaa agcagagtaa gcacaacaca gtattttagg ttatgtttcc    180

cctatctcgt cacggacagc tcacaagtta atgtgattta tctcactata gatacgaaga    240

acatggagta tcctacatcc aaaggaagtg cccatgaagt tgtggagcat cgctacgatt    300

tgtgaccaaa tttgggtgca tgtgggcaat cgtattacag ccaccctgtt gttgatctat    360

atcgactatt atccgacgat atttatcatt atattatgac tagttagttt gtagattttg    420

agagggcaac ataagaagca atccagctta acctgttatg ttcttgatgg tagattctag    480

ttcatgtgtt gaatctgttc tccctgctgt agaatgtatc gagttgctgc tctctactct    540

gtacttttag aatacctttt caatcatttg gagtcagctg attgttgtac tacttatacg    600

ccacctgatt agtcatgtca acaattaaac ttgagcactg gttaagttaa gagtggcctg    660

attgtagttg ataatcacat tttattcgta gacattgtat gctggatctt tatcagccac    720

cgtcagatca tcctctgtaa taaatcttca tcagacgtgt gtgccaatcg caaggaacac    780

gaaatgcatc cgaaatgtta ctctgagtta atcaatacta taattcttgg tcaaattaat    840

tatttatatc tataaagttt aaattaaatt taggaaaatg aattcatgca aatcttgtgg    900

taagttgtca atttcataaa aaatccagct tactactccc tttttaggag tgtgttgtgg    960

ctgcacactt ctgccttttg atatatacgg ttctattctc ggtgtactcc tttattatta   1020

ttaaaacaat cccagttact tggtaagtgc taatcacgaa tcaaagtcaa cataacaaat   1080

catgtgcgta cagctataac tcgattacac aaacaacaaa attcatattt gaacataaat   1140

ccagttgtag catatctggt agtataaagt tttttttttg tatagaagag ttttaatttc   1200

tgtaagtttt ggaaagcatt taatcctaga aattgtagtg tagctcaact aaaaaataaa   1260

tgaacttgaa tcgaaattgg gttgtatcat aaatctttac cactcaaacg aatatttatc   1320

ctaaaccaca aatgactctt ttcatcaagg aatgttttgt tttcagcatt ttaaaaaaaa   1380

acttttctaa tatggtttc atgtttcgtt cttttgaaat ttaacatcta tttaatttgc    1440

acggctccat aaattcaacg gatacatatt ctgaataatt actaaggagg catatatcgg   1500

ctctcttaat acaaccgctt gtttctcaaa atttattttg agttttgtct acacattctc   1560

aaggacggta caaacacact atagatgttc acaatttttt ttttctaaag ttgattgatg   1620

gacaaatgtt tgaacatata aacatataag cactgaatat ttgcttatgc aggaggtatt   1680

tatatcaagt tcgatacttt actaccatag tccctaggac actaaaatgc cttcaatgat   1740

ctgatgaagc ctaagagaga atattgatca gtggagcgac ttgcaactac acatggcaca   1800
```

```
agtagactag acacggtata tattcatatt aacttgttaa aattttacta cttaacagtt   1860

cacttgtggt gcatccatat caattcttac ttacacaata tttgtaaaaa caacctaaca   1920

ctataggatg acctagacaa cctttatgtc aatcacactt agaagatgat cgtcttttta   1980

ataaataatg tgtactacac accatgctct ccatatagat caagatctac aaacccttcc   2040

acttataaac cttaccacca aaaactcatt aagttgcttc atttatctat gctattaaga   2100

aaaaaactta tttcgtttat gccatttcta gaaatggcta gtcacactat tcacaatatt   2160

atataataaa taaaagtttc aaatattcat ccaccaaaaa tcatcaagtc gtgggactta   2220

tatgttaatt agagaagtcc ctttgggtgc aatcgatttt ggaaacccta aattttttct   2280

atacatagaa gagagagatg tctagttgca attgcttttg cgatgtgcca accacccttc   2340

tagctttcat ccacgtctac ttaattgcca ttcttcttct tctttttctt cactattact   2400

acctcctatc ttagcgaatc ttcttcttct tcactattac tacctcccac cttagtgaat   2460

tcatcctcat tgttcacaat gacattgcta agttaactag gtatgctaag tacacaatta   2520

gaatataacc tagagccttt gtttccatca tacttaaaag atgacatttt tatatagata   2580

aagtgtgcta ctcacaaggc ttactatata tatgtatgat acacacaaac tccacaaccc   2640

aaaactcttt caagttgtgt ggcccatcta tgctattaaa aagcccattt agcccatcca   2700

acatgagaaa ccctagggtt ttttccctat aaaagatacc taggttattg ttgcttttcc   2760

accccgcccg ccgccgctcc ctattcctat ttaatcccat ctctcttcct catcaccgct   2820

ctcctctctc caggcaagag gtacgcactt tttgtttcgg atttgaaatc tttgcttcgt   2880

tttactatca ttggtcataa gttctttttt gaagatgttt gagaataagt ttatcattga   2940

gattatcgtc acttgtgata ggaagtacgc aacctcaagc cggacaagac gtgagcaaag   3000
```

<210> SEQ ID NO 190
<211> LENGTH: 2023
<212> TYPE: DNA
<213> ORGANISM: Oryza sativa
<220> FEATURE:
<221> NAME/KEY: misc_feature
<223> OTHER INFORMATION: Ceres Promoter pOsMEA

<400> SEQUENCE: 190

```
gagagcagaa catagtagcc gctgttttct gggggtgcaa tttgtgcaag atcgctatcc     60

ttatggacca tgcaagcacc aagcaatatt aagccaggtc caacagcggt cttggggaat    120

tcagaaatga gcttaaaaac ctccttgagc tggccagctc agccaaggag gtccatcatg    180

catgtgcatg ctcaatactt ggaattattg caaaatgatc ggtcattgac tggaagactt    240

tgcgcccttc ctcagccaac cttatgtggc tgcatgcata gagtaccaac aggaaggtag    300

cgtttgttgg aataaggttt gcatccagca tgtccttgta gagcttcaaa gcctcagcac    360

cttggcccat gaaggccata tccagctaat tgcattccat gagaccacat tcttgctatc    420

catactgttg aagtgaagat gctccgagct tcggaaatgc ttccacacta tgcatacatg    480

tcaatgagca ctgtcatgac ataaacattg ggccccaagt cctcctcagc gataatccta    540

tgcagccact ttcccaggga caaagctcca agctgtgcac acgctgaaag agagctagaa    600

atgatgattg gatttggtca cacgctaagt accagcattt gctcaaagag ggcaattgcc    660

atctccgtcc agccattcta ggcataccct ggtattattg ctttccatga ttccgattcc    720

gtggtcttct atggcatcgc attgaaggcc ttccttgcag actccatatc atttaaccta    780

cagtacaata tggtaattgc tgtcgacact ggagaattcg cagtaaatcc agacttgaga    840
```

```
ggaccatgta agcattgatc aagcagttca ttcccaaaca gactatacgg gatcagtgcc    900

agtgctcgag tttggcttca attccaaggc catcaaccca ataaacagat taactgatga    960

accaaccatg caattcgccg agcaaacata gattaagcat tgtaggcaac caaatctgga   1020

ttctccatca agtcaaagag acgccatgca gaattccaca tccccgctgt atacaccgag   1080

atcaaccggt cagaacatgc tcatactccg ccaaccctct cttcagaaca tgctcatact   1140

ccgccaaccc tctcttctct gcaagaggca tcctccccaa ttccccattg ttatatctgt   1200

tgctggtaag accgttgcca gcgtggttgt gtcagaccga acagactctg cactcgccat   1260

cctcacgaac gactccaggg cctccgaacc aggaagcccg gccggccatc agcgtgttcc   1320

acataacggt atccggcgac tgcacagtgt cgaacacctt gcgtgcgtgg tcacctctgg   1380

acagcatgaa gcgtacaggc tacagcttgg ccaatgcgga cgccacgaac gtgtcggcgg   1440

cgtaacccgc gcgtgcagcg cgccgcgcgc gggctgcgga gtcggttgga gacgacacgc   1500

cgccgccatg agagcaatga gcgaggtggc ggcgaaggcg aaggagaagt agtcgaggca   1560

agcggaagag aaggcggcag cggagaaagc gatcggggcg gcggaggagg tgggtgggag   1620

ggagggacgc gtagcggagg tcggaggagg agggagctga ggtttccggg gcgggggtcg   1680

agagggtagt gtacggaggc gagggacacg gcgaggatct ggtcgaggta gcgcagtgtg   1740

aaggaaagcg cgatgaggcg gagggcgccg gcgaagagcg gcgcggcgga tagcgggagg   1800

aggcggcgcc ggcggggtct catccgattg gaaacagatt gggaaggggg agggggtagg   1860

aatacgtggc gtcggcagta ttaggtagag agagaaaccc tttccatcct ttgtctctta   1920

gccccgaagg agagagaaaa atcagaaaaa aaaaaccctc cgcgtgtggg ggaagcagag   1980

ctccggacgc tggcgccgct cgcgccaccg cacccgcacc gcc                     2023
```

<210> SEQ ID NO 191
<211> LENGTH: 2034
<212> TYPE: DNA
<213> ORGANISM: Oryza sativa
<220> FEATURE:
<221> NAME/KEY: misc_feature
<223> OTHER INFORMATION: Ceres Promoter pOsYp102

<400> SEQUENCE: 191

```
gaacgaccca aacgcgtaaa tggtggtact ggtttccctg ctttgccgag taccagcagc     60

cacgaagaac gttacacaat cgagtacaaa atctataaga gcaagtttaa tagcatagcc    120

aaatactacc tctaaatcat ctatagccaa tttaatagtt catttattca ataattactt    180

ataaacatat actacaatca ttaatatatg gtcttacttc ttatacacat aatattttgg    240

agtccgtgtt acagctggct ataaatataa gggattttgg ttggatgtgg tacatcctat    300

tataatgaat ctagacatga aacctgtcca aattcatcgt gctaggatac gccacatcta    360

accaaaatct cttatcttta gggatggaga gagtaataat taaatgaagc taggtagagt    420

ttcccggtca atacgcttgc gtgtgcttat aagagcatgg ccaacagttt cccgatactc    480

ttcccaatat cagttttgag gagttttgtt ggaaaaaatc gctccaacag tagacctaaa    540

tcacccctaa aagcttggcg tttccaaacc cgcatatttc gttctccact tgtagggaag    600

agactcggcg cccaatcctt caaccgcatg cacttcgcgc gcgctgtgtg aaaattttcc    660

taccaggttc ttctttgtgc gttcgtctac ctgtgagtca atccatcacg ccagcagcct    720

catcttcccc gcagctgtct gggaaagcag ccatggctcc cccaagcttc cccagcgtcg    780

acattttttt ctcagcggca gcgccagacc catctccaac ccaattgggc ggaccttcgt    840
```

```
cggcgctccc ccagcaccac caccgactcg aatcggccgt cgcccctatt catctccaat    900

cgtccctcga ccctaccgca tcctgcagca cagcctgtct ctcgcgtcag actggcgctg    960

cgctcccccc ggtaatgtgc aggcgacaaa ggccccatgc gatgcgacca gcagccggcg   1020

acaaccggag gtgcccagtc gctggccttc atcgaatcat cgtgcacctc ggtcggagtc   1080

gatttctgat tgttgctgct gctcaaatct ggagcttgct attgctgaga actgcttggt   1140

ggtggtactg gaaatttgtt gtttgctggc tgatgaaaac tgttgttctt tgctgctaaa   1200

aactgctgct tgctagtact gaaaagtact attgcagctg ctgaaatatc ttgctgcttg   1260

ctgctgaaaa cttcaagttg ttaacaccgt tcacactaaa aaagctgaaa ttttttttct   1320

gggctgaaaa ccccattgtt gatgattgca gaaccaatat ttttccatgt aaaatacagg   1380

agatcgtggt aataatcaag tgaaatatca ttttggggca aatactcaga tcgtacctga   1440

agccaatgga aacattgttc aatgcttaaa ctgtcagtta tgatgtcaaa gagattgatc   1500

actgaatgtc ctgaaaggag ccgtgaggag gatgcagcat tgcagcgtgc gcgagcgtga   1560

gtggaggaga ggaatgacga ttctgttggt agttgtcgat gtggcctact ttttttgttt   1620

tgaggattaa attttgggaa tctcttggag ataaaaggta ttctcatacc ttaaatcctt   1680

tttagagatc taaaaaaaat gatttagggg attgaatttt gggtggctgt tggtgatgct   1740

ctaagttgca catcctgggg aaaaacctcc ctaatccatc agcaaaccga tcaaccaccc   1800

acgacaagtc gacgccaccg tttttttttt ctccctccta agtcctaacc ccacaaaaat   1860

cccgcgaact ttcgtctcac cacgcgccgc gtgcccccta caaataccaa acaacaccca   1920

ccacgtccac tcacaaacca cgcaggaaac ctcagaaaat caccgtacgc gacgcgggcc   1980

caagaaaacc ccgacagaaa ccgcgcagca gcaacaccac caccggcgtc ggag         2034
```

<210> SEQ ID NO 192
<211> LENGTH: 1877
<212> TYPE: DNA
<213> ORGANISM: Oryza sativa
<220> FEATURE:
<221> NAME/KEY: misc_feature
<223> OTHER INFORMATION: Ceres Promoter pOsYp285

<400> SEQUENCE: 192

```
ggcccgagtt aaacgatctt ccacgtgtca gcgaatccta gtcgttcgat gaatctgaat     60

ctgacttgtg gtggttggac ggccacgtgt taaaaaaggg aaacgtccgc atcacccgat    120

gctgggacat ttgcaatttc gatccagctg tagattgacc agttgttact ctcttttttt    180

taacaccata caaacgtaat actccctctg tcccaaaata taagtatttt ttttaacctc    240

ggttcagtct tcgaggtgct actttgacca ataatattta taaaaataag atgttttaaa    300

taaagagagt tgcatattat gatagctcgt ttaatgataa acaaagtacc atcaaattta    360

catgattaat ctttttaatt tatttgctat taatagttaa aatttaaaaa gtttgacttc    420

acactgttct aaaaatactt atattttggg acggagggag tacacattag agcaggtaca    480

atagcagact agtagccagc tataaacata ttttaatgag ataaaagatg agagagaaca    540

gcgggctaca gatctgtagc cagctgcagc acggactcca agacattgtg tgtgtatgac    600

aggtgggacc atatattaat agtacagtaa gtaactattg tatgaattgg ctattagatt    660

agctataggt gaattgtagc tagtagtggg ctatactatt gaacttactc ttatatctct    720

caatatctcc agaaaactag gacgatatat attgatatta acaaagtcat catagatatc    780

tcgctatcga catatatatt acctatcact gaaaaaataa ttaatcataa atgcaagcac    840
```

```
atatactacg ttcaacactg aatgtaggta gattggtaga cgggttccac cgcaagaaaa    900

gcattgcacc agtgaagaaa gaaacatcgg aatttgtatg tagtttgttg tttgatgaat    960

tcttttgatt aaaaaaaact aaaatcagag ttgattcagt taatggtgtt gcctacgata   1020

tacttccata tcatgatatc actgtagact atgaatcata tctttaatta aaactaaatc   1080

aagaaattaa gtatgagacc tcaactcaat gaagaatttc tagttgaaaa acattcctag   1140

tgtgcgttcg gatggaggta gggatcttct ctccgttcat ataaaaccgg atggttcatt   1200

agaacatgat taattaagca acagttaatc taaaaataaa ttaatatttt ttaagaaatt   1260

tttgtataga gatcttttga aaaaaataca ttggttagaa agcatactaa taaaaagaga   1320

aaaataagaa catagtacta tagtagaaaa tgagaacttg gagtatttga gaggatggga   1380

aataagaaga ttaagaagat gcgtaaagtg aacggttaac gcatgattga ttaattaaat   1440

attaattatt ttaaatttgg aaaataaatt agtatgattt ttaagcaaca tatatatata   1500

tatatatata tatatagaaa aacatagttt tagaaaatat aagcgtgtaa aacgatatgc   1560

aggaacgaaa cgttgagcat tcaaaatttc aaattgaaca tatgaatcaa gagagaataa   1620

aaaaagaggc cttctaggct ggcatggaca attggacatg ttttcaacta gggtttcaag   1680

cttcgagcat ccacttttgt ccttgcaaac tttatacggc aaggcccgtg aatctagccc   1740

cccacaccac cccacccgcc cgcgccgcgc ggccgcctcg cctcccctcc cttctcctcc   1800

tctccgcccc cgccgccagg ccgtccacct ccgccgtctc ctcccccatt cgcacccaag   1860

gcgctggcgc ggaaggc                                                  1877
```

<210> SEQ ID NO 193
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0565

<400> SEQUENCE: 193

```
caccaaatat agtgttattt caatactaaa atggtgttat ggttggagat gccctaaaga     60

taaacatgac gagacacgag atttattaat ttcttgatca accataactt aataacttaa    120

tattaatttc acttaataat ttccaattaa gtgaatcttt acttcaccaa aagttcctaa    180

cgaactctta ttttctagca tcaatattac catgaactag catcaatact atcatgaaaa    240

attcctactt cctatccaac tcttaataac aatgctagtc ttaacaatat tcatcaaaaa    300

cttgatatag accttctaac ttagccacga ctagtatcgg tgaataccaa aattaatgta    360

ttcatgagaa cttgagattt ctctaatgta ttcttgttac taaacaagta acaacactca    420

agaaatatca tgatcaaata ttttactcat aaactccata tttcacattt tgaaaatttt    480

aaacagcaaa tcacattgaa ttttcgtggt aaaagtattt aaaattgaaa aatagcagct    540

cctgatttca atgtataaat ttatctttat atggtttatg tctccaactt attttaaaaa    600

agagagaaag agcacccaaa aggtgaccgt ttgaaattcg aatttatttc cgtttgaaat    660

tcgaattcaa aaaaagtaaa ccgaaccgag tctcgttact gactgtcaca cattgtttcc    720

ctaaaagcta attaacccat acgtggcgta atataacagg tcagtgatca atactaaata    780

acagacatac acctttaaaa ttcgtgcacg ctccaaaaca aaatctacac ttcaaaatca    840

acggtcacga tcattcctca aatttcaaaa aattatttaa cctcacttcc ttcgctttgt    900

ttttaaaacc tctctctctt tctctttctc tttcgccatt aaaactctgt ttcctttttc    960
```

agagattctc agagaagatt cattttaccc taagaaaaaa 1000

<210> SEQ ID NO 194
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0015

<400> SEQUENCE: 194
ttgagcctta ttgttgttat tgacttttag ccaatagaaa gagatggaaa ttcaataatt 60
atccacaaaa ttccaaatca ttggtgtaca aaaagatcta aggctgttat attttcaaaa 120
aagaaagaaa agaaatgcaa caaatatgga ttaaactgtg gtttgtaaat tgagctttgc 180
atgaaaactt tatcactatg atttcactac tccatattta ttgactaaag tggcactaat 240
gaatttctta atcatgaaat cttgtatcaa aaagtactaa aataaacatg acattggcaa 300
ttaggaaaat tctaaattag aaattagtaa aaatgaaagg tgaaagggaa agatgatgat 360
atgaattggt tggtgaccag gagaaatgta tcccgatttt tgcagacact ttcagtgtcc 420
ccattcatat aattatggcc cacctcgtta agatttttca ttcaccacca taacaagatc 480
taagcttaga tttcatgtaa ttaaacatat aatatacttg ccaatactat ctaataaagt 540
atacttaagc aaaaattatt actctagtgt aaggcgatga aatataagtt tagttgaaaa 600
tttatgtcga tataacaaag tataatgaat taagaccttg gttttcgatt aacaaactaa 660
ttaaacacta gttttgccta ataaaaccgg gaatcgtatt caaaaccgaa cgacaaaaca 720
agggacaagt tgagagacaa aaccaaatca gcatctttct tccagaaatg tcatgaccac 780
atgacgtcat cttgaccctt cttcattgtg atatctgtgg ataaagcgca cgtgtttaat 840
tcacgaacct tcgtagtaac gaaaaatcca caactttcat attttttaat tacccactaa 900
actaaaacaa atttggaaaa acatgaaaaa ctttttcttt ttttccaggt tcgtgaacct 960
cgtaccctct atataaacct cttaaccacc ttccacata 999

<210> SEQ ID NO 195
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0087

<400> SEQUENCE: 195
tgaattgagt aaaatgtgtt ttcaaacagt taggtggtag aaggtaaagg taataacatc 60
atgatcttac taaaagaatt gttgcatact aactatcaat attctcaaca acataatata 120
atgttttttt aggtaatttt ccattttaat tttttgtgat taaacaatta aacaactcga 180
atgatgatga taaaaaaaaa aaattaacaa ctcgaataag ttaaagtagc aatacacatg 240
tcgttcaatt caaccaataa agtaagactt atatttttaa gaagttgact aatagcttaa 300
taagttggaa aacttgtgta gtttcttaat tcccacgtgc agtaagaaat aaaaatgaaa 360
aaaattatta tatccttccc actctgcgac ttttctttta ttttatcaaa tattaaaaag 420
attcatatca cagtttacac attgaaatca taaacgataa ttatgtattt tgtaataaaa 480
agttagttct gaagctcata ctttggatag tcgctagtcg ctaatatgct ccttgtaata 540
attaaagtca ctacgacgca cgtcaaagcc gatatttagg gcttaattga tgcgtgtttt 600
tcttttcata taatagtaat ataaattagt actaataaag tatgatggat ggttgagaca 660

```
gaaaagaaaa aagatgactg tatggtcatc attacaaaga agaatgtatt cttcatgttc    720

ttaagaataa taaaatgtca cttgtaaatc aagttggtaa gcattttgag aactttgttc    780

gatgcaacgt atgatgattt atgtagacaa aagataaaac cgtatcttca actattgcca    840

agaaaagata aaacctaatc tagtcagtct ctcaacataa atacaaccca atagccaaac    900

tgtgtccaat tcggagagaa actaaactaa aacaaaacac aaaagcccaa cataagccca    960

ataaaaccca ttttataaac agaacattac taacactca                           999
```

<210> SEQ ID NO 196
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0093

<400> SEQUENCE: 196

```
atgatgaaca ttctacatat ataattatta tgtttaagca cttagacagc ataaattctt     60

tctaattata taaatctaac cttgttacat tgtacatcta taaattactt gaagaaataa    120

cgagttctat ttctttttaa aaattaaaaa tactatacca tatctcagtg attaagttga    180

accaaaaggt acggaggaga aacaagcatt tgattcttcc ttatttttatt ttattcatct    240

ctcactaatg atggtggaga aaaaaagaaa atacctaaca aacaaatata tattgtcata    300

caaaaatatt tctatatttt tagttaatta gtttatattc ctcacttttc agggcttata    360

taagaaagtg agcaaacaca aatcaaaatg cagcagcaaa tactatcatc acccatctcc    420

ttagttctat tttataattc ctcttctttt tgttcatagc tttgtaatta tagtcttatt    480

tctctttaag gctcaataag aggaggtact attactacac ttctctctac ttttacttgt    540

attttagcat taaaatccta aaatccgttt taaattcaaa aataaactta gagatgttta    600

atctcgattc ggtttttcgg ctttaggaga ataattatat gaaattagta tggatatctt    660

tactagtttc cattcaaatg attctgattt caatctaata ctctcactct ttaattaaac    720

tatatgtagt gtaatttcac actgttaaat ttctaccatg tcatgtatat tagagttgca    780

tagaaaattg taaaacatcc atttgaattc gaatgaaaca aaatgtttta aaataaaatt    840

ttggttttta aaagaaaaat ctaaaactga attatatcgt ttaaccaagt tgtaaaagtc    900

ataaaacgta gtatcttgta aatcgctctt ccacggtcca aatagacttc tagtaataaa    960

caagtaaaac taattttggt ttcttactaa ttttcacaga                         1000
```

<210> SEQ ID NO 197
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0108

<400> SEQUENCE: 197

```
ttagctgaac caggaaattg atctcttata ccagtttccg ggtttagatt ggtttgatgg     60

cgatttgatt aaacccccga aattttatgt cgtagttgtg catagtatta ttattctttg    120

cggacaatag acgtatcggg accaagttct gtagcaaaat tgtataagct taagtttgat    180

gaaatttaaa ggtaatcact aaaacccaaa tgggacaata aaccggtgaa gatttagagt    240

ttttaatttt gactcatgaa tctggagaaa gagccctcgt taaaaggagt gaatcaatcc    300
```

```
atagggggaaa aagttttgtc tttttaaaaa ctaaagaacc aaaccttaat agaagcagct    360
caatgtgtga caactttcca ctggcactaa gataaagtga ctagcgatga gtgcaattat    420
tgaaatagta gatggtaaat attacataca agagtaaaaa tatctttatg tcaatgctta    480
attcagtgtt tctggttaac aagagaaact tctctaactt tcgtaattgg gtcttataaa    540
attttatgca attatgattt taccctttta ctacttttca ttagctttca cgaatctatt    600
ttgacaagag aaatcattag aggtaaacat gctttttggt caagggcctt aacagttcca    660
ccaatcaagc tcaaaagttg tacttaaccg acatcttctg tgaaaacata taattacatg    720
tacaaatcaa aactacctta tgaaataaat agaaatattg cagttcattt ctaatttaac    780
ctcttcaact tttaaaacta tttacatttc tttatgtcat ttctagtcat tttgatgcaa    840
attgtaccat ttatggatta tcttcacaaa tttttaagtt ggtgaaaact ttttggtggg    900
tagttaaaac ttgaaataga aatttacttt accaaaataa actaatgaaa agtaatcact    960
ccactcccta taataagatt tccaacgttc ccactaagc                           999
```

<210> SEQ ID NO 198
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0022

<400> SEQUENCE: 198

```
tagttccatt acaatttcca aatgatttgt tacaaagcta caagattatt cgaaatagga     60
tttcatccat aagagagaat ggtgtggtcg acgctacaat gttgatttat tggttgtggt    120
ttgcatcttg gggatgtcaa atcctaagtt tcaagttctt gtaaaaacgt tttcaggttt    180
ctttaatata ttttaatatt aatgtaaaaa gaaaagatat agcttttgta caaaaaaatt    240
tgtttaatca ctatgtagga ggatgcgatc aaattcatgg aatgatgtat tattagcttt    300
tctatcctca ctctaaaaac aatactatag tgagttaaat aatttgatca tttcaatgta    360
gattaaaatt ttattaaaag aagaaaaatt taaaagccta taacaaaata aaaaaggagg    420
ctcgaggtat gatgggtgta gcagaagagc tggcaacagc tatcgactga gtgattacga    480
actcagtact cagtgttctc agctcacaca ctcttttttt gttctctttc ttttggacag    540
ctttcatttt ctcttttctt ttttctattt tgtttcaaaa ttccatccat attaaaatag    600
gcctgatcat gagaataaag gaaatactaa tgatgagttt ctcaataatg caataagatg    660
caattattat gagctattta ctattgaaaa tgagcaaata aatgtcaaaa cacaatctgg    720
ttaagttaga gcaactccat tgtataggat tcatgtagtt tctaagaaaa caaaatgtat    780
taatatttta cttttacatc caaaaaaacca acttatatga gtaatagaaa cgatcctaat    840
attaggaatt ttagagattt tctctcatct gtttcttaac ttttcaatat ttttattttt    900
taaaattgta tgagtttcta ctaagaaact actgctggag ttggtcttag cttcccaatg    960
cttctccacc tatatatatg catatctcct tcttaaaac                           999
```

<210> SEQ ID NO 199
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0080

<400> SEQUENCE: 199

```
aagcggcaat ttagtaagaa gtactcaaag tatcatttac caaaagtata tggttttggg      60

aagagttgtt agggatgtat tctttctaaa cagatgatat gacgatgttc ttgaaaacta     120

atgttaaaga cggaatctct ggcatcttca ctcgggagat atattaaacc gttgattgta     180

gttagccatg tacttagctt agtgcacaaa taatctgctg caagaaatct ttttctatta     240

taatatctct catttaaaca ttagaacata ttgtttaact tgttcttcta gaaataaaac     300

tgctaatttc ttatggtaaa ctattttcct ttagattgca caatcgaact cgaaaatcta     360

gtggagacta tgtgactatg tttatatata tgaaacctaa atcaaattat cccaataatt     420

gggagacaca aaagaaaaat tacgaaagaa aacaggaaat caaatcaaaa gataaagaga     480

aggtaaaaaa aggcaagaag cactaatgtt taatatttat agttttctcc attaaagaaa     540

aagcgatgat gtgtgttctc atcttttgtg aaagtatata tattgctttt gcttttctca     600

aaagcaaaag actcatccaa caagaacaaa aaaaaaaact aaagctcaat ccaaaagacg     660

aagaatgcat tggatactac aacttctttt tcacttttct ttcaaattta caattatgat     720

tttcacaata cagtttattc aaaaataaat aaaaaaacga ggcatgaaaa taatgattat     780

cctcttcact tattaagcca ctcactataa gcagagcaac tccagaacat agtgagcccc     840

caaaacatta aagcatgatg atgtctaatg atgatgatct tcttcgttcc atttctctaa     900

atttttggga tttctgcgaa gacccttctt ctctttctct tctctgaact tcaagattcg     960

tgtcggacaa atttttgttt ttatttttct gatgttaca                            999
```

<210> SEQ ID NO 200
<211> LENGTH: 3000
<212> TYPE: DNA
<213> ORGANISM: Arabidopsis thaliana
<220> FEATURE:
<221> NAME/KEY: misc_feature
<223> OTHER INFORMATION: Ceres Promoter PR0924

<400> SEQUENCE: 200

```
atctataacg agttaacatg ttgccagttt gaatcaagaa gcttggatga tgaatgaatg      60

gatcggtttg tggtacaatt cttaaaattg tagtagagga gacagagaaa aaacatgata     120

agactttggt atttacaact tgacggagac aagacagtaa gccaaatctg tcacaaaaac     180

actcaaactc ttttctcagt gttttgagtt taaagagaga cttattcact tccccttttcg    240

taacacttat ttgtctccca accaaacagt ttctgtcctt tcccttgtcc tcccacgtgc     300

atctttatat ctcatgactt ttcgtttcta gatcttgaat aatgtcttag tggattaggt     360

ttgttgtcgg taaattaggt gaccgttttt ttcttatatt tggaagatcg cgggatgaag     420

cagatactga gtttcagggc atacacacct aatttgaaaa tcattgttag tccaatttca     480

ctttaatctt gtttacaaaa aaattgatct gaaaatgttg atgggataag taaaaatgta     540

agttttgcta gtagtcatga tataataata gcaaaaccag atcaattttg agcaaaagga     600

agaaacaaaa aacagatcga tcccacgagc aagactaagt gtaaagtggt tcccacaaga     660

gccatatgga tatggtcctt caacttttaa agcccattac ttcagtggtc gacccgacat     720

tacgccacga gtagtcacgc acgcacgact ccgttcacgt gacattcacg ttgatatttc     780

cccctctact ctcttctgct tggttgatct aaaaaacatg aagagaccaa cctaatttca     840

tattaatata tgatatagac ttcatactca acagtcactt tcgtaatcca aatccatatc     900

ttacgaaatt agttcttaat aaaggttgtg gattaagtta taatattgtg ttaagagtta     960

agacacagca tataaccttg taccaacagt gctttattct taaatggaaa caaaacatat    1020
```

```
gtcaatgtca agcatacagc taaaatatca ttatctaata ttaagagtaa aacaagataa   1080

ttaaaaattg aaacaacacc atatttttat agctttactt atcgtatttt tctagtcttc   1140

atggtaattg tgttgcttta ttttgtttat aaatgaattt ggttcgacca gatagtctaa   1200

tatcagtttt taaacactgg ttttaataaa atcatatgtc ggcaattcaa cctgttacgt   1260

tgtatgattg tatcctagtc aaatagggga ggaggtacta gtcgtttcaa ttagtttacg   1320

taatcaatcc aaagaaacta taagctataa agatcctcaa tttgttggtt acaataaaaa   1380

caacagttgt caaaatttat gtttataaaa agtaataact atgttccttc ccatatagag   1440

caaagtacct caggataggc aaaccgtact taatagccct tattcataat ttgatccaac   1500

tcttccccac aaaattgcaa ctgatgaagt caatacttgt atagtgagtc aagctataaa   1560

tgtctagtga tagttttgtc tcttaaaagg ttaacaaaag ttatgacaag ctgaaaaatc   1620

agagtttgct aggagtatta cttacagtta tcagtttaag tatcacattt atagtattgt   1680

atacaatgat tcttaaattc caccttttcc gtgcgaaacc aaattttcta ttggaaacat   1740

agaatgtaaa caaaaatatg ggacgttgtc cgttccaaca ttaaccaaac ttgtctatta   1800

ctaatattcg tgttggtttg atgttggatg tctaaattcg ttgaatcatg tgtctcttga   1860

cgaaatatgc atcttcttat ttcttagtat agatgcactt tatcattctt ttagtacatg   1920

cttaattttt ttttttaaaa tatgttgatt gtcatattgc caaaagtatg aattaaagac   1980

gcacatctaa cacaagttag cagccgtaaa tccttccata aatttatttt gcaagttttg   2040

ctcattatat aatgagcgga atttatgata taatcgtttg taataatgtt atgttttgat   2100

caaaatttga aattaaaagt aggtgagaac ttgttataca gtgtagataa ggtggatctt   2160

gaatataaaa ataaaattta taagatgtat ttaaagcaga aaagcataaa actttagata   2220

aaataatgta aaaatgtgtt agcatcaatg ttgggatatt ggccgacccg aacttaatca   2280

atgtcggaag ccattacttc tctcccaaaa gaccttttc cttcggagaa ctaggaactt   2340

cctcactacc tttcgcttaa cgtgaaagcc ataaatttca tatattcata aaaatcagaa   2400

aatctaaaac tgtttagtat cacctgtttt tggtatagac tattggtttt gtgttacttc   2460

ctaaactata tgatttcgta cttcattgga tcttatagag atgaatattc gtaaaaagat   2520

aagttatctg gtgaaacgtt acttcagtca tgttgggtct agatttacat actactatga   2580

aacattttaa gataataatt atcctagcca actatatgtt ctatattatg ggccaagaag   2640

atatagaact aaaagttcag aatttaacga tataaattac tagtatattc taatacttga   2700

atgattactg ttttagttgt ttagaataaa tagtagcgtg ttggttaaga taccatctat   2760

ccacatctat atttgtgtgg gttacataaa atgtacataa tattatatac atatatatgt   2820

atatttttga taaagccata tattactcct tgacctctgc ccccatttcc ttttactata   2880

aataggaata ctcatgatcc tctaattcag caatcaacac caacgaacac aacctttcc   2940

aaagccaata ataaaagaac aaaagctttt agtttcatca aagacgaagc tgccttagaa   3000
```

<210> SEQ ID NO 201
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0388

<400> SEQUENCE: 201

```
agaagtattc acgcaccaag gttatatttg tagtgacata ttctacaatt atcacatttt     60
```

```
tctcttatgt ttcgtagtcg cagatggtca attttttcta taataatttg tccttgaaca    120
caccaaactt tagaaacgat gatatatacc gtattgtcac gctcacaatg aaacaaacgc    180
gatgaatcgt catcaccagc taaaagccta aaacaccatc ttagttttca ctcagataaa    240
aagattattt gtttccaacc tttctattga attgattagc agtgatgacg taattagtga    300
tagtttatag taaaacaaat ggaagtggta ataaatttac acaacaaaat atggtaagaa    360
tctataaaat aagaggttaa gagatctcat gttatattaa atgattgaaa gaaaaacaaa    420
ctattggttg atttccatat gtaatagtaa gttgtgatga aagtgatgac gtaattagtt    480
gtatttatag taaaacaaat taaaatggta aggtaaattt ccacaacaaa acttggtaaa    540
aatcttaaaa aaaaaaaaag aggtttagag atcgcatgcg tgtcatcaaa ggttcttttt    600
cactttaggt ctgagtagtg ttagactttg attggtgcac gtaagtgttt cgtatcgcga    660
tttaggagaa gtacgtttta cacgtggaca caatcaacgg tcaagatttc gtcgtccaga    720
tagaggagcg atacgtcacg ccattcaaca atctcctctt cttcattcct tcattttgat    780
tttgagtttt gatctgcccg ttcaaaagtc tcggtcatct gcccgtaaat ataaagatga    840
ttatatttat ttatatcttc tggtgaaaga agctaatata aagcttccat ggctaatctt    900
gtttaagctt ctcttcttct tctctctcct gtgtctcgtt cactagtttt ttttcggggg    960
agagtgatgg agtgtgtttg ttgaatagtt ttgacgatca                        1000
```

<210> SEQ ID NO 202
<211> LENGTH: 283
<212> TYPE: DNA
<213> ORGANISM: Arabidopsis thaliana
<220> FEATURE:
<221> NAME/KEY: misc_feature
<223> OTHER INFORMATION: Ceres Promoter PD0901

<400> SEQUENCE: 202

```
caaagtattt gacaagccat atggttttgg atcaaaaagt cggtccaaaa ttaatgtttt     60
atgtgcaaga accgacccat tgtacacacg tgttaacatc ttcaagactt tcatctctat    120
ttttcttttg gtcattaaga tacccattga tccgaatctg ttacattccc acctactttt    180
ttaattttta ctatccactc caaattaaac acaaccgatg attttaataa ttggaagctt    240
tttaaaatat ttctccacgt gcctctttgt gtttgtctat ata                      283
```

<210> SEQ ID NO 203
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0623

<400> SEQUENCE: 203

```
aaagttattg acattttgaa aggaccgtaa atattaccaa aaaactgacg gagttaggat     60
cggccacgta gaaagggaca aagagagaac agtcacggac tcggccagac taagtatggg    120
cctgtctgaa tccaaactca gctaagttcc aaaagcataa agagagatgt gtaatgaaat    180
gaacgtattc tagaaacgaa agcaatgtta tgctttgttt ttgagccaca tgtttttggg    240
agatggagag aatctttttt acgtttttaa cctaacccac ttggcacttg gccaaaaaag    300
tgagaagaaa ctgtggcgaa tgagtaggcc acgccatgga ctttgttcct tgtccttcaa    360
aagttaaatt tatgttatgc gtggggacaa tctaagcaac gtggttcctt taaatatcgc    420
```

```
agcttcctct tttacacttt tggagcctac gtgttttgtt ttggaccggc caaatacacg    480

agtcagtcag tttagaaata atttggatgt ccaaaaatct tggagatcca aataaaataa    540

ttagcatgtt ttagttcata agaatatgaa atgtagataa actgtctata ttaatttttc    600

catagaattg gctttttatc gaggtgatgt acttaatgac tttgttgatt actactcgta    660

taacaataaa gaatatgata ctatgtgaga cttataatga atttggtgtg tgttaattaa    720

tccagttgaa acagtttaat aacaaatcag aataaaaatt gtagtaagaa aatttgaacg    780

ctgatccttc aacctagata gtgaaccttt caaatactat atgattcacg tgtaatgttt    840

ttgaccgttg gttattttg tgtgaactat attaacttat caatatcgaa aggctaaata    900

agtaaataac taaaagaaag ttcaggaaac aactcgacct aatgacctat catttctgat    960

cacccgtcct ataaatacat acgtaagatc attcgttact                         1000
```

```
<210> SEQ ID NO 204
<211> LENGTH: 33
<212> TYPE: PRT
<213> ORGANISM: Artificial Sequence
<220> FEATURE:
<223> OTHER INFORMATION: Truncated version of Ceres CLONE ID no.
      100021733
<220> FEATURE:
<221> NAME/KEY: misc_feature
<223> OTHER INFORMATION: Ceres CLONE ID no. 100021733_T
<220> FEATURE:
<221> NAME/KEY: misc_feature
<222> LOCATION: (1)..(33)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 204

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys


<210> SEQ ID NO 205
<211> LENGTH: 33
<212> TYPE: PRT
<213> ORGANISM: Artificial Sequence
<220> FEATURE:
<223> OTHER INFORMATION: Truncated version of Ceres CLONE ID no. 1036726
<220> FEATURE:
<221> NAME/KEY: misc_feature
<223> OTHER INFORMATION: Ceres CLONE ID no. 1036726_T
<220> FEATURE:
<221> NAME/KEY: misc_feature
<222> LOCATION: (1)..(33)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 205

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30
```

Lys

<210> SEQ ID NO 206
<211> LENGTH: 33
<212> TYPE: PRT
<213> ORGANISM: Artificial Sequence
<220> FEATURE:
<223> OTHER INFORMATION: Truncated version of Ceres CLONE ID no. 1482731
<220> FEATURE:
<221> NAME/KEY: misc_feature
<223> OTHER INFORMATION: Ceres CLONE ID no. 1482731_T
<220> FEATURE:
<221> NAME/KEY: misc_feature
<222> LOCATION: (1)..(33)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 206

```
Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ser Lys Ile Gln Asp
            20                  25                  30

Lys
```

<210> SEQ ID NO 207
<211> LENGTH: 80
<212> TYPE: PRT
<213> ORGANISM: Artificial Sequence
<220> FEATURE:
<223> OTHER INFORMATION: Truncated version of Ceres CLONE ID no. 1554560
<220> FEATURE:
<221> NAME/KEY: misc_feature
<223> OTHER INFORMATION: Ceres CLONE ID no. 1554560_T
<220> FEATURE:
<221> NAME/KEY: misc_feature
<222> LOCATION: (17)..(78)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 207

```
Met Ala Leu Ala Glu Ala Asp Asp Gly Ala Val Val Phe Gly Glu Glu
1               5                   10                  15

Gln Glu Ala Leu Val Leu Lys Ser Trp Ala Val Met Lys Lys Asp Ala
            20                  25                  30

Ala Asn Leu Gly Leu Arg Phe Phe Leu Lys Val Phe Glu Ile Ala Pro
        35                  40                  45

Ser Ala Lys Gln Met Phe Ser Phe Leu Arg Asp Ser Asp Val Pro Leu
    50                  55                  60

Glu Lys Asn Pro Lys Leu Lys Thr His Ala Met Ser Val Phe Val Met
65                  70                  75                  80
```

<210> SEQ ID NO 208
<211> LENGTH: 77
<212> TYPE: PRT
<213> ORGANISM: Artificial Sequence
<220> FEATURE:
<223> OTHER INFORMATION: Truncated version of Ceres CLONE ID no. 1802327
<220> FEATURE:
<221> NAME/KEY: misc_feature
<223> OTHER INFORMATION: Ceres CLONE ID no. 1802327_T

```
<220> FEATURE:
<221> NAME/KEY: misc_feature
<222> LOCATION: (14)..(75)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 208

Met Ala Leu Ala Glu Gly Asn Val Ile Phe Gly Glu Glu Gln Glu Ala
1               5                   10                  15

Leu Val Leu Lys Ser Trp Ala Leu Met Lys Lys Asp Ser Ala Asp Leu
            20                  25                  30

Gly Leu Arg Phe Phe Leu Lys Ile Phe Glu Ile Ala Pro Ser Ala Lys
        35                  40                  45

Gln Met Phe Ser Phe Leu Arg Asp Ser Asp Val Pro Leu Glu Lys Asn
    50                  55                  60

Pro Lys Leu Lys Asn His Ala Met Ser Val Phe Val Met
65                  70                  75


<210> SEQ ID NO 209
<211> LENGTH: 77
<212> TYPE: PRT
<213> ORGANISM: Artificial Sequence
<220> FEATURE:
<223> OTHER INFORMATION: Truncated version of Ceres CLONE ID no. 1876458
<220> FEATURE:
<221> NAME/KEY: misc_feature
<223> OTHER INFORMATION: Ceres CLONE ID no. 1876458_T
<220> FEATURE:
<221> NAME/KEY: misc_feature
<222> LOCATION: (14)..(75)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 209

Met Ala Leu Ala Glu Gly Asn Val Ile Phe Gly Glu Glu Gln Glu Ala
1               5                   10                  15

Leu Val Leu Lys Ser Trp Ala Leu Met Lys Lys Asp Ser Ala Asp Leu
            20                  25                  30

Gly Leu Arg Phe Phe Leu Lys Ile Phe Glu Ile Ala Pro Ser Ala Lys
        35                  40                  45

Gln Met Phe Ser Phe Leu Arg Asp Ser Asp Val Pro Leu Glu Lys Asn
    50                  55                  60

Pro Lys Leu Lys Thr His Ala Met Ser Val Phe Val Met
65                  70                  75


<210> SEQ ID NO 210
<211> LENGTH: 79
<212> TYPE: PRT
<213> ORGANISM: Artificial Sequence
<220> FEATURE:
<223> OTHER INFORMATION: Truncated version of Ceres CLONE ID no. 1879148
<220> FEATURE:
<221> NAME/KEY: misc_feature
<223> OTHER INFORMATION: Ceres CLONE ID no. 1879148_T
<220> FEATURE:
<221> NAME/KEY: misc_feature
<222> LOCATION: (16)..(77)
<223> OTHER INFORMATION: Pfam Name: Globin
      Pfam Description: Globin
```

```
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 210

Met Ala Leu Ala Asp Gly Asn Gly Ala Ala Ile Phe Gly Glu Glu Gln
1               5                   10                  15

Glu Ala Leu Val Leu Lys Ser Trp Ala Leu Met Lys Lys Asp Ser Ala
            20                  25                  30

Asp Leu Gly Leu Arg Phe Phe Leu Lys Ile Phe Glu Ile Ala Pro Ser
        35                  40                  45

Ala Lys Gln Met Phe Ser Phe Leu Arg Asp Ser Asp Val Pro Leu Glu
    50                  55                  60

Lys Asn Pro Lys Leu Lys Thr His Ala Met Ser Val Phe Val Met
65                  70                  75


<210> SEQ ID NO 211
<211> LENGTH: 33
<212> TYPE: PRT
<213> ORGANISM: Artificial Sequence
<220> FEATURE:
<223> OTHER INFORMATION: Truncated version of Ceres CLONE ID no. 1884696
<220> FEATURE:
<221> NAME/KEY: misc_feature
<223> OTHER INFORMATION: Ceres CLONE ID no. 1884696_T
<220> FEATURE:
<221> NAME/KEY: misc_feature
<222> LOCATION: (1)..(33)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 211

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys


<210> SEQ ID NO 212
<211> LENGTH: 76
<212> TYPE: PRT
<213> ORGANISM: Artificial Sequence
<220> FEATURE:
<223> OTHER INFORMATION: Truncated version of Ceres CLONE ID no. 1916866
<220> FEATURE:
<221> NAME/KEY: misc_feature
<223> OTHER INFORMATION: Ceres CLONE ID no. 1916866_T
<220> FEATURE:
<221> NAME/KEY: misc_feature
<222> LOCATION: (13)..(74)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 212

Met Ala Thr Tyr Glu Gly Lys Val Phe Thr Glu Glu Gln Glu Ala Leu
1               5                   10                  15

Val Val Lys Ser Trp Thr Val Met Lys Lys Asn Ala Ala Glu Leu Gly
            20                  25                  30
```

```
Leu Lys Phe Phe Leu Lys Ile Phe Glu Ile Ala Pro Ser Ala Lys Lys
        35                  40                  45

Leu Phe Ser Phe Leu Arg Asp Ser Asn Val Pro Leu Glu Gln Asn Thr
    50                  55                  60

Lys Leu Lys Pro His Ala Met Ser Val Phe Val Met
65                  70                  75


<210> SEQ ID NO 213
<211> LENGTH: 33
<212> TYPE: PRT
<213> ORGANISM: Artificial Sequence
<220> FEATURE:
<223> OTHER INFORMATION: Truncated version of Ceres CLONE ID no. 1950105
<220> FEATURE:
<221> NAME/KEY: misc_feature
<223> OTHER INFORMATION: Ceres CLONE ID no. 1950105_T
<220> FEATURE:
<221> NAME/KEY: misc_feature
<222> LOCATION: (1)..(33)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 213

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys


<210> SEQ ID NO 214
<211> LENGTH: 79
<212> TYPE: PRT
<213> ORGANISM: Artificial Sequence
<220> FEATURE:
<223> OTHER INFORMATION: Truncated version of Ceres CLONE ID no. 1990746
<220> FEATURE:
<221> NAME/KEY: misc_feature
<223> OTHER INFORMATION: Ceres CLONE ID no. 1990746_T
<220> FEATURE:
<221> NAME/KEY: misc_feature
<222> LOCATION: (16)..(77)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 214

Met Ala Leu Ala Glu Gly Asn Gly Ala Ala Ile Phe Gly Glu Glu Gln
1               5                   10                  15

Glu Ala Leu Val Leu Lys Ser Trp Ala Leu Met Lys Lys Asp Ser Ala
            20                  25                  30

Asp Leu Gly Leu Arg Phe Phe Leu Lys Ile Phe Glu Ile Ala Pro Ser
        35                  40                  45

Ala Lys Gln Met Phe Ser Phe Leu Arg Asp Ser Asp Val Pro Leu Glu
    50                  55                  60

Lys Asn Pro Lys Leu Lys Thr His Ala Met Ser Val Phe Val Met
65                  70                  75


<210> SEQ ID NO 215
```

```
<211> LENGTH: 79
<212> TYPE: PRT
<213> ORGANISM: Artificial Sequence
<220> FEATURE:
<223> OTHER INFORMATION: Truncated version of Ceres CLONE ID no. 2033803
<220> FEATURE:
<221> NAME/KEY: misc_feature
<223> OTHER INFORMATION: Ceres CLONE ID no. 2033803_T
<220> FEATURE:
<221> NAME/KEY: misc_feature
<222> LOCATION: (16)..(77)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 215

Met Ala Leu Ala Glu Gly Asn Gly Ala Ala Ile Phe Gly Glu Glu Gln
1               5                   10                  15

Glu Ala Leu Val Leu Lys Ser Trp Ala Leu Met Lys Lys Asp Ser Ala
            20                  25                  30

Asp Leu Gly Leu Arg Phe Phe Leu Lys Ile Phe Glu Ile Ala Pro Ser
        35                  40                  45

Ala Lys Gln Met Phe Ser Phe Leu Arg Asp Ser Asp Val Pro Leu Glu
    50                  55                  60

Lys Asn Pro Lys Leu Lys Thr His Ala Met Ser Val Phe Val Met
65                  70                  75


<210> SEQ ID NO 216
<211> LENGTH: 33
<212> TYPE: PRT
<213> ORGANISM: Artificial Sequence
<220> FEATURE:
<223> OTHER INFORMATION: Truncated version of Ceres CLONE ID no. 2034916
<220> FEATURE:
<221> NAME/KEY: misc_feature
<223> OTHER INFORMATION: Ceres CLONE ID no. 2034916_T
<220> FEATURE:
<221> NAME/KEY: misc_feature
<222> LOCATION: (1)..(33)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 216

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys


<210> SEQ ID NO 217
<211> LENGTH: 33
<212> TYPE: PRT
<213> ORGANISM: Artificial Sequence
<220> FEATURE:
<223> OTHER INFORMATION: Truncated version of Ceres CLONE ID no. 513071
<220> FEATURE:
<221> NAME/KEY: misc_feature
<223> OTHER INFORMATION: Ceres CLONE ID no. 513071_T
<220> FEATURE:
<221> NAME/KEY: misc_feature
<222> LOCATION: (1)..(33)
<223> OTHER INFORMATION: Pfam Name: ubiquitin
```

```
      Pfam Description: Ubiquitin family
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 217

Met Gln Ile Phe Val Lys Thr Leu Thr Gly Lys Thr Ile Thr Leu Glu
1               5                   10                  15

Val Glu Ser Ser Asp Thr Val Asp Asn Val Lys Ala Lys Ile Gln Asp
            20                  25                  30

Lys


<210> SEQ ID NO 218
<211> LENGTH: 33
<212> TYPE: PRT
<213> ORGANISM: Artificial Sequence
<220> FEATURE:
<223> OTHER INFORMATION: Truncated version of Ceres CLONE ID no. 522921
<220> FEATURE:
<223> OTHER INFORMATION: Ceres CLONE ID no. 522921_T
<220> FEATURE:
<221> NAME/KEY: misc_feature
<222> LOCATION: (1)..(33)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 218

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys


<210> SEQ ID NO 219
<211> LENGTH: 76
<212> TYPE: PRT
<213> ORGANISM: Artificial Sequence
<220> FEATURE:
<223> OTHER INFORMATION: Truncated version of Ceres CLONE ID no. 546001
<220> FEATURE:
<221> NAME/KEY: misc_feature
<223> OTHER INFORMATION: Ceres CLONE ID no. 546001_T
<220> FEATURE:
<221> NAME/KEY: misc_feature
<222> LOCATION: (13)..(74)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 219

Met Thr Thr Thr Leu Glu Arg Gly Phe Ser Glu Glu Gln Glu Ala Leu
1               5                   10                  15

Val Val Lys Ser Trp Asn Val Met Lys Lys Asn Ser Gly Glu Leu Gly
            20                  25                  30

Leu Lys Phe Phe Leu Lys Ile Phe Glu Ile Ala Pro Ser Ala Gln Lys
        35                  40                  45

Leu Phe Ser Phe Leu Arg Asp Ser Thr Val Pro Leu Glu Gln Asn Pro
    50                  55                  60
```

```
Lys Leu Lys Pro His Ala Val Ser Val Phe Val Met
65                  70                  75


<210> SEQ ID NO 220
<211> LENGTH: 76
<212> TYPE: PRT
<213> ORGANISM: Artificial Sequence
<220> FEATURE:
<223> OTHER INFORMATION: Truncated version of Ceres CLONE ID no. 651581
<220> FEATURE:
<221> NAME/KEY: misc_feature
<223> OTHER INFORMATION: Ceres CLONE ID no. 651581_T
<220> FEATURE:
<221> NAME/KEY: misc_feature
<222> LOCATION: (13)..(74)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 220

Met Glu Ser Glu Gly Lys Ile Val Phe Thr Glu Glu Gln Glu Ala Leu
1               5                   10                  15

Val Val Lys Ser Trp Ser Val Met Lys Lys Asn Ser Ala Asp Leu Gly
            20                  25                  30

Leu Lys Leu Phe Ile Lys Ile Phe Glu Ile Ala Pro Thr Ala Lys Lys
        35                  40                  45

Leu Phe Ser Phe Leu Arg Asp Ser Pro Ile Pro Ala Glu Gln Asn Pro
    50                  55                  60

Lys Leu Lys Pro His Ala Met Ser Val Phe Val Met
65                  70                  75


<210> SEQ ID NO 221
<211> LENGTH: 77
<212> TYPE: PRT
<213> ORGANISM: Artificial Sequence
<220> FEATURE:
<223> OTHER INFORMATION: Truncated version of Ceres CLONE ID no. 839727
<220> FEATURE:
<221> NAME/KEY: misc_feature
<223> OTHER INFORMATION: Ceres CLONE ID no. 839727_T
<220> FEATURE:
<221> NAME/KEY: misc_feature
<222> LOCATION: (14)..(75)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 221

Met Ser Ala Ala Glu Gly Ala Val Val Phe Ser Glu Glu Lys Glu Ala
1               5                   10                  15

Leu Val Leu Lys Ser Trp Ala Ile Met Lys Lys Asp Ser Ala Asn Leu
            20                  25                  30

Gly Leu Arg Phe Phe Leu Lys Ile Phe Glu Ile Ala Pro Ser Ala Arg
        35                  40                  45

Gln Met Phe Pro Phe Leu Arg Asp Ser Asp Val Pro Leu Glu Thr Asn
    50                  55                  60

Pro Lys Leu Lys Thr His Ala Val Ser Val Phe Val Met
65                  70                  75


<210> SEQ ID NO 222
```

```
<211> LENGTH: 76
<212> TYPE: PRT
<213> ORGANISM: Artificial Sequence
<220> FEATURE:
<223> OTHER INFORMATION: Truncated version of Public GI ID no. 11095158
<220> FEATURE:
<221> NAME/KEY: misc_feature
<223> OTHER INFORMATION: Public GI ID no. 11095158_T
<220> FEATURE:
<221> NAME/KEY: misc_feature
<222> LOCATION: (13)..(76)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 222

Met Gly Thr Leu Asp Thr Lys Gly Phe Thr Glu Glu Gln Glu Ala Leu
1               5                   10                  15

Val Val Lys Ser Trp Asn Ala Met Lys Lys Asn Ser Ala Glu Leu Gly
            20                  25                  30

Leu Lys Leu Phe Leu Lys Ile Phe Glu Ile Ala Pro Ser Ala Gln Lys
        35                  40                  45

Leu Phe Ser Phe Leu Lys Asp Ser Lys Val Pro Leu Glu Gln Asn Thr
    50                  55                  60

Lys Leu Lys Pro His Ala Met Ser Val Phe Leu Met
65                  70                  75


<210> SEQ ID NO 223
<211> LENGTH: 71
<212> TYPE: PRT
<213> ORGANISM: Artificial Sequence
<220> FEATURE:
<223> OTHER INFORMATION: Truncated version of Public GI ID no. 12963875
<220> FEATURE:
<221> NAME/KEY: misc_feature
<223> OTHER INFORMATION: Public GI ID no. 12963875_T
<220> FEATURE:
<221> NAME/KEY: misc_feature
<222> LOCATION: (8)..(69)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 223

Met Ser Ser Phe Ser Glu Glu Gln Glu Ala Leu Val Val Lys Ser Trp
1               5                   10                  15

Gly Ser Met Lys Lys Asp Ala Gly Glu Trp Gly Leu Lys Phe Phe Leu
            20                  25                  30

Lys Ile Phe Glu Ile Ala Pro Ser Ala Lys Lys Met Phe Ser Phe Leu
        35                  40                  45

Lys Asp Ser Asn Val Pro Leu Asp Gln Asn Pro Lys Leu Lys Ile His
    50                  55                  60

Ala Lys Ser Val Leu Val Met
65                  70


<210> SEQ ID NO 224
<211> LENGTH: 84
<212> TYPE: PRT
<213> ORGANISM: Artificial Sequence
<220> FEATURE:
<223> OTHER INFORMATION: Truncated version of Public GI ID no. 14701800
```

<220> FEATURE:
<221> NAME/KEY: misc_feature
<223> OTHER INFORMATION: Public GI ID no. 14701800_T
<220> FEATURE:
<221> NAME/KEY: misc_feature
<222> LOCATION: (21)..(82)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 224

```
Met Ala Leu Val Glu Gly Asn Asn Gly Val Ser Gly Gly Ala Val Ser
1               5                   10                  15

Phe Ser Glu Glu Gln Glu Ala Leu Val Leu Lys Ser Trp Ala Ile Met
            20                  25                  30

Lys Lys Asp Ser Ala Asn Ile Gly Leu Arg Phe Phe Leu Lys Ile Phe
        35                  40                  45

Glu Val Ala Pro Ser Ala Ser Gln Met Phe Ser Phe Leu Arg Asn Ser
    50                  55                  60

Asp Val Pro Leu Glu Lys Asn Pro Lys Leu Lys Thr His Ala Met Ser
65                  70                  75                  80

Val Phe Val Met
```

<210> SEQ ID NO 225
<211> LENGTH: 76
<212> TYPE: PRT
<213> ORGANISM: Artificial Sequence
<220> FEATURE:
<223> OTHER INFORMATION: Truncated version of Public GI ID no. 15226675
<220> FEATURE:
<221> NAME/KEY: misc_feature
<223> OTHER INFORMATION: Public GI ID no. 15226675_T
<220> FEATURE:
<221> NAME/KEY: misc_feature
<222> LOCATION: (13)..(74)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 225

```
Met Glu Ser Glu Gly Lys Ile Val Phe Thr Glu Glu Gln Glu Ala Leu
1               5                   10                  15

Val Val Lys Ser Trp Ser Val Met Lys Lys Asn Ser Ala Glu Leu Gly
            20                  25                  30

Leu Lys Leu Phe Ile Lys Ile Phe Glu Ile Ala Pro Thr Thr Lys Lys
        35                  40                  45

Met Phe Ser Phe Leu Arg Asp Ser Pro Ile Pro Ala Glu Gln Asn Pro
    50                  55                  60

Lys Leu Lys Pro His Ala Met Ser Val Phe Val Met
65                  70                  75
```

<210> SEQ ID NO 226
<211> LENGTH: 76
<212> TYPE: PRT
<213> ORGANISM: Artificial Sequence
<220> FEATURE:
<223> OTHER INFORMATION: Truncated version of Public GI ID no. 15824736
<220> FEATURE:
<221> NAME/KEY: misc_feature
<223> OTHER INFORMATION: Public GI ID no. 15824736_T
<220> FEATURE:
<221> NAME/KEY: misc_feature
<222> LOCATION: (13)..(74)
<223> OTHER INFORMATION: Pfam Name: Globin
Pfam Description: Globin
<220> FEATURE:
<221> NAME/KEY: misc_feature
<223> OTHER INFORMATION: Functional homolog of Ceres Clone ID no. 30469
given in SEQ ID NO: 7

<400> SEQUENCE: 226

Met Ala Thr Tyr Glu Gly Lys Val Phe Thr Glu Glu Gln Glu Ala Leu
1 5 10 15

Val Val Lys Ser Trp Thr Val Met Lys Lys Lys Thr Ala Glu Leu Gly
20 25 30

Leu Lys Phe Phe Leu Lys Ile Phe Glu Ile Ala Pro Ser Ala Lys Lys
35 40 45

Leu Phe Ser Phe Leu Arg Asp Ser Asn Val Pro Leu Glu Gln Asn Thr
50 55 60

Lys Leu Lys Pro His Ala Met Ser Val Phe Val Met
65 70 75

<210> SEQ ID NO 227
<211> LENGTH: 76
<212> TYPE: PRT
<213> ORGANISM: Artificial Sequence
<220> FEATURE:
<223> OTHER INFORMATION: Truncated version of Public GI ID no. 30909306
<220> FEATURE:
<221> NAME/KEY: misc_feature
<223> OTHER INFORMATION: Public GI ID no. 30909306_T
<220> FEATURE:
<221> NAME/KEY: misc_feature
<222> LOCATION: (13)..(74)
<223> OTHER INFORMATION: Pfam Name: Globin
Pfam Description: Globin
<220> FEATURE:
<221> NAME/KEY: misc_feature
<223> OTHER INFORMATION: Functional homolog of Ceres Clone ID no. 30469
given in SEQ ID NO: 7

<400> SEQUENCE: 227

Met Glu Ser Glu Gly Lys Ile Val Phe Thr Glu Glu Gln Glu Ala Leu
1 5 10 15

Val Val Lys Ser Trp Ser Val Met Lys Lys Asn Ser Ala Asp Leu Gly
20 25 30

Leu Lys Leu Phe Ile Lys Ile Phe Glu Ile Ala Pro Thr Ala Lys Lys
35 40 45

Leu Phe Ser Phe Leu Arg Asp Ser Pro Ile Pro Ala Glu Gln Asn Pro
50 55 60

Lys Leu Lys Pro His Ala Met Ser Val Phe Val Met
65 70 75

<210> SEQ ID NO 228
<211> LENGTH: 73
<212> TYPE: PRT
<213> ORGANISM: Artificial Sequence
<220> FEATURE:
<223> OTHER INFORMATION: Truncated version of Public GI ID no. 37903656
<220> FEATURE:
<221> NAME/KEY: misc_feature
<223> OTHER INFORMATION: Public GI ID no. 37903656_T
<220> FEATURE:
<221> NAME/KEY: misc_feature
<222> LOCATION: (10)..(71)
<223> OTHER INFORMATION: Pfam Name: Globin
Pfam Description: Globin <220> FEATURE:
<221> NAME/KEY: misc_feature
<223> OTHER INFORMATION: Functional homolog of Ceres Clone ID no. 30469
given in SEQ ID NO: 7

<400> SEQUENCE: 228

Met Glu Gly Lys Val Phe Thr Glu Glu Gln Glu Thr Leu Val Val Lys
1 5 10 15

Ser Trp Gly Val Met Lys Lys Asn Ala Ala Glu Leu Gly Leu Lys Phe
20 25 30

Phe Leu Lys Ile Phe Glu Ile Ala Pro Ser Ala Gln Lys Leu Phe Ser
35 40 45

Phe Leu Arg Asp Ser Asp Ile Pro Leu Glu Lys Asn Pro Lys Leu Lys
50 55 60

Pro His Ala Met Ser Val Phe Val Met
65 70

<210> SEQ ID NO 229
<211> LENGTH: 76
<212> TYPE: PRT
<213> ORGANISM: Artificial Sequence
<220> FEATURE:
<223> OTHER INFORMATION: Truncated version of Public GI ID no. 62548111
<220> FEATURE:
<221> NAME/KEY: misc_feature
<223> OTHER INFORMATION: Public GI ID no. 62548111_T
<220> FEATURE:
<221> NAME/KEY: misc_feature
<222> LOCATION: (13)..(74)
<223> OTHER INFORMATION: Pfam Name: Globin
Pfam Description: Globin
<220> FEATURE:
<221> NAME/KEY: misc_feature
<223> OTHER INFORMATION: Functional homolog of Ceres Clone ID no. 30469
given in SEQ ID NO: 7

<400> SEQUENCE: 229

Met Ala Thr Tyr Glu Gly Lys Val Phe Thr Glu Glu Gln Glu Ala Leu
1 5 10 15

Val Val Lys Ser Trp Thr Val Met Lys Lys Asn Ala Ala Glu Leu Gly
20 25 30

Leu Lys Phe Phe Leu Lys Ile Phe Glu Ile Ala Pro Ser Ala Lys Lys
35 40 45

Leu Phe Ser Phe Leu Arg Asp Ser Asn Val Pro Leu Glu Gln Asn Thr
50 55 60

Lys Leu Lys Pro His Ala Met Ser Val Phe Val Met
65 70 75